(12) United States Patent
Gleiberman et al.

(10) Patent No.: US 10,265,390 B2
(45) Date of Patent: Apr. 23, 2019

(54) USE OF TOLL-LIKE RECEPTOR AGONIST FOR TREATING CANCER

(71) Applicant: Cleveland BioLabs, Inc., Buffalo, NY (US)

(72) Inventors: Anatoli Gleiberman, East Aurora, NY (US); Lyudmila Burdelya, Lancaster, NY (US); Andrei Gudkov, East Aurora, NY (US)

(73) Assignee: CLEVELAND BIOLABS, INC., Buffalo, NY (US)

( * ) Notice: Subject to any disclaimer, the term of this patent is extended or adjusted under 35 U.S.C. 154(b) by 0 days.

(21) Appl. No.: 16/014,419

(22) Filed: Jun. 21, 2018

(65) Prior Publication Data

US 2018/0344823 A1 Dec. 6, 2018

Related U.S. Application Data

(63) Continuation of application No. 15/631,427, filed on Jun. 23, 2017, now Pat. No. 10,034,926, which is a continuation of application No. 15/241,757, filed on Aug. 19, 2016, now abandoned, which is a continuation of application No. 14/949,441, filed on Nov. 23, 2015, now abandoned, which is a continuation of application No. 13/979,104, filed as application No. PCT/US2012/020844 on Jan. 10, 2012, now Pat. No. 9,376,473.

(60) Provisional application No. 61/431,313, filed on Jan. 10, 2011.

(51) Int. Cl.
| C07K 14/195 | (2006.01) |
| C07K 14/255 | (2006.01) |
| A61K 38/16 | (2006.01) |
| A61K 39/02 | (2006.01) |
| A61K 39/112 | (2006.01) |
| A61K 39/00 | (2006.01) |
| A61K 39/395 | (2006.01) |
| C07K 16/28 | (2006.01) |
| C07K 14/705 | (2006.01) |

(52) U.S. Cl.
CPC ........ *A61K 39/0011* (2013.01); *A61K 38/164* (2013.01); *A61K 39/39533* (2013.01); *A61K 39/39558* (2013.01); *C07K 14/195* (2013.01); *C07K 14/255* (2013.01); *C07K 16/2878* (2013.01); *A61K 39/02* (2013.01); *A61K 39/0275* (2013.01); *A61K 2039/5158* (2013.01); *A61K 2039/545* (2013.01); *A61K 2039/57* (2013.01); *A61K 2039/572* (2013.01); *A61K 2039/585* (2013.01); *C07K 14/705* (2013.01)

(58) Field of Classification Search
CPC ...... A61K 2300/00; A61K 2039/55516; A61K 2039/55561; A61K 38/00; A61K 2039/55594; A61K 38/164; C07K 14/00; C07K 14/255; C07K 14/195
See application file for complete search history.

(56) References Cited

U.S. PATENT DOCUMENTS

| 4,554,101 A | 11/1985 | Hopp |
| 5,399,494 A | 3/1995 | Kaper et al. |
| 5,693,476 A | 12/1997 | Scheller |
| 6,130,082 A | 10/2000 | Majarian et al. |
| 7,404,963 B2 | 7/2008 | Sotomayor et al. |
| 7,638,485 B2 | 12/2009 | Gudkov |
| 7,794,731 B2 | 9/2010 | Mizel et al. |
| 8,007,812 B2 | 8/2011 | Gudkov et al. |
| 8,106,005 B2 | 1/2012 | Gudkov |
| 8,287,882 B2 | 10/2012 | Gudkov et al. |
| 8,324,163 B2 | 12/2012 | Gudkov et al. |
| 8,580,321 B2 | 11/2013 | Gudkov et al. |
| 9,376,473 B2 * | 6/2016 | Gleiberman ......... A61K 38/164 |
| 10,034,926 B2 * | 7/2018 | Gleiberman ......... A61K 38/164 |
| 2002/0009747 A1 | 1/2002 | Miller et al. |
| 2003/0044429 A1 | 3/2003 | Aderem et al. |
| 2005/0147627 A1 | 7/2005 | Aderem et al. |
| 2005/0266391 A1 | 12/2005 | Bennett et al. |
| 2006/0275255 A1 | 12/2006 | Gudkov |
| 2007/0202551 A1 | 8/2007 | Gudkov |
| 2007/0269406 A1 | 11/2007 | Ichim |
| 2008/0124361 A1 | 5/2008 | Mizel et al. |
| 2008/0182797 A1 | 7/2008 | Nudler et al. |
| 2009/0011982 A1 | 1/2009 | Gudkov et al. |
| 2009/0081157 A1 | 3/2009 | Kornbluth et al. |
| 2009/0123467 A1 | 5/2009 | Bedi et al. |
| 2009/0175880 A1 | 7/2009 | Keler et al. |

(Continued)

FOREIGN PATENT DOCUMENTS

| WO | 1992005816 | 4/1992 |
| WO | 1993018150 | 9/1993 |

(Continued)

OTHER PUBLICATIONS

Kim et al. Increased expression of toll-like receptor 5 during progression of cervical neoplasia. Int J Gynecol Cancer 18: 30--305, 2008.*
Nishimura et al. Tissue-specific mRNA expression profiles of human toll-like receptors and related genes. Biol Pharm Bull 28(5): 886-892, 2005.*
Skerrett et al. Redundant toll-like receptor signaling in the pulmonary host response to Pseudomonas aeruginosa. Am J Physiol Lung Cell Mol Physiol 292: L312-L322, 2007.*

(Continued)

*Primary Examiner* — Bridget E Bunner
(74) *Attorney, Agent, or Firm* — Morgan, Lewis & Bockius LLP

(57) ABSTRACT

The present invention is directed to methods and agents used for treating cancer in Toll-Like Receptor 5-expressing tissues by providing a Toll-Like Receptor agonist such as flagellin. The present invention also relates to protecting the liver from a liver toxicity using a Toll-like receptor agonist.

19 Claims, 44 Drawing Sheets

Specification includes a Sequence Listing.

(56) References Cited

U.S. PATENT DOCUMENTS

| | | | |
|---|---|---|---|
| 2009/0246303 A1 | 10/2009 | Gudkov et al. | |
| 2010/0056454 A1 | 3/2010 | Gudkov | |
| 2011/0319595 A1 | 12/2011 | Gudkov et al. | |
| 2013/0004515 A1 | 1/2013 | Gudkov et al. | |
| 2013/0324462 A1 | 12/2013 | Gudkov et al. | |

FOREIGN PATENT DOCUMENTS

| | | |
|---|---|---|
| WO | 1999029312 | 6/1999 |
| WO | 2001040280 | 6/2001 |
| WO | 2001055210 | 8/2001 |
| WO | 2002044363 | 6/2002 |
| WO | 2003027251 | 4/2003 |
| WO | 2003028659 | 4/2003 |
| WO | 2004086039 | 10/2004 |
| WO | 2005056041 | 6/2005 |
| WO | 2005056042 | 6/2005 |
| WO | 2005056054 | 6/2005 |
| WO | 2005056055 | 6/2005 |
| WO | 2005057218 | 6/2005 |
| WO | 2006066214 | 6/2006 |
| WO | 2006069198 | 6/2006 |
| WO | 2007030581 | 3/2007 |
| WO | 2008157473 | 12/2008 |
| WO | 2009102818 | 8/2009 |
| WO | 2010133885 | 11/2010 |
| WO | 2011027222 | 3/2011 |
| WO | 2011044246 | 4/2011 |

OTHER PUBLICATIONS

Zarember et al. Tissue expression of human toll-like receptors and differential regulation of toll-like receptor mRNAs in leukocytes in response to microbes, their products, and cytokines. J Immunol 168: 554-561, 2002.*

Zhou et al. Toll-like receptor expression in normal ovary and ovarian tumors. Cancer Immunol Immunother 58: 1375-1385, 2009.*

Pashenkov et al. "Phase II trial of a toll-like receptor 9-activating oligonucleotide in patients with metastatic melanoma" J Clin Oncol 24: 5716-5724 2006.

Patchen M. L. "Amifostine plus granulocyte colony-stimulating factor therapy enhances recovery from supralethal radiation exposures: preclinical experience in animals models" European Journal of Cancer 31A(1):S17-S21 (1995).

Rensing-Ehl et al., Local Fas/APO-1 )(CD95) Ligand-Mediated Tumor Cell Killing in vivo, Eur J Immunol, 1995, vol. 25, pp. 2253-2258.

Rhee et al. "Toll-like receptor 5 engagement modulates tumor development and growth in a mouse xenograft model of human colon cancer" Gastroenterology Aug. 2008; 135(2): 518-528.

Samatey F. A. et al. "Structure of the bacterial flagellar protofilament and implications for a switch for supercoiling" Nature 410:331-337 (2001).

Satyamitra M. et al. "In vivo postirradiation protection by a vitamin E analog a-TMG" Radiation Research 160(6):655-661 (2003).

Schmidt et al. "Intratumoural injection of the toll-like receptor-2/6 agonist 'macrophage-activating lipopeptide-2' in patients with pancreatic carcinoma: a phase I/II trial" Brit J Cancer 97: 598-604 2007.

Sebastiani G. et. al. "Cloning and characterization of the murine Toll-like Receptor 5 (Tlr5) gene: sequence and mRNA expression studies in *Salmonella*-susceptible MOLF/Ei mice" Genomics 64(3):230-240 (2000).

Seed T. et al. "New strategies for the prevention of radiation injury: possible implications for countering radiation hazards of long-term space travel" Journal of Radiation Research 43:S239-S244 (2002).

Selander R. K. et al. "Molecular evolutionary genetics of the cattle-adapted serovar *Salmonella dublin*" Journal of Bacteriology 174(11):3587-3592 (1992).

Service R. F. "Tumor-Killer Made; How Does It Work?" Science 274:2009 (1996).

Sfondrini et al. "Antitumor Activity of the TLR-5 Ligand Flagellin in Mouse Models of Cancer" The Journal of Immunology 2006 176:6624-6630.

Smith K. D. et al. "Toll-like receptor 5 recognizes a conserved site on flagellin required for protofilament formation and bacterial motility" Nature Immunology 4(12):1247-1253 (2003).

Song et al. "Flagellin promotes the proliferation of gastric cancers via the Toll-like receptor 5" Int J Mol Med 28:115-119 2011.

Spadaro J. A. et al. "Radioprotectant combinations spare radiation-induced damage to the physis more than fractionation alone" Int. J. Radiat. Biol. 81(10):759-765 (2005) Abstract.

Sredni B. et al. "The immunomodulator AS101 administered orally as a chemoprotective and radioprotective agent" Int. J. Immunopharmacol. 14(4):613-619 (1992).

Streeter P. R. et al. "Activation of the G-CSF and Flt-3 receptors protects hematopoietic stem cells from lethal irradiation" Experimental Hematology 31(11):1119-1125 (2003).

Symon Z. et al. "Selective radioprotection of hepatocytes by systemic and portal vein infusions of amifostine in a rat liver tumor model" Int. J. Radiation Oncology Biol. Phys. 50(2):473-478 (2001).

Tallant T. et al. "Flagellin acting via TLR5 is the major activator of key signaling pathways leading to NF-KB and proinflammatory gene program activation in intestinal epithelial cells" BMC Microbiology 4(1):33 (2004).

Timmer et al. "Fas receptor-mediated apoptosis: a clinical application?" J Pathol 196: 125-134 2002.

Trauth et al. "Monoclonal antibody-mediated tumor regression by induction of apoptosis" Science 245: 301-305 1989.

Tsujimoto H. et al. "Flagellin enhances NK cell proliferation and activation directly and through dendritic cell-NK cell Interactions" Journal of Leukocyte Biology 78(4):888-897 (2005).

Vasquez R. J. et al. "Nanomolar concentrations of nocodazole alter microtubule dynamic instability in vivo and in vitro" Molecular Biology of the Cell 8(6):973-985 (1997).

Vijay-Kumar et al. "Flagellin Treatment Protects against Chemicals Bacteria Viruses and Radiation" The Journal of Immunology 2008 180:8280-8285.

Waddick K. G. et al. "In vitro and in vivo antileukemic activity of B43-pokeweed antiviral protein against radiation-resistant human B-cell precursor leukemia cells" Blood 86(11):4228-4233 (1995).

Watson A. J. et al. "Lessons from genetically engineered animal models. VII. Apoptosis in intestinal epithelium: lessons from transgenic and knockout mice" Am. J. Physiol. Gastrointest. Liver Physiol. 278(1):G1-G5 (2000).

Wheeler C. M. "Preventative vaccines for cervial cancer" Salud Publica de Mexico 39(4) (1997) 9 pages.

Whitnall M. H. et al. "In vivo radioprotection by 5-androstenediol: stimulation of the innate immune system" Radiation Research 156(3):283-293 (2001).

Wolska et al. "Toll-like receptors and their role in carcinogensis and anti-tumor treatment" Cell Mol Biol Letters 14:248-272 2009.

Wong G. H. W. "Protective roles of cytokines against radiation: induction of mitochondrial MnSOD" Biochimica et Biophysica Acta 1271:205-209 (1995).

Yang et al. "Antigen replacement of domains D2 and D3 in flagellin promotes mucosal IgA production and attenuates flagellin-induced inflammatory response after intranasal immunization" Human Vaccines and Immunotherap 9:5 1084-1092 2013.

Alavanja M. CR. "Biologic damage resulting from exposure to tobacco smoke from radon: implication for preventive interventions" Oncogene 21:7365-7375 (2002).

Andreassen C. N. et al. "Chemical radioprotection: a critical review of amifostine as a cytoprotector in radiotherapy" Seminars in Radiation Oncology 13(1):62-72 (2003).

Androstenediol and Androstenedione Wikipedia (online). URL: < http://en.wikipedia.org/wiki/Androstenediol> [Retrieved from the Internet: Dec. 5, 2006] 4 pages.

Bachmann M. F. et al. "Recall proliferation potential of memory CD8+ T cells and antiviral protection" The Journal of Immunology 175:4677-4685 (2005).

Ben-Yedidia T. et al. "Intranasal administration of peptide vaccine protects human/mouse radiation chimera from influenza infection" International Immunology 11(7):1043-1051 (1998).

(56) References Cited

OTHER PUBLICATIONS

Booth D. et. al. "Transforming growth factor-B3 protects murine small intestinal crypt stem cells and animal survival after irradiation possibly by reducing stem-cell cycling" Int. J. Cancer 86(1):53-59 (2000).
Borges H. L. et al. "DNA damage-induced cell death: lessons from the central nervous system" Cell Research 18:17-26 (2008).
Bulinski J. C. et al. "Overexpression of MAP4 inhibits organelle motility and trafficking in vivo" Journal of Cell Sciences 110:3055-3064 (1997).
Burdelya L. G. et al. "An agonist of toll-like receptor 5 has radioprotective activity in mouse and primate models" Science 320:226-230 (2008).
Cai et al. "Activation of toll-like receptor 5 on breast cancer cells by flagellin suppresses cell proliferation and tumor growth" Cancer Res 71 (7): 2466-2475 2011.
Cai et al. "Activation of toll-like receptor 5 on breast cancer cells by flagellin suppresses tumor development and growth" Cancer Res 70: #3819 Apr. 2010.
Carnes B. A. et al. "Mortality of atomic bomb survivors predicted from laboratory animals" Radiation Research 160(2):159-167 (2003) Abstract.
Caron G. et. al. "Direct stimulation of human T cells via TLR5 and TLR7/8: Flagellin and R-848 up-regulate proliferation and IFN-γ production by memory CD4+ T cells" The Journal of Immunology 175(3):1551-1557 (2005).
Dummer et al. "An exploratory study of systemic administration of the toll-like receptor-7 agonist 852A in patients with refractory metastic melanoma" Clin Cancer Res 14(3): 856-864 2008.
Eaves-Pyles T. D. et al. "*Salmonella flagellin*-dependent proinflammatory responses are localized to the conserved amino and carboxyl regions of the protein" The Journal of Immunology 167(12):7009-7016 (2001).
Eaves-Pyles T. et al. "Flagellin a novel mediator of *Salmonella*-induced epithelial activation and systemic inflammation: IKBa degradation induction of nitric oxide synthase induction of proinflammatory mediators and cardiovascular dysfunction" The Journal of Immunology 166(2):1248-1260 (2001).
Efferson C. L. et al. "Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15" Anticancer Research 25:715-724 (2005).
Egan L. J. et al. "IkB-kinase13-dependent NF-k13 activation provides radioprotection to the intestinal epithelium" PNAS 101(8):2452-2457 (2004).
Elewaut D. et al. "NF-KB is a central regulator of the intestinal epithelial cell innate immune response induced by infection with enteroinvasive bacteria" The Journal of Immunology 163:1457-1466 (1999).
Etter et al. "The combination of chemotherapy and intraperitoneal MegaFas ligand improves treatment of ovarian carcinoma" Gynecologic Oncol 107: 14-21 2007.
Foldes G. et al. "Toll-like receptor modulation in cardiovascular disease: a target for intervention?" Expert Opinion on Investigational Drugs 15(8):857-871 (2006).
Fukuzawa N. et al. "A TLR5 agonist inhibits acute renal ischemic failure" The Journal of Immunology 187:3831-3839 (2011).
GenBank databases NCBI Accession No. M84972 Apr. 26, 1993 [online] [retrieved on Sep. 29, 2011] Retrieved from the Internet: <URL: http://www.ncbi.nlm.nih.gov/nuccore/M84972>.
Gewirtz A.T. et. al. "Cutting edge: Bacterial flagellin activates basolaterally expressed TLR5 to induce epithelial proinflammatory gene expression" The Journal of Immunology 167(4):1882-1885 (2001).
Grdina D. J. et al. "Relationships between cytoprotection and mutation prevention by WR-1065" Military Medicine 167(2):51-53 (2002).
Guan K. L. et al. "Eukaryotic proteins expressed in *Escherichia coli*: an improved thrombin cleavage and purification procedure of fusion proteins with glutathione S-transferase" Analytical Biochemistry 192:262-267 (1991).
Gudkov A. V. et al. "The role of p53 in determining sensitivity to radiotherapy" Nat. Rev. Cancer 3:117-129 (2003).
Guicciardi et al., Life and Death by Death Receptors, FASEB J, 2009, vol. 23, No. 6, pp. 1625-1637.
Haimovitz-Friedman A. et al. "Ionizing radiation acts on cellular membranes to generate ceramide and apoptosis" J. Exp. Med. 180:525-535 (1994).
Hall "Physics and Chemisty of Radiation Absorption" Radiobiology for the Radiobiologist pp. 5-15 5th ed. Lippincott Williams and Wilkins Philadelphia PA (2000).
Herbert J. M. et al. "Involvement of u-PA in the anti-apoptotic activity of TGF-beta for vascular smooth muscle cells" FEBS Letters 413(3):401-404 (1997).
Honko A. N. et al. "Effects of flagellin on innate and adaptive immunity" Immunologic Research 33(1):83-101 (2005).
Jung C. W. et al. "Antiproliferative effect of a vitamin D3 analog EB1089 on HL-60 cells by the induction of TGF-beta receptor" Leukemia Research 23(12):1105-1112 (1999).
Kemp G. et al. "Amifostine pretreatment for protection against cyclophosphamide-induced and cisplatininduced toxicities: results of a randomized control in patients with advanced ovarian cancer" Journal of Clinical Oncolouv 14(7):2101-2112 (1996).
Krieg A.M. "Development of TLR9 agonists for cancer therapy" J Clinical Invest 117(5): 1184-1194 2007.
Kyte J. et al. "A simple method for displaying the hydropathic character of a protein" J. Mol. Biol. 157:105- 132 (1982).
Lehnert B. E. et al. "A new mechanism for DNA alterations induced by alpha particles such as those emitted by radon and radon progeny" Environmental Health Perspectives 105(5):1095-1101 (1997).
Li G. et al. "A special issue on DNA damage responses and genome maintenance" Cell Research 18(1):1-2 (2008).
Li J. et al. "Evolutionary origin and radiation of the avian-adapted non-motile salmonellae" Journal of Medical Microbiology 38(2):129-139 (1993).
McQuiston J. R. et al. "Sequencing and comparative analysis of flagellin genes fliC fljB and flpA from *Salmonella*" Journal of Clinical Microbiology 42(5):1923-1932 (2004).
Melby T. E. et al. "The symmetrical structure of structural maintenance of chromosomes (SMC) and MukB proteins: Long antiparallel coiled coils folded at a flexible hinge" The Journal of Cell Biology 142(6):1595-1604 (1998).
Mercurio F. et al. "NF-kB as a primary regulator of the stress response" Oncogene 18:6163-6171 (1999).
Murley J. S. et al. "Delayed cytoprotection after enhancement of Sod2 (MnSOD) gene expression in SA-NH mouse sarcoma cells exposed to WR-1065 the active metabolite of amifostine" Radiation Research 158(1):101-109 (2002).
Murley J. S. et al. "Delayed radioprotection by NFKB-mediated induction of Sod2 (MnSOD) in SA-NH tumor cells after exposure to clinically used thiol-containing drugs" Radiation Research 162(5):536-546 (2004).
Mutlu-Turkoglu U. et al. "The effect of selenium and/or vitamin E treatments on radiation-induced intestinal injury in rats" Life Sciences 66(20):1905-1913 (2000).
Neish A. S. "TLRS in the Gut. II. Flagellin-induced inflammation and antiapoptosis" American Journal of Physiology: Gastrointestinal and Liver Physiology 292(2):G462-G466 (2006).
Newton S. M. C. et al. "Immune response to cholera toxin epitope inserted in *Salmonella flagellin*" Science 244:70-72 (1989).
Offringa "Tumour immunology—Exploitation of the weapon of immune destruction for cancer therapy: taking aim before firing" Current Opinion in Immunology 2005 17:159-162.
Panda D. et al. "Stabilization of microtubule dynamics by estramustine by binding to a novel site in tubulin: A possible mechanistic basis for its antitumor action" Proc. Natl. Acad. Sci. USA 94(20):10560-10564 (1997).

\* cited by examiner

FIGURE 4A

AA'
Nucleotide sequence (990 bp): SEQ ID NO: 7

ATGCGGGGTTCTCATCATCATCATCATCATGGTATGGCTAGCATGACTGGTGGACAGCAA
ATGGGTCGGGATCTGTACGACGATGACGATAAGGATCCAATGGCACAAGTCATTAATACA
AACAGCCTGTCGCTGTTGACCCAGAATAACCTGAACAAATCTCAGTCTTCACTGACTTCC
GCTATTGAGCGCCTGTCTTCGGGCCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGACTAACTCTGATTCT
GATCTGAAATCTATCCAGGATGAAATTCAGCAACGTCTGGAAGAAATCGATCCCGTTTCT
AATCAGACTCAATTTAACGGTGTAAAGCTCCTCTGTCAGGACAACCAGATGAAAATCCAG
GTTGGTGCTAACGATGGTGAAACCATTACCATCGATCTGCAAAAAATCGATGTGAAATCT
CTGGGCCTTGATGGCTTCAATGTTAATCCCCCGGGAATTTCCGGTGGTGGTGGTGGAATT
CTAGACTCCATGGGTACATTAATCAATGAAGACGCTGCCGCAGCAAAGAAAGTACCGCT
AACCCACTGGCTTCAATTGATTCTGCATTGTCAAAAGTGGACGCAGTTCGTTCTTCTCTC
GGGGCAATTCAAAACCGTTTTGATTCAGCCATTACCAACCTTTGG
Protein sequence (329 AA): SEQ ID NO: 8

MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLDGFNVNSPGISGGGGGILDSMGTLINEDAAAKKSTANPLASIDSALSKVDAVRSSLGAIQNRFD
SAITNLQNTVTNLNSARGRIEDADYATEVSNMSRAQILQQAGTSVLAQANQVPQNVLSLLR

AB'
Nucleotide sequence (825 bp): SEQ ID NO: 9

ATGCGGGGTTCTCATCATCATCATCATCATGGTATGGCTAGCATGACTGGTGGACAGCAA
ATGGGTCGGGATCTGTACGACGATGACGATAAGGATCCAATGGCACAAGTCATTAATACA
AACAGCCTGTCGCTGTTGACCCAGAATAACCTGAACAAATCTCAGTCTTCACTGACTTCC
GCTATTGAGCGCCTGTCTTCGGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGACTAACTCTGATTCT
GATCTGAAATCTATCCAGGATGAAATTCAGCAACGTCTGGAAGAAATCGATCCCGTTTCT
AATCAGACTCAATTTAACGGTGTAAAGCTCCTCTGTCAGGACAACCAGATGAAAATCCAG
GTTGGTGCTAACGATGGTGAAACCATTACCATCGATCTGCAAAAAATCGATGTGAAATCT
CTGGGCCTTGATGGCTTCAATGTTAATCCCCCGGGAATTTCCGGTGGTGGTGGTGGAATT
CTAGACTCCATGGGTACATTAATCAATGAAGACGCTGCCGCAGCAAAGAAAGTACCGCT
AACCCACTGGCTTCAATTGATTCTGCATTGTCAAAAGTGGACGCAGTTCGTTCTTCTCTC
GGGGCAATTCAAAACCGTTTTGATTCAGCCATTACCAACCTTTGG
Protein sequence (274 AA): SEQ ID NO: 10

MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLDGFNVNSPGISGGGGGILDSMGTLINEDAAAKKSTANPLASIDSALSKVDAVRSSLGAIQNRFD
SAITNL

FIGURE 4B

BA'
Nucleotide sequence (831 bp): SEQ ID NO: 11

ATGCGGGGTTCTCATCATCATCATCATGGTATGGCTAGCATGACTGGTGGACAGCAA
ATGGGTCGGATCTGTACGACGATGACGATAAGGATCCTTCACTTCTAATATCAAAGGC
CTGACTCAGGCTTCCCGTAACGCTAACGACGGCATTTCTATTGCCCAGACCACTGAAGGT
GCGCTGAATGAAATCAACAACAACCTGCAGCCTGTGCGTGAGTTGTCGTTCAGGCCACT
AACCGGGACTAACTCTGATTCCGATTTGAAATCTATCCAGGATGAAATCAGCAACGTCTG
GAAGAAATCGATCGTTCTAATCAGACTCAATTTAACGGTGTTAAAGTCCTCTCTCAG
GACAACCAGATGAAAATCCAGGTTGGTGCTAACGATGGTGAAAGCATTACCATCGATCTG
CAAAAAATTGATGTGAAAAGCCTTGGCCTTGATGGCTTCAATGTTAATTCCCGGGAATT
TCCGGTGGTGGTGGTGGAATTCTAGACTCCATGGCTACATTAATGAATGAAGACGCTGCC
GCAGCCAAGAAAGTACCGCTAACCCACTGGCTTGAATTGATTCTGCATTGTGAAAGTG
GACGCCAGTTCGTTCTTCTCTCGGGCAATTCAAAACCGTTTTGATTCAGCCATTACCAAC
CTTGGGAATACGGTAACCAATCTGAATCCGCGTGTAGCCGTATGAAGATGCTGACTAT
GCAACGGAGTTTCTAATATGTCTAAAGCCAGATTCTGCAGCAGCGTGGAGTTCGTT
CTGGCGCAGGCTAACCAGGTTCCGGAAAACGTCCTCTTCTTTACTGCGTTAG

Protein sequence (276 AA): SEQ ID NO: 12

MRGSHHHHHHGMASMTGGQQMGRDLYDDDDKDPFTSNIEGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLDGFNVNSPGISGGGGGILDSMGTLINEDAAAAKKSTANPLASIDSALSKVD
AVRSSLGAIQNRFDSAITNLGNTVTNLNSARSRIEDADYATEVSNMSKAQTLQQAGTSVLAQANQVP
QNVLSLLR

BB'
Nucleotide sequence (666 bp): SEQ ID NO: 13

ATGCGGGGTTCTCATCATCATCATCATCATGGTATGGCTAGCATGACTGGTGGACAGCAA
ATGGGTCGGGATCTGTACGACGATGACGATAAGGATCCTTCACTTCTAATATCAAAGGC
CTGACTCAGGCTTCCCGTAACGCTAACGACGGCATTTCTATTGCCCAGACCACTGAAGGT
GCGCTGAATGAAATCAACAACAACCTGCAGCCTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGTGTTTCTAATCAGACTCAATTTAACGGTGTTAAAGTCCTCTCTCAG
GACAACCAGATGAAAATCCAGGTTGGTGCTAACGATGGTGAAAGCCATTACCATCGATCTG
CAAAAAATTGATGTGAAAAGCCTTGGCCTTGATGGCTTCAATGTTAATTCCCGGGAATT
TCCGGTGGTGGTGGTGGAATTCTAGACTCCATGGGTACATTAATCAATGAAGACGCTGCC
GCAGCCAAGAAAGTACCGCTAACCCACTGGCTTGAATTGATTCTGCATTGTGAAAGTG
GACGCCAGTTCGTTCTTCTCTCGGGCAATTCAAAACCGTTTTGATTCAGCCATTACCAAC
CTTTAG

Protein sequence (221 AA): SEQ ID NO: 14

MRGSHHHHHHGMASMTGGQQMGRDLYDDDDKDPFTSNIEGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLDGFNVNSPGISGGGGGILDSMGTLINEDAAAAKKSTANPLASIDSALSKVD
AVRSSLGAIQNRFDSAITNL

FIGURE 4C

CA'
Nucleotide sequence (603 bp): SEQ ID NO: 15

ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGT
CTGACTCAGGCTTCCCGTAACGCTAACGACGGCATTTCTATTGCCCAGACCACTGAAGGT
GCACTGAATGAAATCAACAACAACCTGCAGCGTGTGCGTGAGTTGTCTGTTCAGGCCACT
TCCCCGGGAATTTCCGGTGGTGGTGGTGGAATTCTAGACTCCATGGTTACATTAATCAAT
GAAGACGCTGCCGCACCAAGAAAAGTACCGCTAACCCACTGGCTTCAATTGATTCTGCA
TTGTCAAAAGTGGACGCAGTCCGTTCTTCTCTGGGGCAATTCAAAACCGTTTTGATTCA
GCCATTACCAACCTGGCAATACGGTAACAATCTGAACTCCGCCGGTAGCCGTATCGAA
GATGCTGACTATGCTACGGAAGTTTCTAATATGTCTAAACGTGAGATTCTGCAGCAGGCT
GGTACTTCCGTTCTTGCTCAGGCTAACCAGGTTCCGCAAAACGTCCTTTCTCTTACTGCGT
TAG

Protein sequence (200 AA): SEQ ID NO: 16

MRGSHHHHHHGMASMTGGQQMGRDLYDDDDKDPFTSNIKGLTQASRNANDGISIAQTTEGALNEINN
NLQRVRELSVQATSPGISGGGGGILDSMGTLINEDAAAARKSTANPLASIDSALSKVDAVRSSLGAI
QNRFDSAITNLQNTVTNLNSARSRIEDADYATEVSNMSKAQILQQAGTSVLAQANQVPQNVLSLLR

CB'
Nucleotide sequence (438 bp): SEQ ID NO: 17

ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGC
CTGACTCAGGCTTCCCGTAACGCTAACGACGGCATTTCTATTGCCCAGACCACTGAAGGT
GCGCTGAATGAAATCAACAACAACCTGCAGCGTGTGCGTGAGTTGTCTGTTCAGGCCACT
TCCCCGGGAATTTCCGGTGGTGGTGGTGGAATTCTAGACTCCATGGTTACATTAATCAAT
GAAGACGCTGCCGCAGCCAAGAAAAGTACCGCTAACCCACTGGCTTCAATTGATTCTGCA
TTGTCAAAAGTGGACGCAGTTCGTTCTTCTCTGGGGCAATTCAAACGGTTTGATTCA
GCCATTACCAACCTTTAG

Protein sequence (145 AA): SEQ ID NO: 18

MRGSHHHHHHGMASMTGGQQMGRDLYDDDDKDPFTSNIKGLTQASRNANDGISIAQTTEGALNEINN
NLQRVRELSVQATSPGISGGGGGILDSMGTLINEDAAAARKSTANPLASIDSALSKVDAVRSSLGAI
QNRFDSAITNL

A
Nucleotide sequence (639 bp): SEQ ID NO: 19

ATGCGGGGTTCTCATCATCATCATCATCATGGTATGGCTAGCATGACTGGTGGACAGCAA
ATGGGTCGGGATCTGTACGACTGACCGATAAGGATCCGATGGCACAAGTCATTAATACA
AACAGCCTGTCGCTGTTGACCCAGAATAACTTGAACAAATCTCAGTCCTCACTGAGTTCC
GCTATTGAGCGTCTCTCCTCTGGTCTACGTATCAACAGCGCGAAAGACGATGCCGCAGGG
CAGGCGATTGCTAACCGCTTCACTTCTAATATCAAAGGTCTGACTCAGGCTTCCCGGAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCT
GATCTCAAATCTATCCAGGATGAAATTCAGCAACGTCTGGAAGAAATCGATCGGGTTTCT
AATCAGACTCAATTTAACGGCGTTAAGGTCCTGTCTCAGGACAACCAGATGAAAATCCAG
GTTGGTGCTAACGATGGTGAAACCATTACCATCGATCTGCAAAAAATTGATGTGAAAAGC
CTTGGGCTTGATGGCTTCAATGTTAATTCCCCGGGATCA

Protein sequence (212 AA), last three amino acids are derived from primer and pRSETb polylinker:

MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLDGFNVNSPG  SEQ ID NO: 20

FIGURE 4D

B
Nucleotide sequence (480 bp): SEQ ID NO: 21
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGT
CTGACTCAGGCTTCCCGTAACGCTAACGACGGGATTTCTATTGCGCAGACCACTGAAGGT
GCCCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTAACGGTGTTAAAGTCCTGTCTCAG
GACAACCAGATGAAAATCCAGGTTTGTGCTAACGATTGCGAAACCATTACCATCGATCTG
CAAAAAATTGATGTGAAAAGCCTTGGCCTTGATGGCTTTAATGTTAATTCCCCGGGATGA
Protein sequence (159 AA), last three amino acids are derived from primer and pRSETb polylinker:
MRGSHHHHHHGMASMTGGQQMGRDLYDDDDKDPFTSNIKGLTQASRNANDGISIAQTTEGALNEINN
NLQRVRELSVQATNGTNSDSDLKSIQDEIQQRLEEIDRVSNQTQFNGVKVLSQDNQMKIQVCANDCE
TITIDLQKIDVKSLGLDGFNVNSPG SEQ ID NO: 22

C
Nucleotide sequence (252 bp): SEQ ID NO: 23
ATGCGGGGTTCTCATCATCATCATCATCATGGTATGGCTAGCATGACTGGTGGACAGCAA
ATGGGTCGGGATCTGTACGACGATGACGATAAGGATCCGTTCACTTCTAATATCAAAGGT
CTGACTCAGGCTTCCCGTAACGCTAACGACGGGATTTCTATTGCGCAGACCACTGAAGGT
GCCCTGAATGAAATCAACAACAACCTGCAGCGTGTGCGTGAGTTGTCTGTTCAGGCCACT
TCCCCGGGATGA
Protein sequence (83 AA), last three amino acids are derived from primer and pRSETb polylinker:
MRGSHHHHHHGMASMTGGQQMGRDLYDDDDKDPFTSNIKGLTQASRNANDGISIAQTTEGALNEINN
NLQRVRELSVQATSPG SEQ ID NO: 24

GST-A'
Nucleotide sequence (1038 bp), GST highlighted: SEQ ID NO: 25

ATGTCCCCTATACTAGGTTATTGGAAAATTAAGGGCCTTGTGCAACCCACTCGACTTCTT
TTGGAATATCTTGAAGAAAAATATGAAGAGCATTTGTATGAGCGCGATGAAGGTGATAAA
TGGCGAAACAAAAAGTTTGAATTGGGTTTGGAGTTTCCCAATCTTCCTTATTATATTGAT
GGTGATGTTAAATTAACACAGTCTATGGCCATCATACGTTATATAGCTGACAAGCACAAC
ATGTTGGGTGGTTGTCCAAAAGAGCGTGCAGAGATTTCAATGCTTGAAGGAGCGGTTCTG
GATATTAGATACGGTGTTTCGAGAATTGCATATAGTAAAGACTTTGAAACTCTCAAAGTT
GATTTTCTTAGCAAGCTACCTGAAATGCTGAAAATGTTCGAAGATCGTTTATGTCATAAA
ACATATTTAAATGGTGATCATGTAACCCATCCTGACTTCATGTTGTATGACGTCCTTGAT
GTTGTTTTATACATGGACCCAATGTGCCTGGATCCGTTCCCAAAATTAGTTTGTTTTAAA
AAACGTATTGAAGCTATCCCACAAATTGATAAGTACTTGAAATCCAGCAAGTATATAGCA
TGGCCTTTGCAGGGCTGGCAAGCCACGTTTGGTGGTGGCGACCATCCTCCAAAATCGGAT
CTGGTTCCGCGTGGATCCCCGGGAATTTCCGGTGGTGGTGGTGGAATTCTAGACTCCATG
GGTACATTAATCAATGAAGACGCTGCCGCACCCAAGAAAAGTACCGCTAACCCACTCGCT
TCAATTGATTCTGCATTGTCAAAAGTGGACGCAGTTCGTTCTTCTCTCGGGGCAATTCAA
AACCGTTTTGATTCAGCCATTACCAACCTTGGCAATACGGTAACCAATCTGAACTCCGCG
CGTAGCCCGATCGAAGATGCTGACTATGCAACGGAAGTTTCTAATATGTCTAAAGCGCAG
ATTCTGCAGGCTGGTACTTCCGTTCTGGCGCAGGCTAACCAGGTTCCGAAAACGTC
CTTCTTACGGGTTAG
Protein sequence (345 AA): SEQ ID NO: 26
MSPILGYWKIRGLVQPTRLLLEYLEERYEEHLYERDEGDKWRNKKFELGLEFPNLPYYIDGDVKLTQ
SMAIIRYIADKHNMLGGCPKERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKRIEAIPQIDKYLKSSKYIAW
PLQGWQATFGGGDHPPKSDLVPRGSPGISGGGGGILDSMGTLINEDAAAKKSTANPLASIDSALSK
VDAVRSSLGAIQNRFDSAITNLGNTVTNLNSARSPIEDADYATEVSNMSKAQILQAGTSVLAQANQ
VPQNVLSLLR

FIGURE 4E

GST-B'
Nucleotide sequence (873 bp), GST highlighted: SEQ ID NO: 27
ATGTCCCCTATACTAGGTTATTGGAAAATTAAGGGCCTTGTGCAACCCACTCGACTTCTT
TTGGAATATCTTGAAGAAAAATATGAAGAGCATTTGTATGAGCGCGATGAAGGTGATAAA
TGGCGAAACAAAAAGTTTGAATTGGGTTTGGGAGTTCCCAATCTTCCTTATTATATTGAT
GGTGATGTTAAATTACACAGTCTATGGCCATCATACGTTATATAGCTGACAAGCACAAC
ATGTTGGGTGGTTGTCCAAAAGAGCGTGCAGAGATTTCAATGCTTGAAGGAGCGGTTTTG
GATATTAGATACGGTGTTTCGAGAATTGCATATAGTAAAGACTTTGAAACTCTCAAAGTT
GATTTTCTTAGCAAGCTACCTGAAATGCTGAAAATGTTCGAAGATCGTTTATGTCATAAA
ACATATTTAAATGGTGATCATGTAACCCATCCTGACTTCATGTTGTATGACGCTCTTGAT
GTTGTTTTATACATGGACCCAATGTGCCTGGATGCCGTTCCCAAAATTAGTTTGTTTTAAA
AAACGTATTGAAGCTATCCCACAAATTGATAAGTACTTGAAATCCAGCAAGTATATAGCA
TGGCCTTTGCAGGGCTGGCAAGCCACGTTTGGTGGTGGCGACCATCCTCCAAAATCGGAT
CTGGTTCCGCGTGGATCCCCGGGAATTTCCGGTGGTGGTGGTGGAATTCTAGACTCCATG
GGTACATTAATCAATGAAGACGCTGCCGCAGCCAAGAAAAGTACGGCTAACCCACTGGCT
TCAATTGATTCTGCATTGTCAAAAGTGGACGCAGTTCGTTCTTCTCTTGGGGCAATTCAA
AACCGTTTTGATTCAGCCATTACCAACCTTTAG
Protein sequence (290 AA): SEQ ID NO: 28
MSPILGYWKIKGLVQPTRLLEYLEEKYEEHLYERDEGDKWRNKKFELGLEFPNLPYYIDGDVKLTQ
SMAIIRYIADKHNMLGGCPKERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKRIEAIPQIDKYLKSSKYIAW
PLQGWQATFGGDHPPKSDLVPRGSPGISGGGGILDSMGTLINEDAAAAKKSTANPLASIDSALSK
VDAVRSSLGAIQNRFDSAITNL AA'n1-170
Nucleotide sequence (972 bp): SEQ ID NO: 29
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAACGTCTGTCCTCTGGCCTGCGTATCAACAGTGCGAAAGACGATGCGGCAGGC
CAGGCGATTGCTAACCGCTTCACTTCTAATATCAAAGGTCTGACTCAGGCTTCCCGTAAC
GCTAACGACGGCATTTCTATTGCGCAGACCACTGAAGGCGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTGTCTCAGGACAACCAGATGAAAATCCAG
GTTGGTGCTAACGATGGTGAAACCATTACCATCGATCTGCAAAAAATTGATGTGAAAAGC
CTTGGCCTTATCCCGGGAATTTCCGGTGGTGGTGGTGGAATTCTAGACTCCATGGGTACA
TTAATCAATGAAGACGCTGCCGCAGCCAAGAAAAGTACGGCTAACCCACTGGCTTCAATT
GATTCTGCATTGTCAAAAGTGGACGCAGTTCGTTCTTCTCTTGGGGCAATTCAAAACCGT
TTTGATTCAGCCATTACCAACCTTTGGCAATACGGTAACCAATCTGAACTCCGCGCGTAGC
CGTATCGAAGATGCTGACTATGCAACGGAAGTTTCTAATATGTCTAAAGCGCAGATTCTG
CAGCAGGCTGGTACTTCGGTTCTGGCGCAGGCTAACCAGTGTCCGCAAAACGTCCTCTCT
TTACTGCGTTAG
Protein sequence (323 AA): SEQ ID NO: 30
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
CTNSDSDLKSIQDEIQQRLEEIDRVSNQTQFNGVKVLSQDNQMKIQVGANDGETITIDLQKIDVKSL
GLIPGISGGGGILDSMGTLINEDAAAAKKSTANPLASIDSALSKVDAVRSSLGAIQNRFDSAITNL
GNTVTNLNSARSRIEDADYATEVSNMSKAQILQQAGTSVLAQANQVPQNVLSLLR

FIGURE 4F

AA'n1-163
Nucleotide sequence (951 bp): SEQ ID NO: 33
ATKCGGGTTCTCATCATCATCATCATCATGGTATGGCTAGCATGACTGGTGGACAGCAA
ATGGGTCGGGATCTCTACGACGATGACGATAAGGATCCGATGGCACAAGTCATTAATACA
AACAGCCTGTCGCTCTGACCCAGAATAACTGAACAAATCTCAGTCCTCACTCAGTTCC
GCTATTGAGCGTCTGTCGTCTGGTCTGCGTATCAACAGCGCGAAAGACGATGCGGCAGGC
CAGCCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATTAACAAC
AACCTGCAGGCGTGTCGGTGAGTTGTCTGTTCAGGCGACTAACGGGACTAACTCTGATTCC
GATCTGAAATCTATCCAGGACGAAATTCAGCAACTGGAAGAAATCGATCGCGTTTCT
AATCAGACTCAATTTAACGGTGTTAAAGTCCTGTCTCAGGACAACCAGATGAAAATCCAG
GTTGGTGCTAACGATGGTGAAACCATTACCATCGATCTTCAAAAAATTATCCCGGGAATT
TCCGGTGGTGGTGGTGGAATTCTAGACTCCATGGGTACATTAATGAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTGGCAATACGGTAACCAATCTGAACTCCGCGCGTAGCCGATCAAGATGCTGACTAT
GCAACGGAAGTTTCTAATATGTCTAAACGGCAGATTCTCCAGCAGGCTGGTACTTCCGTT
CTGGCGCAGGCTAACCAGGTTCCGCAAGACGTCCTGTCTTTACTGCGTTAG
Protein sequence (316 AA): SEQ ID NO: 34
*MRGSHHHHHHGMASMTGGQQMGRDLYDDDDKDPM*AQVINTNSLSLLTQNNLNKSQSSLSSAIERLSS
GLRINSAKEDAAGQAIANRFTSNIKGLTQASRNANDGISIAQTTEGALNEINNNLQEVRELSVQATN
GTNSDSDLKSIQDEIQQRLEEIDRVSNQTQFNGVKVLSQDNQMKIQVGANDGETTITIDLQKIIPGIS
GGGGGILDSMGTLINEDAAAAKKSTANPLASIDSALSKVDAVRSSLGAIQNRFDSAITNLGNTVTNL
NSARSRIEDADYATEVSNMSKAQILQQAGTSVLAQANQVPQNVLSLLR AA'n54-170
Nucleotide sequence (813 bp): SEQ ID NO: 31
ATGCGGGGTTCTCATCATCATCATCATCATGGTATGGCTAGCATGACTGGTGGACAGCAA
ATGGGTCGGGATCTCTACGACGATGACGATAAGGATCCGTTCACTTCTAATATCAAAGGC
CTGACTCAGGCTTCCCGTAACGCTAACGACGGCATTTCTATTGCGCAGACCACTGAAGGT
GCGCTGAATGAAATTAACAACAACCTGCAGGCGTGTCGGTGAGTTGTCTGTTCAGGCGACT
AACGGGACTAACTCTGATTCCGATCTGAAATCTATCCAGGATGAAATTCAGCAACTGCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTGTATGTGAAAAGCCTTGCTTATCCCGGGAATTTCCGGTGGTGGTGGTGGA
ATTCTAGACTCCATGGGTACATTAATGAATGAAGACGCTGCCGCAGCCAAGAAAAGTACC
GCTAACCCACTGGCTTCAATTGATTCTGCATTGTCAAAAGTGGACGCAGTTCGTTCTTCT
CTGGGGCAATTCAAAACCGTTTGATTCAGCCATTACCAACCTTGGCAATACGGTAACC
AATCTGAACTCCGCGCGTAGCCGATCAAGATGCTGACTATGCAACGGAAGTTTCTAAT
ATGTCTAAACGGCAGATTCTCCAGCAGGCTGGTACTTCCGTTCTGGCGCAGGCTAACCAG
GTTCCGCAAAACGTCCTGTCTTTACTGCGTTAG Protein sequence (270 AA): SEQ ID NO: 32
*MRGSHHHHHHGMASMTGGQQMGRDLYDDDDKDPF*TSNIKGLTQASRNANDGISIAQTTEGALNEINN
NLQPVRELSVQATNGTNSDSDLKSIQDEIQQRLEEIDRVSNQTQFNSVKVLSQDNQMKIQVGANDGE
TITIDLQSIDVRSLQLIPGISGGGGGILDSMGTLINEDAAAAKKSTANPLASIDSALSKVDAVRSSL
GAIQNRFDSAITNLGNTVTNLNSARSRIEDADYATEVSNMSKAQILQQAGTSVLAQANQVPQNVLSL
LR

FIGURE 4G

AA'n54-163
Nucleotide sequence (792 bp): SEQ ID NO: 35
ATGCGGGGTTCTCATCATCATCATCATCATGGTATGGCTAGCATGACTGGTGGACAGCAA
ATGGGTCGGGATCTGTACGACGATGACGATAAGGATCCTTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTCCGTGAGTTGTCTGTTCAGGCCACT
AACGGGACTAACTCTGATTCGGATCTGAAATCTATCCAGGATGAAATTCAGCAACGTCTC
GAAGAAATCGATCGCGTTTCTAATCAGACCCAATTTAACGGTGTTAAAGTCCTGTCTCAG
GACAACCAGATGAAATCCAGGTTGCTGCTAACGATGGTGAAACCATTACCATCGATCTG
CAAAAAATTATCCCGGGAATTTCCGGTGGTGGTGGTGGAATTCTAGACTCCATGGGTACA
TTAATCAATGAAGACGCTGCGGCAGCCAAGAAAAGTACGGCTAACCCACTGGCTTCAATT
GATTCTGCATTGTCAAAAGTGGACGCAGTTCGTTCTTCTCTGGGGCAATTCAAAACCGTT
TTTGATTCAGCCATTACCAACGTTGGCAATACGGTAACCAATCTGAACTCCGCGCGTAGC
CGTATCGAAGATGCTGACTATGCAACGGAAGTTTCTAATATGTCTAAAGCCCAGATTCTG
CAGCAGGCTGGTACTTCCGTTCTGGCGCAGGCTAACCAGGTTCCGCAAAACGTCCTCTCT
TTACTGCGTTAG
Protein sequence (263 AA): SEQ ID NO: 36
MRGSHHHHHHGMASMTGGQQMGRDLYDDDDKDPFTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIIPGISGGGGGILDSMGTLINEDAAAAKKSTANPLASIDSALSKVDAVRSSLGAIQNRF
DSAITNLSNTVTNLNSARSRIEDADYATEVSNMSKAQILQQAGTSVLAQANQVPQNVLSLLR AB'n1-170 (or AA'n1-170c402-450)
Nucleotide sequence (807 bp): SEQ ID NO: 37
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTCTTGACCCAGAATAACCTGAACAAATCTCAGTCCTTACTGAGTTCC
GCTATTGAGCGTCTGTCTTCTGGCCTGCGTATCAACAGCGCGAAGGACGATGCCGCAGGC
CAGGCGATTGCTAACCGTTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTCCGTGAGTTGTCTGTTCAGGCCACTAACGGGACTAACTCTGATTCG
GATCTGAAATCTATCCAGGATGAAATTCAGCAACGTCTGGAAGAAATCGATCGCGTTTCT
AATCAGACCCAATTTAACGGTGTTAAAGTCCTGTCTCAGGACAACCAGATGAAAATCCAG
GTTGCTGCTAACGATGGTGAAACCATTACCATCGATCTGCAAAAAATTGATGTGAAAGC
CTTGGCCCTTATCCCGGGAATTTCCGGTGGTGGTGGTGGAATTCTAGACTCCATGGGTACA
TTAATCAATGAAGACGCTGCGGCAGCCAAGAAAAGTACGGCTAACCCACTGGCTTCAATT
GATTCTGCATTGTCAAAAGTGGACGCAGTTCGTTCTTCTCTGGGGCAATTCAAAACCGT
TTTGATTCAGCCATTACCAACCTTTAG
Protein sequence (268 AA): SEQ ID NO: 38
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLIPGISGGGGGILDSMGTLINEDAAAAKKSTANPLASIDSALSKVDAVRSSLGAIQNRFDSAITNL

FIGURE 4H

AB'n1-163 (or AA'n1-163c402-450)
Nucleotide sequence (786 bp): SEQ ID NO: 39
ATGCGGGGTTCTCATCATCATCATCATGGTATGGCTAGCATGACTGGTGGACAGCAA
ATGGGTCGGGATCTGTATGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAACGTCTGTCCTCTGGTCTCCGTATCAACAGCGCCAAAGACGATGCGGCAGGC
CAGGGGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGGGTGAGTTGTCTGTTCAGGCCACTAACGGGACTAACTCTGATTCC
GATCTGAAATCTATCCAGGATGAAATTCAGCAACGTCTGGAAGAAATCGATCGTGTTTCT
AATCAGACTCAATTTAACGGTGTTAAAGTCCTCTCTCAGGACAATCAGATGAAAATCCAG
GTTGGTGCTAACGATGGTGAAACCATTACTATCGATCTGCAAAAATTATCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTC
GACGCAGTTCGTTCTTCTCTCGGGGCAATTCAAAACCGTTTTGATTCAGCCATTACCAAC
CTTTAG
Protein sequence (261 AA): SEQ ID NO: 40
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIIPGIS
GGGGGILDSMGTLINEDAAAAKKSTANPLASIDSALSKVDAVRSSLGAIQNRFDSAITNL AA'n1-129
Nucleotide sequence (849 bp): SEQ ID NO: 41
ATGCGGGGTTCTCATCATCATCATCATCATGGTATGGCTAGCATGACTGGTGGACAGCAA
ATGGGTCGGGATCTGTATGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAACGTCTGTCCTCTGGTCTCCGTATCAACAGCGCCAAGACGATGCGGCAGGC
CAGGGGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGTGTTTCT
AATCAGACTCAATCCCGGGAATTTCCGGTGGTGGTGGTGGAATTCTAGACTCCATGGGTACATTA
ATCAATGAAGACGCTGCCGCAGCCAAGAAAAGTACCGCTAACCCACTGGCTTCAATTGAT
TCTGCATTGTCAAAAGTCGACGCAGTTCGTTCTTCTCTCGGGGCAATTCAAAACCGTTTT
GATTCAGCCATTACCAACCTTGGCAATACGGTAACCAATCTGAACTCCGCGCGTACCCGT
ATCGAAGATGCTGACTATGCAACGGAAGTTTCTAATATGTCGAAAGCGCAGATTCTGCAG
CAGGCTTGTACTTCTGTTCTGGCCCAGGCTAACCAGGTTCCGCAAAACGTCCTCTCTTTA
CTTCGTTAG
Protein sequence (282 AA): SEQ ID NO: 42
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQIPGISGGGGGILDSMGTLINEDAAAAKKSTANPLASIDS
ALSKVDAVRSSLGAIQNRFDSAITNLGNTVTNLNSARSRIEDADYATEVSNMSKAQILQQACTSVLA
QANQVPQNVLSLLR

FIGURE 4I

AA'n54-129
Nucleotide sequence (690 bp): SEQ ID NO: 43
ATGCGGGGTTCTCATCATCATCATCATCATGGTATGGCTAGCATGACTGGTGGACAGCAA
ATGGGTCGGGATCTGTATGACGATGACGATAAGGATCCGTTCACTTCTAATATCAAAGGC
CTGACTCAGGCTTCCCGTAACGCTAACGACGGTATTTCTATTGCGCAGACCACTGAAGGT
GCGCTGAATGAAATAAACAACAACCTGCAGCGTGTTCGTGAGTTGTCTGTTCAGGCCACT
AATGGGACTAACTCTGATTCGATCTGAAATCTATCCAGGATGAAATTCAGCAACGTCTG
GAACAAATCGATCGCGTTTCTAATCAGATCCCGGGAATTTCCGGTGGTGGTGGTGGAATT
CTAGACTCCATGGGTACATTAATCAATGAAGACGCTGCCGCAGCCAAGAAAAGTACGGCT
AACCCACTGGCTTCAATTGATTCTGCATTGTCAAAAGTGGACGCAGTCCGTTCTCTCTTG
GGGGCAATTCAAAATCGTTTTGATTCAGCCATTACTAACCTTAACGAATACGGTAACGAAT
GTGAACTCCGCGGTAGCGCGTATCGAAGATGCTGACTATGCAACGGAAGTTTCTAATATG
TCTAAAGCGCAGATTCTGCAGCAGGCTGGTACTTCCGTTCTGGCGCAGGCTAACCAGGTT
CCGCAAAACGTGCTGTCTTTACTCGGTTAG
Protein sequence (229 AA): SEQ ID NO: 44
MRGSHHHHHHGMASMTGGQQMGRDLYDDDDKDPFTSNIKGLTQASRNANDGISIAQTTEGALNEINN
NLQRVRELSVQATNGTNSDSDLKSIQDEIQQRLEEIDRVSNQIPGISGGGGGILDSMGTLINEDAAA
AKKSTANPLASIDSALSKVDAVRSSLGAIQNRFDSAITNLGNTVTNLNSARSRIEDADYATEVSNMS
KAQILQQAGTSVLAQANQVPQNVLSLLR AB'n1-129
Nucleotide sequence (684 bp): SEQ ID NO: 45
ATGCGGGGTTCTCATCATCATCATCATCATGGTATGGCTAGCATGACTGGTGGACAGCAA
ATGGGTCGGGATCTGTATGACGATGACGATAAGGATCCGATGGCACAAGTTATTAATACA
AACAGCCTGTCGCTGTTGACCCAGAATAACCTGAACAAATCTCAGTCTTCACTGAGTTCC
GCTATTGAGCGTCTGTCCTGTGGTCTGCGTATTAACAGCGCTGAAGACGATGCGGCAGGC
CAGGCGATTGCTAACGCGTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTCCGTGAGTTGTCTGTTCAGGCCACTAACGGGACTAACTCTGATTCG
GATCTGAAATCTATCCAGGATGAAATTCAGCAACGTCTGGAAGAAATCGATCGCGTTTCT
AATCAGATCCCGGGAATTTCCGGTGGTGGTGGTGGAATTCTAGACTCCATGGGTACATTA
ATCAATGAAGACGCTGCCGCAGCCAAGAAAAGTACGGCTAACCCACTGGCTTCAATTGAT
TCTGCATTGTCAAAAGTGGACGCAGTCCGTTCTTCTCTGGGGGCAATTCAAAACCGTTTT
GATTCAGCCATTACCAACCTTTAG
Protein sequence (227 AA): SEQ ID NO: 46
MRGSHHHHHHGMASMTGGQQMGRDLYDDDDKDPMAQVINTNSLSLLTQNNLNKSQSSLSSAIERLSS
GLRINSAEDDAAGQAIANEFTSNIKGLTQASRNANDGISIAQTTEGALNEINNNLQRVRELSVQATN
GTNSDSDLKSIQDEIQQRLEEIDRVSNQIPGISGGGGGILDSMGTLINEDAAAAKKSTANPLASIDS
ALSKVDAVRSSLGAIQNRFDSAITNL

FIGURE 4J

AB'n54-129
Nucleotide sequence (525 bp): SEQ ID NO: 47
ATGCGGGGTTCTCATCATCATCATCATGGTATGGCTAGCATGACTGGTGGACAGCAA
ATGGGTCGGGATCTGTACGACGATGACGATAAGGATCCCTTCACTTCTAATATCAAAGGC
CTGACTCAGGCTTCCCGTAACGCTAACGACGGCATTTCTATTGCCCAGACCACTGAAGGT
GCCCTGAATGAAATCAACAACCTGCAGCGTGTTCGTGAACTTTCTGTTCAGGCCACT
AACGGCACTAACTCTGATTCCGGTCTGAAATCTATTCAGGATGAAATTCAGCAACGTCTC
GAAGAAATCGATCGCGTTTCTAATCAGATCCCGGGAATTTCCGGTGGTGGTGGTGGAATT
CTAGACTCCATGGGTACATTAATCAATGAAGACGCTGCCGCAGCCAAGAAAAGTACCGCT
AACCCGCTGGCTTCAATTGATTCTGCATTGTCAAAAGTGGACGCAGTTCGTTCTTCTCTG
GGGGCAATCAAAACCGTTTTGATTCAGGCATTACCAACGTTTAG
Protein sequence (174 AA): SEQ ID NO: 48
MRGSHHHHHHGMASMTGGQQMGRDLYDDDDKDPFTSNIKGLTQASRNANDGISIAQTTEGALNEINN
NLQRVRELSVQATNGTNSDGDLKSIQDEIQQRLEEIDRVSNQIPGISGGGGGILDSMGTLINEDAAA
AKKSTANPLASIDSALSKVDAVRSSLGAIQNRFDSAITNL AA'n1-100
Nucleotide sequence (762 bp): SEQ ID NO: 49
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATCGAGCGTCTGTCCTCTGGTCTGCGTATCAACAGTGCGGAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCCCAGACCACTGAAGGTGCCCTGAATGAAATCAACAAC
CTGCAGCGTGTCCGTGAGTTGTCTGTTCAGGCCACTATCCCGGGAATTTCCGGTGGT
GGTGGTGGAATTCTAGACTCCATGGGTACATTAATCAATGAAGACGCTGCCGCAGCCAAG
AAAAGTACCGCTAACCCGCTGGCTTCAATTGATTCTGCATTGTCAAAAGTGGACGCAGTT
CGTTCTTCTCTGGGGGCAATCAAAACCGTTTTGATTCAGGCATTACCAACCTTGGCAAT
ACCGTAACCAATCTGAACTCCGCGCCTAGCCGTATCGAAGATGCTGACTATGCAACCGAA
GTTTCTAATATGTCTAAAGCGCAGATTCTGCAGCAGGCTGGTACTTCCGTTCTGGCCCAG
GCTAACCAGGTTCCAGAAAACGTCCTGTCTTTACTGCGTTAG
Protein sequence (253 AA): SEQ ID NO: 50
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNLQRVRELSVQATI
PGISGGGGGILDSMGTLINEDAAAAKKSTANPLASIDSALSKVDAVRSSLGAIQNRFDSAITNLGNT
VTNLNSARSRIEDADYATEVSNMSKAQILQQAGTSVLAQANQVPQNVLSLLR AB'n1-100
Nucleotide sequence (597 bp): SEQ ID NO: 51
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCCCAGACCACTGAAGGTGCCCTGAATGAAATCAACAAC
CTGCAGCGTGTCCGTGAGTTGTCTGTTCAGGCCACTATCCCGGGAATTTCCGGTGGT
GGTGGTGGAATTCTAGACTCCATGGGTACATTAATCAATGAAGACGCTGCCGCAGCCAAG
AAAAGTACCGCTAACCCGCTGGCTTCAATTGATTCTGCATTGTCAAAAGTGGACGCAGTT
CGTTCTTCTCTGGGGGCAATCAAAACCGTTTTGATTCAGGCATTACCAACGTTTAG
Protein sequence (198 AA): SEQ ID NO: 52
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDGISIAQTTEGALNEINNLQRVRELSVQATI
PGISGGGGGILDSMGTLINEDAAAAKKSTANPLASIDSALSKVDAVRSSLGAIQNRFDSAITNL

FIGURE 4K

AA'n1-70
Nucleotide sequence (672 bp): SEQ ID NO: 53
ATGCGGGGTTCTCATCATCATCATCATGGTATGGCTAGCATGACTGGTGGACAGCAA
ATGGGTCGGGATCTGTACGACGATGACGATAAGGATCCATGGCAAAGTCATTAATACA
AACAGCCTGTCGCTGTTGACCCAGAATAACCTGAACAAATCTCAGTCCTGACTGAGTTCC
GCTATTGAGCGTCTGTCCTCTGGTCTGCGTATCAACAGCGCAAAGACGATGCGGCAGGT
CAGGCGATTGCTAACCGTTTCACTTCTAATATCAAAGGCCTGACTCAGGCTTCCCGTAAC
GCTAACGACATCCCGGGAATTTCCGGTGGTGGTGGTGGAATTCTAGACTCCATGGCTACA
TTAATCAATGAAGACGCTGCCGCAGCCAAGAAAAGTACGGCTAACCCACTGCTTCAATT
GATTCTGCATTGTCAAAGTGGACGCAGTTCGTTCTTCTCTGGGGCAATTCAAAACCGT
TTTGATTCAGCCATTACCAACGTTGGCAATACGGTAACCAATCTGAACTGGGCGTTACC
CGTATCGAAGATGCTGACTATGCAACCGAAGTTTCTAATATGTCTAAAGCGCAGATTCTG
CAGGCAGGCTGTACTTCGGTCTGGCGCAGGCTAACCAGGTTCCGCAAAACGTTCTCTCT
TTACTGCGTTAG
Protein sequence (223 AA): SEQ ID NO: 54
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDIPGISGGGGGILDSMGTLINEDAAAAKKSTA
NPLASIDSALSKVDAVRSSLGAIQNRFDSAITNLGNTVTNLNSARSRIEDADYATEVSNMSKAQILQ
QAGTSVLAQANQVPQNVLSLLR AB'n1-70
Nucleotide sequence (507 bp): SEQ ID NO: 55
ATGCGGGGTTCTCATCATCATCATCATCATGGTATGGCTAGCATGACTGGTGGACAGCAA
ATGGGTCGGGATCTGTACGACGATGACGATAAGGATCCATGGCAAAGTCATTAATACA
AACAGCCTGTCGCTGTTGACCCAGAATAACCTGAACAAATCTCAGTCCTGACTGAGTTCC
GCTATTGAGCGTCTGTCCTCTGGTCTGCGTATCAACAGCGCAAAGACGATGCGGCAGGT
CAGGCGATTGCTAACCGTTTCACTTCTAATATCAAAGGCCTGACTCAGGCTTCCCGTAAC
GCTAACGACATCCCGGGAATTTCCGGTGGTGGTGGTGGAATTCTAGACTCCATGGCTACA
TTAATCAATGAAGACGCTGCCGCAGCCAAGAAAAGTACGGCTAACCCACTGCTTCAATT
GATTCTGCATTGTCAAAGTGGACGCAGTTCGTTCTTCTCTGGGGCAATTCAAAACCGT
TTTGATTCAGCCATTACCAACGTTTAG
Protein sequence (168 AA): SEQ ID NO: 56
MRGSHHHHHHGMASMTGGQQMGRDLYDDDDKDPMAQVINTNSLSLLTQNNLNKSQSSLSSAIERLSS
GLRINSAKDDAAGQAIANRFTSNIKGLTQASRNANDIPGISGGGGGILDSMGTLINEDAAAAKKSTA
NPLASIDSALSKVDAVRSSLGAIQNRFDSAITNL

FIGURE 5A

```
Q53970   1 MAQVINTNSLSLLTQNNLNKSQSSLSSAIERLSSGLRINSAKDDAAGQAIANRFTSNIKGLTQASRNAND SEQ ID NO 118
P72151   1 MALTVNTNIASLNTQRNLNASSNDLNTSLQRLTTGYRINSAKDDAAGLQISNRLSNQISGLNVATRNAND SEQ ID NO 119
Q5X5M6   1 MAQVINTNVASLTAQRNLGVSGNMMQTSIQRLSSGLRINSAKDDAAGLAISQRMTAQIRGMNQAVRNAND SEQ ID NO 120
Q6VMV6   1 MAQVINTNSLSLLTQNNLNKSQSSLSSAIERLSSGLRINSAKDDAAGQAIANRFTANIKGLTQASRNAND SEQ ID NO 121
P13713   1 MAQVINTNSLSLMAQNNLNKSQSSLGTAIERLSSGLRINSAKDDAAGQAISNRFTANIKGLTQASRNAND SEQ ID NO 122
Q93RK8   1 --MRINHNIAALNTSRQLNAGSNSAAKNMEKLSSGLRINRAGDDAAGLAISEKMRSQIRGLDMASKNAQD SEQ ID NO 123
Q02551   1 --MKVNTNIISLKTQEYLRKNNEGMTQAQERLASGKRINSSLDDAAGLAVVTRMNVKSTGLDAASKNSSM SEQ ID NO 124
Q09012   1 MAQVINTNSLSLLTQNNLNKSQSSLSSAIERLSSGLRINSAKDDAAGQAIANRFTANIKGLTQASRNAND SEQ ID NO 125
Q8GNT8   1 MAQVINTNSLSLMAQNNLNKSQSALGTAIERLSSGLRINSAKDDAAGLAISNRFTANINGLTQASRNAND SEQ ID NO 126
Q9FAE7   1 MASTINTNVSSLTAQRNLSLSQSSLNTSIQRLSSGLRINSAKDDAAGLAISERFTSQIRGLNQAVRNAND SEQ ID NO 127
Q8ZF76   1 MA-VINTNSLSLLTQNNLNKSQSSLGTAIERLSSGLRINSAKDDAAGQAIANRFTSNIKGLTQAARNAND SEQ ID NO 128
Q7N5J4   1 MAQVINTNSLSLLTQNNLNRSQGTLGSAIERLSSGLRINSAKDDAAGQAIANRFTANVRGLTQAARNAND SEQ ID NO 129
O33578   1 -MTTINTNIGAIAAQANMTKVNDQFNTAMTRLSTGLRINAAKDDAAGMAIGEKMTAQVMGLNQAIRNAQD SEQ ID NO 130
Q56826   1 MASVINTNDSALLAQNNLTKSKGILGSAIERLSSGLRINSAKDDAAGQAIANRFTANVKGLTQAARNAND SEQ ID NO 131
P42273   1 MAQVINTNYLSLVTQNNLNRSQSALGNAIERLSSGMRINSAKDDAAGQAIANRFTSNINGLTQAARNAND SEQ ID NO 132
O31059   1 --MVVQHNMQAANASRMLGITTGDQSKSTEKLSSGFKINRAADDAAGLSISEKMRKQIRGLDQASTNASD SEQ ID NO 133
Q7VZC2   1 MAAVINTNYLSLVAQNNLNKSQSALGSAINRLSSGLRINSAKDDAAGLAIANRFTANVKGLTQAARNAND SEQ ID NO 134
Q9F4A4   1 --MIINHNMNALNAHRNMMGNIATAGKSMEKLSSGLRINRAGDDAAGLAISEKMRGQIRGLDQASRNAQD SEQ ID NO 135
Q8P9C4   1 MAQVINTNVMSLNAQRNLNTNSSSMALSIQQLSSGLRKRITSASVDAAGLAISERFTTQIRGLDVASRNAND SEQ ID NO 136
Q82UA3   1 MPQVINTNIASLNAQRNLNVSQNSLSTALQRLSSGLRINSAKDDAAGLAISERMTSQIRGMNQAARNAND SEQ ID NO 137
Q84IC5   1 -GFRINTNGASLNAQVNAGLNSRNLDSSLARLSSGLRINSAADDASGLAIADSLKTQANSLGQAINNAND SEQ ID NO 138
           ::  *    :  :              :*::*  :* . :  **:*     :       .:   *   *:..

Q53970  71 GISIAQTTEGALNEINNNLQRVRELSVQATNGTNSDSDLKSIQDEIQQRLEEIDRVSNQTQFNGVKVLSQ SEQ ID NO 118
P72151  71 GISLAQTAEGALQQSTNILQRIRDLALQSANGSNSDADRAALQKEVAAQQAELTRISDTTTFGGRKLLDG SEQ ID NO 119
Q5X5M6  71 GISLAQVAEGAMQETTNILQRMRELSVQAANSTNNSSDRASIQSEISQLKSELERIAQNTEFNGQRILDG SEQ ID NO 120
Q6VMV6  71 GISVAQTTEGALNEINNNLQRVRELTVQATNGTNSDSDLSSIQAEITQRLEEIDRVSEQTQFNGVKVLAE SEQ ID NO 121
P13713  71 GISLAQTTEGALNETHSILQRMSELATQAANDTNTDSDRSELQKEMDQLASEVTRISTDTEFNTKKLLDG SEQ ID NO 122
Q93RK8  69 GISLIQTSEGALNETHSILQRMSELATQAANDTNTDSDRSELQKEMDQLASEVTRISTDTEFNTKKLLDG SEQ ID NO 123
Q02551  71 GIDLLQTADSALSSMSSILQRMRQLAVQSSNGSFSDEDRKQYTAEFGSLIKELDHVADTTNYNNIKLLDQ SEQ ID NO 124
Q09012  69 GISVAQTTEGALSEINNNLQRIRELSVQATNGTNSDSDLNSIQDEITQRLSEIDRVSNQTQFNGVKVLAS SEQ ID NO 125
Q8GNT8  71 GISLAQTEGALNEVNDNLQRIRRLTVQAQNGSNSSSDLQSIQDEITQRLSEIDRISQQTDFNGVKVLSK SEQ ID NO 126
Q9FAE7  71 GISLAQTAEGALKSTGDILQRVRELAVQSANATNSSGDRKAIQAEVGQLLSEMDRIAGNTEFNGQKLLDG SEQ ID NO 127
Q8ZF76  70 GISIAQTTEGSLNEINNNLQRVRELTVQAQNGSNSSSDLDSIQDEISLRLAEIDRVSDQTQFNGKKVLAE SEQ ID NO 128
Q7N5J4  71 GISIAQTTEGALNEINTNLQRIRELTVQSQNGSNSESDIKSIQEEVTQRLKEIDRISEQTQFNGVRVLRE SEQ ID NO 129
O33578  70 GKNLVDTTEGAHVEVSSMLQRLRELAVQSSNDTNTAADRGSLAAEGKQLIAEINRVAESTTFNGMKVLDG SEQ ID NO 130
Q56826  71 GISIAQTTEGALNEINNNLQRIRELTVQSENGSNSKSDLDSIQKEVTQRLEEIDRISTQTQFNGIKVLNG SEQ ID NO 131
P42273  71 GISVSQTTEGALNEINNNLQRIRELTVQAKNGTNSNSDINSIQNEVNQRLDEINRVSEQTQFNGVKVLSG SEQ ID NO 132
O31059  69 GISAVQTAEGALTEVHSMLQRMNELAVQAANGTNSESDRSSIQDEINQLTTEIDRVAETTKFNETYLLKG SEQ ID NO 133
Q7VZC2  71 GISIAQTTEGALNEINNNLQRIRELTVQASNGTNSASDIDSIQQEVNQRLEEINRIAEQTDFNGIKVLKS SEQ ID NO 134
Q9F4A4  69 GISLIQTAEGALAETHSILQRMRELSVQSANDTNVAVDRTAIQDEINSLTEBINRISGDTEFNTQKLLDG SEQ ID NO 135
Q8P9C4  71 GISLAQTAEGAMVEIGNNLQRIRELSVQSANATNSATDREALNSEVKQLTSEIDRVANQTSFNGTKLLNG SEQ ID NO 136
Q82UA3  71 GISLAQTAEGALVEIGNNLQRIRELAVQSANATNSEDDREALQKEVTQLIDEIQRVGEQTSPNGTKLLDG SEQ ID NO 137
Q84IC5  70 ANSMLQIADKAMDEQLKILDTIKVKATQAAQDGQTAKTRAMIQGEINKLMEELDNIANTTTYNGKQLLSG SEQ ID NO 138
           . .  :  ::   .       *:     : *:  :         *          *:  ..   * :.   :*
```

FIGURE 5B

```
Q53970  141  DNQ-MK--IQVGANDG--------------ETITIDLQ---------KID-VKSLG----LDGFN  SEQ ID NO 118
P72151  141  SFGTTS--FQVGSNAY--------------ETIDISLQNASASAIGSYQVG-SNGAGTVASVAGTA SEQ ID NO 119
Q5X5M6  141  SFSGAS--FQVGANSN--------------QTINFSIG---------SIK-ASSIGGIATATGTE  SEQ ID NO 120
Q6VMV6  141  NNE-MK--IQVGANDG--------------ETITINLA---------KID-AKTLG----LDGFN  SEQ ID NO 121
P13713  141  DQK-LT--IQVGANDG--------------ETTDIDLK---------KID-AKQLG----MDTF-  SEQ ID NO 122
Q93RK8  139  TAQNLT--FQIGANEG--------------QTMSLSIN---------KMD-SE---------SLK  SEQ ID NO 123
Q02551  139  TATGAATQVSIQASDKAN------------DLINIDLFNAKGLSAGTITLGSGSTVAGYSALSVAD SEQ ID NO 124
Q09012  141  DQT-MK--IQVGANDG--------------ETIEIALD---------KID-AKTLG----LDNFS  SEQ ID NO 125
Q8GNT8  141  DQK-LT--IQVGANDG--------------ETIDIDLK---------KID-KEALN----LDKFN  SEQ ID NO 126
Q9FAE7  141  SFGSAT--FQVGANAN--------------QTITATTGNFRTNNY-GAQLT-ASASG--AATSGAS SEQ ID NO 127
Q8ZF76  140  NTT-MS--IQVGANDG--------------ETIDINLQ---------KID-SKSLG----LGSYS  SEQ ID NO 128
Q7N5J4  141  DSK-MT--IQVGANDN--------------EVIDIDLK---------KID-KEALN----LGKFT  SEQ ID NO 129
O33578  140  SFTGKQ--LQIGADSG--------------QTMAINVDSAAATDIGAHKISSASTVVADAALTDTT SEQ ID NO 130
Q56826  141  DVTEMK--IQVGANDN--------------ETIGIKLG---------KIN-SEKLN----LKEFS  SEQ ID NO 131
P42273  141  EKSKMT--IQVGTNDN--------------EVIEFNLD---------KID-NDTLG----VASDK  SEQ ID NO 132
O31059  139  GNGDRT--VRVYAHDAGLVGSLSQNTTKATFQMRKLEIGDSYTIGGTTYKIG-AETVK--BAMTALK SEQ ID NO 133
Q7VZC2  141  NATDMTLSIQVGAKDN--------------ETIDIKID---------RNS-NWNLY----DAVGT  SEQ ID NO 134
Q9F4A4  139  GFKG-E--FQIGANSN--------------QTVKLDIG---------NMS-AA---------SLG  SEQ ID NO 135
Q8P9C4  141  DFSGAL--FQVGADAG--------------QTIGINS---------IVDAN-VDSLG--KANFAAS SEQ ID NO 136
Q82UA3  141  SFASQI--FQVGANEG--------------ETIDFTD---------------------------  SEQ ID NO 137
Q84IC5  140  SFSNAQ--FQIGDKAN--------------QTVNATIG---------STN-SAKVGQTRFETGAV  SEQ ID NO 138
                 . :                              :
```

FIGURE 5C

```
Q53970  418  PLASIDSAISKVDAVRSSEGAIQNRFDSAITNLGNTVTNLNSARSRIEDADYATEVSNMSKAQILQQAGTSVLAQANQVPQNVLSLLR--  SEQ ID NO 139
P72151  401  AIAVDNALAAIDAQRADEGAVQNRFKNTIDNLTNISENATNARSRIKDTFAAETAALSKNQVLQQAGTAIIAQANQLPQAVLSLLR--  SEQ ID NO 140
Q5X5M6  387  AIKRIDAAINSVNSNRANVGALQNRFESTIAMLQNVSDNLSAARSRIQDADYAAEMASLTKNQILQQAGTAMLAQANSLPQSVLSLLGR-  SEQ ID NO 141
Q6VMV6  400  PLETIDKALAKVDNLRSDEGAVQNRFDSAITNLGNTVNNLSSARSRIEDADYATEVSNMSRAQILQQAGTSVLAQANQTTQNVLSLLQG-  SEQ ID NO 142
P13713  264  PLATLDKALAQVDGLRSSEGAVQNRFDSVINNLNSTVNNLSASQSRIQDADYATEVSNMSRANILQQAGTSVIAQANQSTQNVLSLLR--  SEQ ID NO 143
Q93RK8  245  ALTTKTAIDTVSSERAKLREHTINNLGTSSENITSAESRIRDVDMASEMEYTKNNILTQASQAMLAQANQQPQQVLQLLKG--  SEQ ID NO 144
Q02551  481  VIGLADAALTKIMKQRADVGAYYNRLEYTAKGLMGAYENMQASESRIRDADMABEVVSLTTKQILVQSGTAMLAQANMKPNSVLKLLQQI  SEQ ID NO 145
Q09012  437  PLSKLDEAIAKVDKLRSSEGAVQNRFDSAITNLGNTVNDLSSARSRIEDADYATEVSNMSRAQILQQAGTSVLAQANQTTQNVLSLLR--  SEQ ID NO 146
Q8GNT8  329  PLATLDKAISQVDDLRSGLGAVQNRFDSVINNLNSTVNNLQSTSENMSASRSRIQDADFAAETANLSRSQILQQAGTAMVAQANQLPQGVLSLLK-  SEQ ID NO 147
Q9FAE7  405  ALKIIDAALSAVNGQRASEGALQSRFETTVNNLQSTSENMSASRSRIQDADFAAETANLSRSQILQQAGTAMVAQANQLPQGVLSLLK-  SEQ ID NO 148
Q8ZF76  282  PLETIDDAIKQVDGLRSSEGAVQNRFESSAVTNLNNTVTNLITSARSRIEDADYATEVSNMSRAQILQQAGTSVLSQANQVPQTVLSLLN-  SEQ ID NO 149
Q7N5J4  268  PLETIDSALAQVDSLRSSEGAIQNRLESTVNNLNNTVNNLSAARSRIEDADYATEVSNMSRGQILQQAGTAVLAQANQVPQNVMSLLR--  SEQ ID NO 150
O33578  405  AIGVIDVAISKISQSRSEEGAVSNRLDSTISNLINISTSVQAAKSQVMDADFAAESTNLARSQILSQASTAMLAQANSSKQNVLSLLRG-  SEQ ID NO 151
Q56826  226  PLDTIDKAIAQVDDMRSSEGAVQNRLESTVNNLNNTVNNLSAARSRIEDADYAVEVSNMSRGQILQQAGTSVLAQANQVPQTVLSLLR--  SEQ ID NO 152
P42273  280  ALATIDNATSKVDESRSKLGAIQNRFQSTINNLNNTVNNLSASRSRILDADYATEVSNMSKNQILQQAGTAVLAQANQVPQTVLSLLR--  SEQ ID NO 153
O31059  385  AIDALSDALAKVSAQRSALGSIQNRLEHSIANLDNVENTNAAESRIRDTDMADEMVTYSKNNIIMQAGQSMLAQANQATQGVLSILQ--  SEQ ID NO 154
Q7VZC2  304  ALSKLDDAMKAVDEQRSSEGAIQNRFESTVANLNNTITNLSAARSRIEDSDYATEVSNMTKNQILQQAGTSVLAQANQVPQNVLSLLR--  SEQ ID NO 155
Q9F4A4  326  SIKTINSALEQVSTQRSKLGAVQNRLEHTINNLTSSENLTAAESRVRDVDMAKEMAFSKNNILSQAAQAMLGQANQPQGVLQLLR--  SEQ ID NO 156
Q8P9C4  312  ALELVEKAITSVNSSRADVGAVQNRFTSTIANLAATSENLTASRSRIADTDYAKTTAELTRTQILQQAGVMLAQAKSVPQNVLSLLQ--  SEQ ID NO 157
Q82UA3  192  ----LDDALKIVNSTRADLGAIQNRFSSAIANLQTSAERNLSASRSRIQDADFAAETAALTRAQILQQAGVAMLSQANALPNNVLSLLR--  SEQ ID NO 158
Q84IC5  403  VMDIATAANLDTIRANIGATQNQITSTINNISVTQVNVKAAESQIRDVDFASESANYSKANILAQSGSYAMAQANAASQNVLRLLQ--  SEQ ID NO 159
                *     :            *:           :           :*:: * ***      ::*:    ..:**:**  .  ::*::   :* ::*
```

FIGURE 6

Homo Sapiens TLR5

```
  1  mgdhldlllg  vvlmagpvfg  ipscsfdgri  afyrfcnltq  vpqvlntter  lllsfnyirt
 61  vtassfpfle  qlqllelgsq  ytpltidkea  frnlpnlril  dlgsskiyfl  hpdafqglfh
121  lfelrlyfcg  lsdavlkdgy  frnlkaltrl  dlsknqirsl  ylhpsfgkln  slksidfssn
181  qiflvcehel  eplqgktlsf  fslaanslys  rvsvdwgkcm  npfrnmvlei  ldvsgngwtv
241  ditgnfsnai  sksqafslil  ahhimgagfg  fhnikdpdqn  tfaglarssv  rhldlshgfv
301  fslnsrvfet  lkdlkvinla  ynkinkiade  afygldnlqv  lnlsynllge  lyssnfyglp
361  kvayidlqkn  hialiqdqtf  kfleklqtld  lrdnalttih  fipsipdifl  sgnklvtlpk
421  inltanlihl  senrlenldi  lyfllrvphl  qililnqnrf  sscsgdqtps  enpsleqlfl
481  genmlqlawe  telcwdvfeg  lshlqvlyln  hnylnslppg  vfshltalrg  lslnsnrltv
541  lshndlpanl  eildisrnql  lapnpdvfvs  lsvldithnk  ficecelstf  inwlnhtnvt
601  iagppadiyc  vypdsfsgvs  lfslstegcd  eeevlkslkf  slfivctvtl  tlflmtiltv
661  tkfrgfcfic  yktaqrlvfk  dhpqgtepdm  ykydaylcfs  skdftwvqna  likhldtqys
721  dqnrfnlcfe  erdfvpgenr  ianiqdaiwn  srkivclvsr  hflrdgwcle  afsyaqgrcl
781  sdlnsalimv  vvgslsqyql  mkhqsirgfv  qkqqylrwpe  dfqdvgwflh  klsqqilkke
841  kekkkdmnip  lqtvatis  (SEQ ID NO: 117)
```

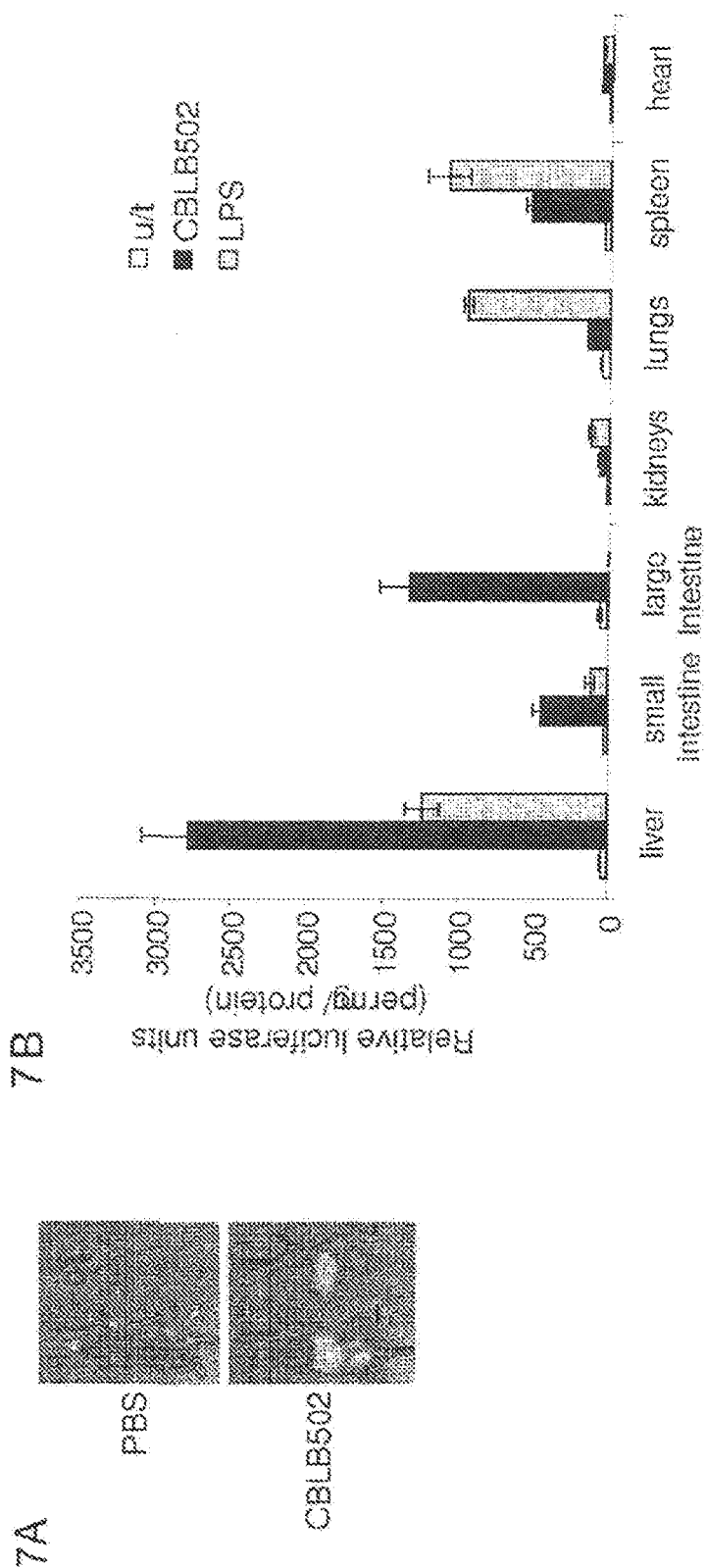

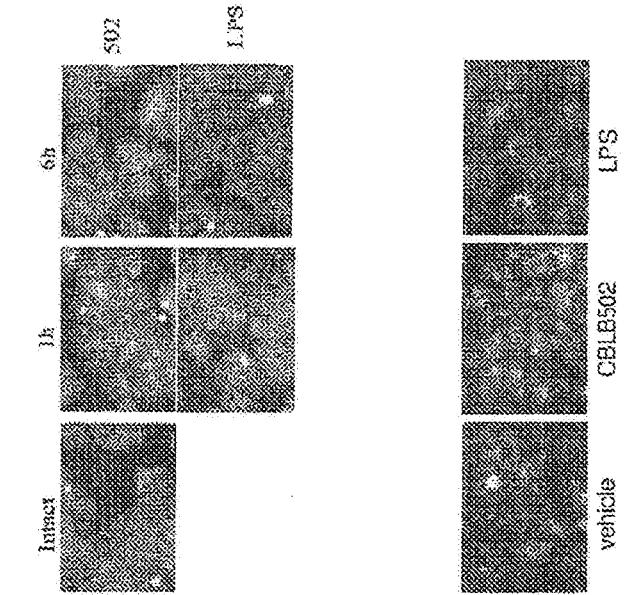
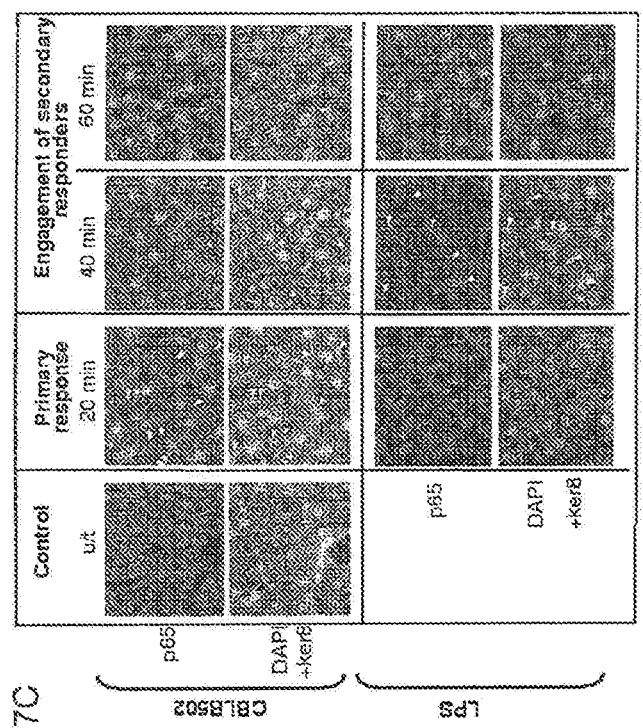
FIGURE 7C-E

FIGURE 8A-D
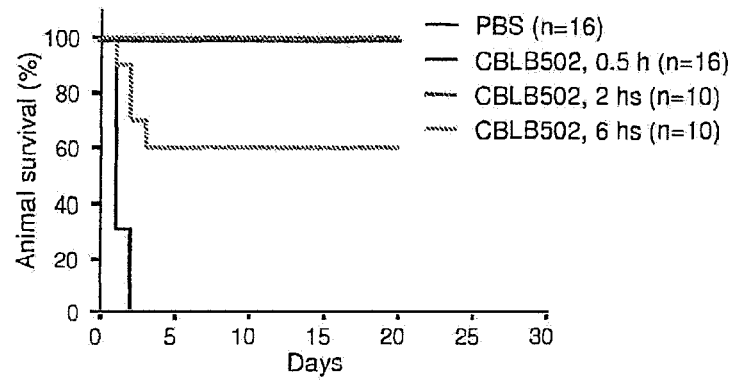
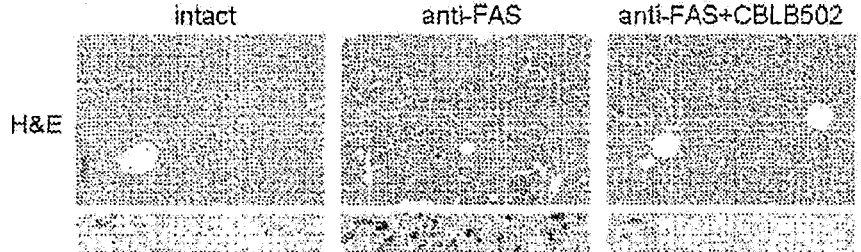
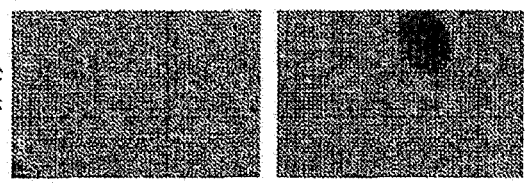

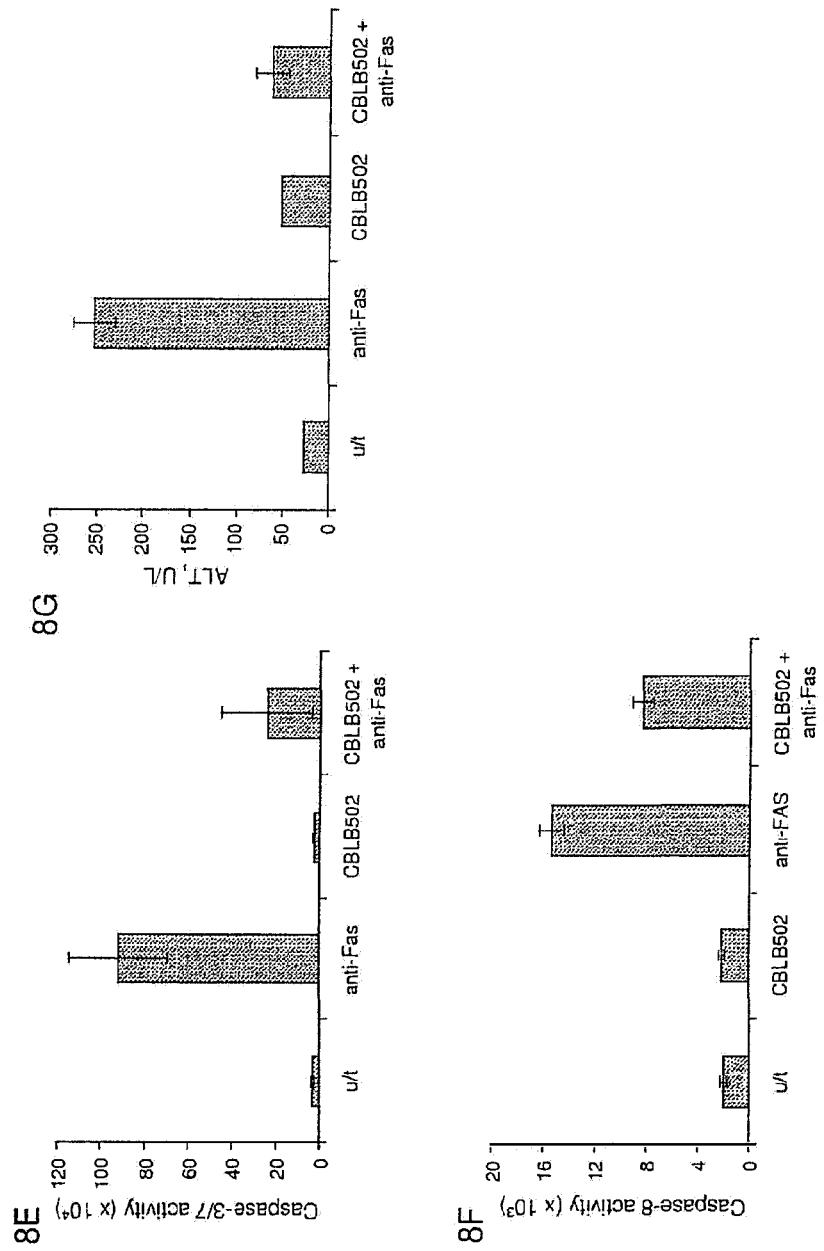
FIGURE 8E-G

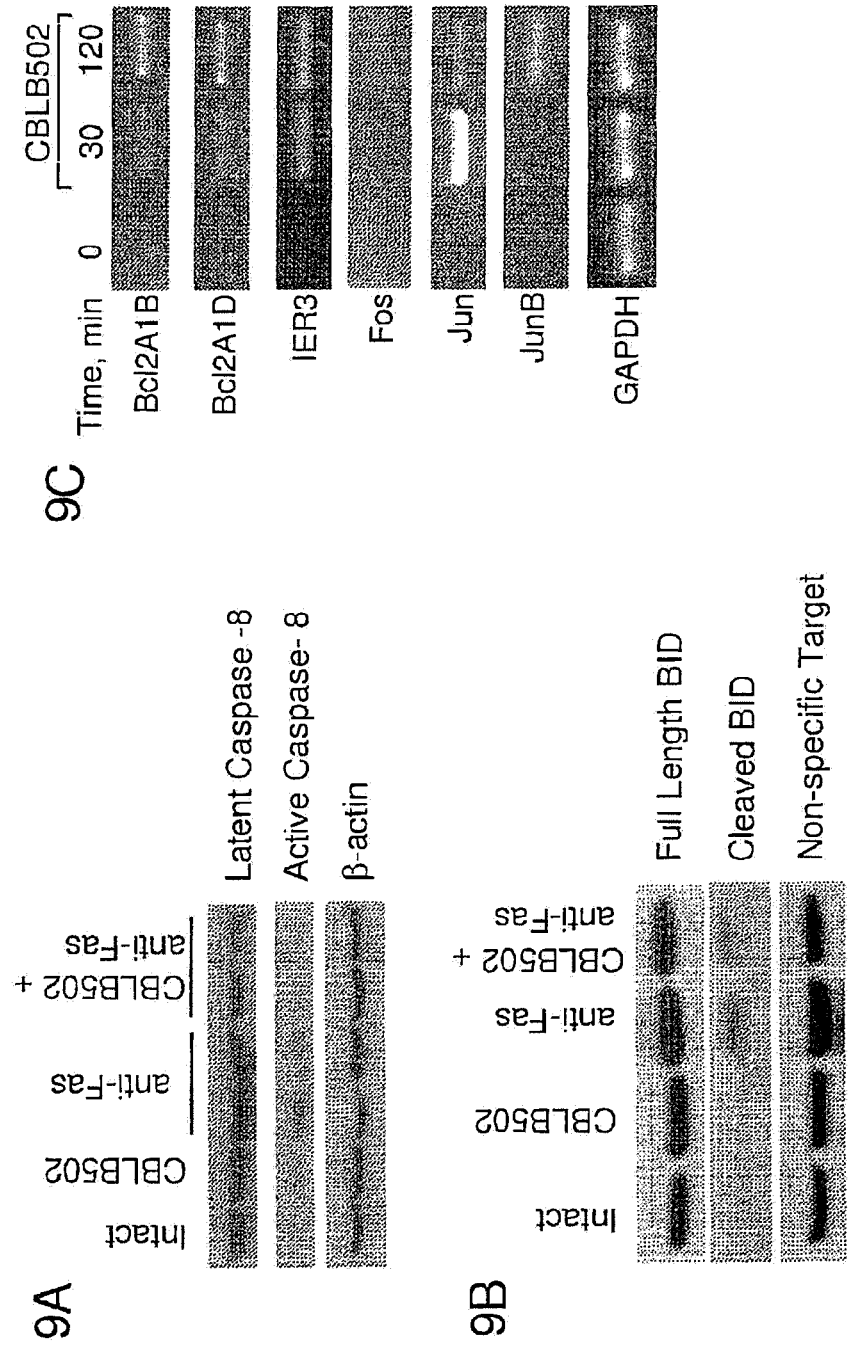
FIGURE 9A-C

FIGURE 9D-G
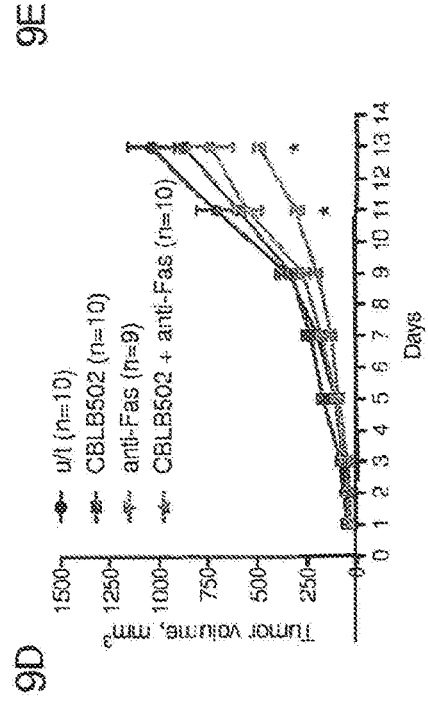
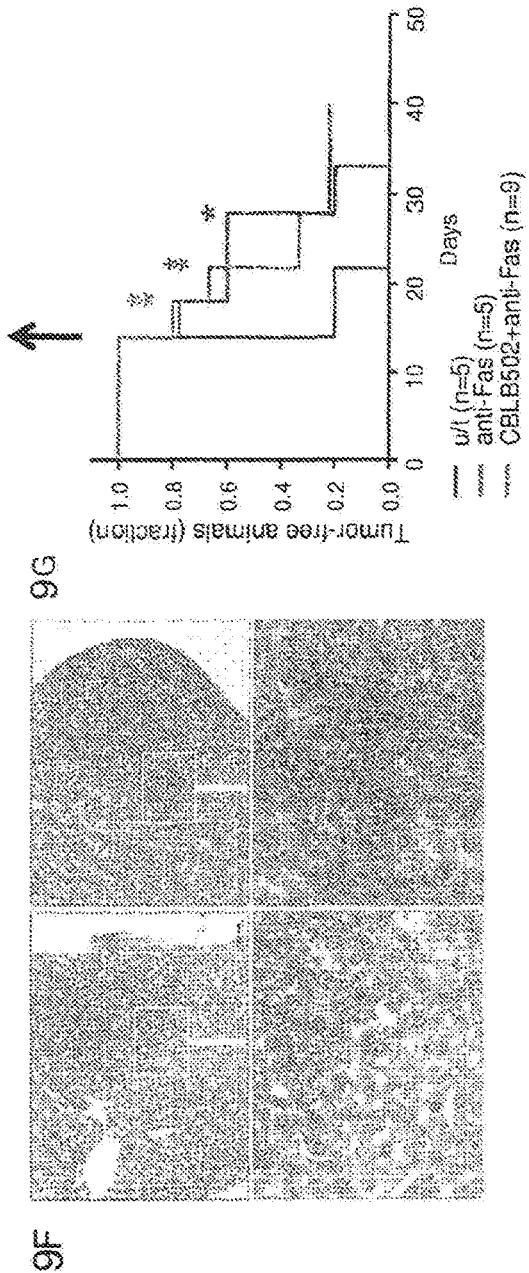

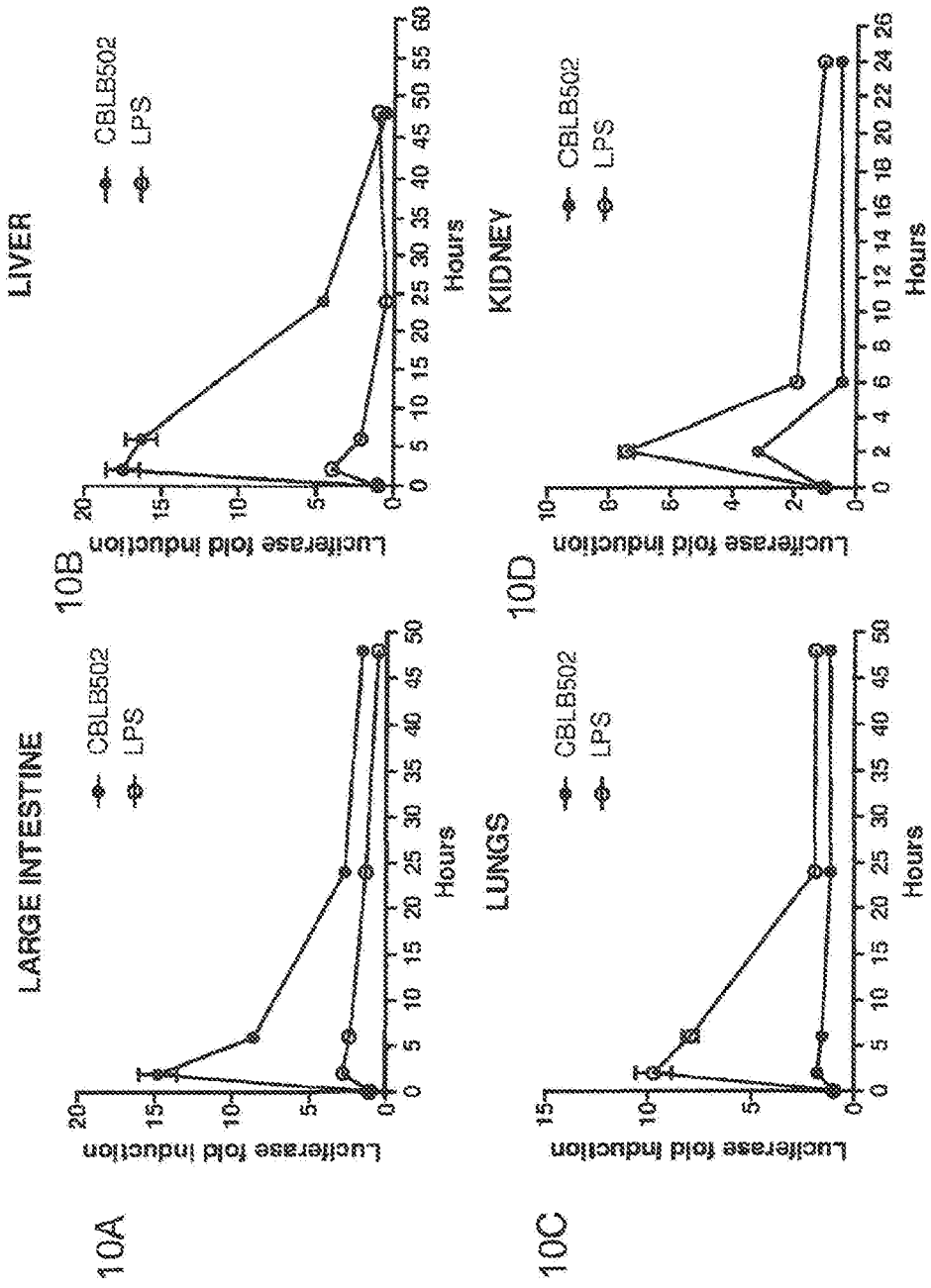
FIGURE 10A-D

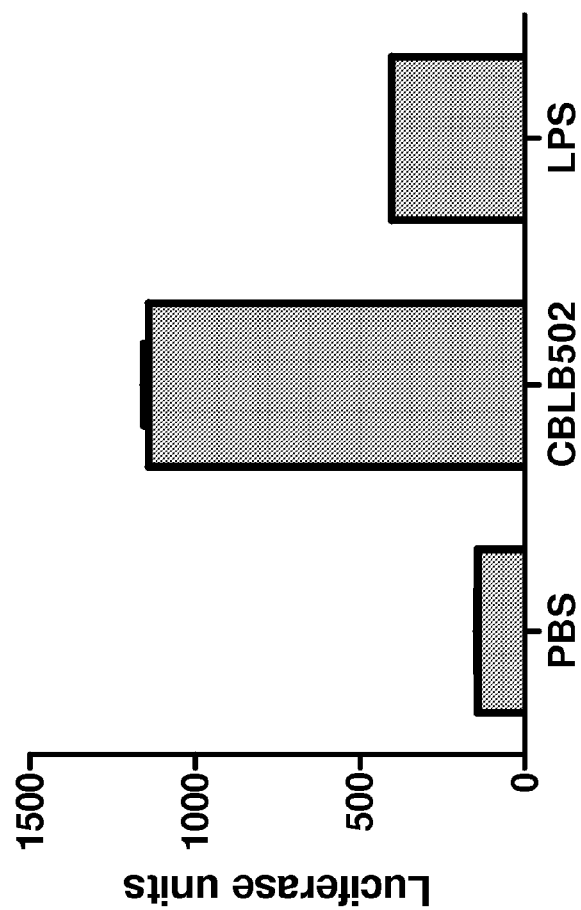

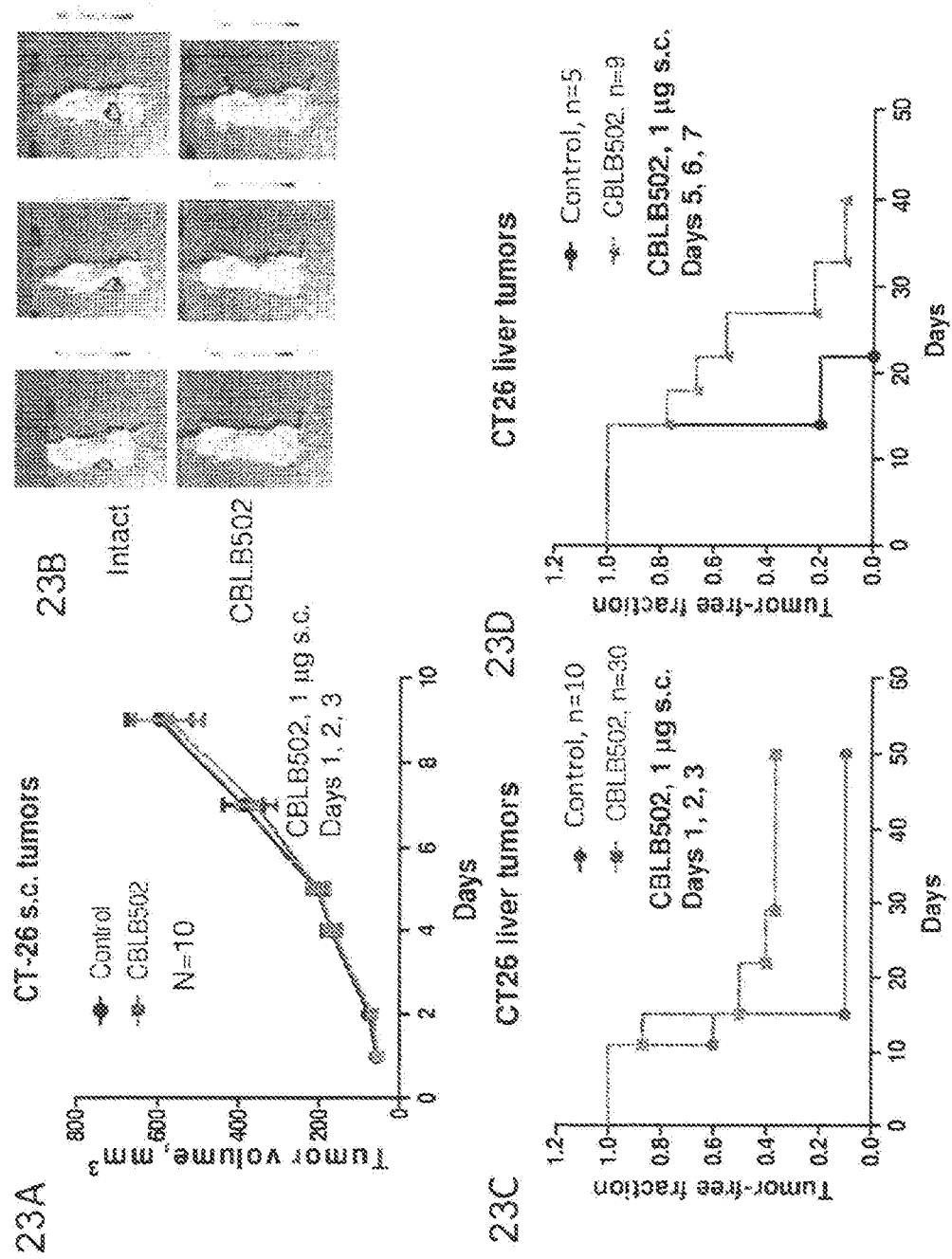
FIGURE 23A-D

FIGURE 24A-B
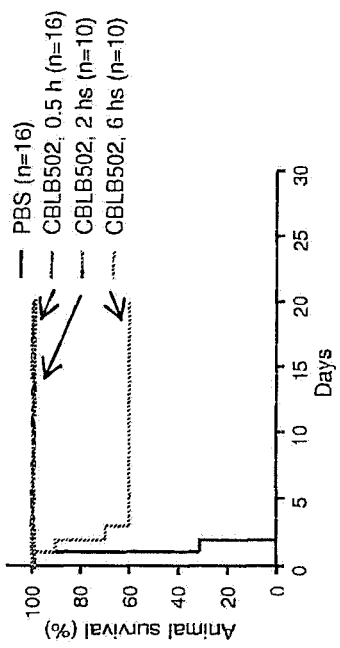
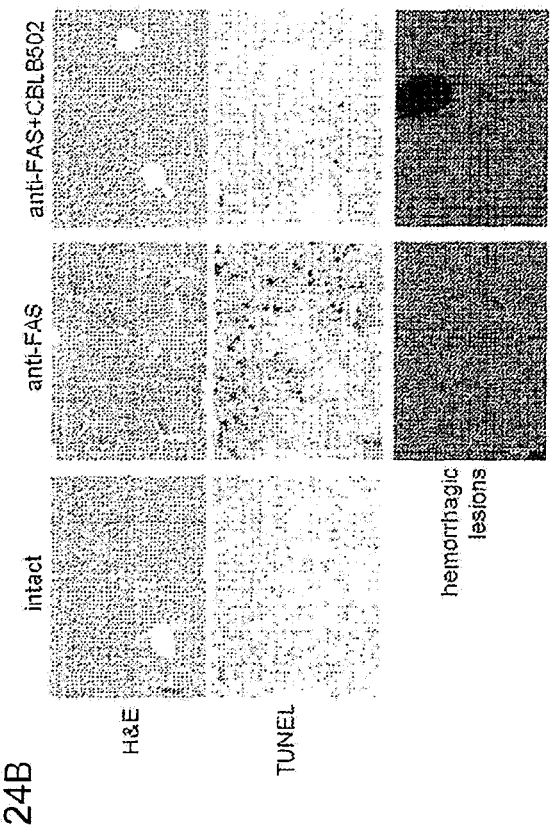

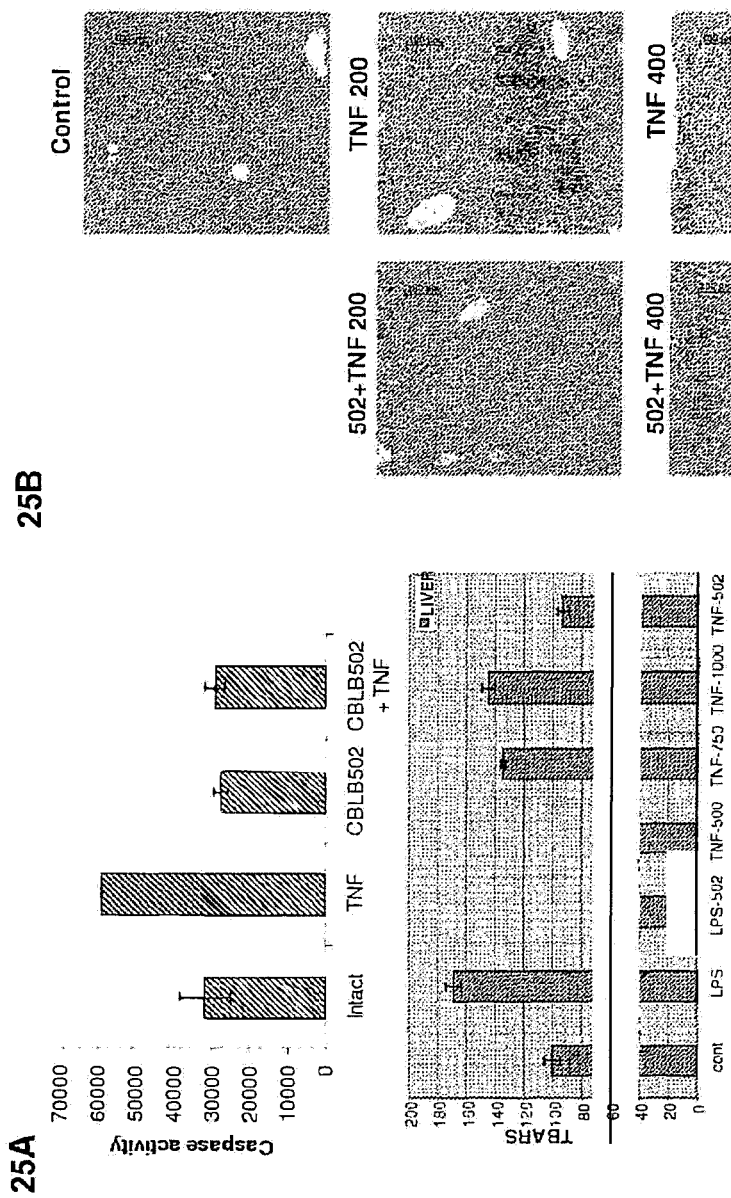
FIGURE 25A-B

FIGURE 26A-B
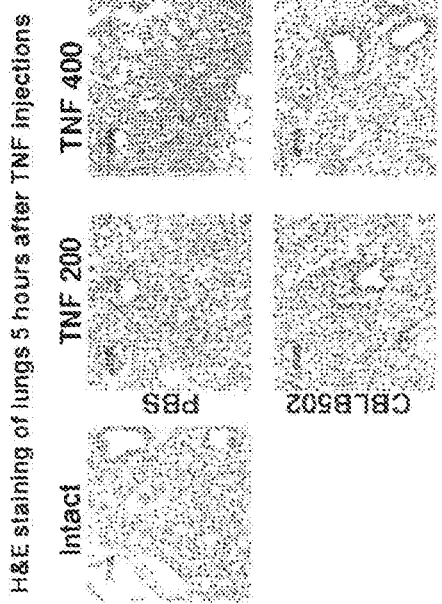
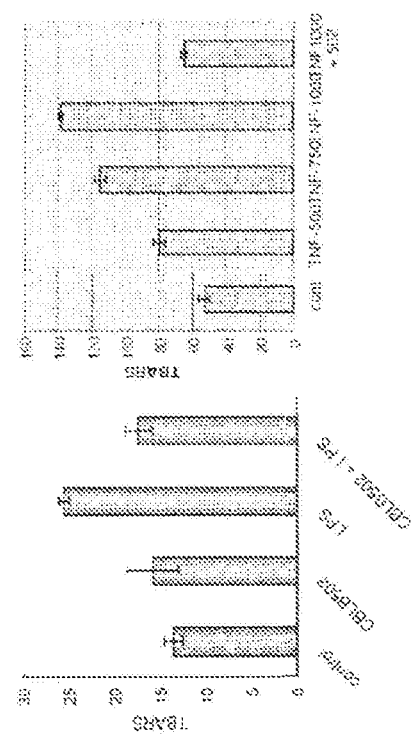

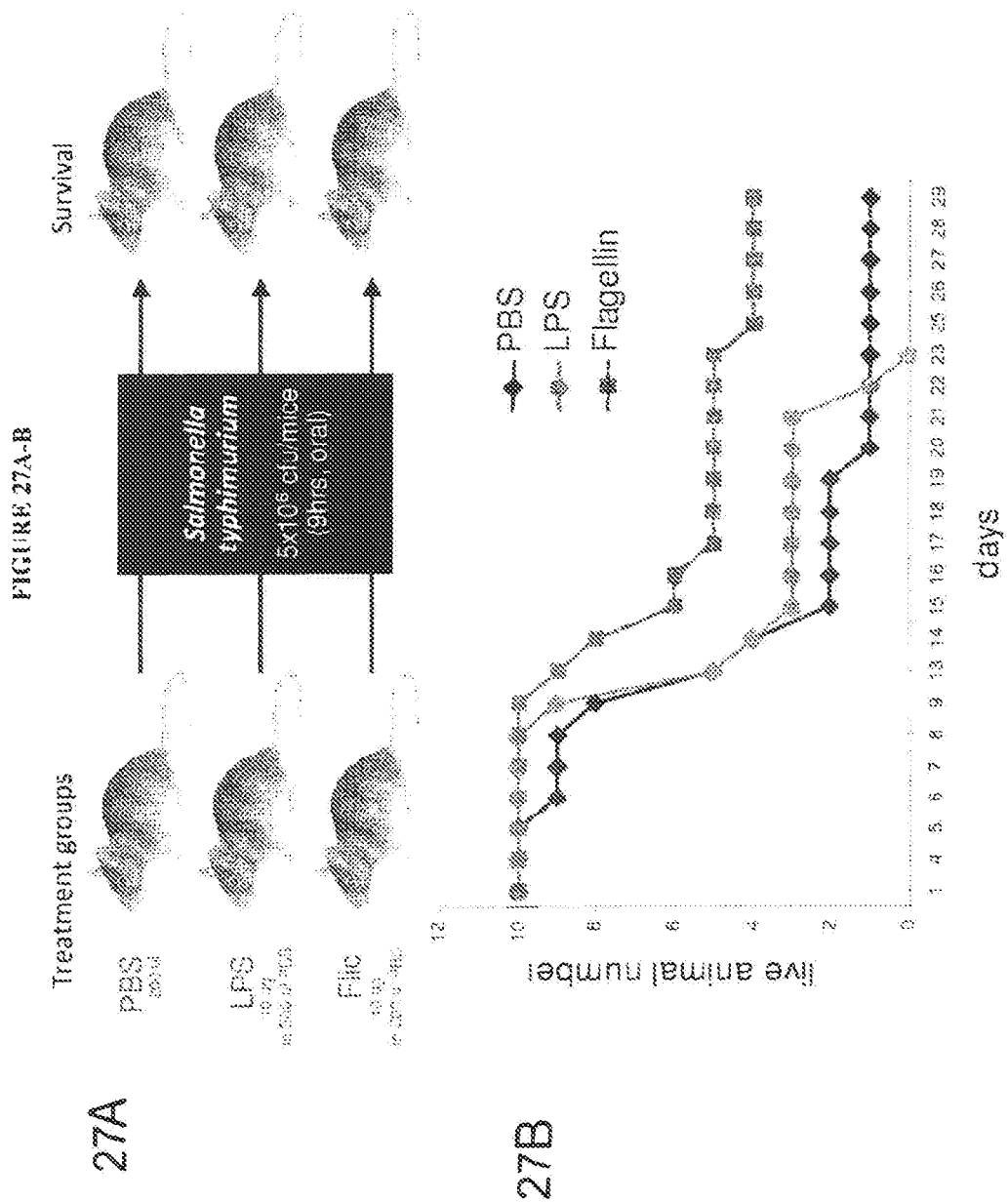

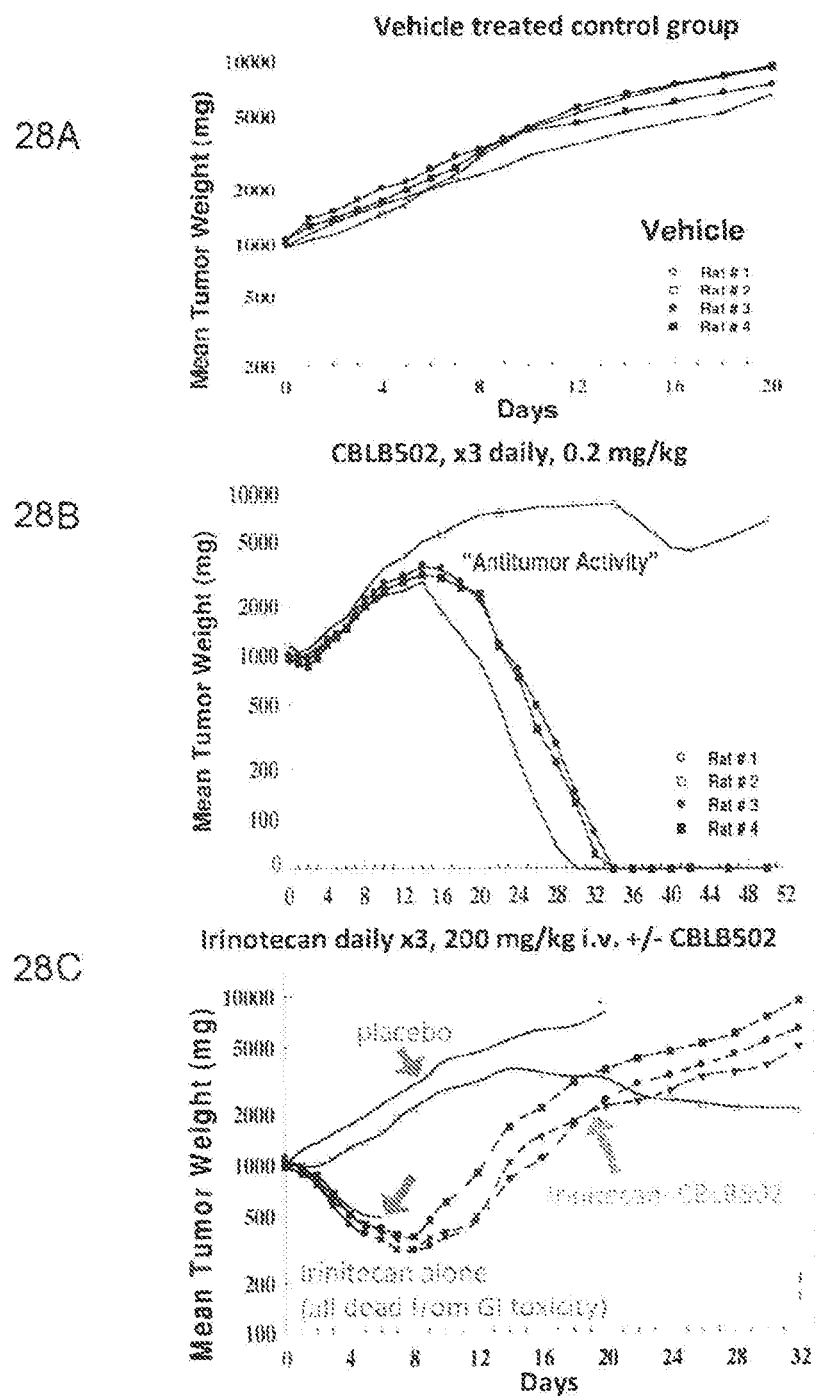

SEQUENCE LISTING

```
<160> NUMBER OF SEQ ID NOS: 159

<210> SEQ ID NO 1
<211> LENGTH: 505
<212> TYPE: PRT
<213> ORGANISM: Salmonella dublin

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Tyr Asp Thr Tyr Ala Ala Gly Ala Asp Lys Tyr Arg Val
        195                 200                 205

Asp Ile Asn Ser Gly Ala Val Val Thr Asp Ala Ala Ala Pro Asp Lys
    210                 215                 220

Val Tyr Val Asn Ala Ala Asn Gly Gln Leu Thr Thr Asp Asp Ala Glu
225                 230                 235                 240

Asn Asn Thr Ala Val Asp Leu Phe Lys Thr Thr Lys Ser Thr Ala Gly
                245                 250                 255
```

```
Thr Ala Glu Ala Lys Ala Ile Ala Gly Ala Ile Lys Gly Gly Lys Glu
            260                 265                 270

Gly Asp Thr Phe Asp Tyr Lys Gly Val Thr Phe Thr Ile Asp Thr Lys
        275                 280                 285

Thr Gly Asp Asp Gly Asn Gly Lys Val Ser Thr Thr Ile Asn Gly Glu
    290                 295                 300

Lys Val Thr Leu Thr Val Ala Asp Ile Ala Thr Gly Ala Ala Asp Val
305                 310                 315                 320

Asn Ala Ala Thr Leu Gln Ser Ser Lys Asn Val Tyr Thr Ser Val Val
                325                 330                 335

Asn Gly Gln Phe Thr Phe Asp Asp Lys Thr Lys Asn Glu Ser Ala Lys
            340                 345                 350

Leu Ser Asp Leu Glu Ala Asn Asn Ala Val Lys Gly Glu Ser Lys Ile
        355                 360                 365

Thr Val Asn Gly Ala Glu Tyr Thr Ala Asn Ala Thr Gly Asp Lys Ile
    370                 375                 380

Thr Leu Ala Gly Lys Thr Met Phe Ile Asp Lys Thr Ala Ser Gly Val
385                 390                 395                 400

Ser Thr Leu Ile Asn Glu Asp Ala Ala Ala Lys Lys Ser Thr Ala
                405                 410                 415

Asn Pro Leu Ala Ser Ile Asp Ser Ala Leu Ser Lys Val Asp Ala Val
            420                 425                 430

Arg Ser Ser Leu Gly Ala Ile Gln Asn Arg Phe Asp Ser Ala Ile Thr
        435                 440                 445

Asn Leu Gly Asn Thr Val Thr Asn Leu Asn Ser Ala Arg Ser Arg Ile
    450                 455                 460

Glu Asp Ala Asp Tyr Ala Thr Glu Val Ser Asn Met Ser Lys Ala Gln
465                 470                 475                 480

Ile Leu Gln Gln Ala Gly Thr Ser Val Leu Ala Gln Ala Asn Gln Val
                485                 490                 495

Pro Gln Asn Val Leu Ser Leu Leu Arg
            500                 505

<210> SEQ ID NO 2
<211> LENGTH: 1518
<212> TYPE: DNA
<213> ORGANISM: Salmonella dublin

<400> SEQUENCE: 2
atggcacaag tcattaatac aaacagcctg tcgctgttga cccagaataa cctgaacaaa      60
tctcagtcct cactgagttc cgctattgag cgtctgtcct ctggtctgcg tatcaacagc     120
gcgaaagacg atgcggcagg ccaggcgatt gctaaccgct tcacttctaa tatcaaaggc     180
ctgactcagg cttcccgtaa cgctaacgac ggcatttcta ttgcgcagac cactgaaggt     240
gcgctgaatg aaatcaacaa caacctgcag cgtgtgcgtg agttgtctgt tcaggccact     300
aacgggacta actctgattc cgatctgaaa tctatccagg atgaaattca gcaacgtctg     360
gaagaaatcg atcgcgtttc taatcagact caatttaacg gtgttaaagt cctctctcag     420
gacaaccaga tgaaaatcca ggttggtgct aacgatggtg aaaccattac catcgatctg     480
caaaaaattg atgtgaaaag ccttggcctt gatgggttca atgttaatgg ccaaaagaa      540 gcgacagtgg gtgatctgaa atccagcttc aagaatgtta cgggttacga cacctatgca     600
gcgggtgccg ataaatatcg tgtagatatt aattccggtg ctgtagtgac tgatgcagca     660
gcaccggata agtatatgt aaatgcagca acggtcagt taacaactga cgatgcggaa      720
```

-continued

```
aataacactg cggttgatct ctttaagacc actaaatcta ctgctggtac cgctgaagcc      780
aaagcgatag ctggtgccat taaaggtggt aaggaaggag atacctttga ttataaaggc      840 gtgacttta  ctattgatac aaaaactggt gatgacggta atggtaaggt ttctactacc      900
atcaatggtg aaaaagttac gttaactgtc gctgatattg ccactggcgc ggcggatgtt      960
aatgctgcta ccttacaatc aagcaaaaat gtttatacat ctgtagtgaa cggtcagttt     1020
acttttgatg ataaaaccaa aaacgagagt gcgaaacttt ctgatttgga agcaaacaat     1080
gctgttaagg gcgaaagtaa aattacagta aatggggctg aatatactgc taacgccacg     1140
ggtgataaga tcaccttagc tggcaaaacc atgtttattg ataaaacagc ttctggcgta     1200
agtacattaa tcaatgaaga cgctgccgca gccaagaaaa gtaccgctaa cccactggct     1260
tcaattgatt ctgcattgtc aaagtggac gcagttcgtt cttctctggg ggcaattcaa     1320
aaccgttttg attcagccat taccaacctt ggcaatacgg taaccaatct gaactccgcg     1380
cgtagccgta tcgaagatgc tgactatgca acggaagttt ctaatatgtc taaagcgcag     1440
attctgcagc aggctggtac ttccgttctg gcgcaggcta accaggttcc gcaaaacgtc     1500
ctctctttac tgcgttaa                                                  1518

<210> SEQ ID NO 3
<211> LENGTH: 16
<212> TYPE: PRT
<213> ORGANISM: Artificial
<220> FEATURE:
<223> OTHER INFORMATION: peptide linker

<400> SEQUENCE: 3

Ser Pro Gly Ile Ser Gly Gly Gly Gly Gly Ile Leu Asp Ser Met Gly
1               5                   10                  15

<210> SEQ ID NO 4
<211> LENGTH: 16
<212> TYPE: PRT
<213> ORGANISM: Artificial
<220> FEATURE:
<223> OTHER INFORMATION: peptide linker

<400> SEQUENCE: 4

Ile Pro Gly Ile Ser Gly Gly Gly Gly Gly Ile Leu Asp Ser Met Gly
1               5                   10                  15

<210> SEQ ID NO 5
<211> LENGTH: 46
<212> TYPE: DNA
<213> ORGANISM: Artificial
<220> FEATURE:
<223> OTHER INFORMATION: peptide linker

<400> SEQUENCE: 5
tccccgggaa tttccggtgg tggtggtgga attctagact ccatgg             46

<210> SEQ ID NO 6
<211> LENGTH: 46
<212> TYPE: DNA
<213> ORGANISM: Artificial
<220> FEATURE:
<223> OTHER INFORMATION: peptide linker

<400> SEQUENCE: 6
atcccgggaa tttccggtgg tggtggtgga attctagact ccatgg             46
```

<210> SEQ ID NO 7
<211> LENGTH: 990
<212> TYPE: DNA
<213> ORGANISM: Salmonella dublin

<400> SEQUENCE: 7

```
atgcggggtt ctcatcatca tcatcatcat ggtatggcta gcatgactgg tggacagcaa      60
atgggtcggg atctgtacga cgatgacgat aaggatccga tggcacaagt cattaataca    120
aacagcctgt cgctgttgac ccagaataac ctgaacaaat ctcagtcctc actgagttcc    180
gctattgagc gtctgtcctc tggtctgcgt atcaacagcg cgaaagacga tgcggcaggc    240
caggcgattg ctaaccgctt cacttctaat atcaaaggcc tgactcaggc ttcccgtaac    300
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagactc aatttaacgg tgttaaagtc ctctctcagg acaaccagat gaaaatccag    540
gttggtgcta cgatggtga aaccattacc atcgatctgc aaaaaattga tgtgaaaagc    600
cttggccttg atgggttcaa tgttaattcc ccgggaattt ccggtggtgg tggtggaatt    660
ctagactcca tgggtacatt aatcaatgaa gacgctgccg cagccaagaa aagtaccgct    720
aacccactgg cttcaattga ttctgcattg tcaaaagtgg acgcagttcg ttcttctctg    780
ggggcaattc aaaaccgttt tgattcagcc attaccaacc ttggcaatac ggtaaccaat    840
ctgaactccg cgcgtagccg tatcgaagat gctgactatg caacgaagt ttctaatatg    900
tctaaagcgc agattctgca gcaggctggt acttccgttc tggcgcaggc taaccaggtt    960
ccgcaaaacg tcctctcttt actgcgttag                                      990
```

<210> SEQ ID NO 8
<211> LENGTH: 329
<212> TYPE: PRT
<213> ORGANISM: Salmonella dublin

<400> SEQUENCE: 8

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160
```

Asn Gln Thr Gln Phe Asn Gly Val Lys Val Leu Ser Gln Asp Asn Gln
              165                 170                 175

Met Lys Ile Gln Val Gly Ala Asn Asp Gly Glu Thr Ile Thr Ile Asp
          180                 185                 190

Leu Gln Lys Ile Asp Val Lys Ser Leu Gly Leu Asp Gly Phe Asn Val
      195                 200                 205

Asn Ser Pro Gly Ile Ser Gly Gly Gly Gly Ile Leu Asp Ser Met
210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
              245                 250                 255

Arg Ser Ser Leu Gly Ala Ile Gln Asn Arg Phe Asp Ser Ala Ile Thr
          260                 265                 270

Asn Leu Gly Asn Thr Val Thr Asn Leu Asn Ser Ala Arg Ser Arg Ile
      275                 280                 285

Glu Asp Ala Asp Tyr Ala Thr Glu Val Ser Asn Met Ser Lys Ala Gln
290                 295                 300

Ile Leu Gln Gln Ala Gly Thr Ser Val Leu Ala Gln Ala Asn Gln Val
305                 310                 315                 320

Pro Gln Asn Val Leu Ser Leu Leu Arg
              325

<210> SEQ ID NO 9
<211> LENGTH: 825
<212> TYPE: DNA
<213> ORGANISM: Salmonella dublin

<400> SEQUENCE: 9
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga atcaacaac     360
aacctgcagc gtgtgcgtga gttgtctgtt caggccacta cgggactaa ctctgattcc     420
gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta acgatggtga accattacc atcgatctgc aaaaaattga tgtgaaaagc     600
cttggccttg atgggttcaa tgttaattcc ccgggaattt ccggtggtgg tggtggaatt     660
ctagactcca tgggtacatt aatcaatgaa gacgctgccg cagccaagaa aagtaccgct     720
aacccactgg cttcaattga ttctgcattg tcaaaagtgg acgcagttcg ttcttctctg     780
ggggcaattc aaaaccgttt tgattcagcc attaccaacc tttag                      825

<210> SEQ ID NO 10
<211> LENGTH: 274
<212> TYPE: PRT
<213> ORGANISM: Salmonella dublin

<400> SEQUENCE: 10

Met Arg Gly Ser His His His His His His Gly Met Ala Ser Met Thr

```
            1               5                  10                 15
          Gly Gly Gln Gln Met Gly Arg Asp Leu Tyr Asp Asp Asp Lys Asp
                        20                  25                  30

Pro Met Ala Gln Val Ile Asn Thr Asn Ser Leu Ser Leu Leu Thr Gln
                        35                  40                  45

Asn Asn Leu Asn Lys Ser Gln Ser Ser Leu Ser Ser Ala Ile Glu Arg
                    50                  55                  60

Leu Ser Ser Gly Leu Arg Ile Asn Ser Ala Lys Asp Asp Ala Ala Gly
          65                  70                  75                  80

Gln Ala Ile Ala Asn Arg Phe Thr Ser Asn Ile Lys Gly Leu Thr Gln
                              85                  90                  95

Ala Ser Arg Asn Ala Asn Asp Gly Ile Ser Ile Ala Gln Thr Thr Glu
                          100                 105                 110

Gly Ala Leu Asn Glu Ile Asn Asn Asn Leu Gln Arg Val Arg Glu Leu
                          115                 120                 125

Ser Val Gln Ala Thr Asn Gly Thr Asn Ser Asp Ser Asp Leu Lys Ser
                      130                 135                 140

Ile Gln Asp Glu Ile Gln Gln Arg Leu Glu Glu Ile Asp Arg Val Ser
          145                 150                 155                 160

Asn Gln Thr Gln Phe Asn Gly Val Lys Val Leu Ser Gln Asp Asn Gln
                              165                 170                 175

Met Lys Ile Gln Val Gly Ala Asn Asp Gly Glu Thr Ile Thr Ile Asp
                          180                 185                 190

Leu Gln Lys Ile Asp Val Lys Ser Leu Gly Leu Asp Gly Phe Asn Val
                          195                 200                 205

Asn Ser Pro Gly Ile Ser Gly Gly Gly Gly Ile Leu Asp Ser Met
                      210                 215                 220

Gly Thr Leu Ile Asn Glu Asp Ala Ala Ala Lys Lys Ser Thr Ala
          225                 230                 235                 240

Asn Pro Leu Ala Ser Ile Asp Ser Ala Leu Ser Lys Val Asp Ala Val
                          245                 250                 255

Arg Ser Ser Leu Gly Ala Ile Gln Asn Arg Phe Asp Ser Ala Ile Thr
                          260                 265                 270

Asn Leu

<210> SEQ ID NO 11
<211> LENGTH: 831
<212> TYPE: DNA
<213> ORGANISM: Salmonella dublin

<400> SEQUENCE: 11
atgcggggtt ctcatcatca tcatcatcat ggtatggcta gcatgactgg tggacagcaa     60
atgggtcggg atctgtacga cgatgacgat aaggatccgt tcacttctaa tatcaaaggc    120
ctgactcagg cttcccgtaa cgctaacgac ggcatttcta ttgcgcagac cactgaaggt    180
gcgctgaatg aaatcaacaa caacctgcag cgtgtgcgtg agttgtctgt tcaggccact    240
aacgggacta actctgattc cgatctgaaa tctatccagg atgaaattca gcaacgtctg    300
gaagaaatcg atcgcgtttc taatcagact caatttaacg gtgttaaagt cctctctcag    360
gacaaccaga tgaaaatcca ggttggtgct aacgatggtg aaaccattac catcgatctg    420
caaaaaattg atgtgaaaag ccttggcctt gatgggttca atgttaattc cccgggaatt    480
tccggtggtg gtggtggaat tctagactcc atgggtacat taatcaatga agacgctgcc    540
gcagccaaga aaagtaccgc taacccactg gcttcaattg attctgcatt gtcaaaagtg    600
```

```
gacgcagttc gttcttctct gggggcaatt caaaaccgtt ttgattcagc cattaccaac    660
cttggcaata cggtaaccaa tctgaactcc gcgcgtagcc gtatcgaaga tgctgactat    720
gcaacggaag tttctaatat gtctaaagcg cagattctgc agcaggctgg tacttccgtt    780
ctggcgcagg ctaaccaggt tccgcaaaac gtcctctctt tactgcgtta g             831
```

<210> SEQ ID NO 12
<211> LENGTH: 276
<212> TYPE: PRT
<213> ORGANISM: Salmonella dublin

<400> SEQUENCE: 12

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
            35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Asp Gly Phe Asn Val Asn Ser Pro Gly Ile
145                 150                 155                 160

Ser Gly Gly Gly Gly Ile Leu Asp Ser Met Gly Thr Leu Ile Asn
                165                 170                 175

Glu Asp Ala Ala Ala Ala Lys Lys Ser Thr Ala Asn Pro Leu Ala Ser
            180                 185                 190

Ile Asp Ser Ala Leu Ser Lys Val Asp Ala Val Arg Ser Ser Leu Gly
        195                 200                 205

Ala Ile Gln Asn Arg Phe Asp Ser Ala Ile Thr Asn Leu Gly Asn Thr
    210                 215                 220

Val Thr Asn Leu Asn Ser Ala Arg Ser Arg Ile Glu Asp Ala Asp Tyr
225                 230                 235                 240

Ala Thr Glu Val Ser Asn Met Ser Lys Ala Gln Ile Leu Gln Gln Ala
                245                 250                 255

Gly Thr Ser Val Leu Ala Gln Ala Asn Gln Val Pro Gln Asn Val Leu
            260                 265                 270

Ser Leu Leu Arg
        275
```

<210> SEQ ID NO 13
<211> LENGTH: 666
<212> TYPE: DNA
<213> ORGANISM: Salmonella dublin

<400> SEQUENCE: 13

```
atgcggggtt ctcatcatca tcatcatcat ggtatggcta gcatgactgg tggacagcaa    60
atgggtcggg atctgtacga cgatgacgat aaggatccgt tcacttctaa tatcaaaggc   120
ctgactcagg cttcccgtaa cgctaacgac ggcatttcta ttgcgcagac cactgaaggt   180
gcgctgaatg aaatcaacaa caacctgcag cgtgtgcgtg agttgtctgt tcaggccact   240
aacgggacta actctgattc cgatctgaaa tctatccagg atgaaattca gcaacgtctg   300
gaagaaatcg atcgcgtttc taatcagact caatttaacg tgttaaaagt cctctctcag   360
gacaaccaga tgaaaatcca ggttggtgct aacgatggtg aaaccattac catcgatctg   420
caaaaaattg atgtgaaaag ccttggcctt gatgggttca atgttaattc cccgggaatt   480
tccggtggtg gtggtggaat tctagactcc atgggtacat aatcaatga agacgctgcc   540 gcagccaaga aaagtaccgc taacccactg gcttcaattg attctgcatt gtcaaaagtg   600
gacgcagttc gttcttctct ggggcaatt caaaaccgtt tgattcagc cattaccaac   660 ctttag                                                              666
```

<210> SEQ ID NO 14
<211> LENGTH: 221
<212> TYPE: PRT
<213> ORGANISM: Salmonella dublin

<400> SEQUENCE: 14

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Asp Gly Phe Asn Val Asn Ser Pro Gly Ile
145                 150                 155                 160

Ser Gly Gly Gly Gly Ile Leu Asp Ser Met Gly Thr Leu Ile Asn
                165                 170                 175

Glu Asp Ala Ala Ala Ala Lys Lys Ser Thr Ala Asn Pro Leu Ala Ser
            180                 185                 190

Ile Asp Ser Ala Leu Ser Lys Val Asp Ala Val Arg Ser Ser Leu Gly
        195                 200                 205

Ala Ile Gln Asn Arg Phe Asp Ser Ala Ile Thr Asn Leu
    210                 215                 220
```

<210> SEQ ID NO 15
<211> LENGTH: 603
<212> TYPE: DNA
<213> ORGANISM: Salmonella dublin

<400> SEQUENCE: 15

```
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
tccccgggaa tttccggtgg tggtggtgga attctagact ccatgggtac attaatcaat     300
gaagacgctg ccgcagccaa gaaaagtacc gctaacccac tggcttcaat tgattctgca     360
ttgtcaaaag tggacgcagt tcgttcttct ctggggcaa ttcaaaaccg ttttgattca      420
gccattacca accttggcaa tacggtaacc aatctgaact ccgcgcgtag ccgtatcgaa     480
gatgctgact atgcaacgga gtttctaat atgtctaaag cgcagattct gcagcaggct      540
ggtacttccg ttctggcgca ggctaaccag gttccgcaaa acgtcctctc tttactgcgt     600
tag                                                                   603
```

<210> SEQ ID NO 16
<211> LENGTH: 200
<212> TYPE: PRT
<213> ORGANISM: Salmonella dublin
<400> SEQUENCE: 16

```
Met Arg Gly Ser His His His His His His Gly Met Ala Ser Met Thr
 1               5                  10                  15
Gly Gly Gln Gln Met Gly Arg Asp Leu Tyr Asp Asp Asp Lys Asp
             20                  25                  30
Pro Phe Thr Ser Asn Ile Lys Gly Leu Thr Gln Ala Ser Arg Asn Ala
         35                  40                  45
Asn Asp Gly Ile Ser Ile Ala Gln Thr Thr Glu Gly Ala Leu Asn Glu
     50                  55                  60
Ile Asn Asn Asn Leu Gln Arg Val Arg Glu Leu Ser Val Gln Ala Thr
 65                  70                  75                  80
Ser Pro Gly Ile Ser Gly Gly Gly Gly Ile Leu Asp Ser Met Gly
                 85                  90                  95
Thr Leu Ile Asn Glu Asp Ala Ala Ala Lys Lys Ser Thr Ala Asn
            100                 105                 110
Pro Leu Ala Ser Ile Asp Ser Ala Leu Ser Lys Val Asp Ala Val Arg
        115                 120                 125
Ser Ser Leu Gly Ala Ile Gln Asn Arg Phe Asp Ser Ala Ile Thr Asn
    130                 135                 140
Leu Gly Asn Thr Val Thr Asn Leu Asn Ser Ala Arg Ser Arg Ile Glu
145                 150                 155                 160
Asp Ala Asp Tyr Ala Thr Glu Val Ser Asn Met Ser Lys Ala Gln Ile
                165                 170                 175
Leu Gln Gln Ala Gly Thr Ser Val Leu Ala Gln Ala Asn Gln Val Pro
            180                 185                 190
Gln Asn Val Leu Ser Leu Leu Arg
        195                 200
```

<210> SEQ ID NO 17
<211> LENGTH: 438
<212> TYPE: DNA
<213> ORGANISM: Salmonella dublin
<400> SEQUENCE: 17

```
atgcggggtt ctcatcatca tcatcatcat ggtatggcta gcatgactgg tggacagcaa    60
atgggtcggg atctgtacga cgatgacgat aaggatccgt tcacttctaa tatcaaaggc   120
ctgactcagg cttcccgtaa cgctaacgac ggcatttcta ttgcgcagac cactgaaggt   180
gcgctgaatg aaatcaacaa caacctgcag cgtgtgcgtg agttgtctgt tcaggccact   240
tccccgggaa tttccggtgg tggtggtgga attctagact ccatgggtac attaatcaat   300
gaagacgctg ccgcagccaa gaaaagtacc gctaacccac tggcttcaat tgattctgca   360
ttgtcaaaag tggacgcagt tcgttcttct ctgggggcaa ttcaaaaccg tttttgattca  420
gccattacca acctttag                                                 438
```

<210> SEQ ID NO 18
<211> LENGTH: 145
<212> TYPE: PRT
<213> ORGANISM: Salmonella dublin

<400> SEQUENCE: 18

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Phe Thr Ser Asn Ile Lys Gly Leu Thr Gln Ala Ser Arg Asn Ala
        35                  40                  45
Asn Asp Gly Ile Ser Ile Ala Gln Thr Thr Glu Gly Ala Leu Asn Glu
    50                  55                  60
Ile Asn Asn Asn Leu Gln Arg Val Arg Glu Leu Ser Val Gln Ala Thr
65                  70                  75                  80
Ser Pro Gly Ile Ser Gly Gly Gly Gly Ile Leu Asp Ser Met Gly
                85                  90                  95
Thr Leu Ile Asn Glu Asp Ala Ala Ala Ala Lys Lys Ser Thr Ala Asn
            100                 105                 110
Pro Leu Ala Ser Ile Asp Ser Ala Leu Ser Lys Val Asp Ala Val Arg
        115                 120                 125
Ser Ser Leu Gly Ala Ile Gln Asn Arg Phe Asp Ser Ala Ile Thr Asn
    130                 135                 140
Leu
145

<210> SEQ ID NO 19
<211> LENGTH: 639
<212> TYPE: DNA
<213> ORGANISM: Salmonella dublin

<400> SEQUENCE: 19

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggtc tgactcaggc ttcccgtaac   300
gctaacgacg gcatttctat tgcgcagacc actgaaggtg cgctgaatga aatcaacaac   360
aacctgcagc gtgtgcgtga gttgtctgtt caggccacta cgggactaa ctctgattcc   420
gatctgaaat ctatccagga tgaaattcag caacgtctgg aagaaatcga tcgcgtttct   480
```

```
aatcagactc aatttaacgg tgttaaagtc ctgtctcagg acaaccagat gaaaatccag      540
gttggtgcta acgatggtga aaccattacc atcgatctgc aaaaaattga tgtgaaaagc      600
cttggccttg atgggttcaa tgttaattcc ccgggatga                             639
```

```
<210> SEQ ID NO 20
<211> LENGTH: 212
<212> TYPE: PRT
<213> ORGANISM: Salmonella dublin

<400> SEQUENCE: 20
```

| | | | | | | | | | | | | | | | |
|---|---|---|---|---|---|---|---|---|---|---|---|---|---|---|---|
| Met | Arg | Gly | Ser | His | His | His | His | His | His | Gly | Met | Ala | Ser | Met | Thr |
| 1 | | | | 5 | | | | | 10 | | | | | 15 | |
| Gly | Gly | Gln | Gln | Met | Gly | Arg | Asp | Leu | Tyr | Asp | Asp | Asp | Lys | Asp | |
| | | 20 | | | | | 25 | | | | | 30 | | | |
| Pro | Met | Ala | Gln | Val | Ile | Asn | Thr | Asn | Ser | Leu | Ser | Leu | Leu | Thr | Gln |
| | | 35 | | | | | 40 | | | | | 45 | | | |
| Asn | Asn | Leu | Asn | Lys | Ser | Gln | Ser | Ser | Leu | Ser | Ser | Ala | Ile | Glu | Arg |
| | 50 | | | | | 55 | | | | | 60 | | | | |
| Leu | Ser | Ser | Gly | Leu | Arg | Ile | Asn | Ser | Ala | Lys | Asp | Asp | Ala | Ala | Gly |
| 65 | | | | | 70 | | | | | 75 | | | | | 80 |
| Gln | Ala | Ile | Ala | Asn | Arg | Phe | Thr | Ser | Asn | Ile | Lys | Gly | Leu | Thr | Gln |
| | | | | 85 | | | | | 90 | | | | | 95 | |
| Ala | Ser | Arg | Asn | Ala | Asn | Asp | Gly | Ile | Ser | Ile | Ala | Gln | Thr | Thr | Glu |
| | | | 100 | | | | | 105 | | | | | 110 | | |
| Gly | Ala | Leu | Asn | Glu | Ile | Asn | Asn | Asn | Leu | Gln | Arg | Val | Arg | Glu | Leu |
| | | 115 | | | | | 120 | | | | | 125 | | | |
| Ser | Val | Gln | Ala | Thr | Asn | Gly | Thr | Asn | Ser | Asp | Ser | Asp | Leu | Lys | Ser |
| | 130 | | | | | 135 | | | | | 140 | | | | |
| Ile | Gln | Asp | Glu | Ile | Gln | Gln | Arg | Leu | Glu | Glu | Ile | Asp | Arg | Val | Ser |
| 145 | | | | | 150 | | | | | 155 | | | | | 160 |
| Asn | Gln | Thr | Gln | Phe | Asn | Gly | Val | Lys | Val | Leu | Ser | Gln | Asp | Asn | Gln |
| | | | | 165 | | | | | 170 | | | | | 175 | |
| Met | Lys | Ile | Gln | Val | Gly | Ala | Asn | Asp | Gly | Glu | Thr | Ile | Thr | Ile | Asp |
| | | | 180 | | | | | 185 | | | | | 190 | | |
| Leu | Gln | Lys | Ile | Asp | Val | Lys | Ser | Leu | Gly | Leu | Asp | Gly | Phe | Asn | Val |
| | | 195 | | | | | 200 | | | | | 205 | | | |
| Asn | Ser | Pro | Gly | | | | | | | | | | | | |
| | | | 210 | | | | | | | | | | | | |

```
<210> SEQ ID NO 21
<211> LENGTH: 480
<212> TYPE: DNA
<213> ORGANISM: Salmonella dublin

<400> SEQUENCE: 21
```

```
atgcggggtt ctcatcatca tcatcatcat ggtatggcta gcatgactgg tggacagcaa      60
atgggtcggg atctgtacga cgatgacgat aaggatccgt tcacttctaa tatcaaaggt     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta actctgattc cgatctgaaa tctatccagg atgaaattca gcaacgtctg     300
gaagaaatcg atcgcgtttc taatcagact caatttaacg gtgttaaagt cctgtctcag     360
gacaaccaga tgaaaatcca ggttggtgct aacgatggtg aaaccattac catcgatctg     420
caaaaaattg atgtgaaaag ccttggcctt gatgggttca atgttaattc cccgggatga     480
```

<210> SEQ ID NO 22
<211> LENGTH: 159
<212> TYPE: PRT
<213> ORGANISM: Salmonella dublin

<400> SEQUENCE: 22

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Asp Gly Phe Asn Val Asn Ser Pro Gly
145                 150                 155

<210> SEQ ID NO 23
<211> LENGTH: 252
<212> TYPE: DNA
<213> ORGANISM: Salmonella dublin

<400> SEQUENCE: 23
atgcggggtt ctcatcatca tcatcatcat ggtatggcta gcatgactgg tggacagcaa      60
atgggtcggg atctgtacga cgatgacgat aaggatccgt tcacttctaa tatcaaaggt     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
tccccgggat ga                                                         252

<210> SEQ ID NO 24
<211> LENGTH: 83
<212> TYPE: PRT
<213> ORGANISM: Salmonella dublin

<400> SEQUENCE: 24

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Ser Pro Gly

<210> SEQ ID NO 25
<211> LENGTH: 1038
<212> TYPE: DNA
<213> ORGANISM: Salmonella dublin

<400> SEQUENCE: 25

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa     540
aaacgtattg aagctatccc acaaattgat aagtacttga atccagcaa gtatatagca    600
tggcctttgc agggctggca agccacgttt ggtggtggcg accatcctcc aaaatcggat    660
ctggttccgc gtggatcccc gggaatttcc ggtggtggtg gtggaattct agactccatg    720
ggtacattaa tcaatgaaga cgctgccgca gccaagaaaa gtaccgctaa cccactggct    780
tcaattgatt ctgcattgtc aaaagtggac gcagttcgtt cttctctggg ggcaattcaa    840
aaccgttttg attcagccat taccaacctt ggcaatacgg taaccaatct gaactccgcg    900
cgtagccgta tcgaagatgc tgactatgca acggaagttt ctaatatgtc taaagcgcag    960
attctgcagc aggctggtac ttccgttctg cgcaggcta accaggttcc gcaaaacgtc   1020
ctctctttac tgcgttag                                                1038
```

<210> SEQ ID NO 26
<211> LENGTH: 345
<212> TYPE: PRT
<213> ORGANISM: Salmonella dublin

<400> SEQUENCE: 26

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

```
Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
210                 215                 220

Gly Ser Pro Gly Ile Ser Gly Gly Gly Gly Ile Leu Asp Ser Met
225                 230                 235                 240

Gly Thr Leu Ile Asn Glu Asp Ala Ala Ala Lys Lys Ser Thr Ala
                245                 250                 255

Asn Pro Leu Ala Ser Ile Asp Ser Ala Leu Ser Lys Val Asp Ala Val
            260                 265                 270

Arg Ser Ser Leu Gly Ala Ile Gln Asn Arg Phe Asp Ser Ala Ile Thr
275                 280                 285

Asn Leu Gly Asn Thr Val Thr Asn Leu Asn Ser Ala Arg Ser Arg Ile
290                 295                 300

Glu Asp Ala Asp Tyr Ala Thr Glu Val Ser Asn Met Ser Lys Ala Gln
305                 310                 315                 320

Ile Leu Gln Gln Ala Gly Thr Ser Val Leu Ala Gln Ala Asn Gln Val
                325                 330                 335

Pro Gln Asn Val Leu Ser Leu Leu Arg
        340                 345

<210> SEQ ID NO 27
<211> LENGTH: 873
<212> TYPE: DNA
<213> ORGANISM: Salmonella dublin

<400> SEQUENCE: 27
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aaaatcggat     660
ctggttccgc gtggatcccc gggaatttcc ggtggtggtg gtggaattct agactccatg     720
ggtacattaa tcaatgaaga cgctgccgca gccaagaaaa gtaccgctaa cccactggct     780
tcaattgatt ctgcattgtc aaaagtggac gcagttcgtt cttctctggg ggcaattcaa     840
aaccgttttg attcagccat taccaacctt tag                                   873
```

<210> SEQ ID NO 28
<211> LENGTH: 290
<212> TYPE: PRT
<213> ORGANISM: Salmonella dublin

<400> SEQUENCE: 28

```
Met Ser Pro Ile Leu Gly Tyr Trp Lys Ile Lys Gly Leu Val Gln Pro
1               5                   10                  15
Thr Arg Leu Leu Leu Glu Tyr Leu Glu Lys Tyr Glu Glu His Leu
            20                  25                  30
Tyr Glu Arg Asp Glu Gly Asp Lys Trp Arg Asn Lys Lys Phe Glu Leu
                35                  40                  45
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
    130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Asp His Pro Pro Lys Ser Asp Leu Val Pro Arg
    210                 215                 220
Gly Ser Pro Gly Ile Ser Gly Gly Gly Gly Ile Leu Asp Ser Met
225                 230                 235                 240
Gly Thr Leu Ile Asn Glu Asp Ala Ala Ala Lys Lys Ser Thr Ala
                245                 250                 255
Asn Pro Leu Ala Ser Ile Asp Ser Ala Leu Ser Lys Val Asp Ala Val
            260                 265                 270
Arg Ser Ser Leu Gly Ala Ile Gln Asn Arg Phe Asp Ser Ala Ile Thr
        275                 280                 285
Asn Leu
    290
```

<210> SEQ ID NO 29
<211> LENGTH: 972
<212> TYPE: DNA
<213> ORGANISM: Salmonella dublin

<400> SEQUENCE: 29

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
```

-continued

```
gctattgagc gtctgtcctc tggtctgcgt atcaacagcg cgaaagacga tgcggcaggc    240
caggcgattg ctaaccgctt cacttctaat atcaaaggcc tgactcaggc ttcccgtaac    300
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagactc aatttaacgg tgttaaagtc ctctctcagg acaaccagat gaaaatccag    540
gttggtgcta acgatggtga aaccattacc atcgatctgc aaaaaattga tgtgaaaagc    600
cttggcctta tcccgggaat tccggtggt ggtggtggaa ttctagactc catgggtaca    660
ttaatcaatg aagacgctgc cgcagccaag aaaagtaccg ctaacccact ggcttcaatt    720
gattctgcat tgtcaaaagt ggacgcagtt cgttcttctc tgggggcaat tcaaaaccgt    780
tttgattcag ccattaccaa ccttggcaat acggtaacca atctgaactc cgcgcgtagc    840
cgtatcgaag atgctgacta tgcaacggaa gtttctaata tgtctaaagc gcagattctg    900
cagcaggctg gtacttccgt tctggcgcag gctaaccagg ttccgcaaaa cgtcctctct    960
ttactgcgtt ag                                                       972
```

```
<210> SEQ ID NO 30
<211> LENGTH: 323
<212> TYPE: PRT
<213> ORGANISM: Salmonella dublin

<400> SEQUENCE: 30

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Ile Pro Gly Ile Ser
        195                 200                 205

Gly Gly Gly Gly Gly Ile Leu Asp Ser Met Gly Thr Leu Ile Asn Glu
    210                 215                 220
```

```
Asp Ala Ala Ala Ala Lys Lys Ser Thr Ala Asn Pro Leu Ala Ser Ile
225                 230                 235                 240

Asp Ser Ala Leu Ser Lys Val Asp Ala Val Arg Ser Ser Leu Gly Ala
            245                 250                 255

Ile Gln Asn Arg Phe Asp Ser Ala Ile Thr Asn Leu Gly Asn Thr Val
        260                 265                 270

Thr Asn Leu Asn Ser Ala Arg Ser Arg Ile Glu Asp Ala Asp Tyr Ala
    275                 280                 285

Thr Glu Val Ser Asn Met Ser Lys Ala Gln Ile Leu Gln Gln Ala Gly
290                 295                 300

Thr Ser Val Leu Ala Gln Ala Asn Gln Val Pro Gln Asn Val Leu Ser
305                 310                 315                 320

Leu Leu Arg

<210> SEQ ID NO 31
<211> LENGTH: 813
<212> TYPE: DNA
<213> ORGANISM: Salmonella dublin

<400> SEQUENCE: 31
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta ctctgattcc gatctgaaaa tctatccagg atgaaattca gcaacgtctg     300
gaagaaatcg atcgcgtttc taatcagact caatttaacg gtgttaaagt cctctctcag     360
gacaaccaga tgaaaatcca ggttggtgct aacgatggtg aaaccattac catcgatctg     420
caaaaaattg atgtgaaaag ccttggcctt atcccgggaa tttccggtgg tggtggtgga     480
attctagact ccatgggtac attaatcaat gaagacgctg ccgcagccaa gaaaagtacc     540
gctaacccac tggcttcaat tgattctgca ttgtcaaaag tggacgcagt tcgttcttct     600 ctggggggcaa ttcaaaaccg ttttgattca gccattacca accttggcaa tacggtaacc     660
aatctgaact ccgcgcgtag ccgtatcgaa gatgctgact atgcaacgga agtttctaat     720
atgtctaaag cgcagattct gcagcaggct ggtacttccg ttctggcgca ggctaaccag     780
gttccgcaaa acgtcctctc tttactgcgt tag                                  813

<210> SEQ ID NO 32
<211> LENGTH: 270
<212> TYPE: PRT
<213> ORGANISM: Salmonella dublin

<400> SEQUENCE: 32

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80
```

Asn Gly Thr Asn Ser Asp Ser Asp Leu Lys Ser Ile Gln Asp Glu Ile
            85                  90                  95

Gln Gln Arg Leu Glu Glu Ile Asp Arg Val Ser Asn Gln Thr Gln Phe
        100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
        130                 135                 140

Val Lys Ser Leu Gly Leu Ile Pro Gly Ile Ser Gly Gly Gly Gly Gly
145                 150                 155                 160

Ile Leu Asp Ser Met Gly Thr Leu Ile Asn Glu Asp Ala Ala Ala Ala
                165                 170                 175

Lys Lys Ser Thr Ala Asn Pro Leu Ala Ser Ile Asp Ser Ala Leu Ser
                180                 185                 190

Lys Val Asp Ala Val Arg Ser Ser Leu Gly Ala Ile Gln Asn Arg Phe
                195                 200                 205

Asp Ser Ala Ile Thr Asn Leu Gly Asn Thr Val Thr Asn Leu Asn Ser
        210                 215                 220

Ala Arg Ser Arg Ile Glu Asp Ala Asp Tyr Ala Thr Glu Val Ser Asn
225                 230                 235                 240

Met Ser Lys Ala Gln Ile Leu Gln Gln Ala Gly Thr Ser Val Leu Ala
                245                 250                 255

Gln Ala Asn Gln Val Pro Gln Asn Val Leu Ser Leu Leu Arg
            260                 265                 270

<210> SEQ ID NO 33
<211> LENGTH: 951
<212> TYPE: DNA
<213> ORGANISM: Salmonella dublin

<400> SEQUENCE: 33
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga aatcaacaac     360
aacctgcagc gtgtgcgtga gttgtctgtt caggccacta cgggactaaa ctctgattcc     420
gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta acgatggtga accattacc atcgatctgc aaaaaattat cccgggaatt     600
tccggtggtg gtggtggaat tctagactcc atgggtacat taatcaatga agacgctgcc     660
gcagccaaga aaagtaccgc taacccactg gcttcaattg attctgcatt gtcaaaagtg     720
gacgcagttc gttcttctct gggggcaatt caaaaccgtt ttgattcagc cattaccaac     780
cttggcaata cggtaaccaa tctgaactcc gcgcgtagcc gtatcgaaga tgctgactat     840
gcaacggaag tttctaatat gtctaaagcg cagattctgc agcaggctgg tacttccgtt     900
ctggcgcagg ctaaccaggt tccgcaaaac gtcctctctt tactgcgtta g              951

<210> SEQ ID NO 34
<211> LENGTH: 316

<212> TYPE: PRT
<213> ORGANISM: Salmonella dublin

<400> SEQUENCE: 34

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met Ala Gln Val Ile Asn Thr Asn Ser Leu Ser Leu Leu Thr Gln
        35                  40                  45
Asn Asn Leu Asn Lys Ser Gln Ser Ser Leu Ser Ser Ala Ile Glu Arg
50                  55                  60
Leu Ser Ser Gly Leu Arg Ile Asn Ser Ala Lys Asp Asp Ala Ala Gly
65                  70                  75                  80
Gln Ala Ile Ala Asn Arg Phe Thr Ser Asn Ile Lys Gly Leu Thr Gln
                85                  90                  95
Ala Ser Arg Asn Ala Asn Asp Gly Ile Ser Ile Ala Gln Thr Thr Glu
            100                 105                 110
Gly Ala Leu Asn Glu Ile Asn Asn Asn Leu Gln Arg Val Arg Glu Leu
        115                 120                 125
Ser Val Gln Ala Thr Asn Gly Thr Asn Ser Asp Ser Asp Leu Lys Ser
130                 135                 140
Ile Gln Asp Glu Ile Gln Gln Arg Leu Glu Glu Ile Asp Arg Val Ser
145                 150                 155                 160
Asn Gln Thr Gln Phe Asn Gly Val Lys Val Leu Ser Gln Asp Asn Gln
                165                 170                 175
Met Lys Ile Gln Val Gly Ala Asn Asp Gly Glu Thr Ile Thr Ile Asp
            180                 185                 190
Leu Gln Lys Ile Ile Pro Gly Ile Ser Gly Gly Gly Gly Ile Leu
        195                 200                 205
Asp Ser Met Gly Thr Leu Ile Asn Glu Asp Ala Ala Ala Ala Lys Lys
210                 215                 220
Ser Thr Ala Asn Pro Leu Ala Ser Ile Asp Ser Ala Leu Ser Lys Val
225                 230                 235                 240
Asp Ala Val Arg Ser Ser Leu Gly Ala Ile Gln Asn Arg Phe Asp Ser
                245                 250                 255
Ala Ile Thr Asn Leu Gly Asn Thr Val Thr Asn Leu Asn Ser Ala Arg
            260                 265                 270
Ser Arg Ile Glu Asp Ala Asp Tyr Ala Thr Glu Val Ser Asn Met Ser
        275                 280                 285
Lys Ala Gln Ile Leu Gln Gln Ala Gly Thr Ser Val Leu Ala Gln Ala
290                 295                 300
Asn Gln Val Pro Gln Asn Val Leu Ser Leu Leu Arg
305                 310                 315
```

<210> SEQ ID NO 35
<211> LENGTH: 792
<212> TYPE: DNA
<213> ORGANISM: Salmonella dublin

<400> SEQUENCE: 35

```
atgcggggtt ctcatcatca tcatcatcat ggtatggcta gcatgactgg tggacagcaa    60
atgggtcggg atctgtacga cgatgacgat aaggatccgt tcacttctaa tatcaaaggc   120
ctgactcagg cttcccgtaa cgctaacgac ggcatttcta ttgcgcagac cactgaaggt   180
```

```
gcgctgaatg aaatcaacaa caacctgcag cgtgtgcgtg agttgtctgt tcaggccact    240
aacgggacta actctgattc cgatctgaaa tctatccagg atgaaattca gcaacgtctg    300
gaagaaatcg atcgcgtttc taatcagact caatttaacg gtgttaaagt cctctctcag    360
gacaaccaga tgaaaatcca ggttggtgct aacgatggtg aaaccattac catcgatctg    420
caaaaaatta tcccgggaat ttccggtggt ggtggtggaa ttctagactc catgggtaca    480
ttaatcaatg aagacgctgc cgcagccaag aaaagtaccg ctaacccact ggcttcaatt    540
gattctgcat tgtcaaaagt ggacgcagtt cgttcttctc tgggggcaat tcaaaaccgt    600
tttgattcag ccattaccaa ccttggcaat acggtaacca atctgaactc cgcgcgtagc    660
cgtatcgaag atgctgacta tgcaacggaa gtttctaata tgtctaaagc gcagattctg    720
cagcaggctg gtacttccgt tctggcgcag gctaaccagg ttccgcaaaa cgtcctctct    780
ttactgcgtt ag                                                        792
```

<210> SEQ ID NO 36
<211> LENGTH: 263
<212> TYPE: PRT
<213> ORGANISM: Salmonella dublin

<400> SEQUENCE: 36

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Ile
    130                 135                 140

Pro Gly Ile Ser Gly Gly Gly Gly Ile Leu Asp Ser Met Gly Thr
145                 150                 155                 160

Leu Ile Asn Glu Asp Ala Ala Ala Ala Lys Lys Ser Thr Ala Asn Pro
                165                 170                 175

Leu Ala Ser Ile Asp Ser Ala Leu Ser Lys Val Asp Ala Val Arg Ser
            180                 185                 190

Ser Leu Gly Ala Ile Gln Asn Arg Phe Asp Ser Ala Ile Thr Asn Leu
        195                 200                 205

Gly Asn Thr Val Thr Asn Leu Asn Ser Ala Arg Ser Arg Ile Glu Asp
    210                 215                 220

Ala Asp Tyr Ala Thr Glu Val Ser Asn Met Ser Lys Ala Gln Ile Leu
225                 230                 235                 240

Gln Gln Ala Gly Thr Ser Val Leu Ala Gln Ala Asn Gln Val Pro Gln
                245                 250                 255

Asn Val Leu Ser Leu Leu Arg
```

<210> SEQ ID NO 37
<211> LENGTH: 807
<212> TYPE: DNA
<213> ORGANISM: Salmonella dublin

<400> SEQUENCE: 37

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga atcaacaac      360
aacctgcagc gtgtgcgtga gttgtctgtt caggccacta acgggactaa ctctgattcc     420
gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta cgatggtga aaccattacc atcgatctgc aaaaaattga tgtgaaaagc      600
cttggcctta tcccgggaat ttccggtggt ggtggtggaa ttctagactc catgggtaca     660
ttaatcaatg aagacgctgc cgcagccaag aaaagtaccg ctaacccact ggcttcaatt     720
gattctgcat tgtcaaaagt ggacgcagtt cgttcttctc tggggcaat tcaaaaccgt      780
tttgattcag ccattaccaa cctttag                                         807
```

<210> SEQ ID NO 38
<211> LENGTH: 268
<212> TYPE: PRT
<213> ORGANISM: Salmonella dublin

<400> SEQUENCE: 38

```
Met Arg Gly Ser His His His His His His Gly Met Ala Ser Met Thr
 1               5                  10                  15
Gly Gly Gln Gln Met Gly Arg Asp Leu Tyr Asp Asp Asp Lys Asp
             20                  25                  30
Pro Met Ala Gln Val Ile Asn Thr Asn Ser Leu Ser Leu Leu Thr Gln
         35                  40                  45
Asn Asn Leu Asn Lys Ser Gln Ser Ser Leu Ser Ser Ala Ile Glu Arg
     50                  55                  60
Leu Ser Ser Gly Leu Arg Ile Asn Ser Ala Lys Asp Asp Ala Ala Gly
 65                  70                  75                  80
Gln Ala Ile Ala Asn Arg Phe Thr Ser Asn Ile Lys Gly Leu Thr Gln
                 85                  90                  95
Ala Ser Arg Asn Ala Asn Asp Gly Ile Ser Ile Ala Gln Thr Thr Glu
            100                 105                 110
Gly Ala Leu Asn Glu Ile Asn Asn Asn Leu Gln Arg Val Arg Glu Leu
        115                 120                 125
Ser Val Gln Ala Thr Asn Gly Thr Asn Ser Asp Ser Asp Leu Lys Ser
    130                 135                 140
Ile Gln Asp Glu Ile Gln Gln Arg Leu Glu Glu Ile Asp Arg Val Ser
145                 150                 155                 160
Asn Gln Thr Gln Phe Asn Gly Val Lys Val Leu Ser Gln Asp Asn Gln
                165                 170                 175
```

```
Met Lys Ile Gln Val Gly Ala Asn Asp Gly Glu Thr Ile Thr Ile Asp
                180                 185                 190

Leu Gln Lys Ile Asp Val Lys Ser Leu Gly Leu Ile Pro Gly Ile Ser
            195                 200                 205

Gly Gly Gly Gly Gly Ile Leu Asp Ser Met Gly Thr Leu Ile Asn Glu
        210                 215                 220

Asp Ala Ala Ala Lys Lys Ser Thr Ala Asn Pro Leu Ala Ser Ile
225                 230                 235                 240

Asp Ser Ala Leu Ser Lys Val Asp Ala Val Arg Ser Ser Leu Gly Ala
                245                 250                 255

Ile Gln Asn Arg Phe Asp Ser Ala Ile Thr Asn Leu
            260                 265
```

<210> SEQ ID NO 39
<211> LENGTH: 786
<212> TYPE: DNA
<213> ORGANISM: Salmonella dublin

<400> SEQUENCE: 39

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtcgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga atcaacaac     360
aacctgcagc gtgtgcgtga gttgtctgtt caggccacta acgggactaa ctctgattcc     420
gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta cgatggtga aaccattacc atcgatctgc aaaaaattat cccgggaatt     600
tccggtggtg gtggtggaat tctagactcc atgggtacat taatcaatga agacgctgcc     660
gcagccaaga aaagtaccgc taacccactg gcttcaattg attctgcatt gtcaaaagtg     720
gacgcagttc gttcttctct gggggcaatt caaaaccgtt ttgattcagc cattaccaac     780
ctttag                                                                786
```

<210> SEQ ID NO 40
<211> LENGTH: 261
<212> TYPE: PRT
<213> ORGANISM: Salmonella dublin

<400> SEQUENCE: 40

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95
```

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Ile Pro Gly Ile Ser Gly Gly Gly Gly Ile Leu
        195                 200                 205

Asp Ser Met Gly Thr Leu Ile Asn Glu Asp Ala Ala Ala Lys Lys
    210                 215                 220

Ser Thr Ala Asn Pro Leu Ala Ser Ile Asp Ser Ala Leu Ser Lys Val
225                 230                 235                 240

Asp Ala Val Arg Ser Ser Leu Gly Ala Ile Gln Asn Arg Phe Asp Ser
                245                 250                 255

Ala Ile Thr Asn Leu
            260

<210> SEQ ID NO 41
<211> LENGTH: 849
<212> TYPE: DNA
<213> ORGANISM: Salmonella dublin

<400> SEQUENCE: 41
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga aatcaacaac     360
aacctgcagc gtgtgcgtga gttgtctgtt caggccacta acgggactaa ctctgattcc     420
gatctgaaat ctatccagga tgaaattcag caacgtctgg aagaaatcga tcgcgtttct     480
aatcagatcc cggaatttc cggtggtggt ggtggaattc tagactccat gggtacatta     540
atcaatgaag acgctgccgc agccaagaaa agtaccgcta acccactggc ttcaattgat     600
tctgcattgt caaaagtgga cgcagttcgt tcttctctgg gggcaattca aaaccgtttt     660
gattcagcca ttaccaacct tgcaatacg gtaaccaatc tgaactccgc gcgtagccgt     720
atcgaagatg ctgactatgc aacggaagtt tctaatatgt ctaaagcgca gattctgcag     780
caggctggta cttccgttct ggcgcaggct aaccaggttc gcaaaacgt cctctcttta     840 ctgcgttag                                                             849

<210> SEQ ID NO 42
<211> LENGTH: 282
<212> TYPE: PRT
<213> ORGANISM: Salmonella dublin

<400> SEQUENCE: 42

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Ile Pro Gly Ile Ser Gly Gly Gly Gly Ile Leu Asp Ser
                165                 170                 175

Met Gly Thr Leu Ile Asn Glu Asp Ala Ala Ala Ala Lys Lys Ser Thr
            180                 185                 190

Ala Asn Pro Leu Ala Ser Ile Asp Ser Ala Leu Ser Lys Val Asp Ala
        195                 200                 205

Val Arg Ser Ser Leu Gly Ala Ile Gln Asn Arg Phe Asp Ser Ala Ile
    210                 215                 220

Thr Asn Leu Gly Asn Thr Val Thr Asn Leu Asn Ser Ala Arg Ser Arg
225                 230                 235                 240

Ile Glu Asp Ala Asp Tyr Ala Thr Glu Val Ser Asn Met Ser Lys Ala
                245                 250                 255

Gln Ile Leu Gln Gln Ala Gly Thr Ser Val Leu Ala Gln Ala Asn Gln
            260                 265                 270

Val Pro Gln Asn Val Leu Ser Leu Leu Arg
        275                 280

<210> SEQ ID NO 43
<211> LENGTH: 690
<212> TYPE: DNA
<213> ORGANISM: Salmonella dublin

<400> SEQUENCE: 43
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta ctctgattcg atctgaaa tctatccagg atgaaattca gcaacgtctg       300
gaagaaatcg atcgcgtttc taatcagatc ccgggaattt ccggtggtgg tggtggaatt     360
ctagactcca tgggtacatt aatcaatgaa gacgctgccg cagccaagaa aagtaccgct     420
aacccactgg cttcaattga ttctgcattg tcaaaagtgg acgcagttcg ttcttctctg     480

| | | |
|---|---|---|
| ggggcaattc aaaaccgttt tgattcagcc attaccaacc ttggcaatac ggtaaccaat | 540 | |
| ctgaactccg cgcgtagccg tatcgaagat gctgactatg caacggaagt ttctaatatg | 600 | |
| tctaaagcgc agattctgca gcaggctggt acttccgttc tggcgcaggc taaccaggtt | 660 | |
| ccgcaaaacg tcctctcttt actgcgttag | 690 | |

<210> SEQ ID NO 44
<211> LENGTH: 229
<212> TYPE: PRT
<213> ORGANISM: Salmonella dublin

<400> SEQUENCE: 44

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Ile Pro Gly
            100                 105                 110

Ile Ser Gly Gly Gly Gly Ile Leu Asp Ser Met Gly Thr Leu Ile
            115                 120                 125

Asn Glu Asp Ala Ala Ala Ala Lys Lys Ser Thr Ala Asn Pro Leu Ala
130                 135                 140

Ser Ile Asp Ser Ala Leu Ser Lys Val Asp Ala Val Arg Ser Ser Leu
145                 150                 155                 160

Gly Ala Ile Gln Asn Arg Phe Asp Ser Ala Ile Thr Asn Leu Gly Asn
                165                 170                 175

Thr Val Thr Asn Leu Asn Ser Ala Arg Ser Arg Ile Glu Asp Ala Asp
            180                 185                 190

Tyr Ala Thr Glu Val Ser Asn Met Ser Lys Ala Gln Ile Leu Gln Gln
        195                 200                 205

Ala Gly Thr Ser Val Leu Ala Gln Ala Asn Gln Val Pro Gln Asn Val
    210                 215                 220

Leu Ser Leu Leu Arg
225

<210> SEQ ID NO 45
<211> LENGTH: 684
<212> TYPE: DNA
<213> ORGANISM: Salmonella dublin

<400> SEQUENCE: 45

| | | |
|---|---|---|
| atgcggggtt ctcatcatca tcatcatcat ggtatggcta gcatgactgg tggacagcaa | 60 | |
| atgggtcggg atctgtacga cgatgacgat aaggatccga tggcacaagt cattaataca | 120 | |
| aacagcctgt cgctgttgac ccagaataac ctgaacaaat ctcagtcctc actgagttcc | 180 | |
| gctattgagc gtctgtcctc tggtctgcgt atcaacagcg cgaaagacga tgcggcaggc | 240 | |
| caggcgattg ctaaccgctt cacttctaat atcaaaggcc tgactcaggc ttcccgtaac | 300 | |

```
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagatcc cgggaatttc cggtggtggt ggtggaattc tagactccat gggtacatta    540
atcaatgaag acgctgccgc agccaagaaa agtaccgcta acccactggc ttcaattgat    600
tctgcattgt caaaagtgga cgcagttcgt tcttctctgg ggcaattca aaaccgtttt     660 gattcagcca ttaccaacct ttag                                           684
```

<210> SEQ ID NO 46
<211> LENGTH: 227
<212> TYPE: PRT
<213> ORGANISM: Salmonella dublin

<400> SEQUENCE: 46

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Ile Pro Gly Ile Ser Gly Gly Gly Gly Gly Ile Leu Asp Ser
                165                 170                 175

Met Gly Thr Leu Ile Asn Glu Asp Ala Ala Ala Ala Lys Lys Ser Thr
            180                 185                 190

Ala Asn Pro Leu Ala Ser Ile Asp Ser Ala Leu Ser Lys Val Asp Ala
        195                 200                 205

Val Arg Ser Ser Leu Gly Ala Ile Gln Asn Arg Phe Asp Ser Ala Ile
    210                 215                 220

Thr Asn Leu
225
```

<210> SEQ ID NO 47
<211> LENGTH: 525
<212> TYPE: DNA
<213> ORGANISM: Salmonella dublin

<400> SEQUENCE: 47

```
atgcggggtt ctcatcatca tcatcatcat ggtatggcta gcatgactgg tggacagcaa    60
atgggtcggg atctgtacga cgatgacgat aaggatccgt tcacttctaa tatcaaaggc   120
```

| | |
|---|---|
| ctgactcagg cttcccgtaa cgctaacgac ggcatttcta ttgcgcagac cactgaaggt | 180 |
| gcgctgaatg aaatcaacaa caacctgcag cgtgtgcgtg agttgtctgt tcaggccact | 240 |
| aacgggacta actctgattc cgatctgaaa tctatccagg atgaaattca gcaacgtctg | 300 |
| gaagaaatcg atcgcgtttc taatcagatc ccgggaattt ccggtggtgg tggtggaatt | 360 |
| ctagactcca tgggtacatt aatcaatgaa gacgctgccg cagccaagaa aagtaccgct | 420 |
| aacccactgg cttcaattga ttctgcattg tcaaaagtgg acgcagttcg ttcttctctg | 480 |
| ggggcaattc aaaaccgttt tgattcagcc attaccaacc tttag | 525 |

<210> SEQ ID NO 48
<211> LENGTH: 174
<212> TYPE: PRT
<213> ORGANISM: Salmonella dublin

<400> SEQUENCE: 48

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Phe Thr Ser Asn Ile Lys Gly Leu Thr Gln Ala Ser Arg Asn Ala
        35                  40                  45
Asn Asp Gly Ile Ser Ile Ala Gln Thr Thr Glu Gly Ala Leu Asn Glu
    50                  55                  60
Ile Asn Asn Asn Leu Gln Arg Val Arg Glu Leu Ser Val Gln Ala Thr
65                  70                  75                  80
Asn Gly Thr Asn Ser Asp Ser Asp Leu Lys Ser Ile Gln Asp Glu Ile
                85                  90                  95
Gln Gln Arg Leu Glu Glu Ile Asp Arg Val Ser Asn Gln Ile Pro Gly
            100                 105                 110
Ile Ser Gly Gly Gly Gly Gly Ile Leu Asp Ser Met Gly Thr Leu Ile
        115                 120                 125
Asn Glu Asp Ala Ala Ala Ala Lys Lys Ser Thr Ala Asn Pro Leu Ala
    130                 135                 140
Ser Ile Asp Ser Ala Leu Ser Lys Val Asp Ala Val Arg Ser Ser Leu
145                 150                 155                 160
Gly Ala Ile Gln Asn Arg Phe Asp Ser Ala Ile Thr Asn Leu
                165                 170
```

<210> SEQ ID NO 49
<211> LENGTH: 762
<212> TYPE: DNA
<213> ORGANISM: Salmonella dublin

<400> SEQUENCE: 49

| | |
|---|---|
| atgcggggtt ctcatcatca tcatcatcat ggtatggcta gcatgactgg tggacagcaa | 60 |
| atgggtcggg atctgtacga cgatgacgat aaggatccga tggcacaagt cattaataca | 120 |
| aacagcctgt cgctgttgac ccagaataac ctgaacaaat ctcagtcctc actgagttcc | 180 |
| gctattgagc gtctgtcctc tggtctgcgt atcaacagcg cgaaagacga tgcggcaggc | 240 |
| caggcgattg ctaaccgctt cacttctaat atcaaaggcc tgactcaggc ttcccgtaac | 300 |
| gctaacgacg gcatttctat tgcgcagacc actgaaggtg cgctgaatga aatcaacaac | 360 |
| aacctgcagc gtgtgcgtga gttgtctgtt caggccacta cccgggaat tccggtggt | 420 |
| ggtggtggaa ttctagactc catgggtaca ttaatcaatg aagacgctgc cgcagccaag | 480 |

```
aaaagtaccg ctaacccact ggcttcaatt gattctgcat tgtcaaaagt ggacgcagtt    540
cgttcttctc tgggggcaat tcaaaaccgt tttgattcag ccattaccaa ccttggcaat    600
acggtaacca atctgaactc cgcgcgtagc cgtatcgaag atgctgacta tgcaacggaa    660
gtttctaata tgtctaaagc gcagattctg cagcaggctg gtacttccgt tctggcgcag    720
gctaaccagg ttccgcaaaa cgtcctctct ttactgcgtt ag                       762
```

<210> SEQ ID NO 50
<211> LENGTH: 253
<212> TYPE: PRT
<213> ORGANISM: Salmonella dublin

<400> SEQUENCE: 50

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Ile Pro Gly Ile Ser Gly Gly Gly Gly Ile
    130                 135                 140

Leu Asp Ser Met Gly Thr Leu Ile Asn Glu Asp Ala Ala Ala Ala Lys
145                 150                 155                 160

Lys Ser Thr Ala Asn Pro Leu Ala Ser Ile Asp Ser Ala Leu Ser Lys
                165                 170                 175

Val Asp Ala Val Arg Ser Ser Leu Gly Ala Ile Gln Asn Arg Phe Asp
            180                 185                 190

Ser Ala Ile Thr Asn Leu Gly Asn Thr Val Thr Asn Leu Asn Ser Ala
        195                 200                 205

Arg Ser Arg Ile Glu Asp Ala Asp Tyr Ala Thr Glu Val Ser Asn Met
    210                 215                 220

Ser Lys Ala Gln Ile Leu Gln Gln Ala Gly Thr Ser Val Leu Ala Gln
225                 230                 235                 240

Ala Asn Gln Val Pro Gln Asn Val Leu Ser Leu Leu Arg
                245                 250
```

<210> SEQ ID NO 51
<211> LENGTH: 597
<212> TYPE: DNA
<213> ORGANISM: Salmonella dublin

<400> SEQUENCE: 51

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
```

```
gctattgagc gtctgtcctc tggtctgcgt atcaacagcg cgaaagacga tgcggcaggc       240
caggcgattg ctaaccgctt cacttctaat atcaaaggcc tgactcaggc ttcccgtaac       300
gctaacgacg gcatttctat tgcgcagacc actgaaggtg cgctgaatga aatcaacaac       360
aacctgcagc gtgtgcgtga gttgtctgtt caggccacta tcccgggaat ttccggtggt       420
ggtggtggaa ttctagactc catgggtaca ttaatcaatg aagacgctgc cgcagccaag       480
aaaagtaccg ctaacccact ggcttcaatt gattctgcat tgtcaaaagt ggacgcagtt       540
cgttcttctc tggggcaat tcaaaaccgt tttgattcag ccattaccaa cctttag         597
```

<210> SEQ ID NO 52
<211> LENGTH: 198
<212> TYPE: PRT
<213> ORGANISM: Salmonella dublin

<400> SEQUENCE: 52

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Ile Pro Gly Ile Ser Gly Gly Gly Gly Ile
    130                 135                 140

Leu Asp Ser Met Gly Thr Leu Ile Asn Glu Asp Ala Ala Ala Ala Lys
145                 150                 155                 160

Lys Ser Thr Ala Asn Pro Leu Ala Ser Ile Asp Ser Ala Leu Ser Lys
                165                 170                 175

Val Asp Ala Val Arg Ser Ser Leu Gly Ala Ile Gln Asn Arg Phe Asp
            180                 185                 190

Ser Ala Ile Thr Asn Leu
        195
```

<210> SEQ ID NO 53
<211> LENGTH: 672
<212> TYPE: DNA
<213> ORGANISM: Salmonella dublin

<400> SEQUENCE: 53

```
atgcggggtt ctcatcatca tcatcatcat ggtatggcta gcatgactgg tggacagcaa       60
atgggtcggg atctgtacga cgatgacgat aaggatccga tggcacaagt cattaataca      120
aacagcctgt cgctgttgac ccagaataac ctgaacaaat ctcagtcctc actgagttcc      180
gctattgagc gtctgtcctc tggtctgcgt atcaacagcg cgaaagacga tgcggcaggc      240
caggcgattg ctaaccgctt cacttctaat atcaaaggcc tgactcaggc ttcccgtaac      300
```

```
gctaacgaca tcccgggaat ttccggtggt ggtggtggaa ttctagactc catgggtaca        360
ttaatcaatg aagacgctgc cgcagccaag aaaagtaccg ctaacccact ggcttcaatt        420
gattctgcat tgtcaaaagt ggacgcagtt cgttcttctc tgggggcaat tcaaaaccgt        480
tttgattcag ccattaccaa ccttggcaat acggtaacca atctgaactc cgcgcgtagc        540
cgtatcgaag atgctgacta tgcaacggaa gtttctaata tgtctaaagc gcagattctg        600
cagcaggctg gtacttccgt tctggcgcag gctaaccagg ttccgcaaaa cgtcctctct        660
ttactgcgtt ag                                                            672
```

<210> SEQ ID NO 54
<211> LENGTH: 223
<212> TYPE: PRT
<213> ORGANISM: Salmonella dublin

<400> SEQUENCE: 54

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Ile Pro Gly Ile Ser Gly Gly Gly
            100                 105                 110

Gly Ile Leu Asp Ser Met Gly Thr Leu Ile Asn Glu Asp Ala Ala Ala
        115                 120                 125

Ala Lys Lys Ser Thr Ala Asn Pro Leu Ala Ser Ile Asp Ser Ala Leu
    130                 135                 140

Ser Lys Val Asp Ala Val Arg Ser Ser Leu Gly Ala Ile Gln Asn Arg
145                 150                 155                 160

Phe Asp Ser Ala Ile Thr Asn Leu Gly Asn Thr Val Thr Asn Leu Asn
                165                 170                 175

Ser Ala Arg Ser Arg Ile Glu Asp Ala Asp Tyr Ala Thr Glu Val Ser
            180                 185                 190

Asn Met Ser Lys Ala Gln Ile Leu Gln Gln Ala Gly Thr Ser Val Leu
        195                 200                 205

Ala Gln Ala Asn Gln Val Pro Gln Asn Val Leu Ser Leu Leu Arg
    210                 215                 220
```

<210> SEQ ID NO 55
<211> LENGTH: 507
<212> TYPE: DNA
<213> ORGANISM: Salmonella dublin

<400> SEQUENCE: 55

```
atgcggggtt ctcatcatca tcatcatcat ggtatggcta gcatgactgg tggacagcaa        60
atgggtcggg atctgtacga cgatgacgat aaggatccga tggcacaagt cattaataca        120
aacagcctgt cgctgttgac ccagaataac ctgaacaaat ctcagtcctc actgagttcc        180
```

```
gctattgagc gtctgtcctc tggtctgcgt atcaacagcg cgaaagacga tgcggcaggc    240
caggcgattg ctaaccgctt cacttctaat atcaaaggcc tgactcaggc ttcccgtaac    300
gctaacgaca tcccgggaat tccggtggt ggtggtggaa ttctagactc catgggtaca    360
ttaatcaatg aagacgctgc cgcagccaag aaaagtaccg ctaacccact ggcttcaatt    420
gattctgcat tgtcaaaagt ggacgcagtt cgttcttctc tggggggcaat tcaaaaccgt    480 tttgattcag ccattaccaa cctttag                                         507
```

<210> SEQ ID NO 56
<211> LENGTH: 168
<212> TYPE: PRT
<213> ORGANISM: Salmonella dublin

<400> SEQUENCE: 56

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Ile Pro Gly Ile Ser Gly Gly Gly Gly
            100                 105                 110

Gly Ile Leu Asp Ser Met Gly Thr Leu Ile Asn Glu Asp Ala Ala Ala
        115                 120                 125

Ala Lys Lys Ser Thr Ala Asn Pro Leu Ala Ser Ile Asp Ser Ala Leu
    130                 135                 140

Ser Lys Val Asp Ala Val Arg Ser Ser Leu Gly Ala Ile Gln Asn Arg
145                 150                 155                 160

Phe Asp Ser Ala Ile Thr Asn Leu
                165
```

<210> SEQ ID NO 57
<211> LENGTH: 174
<212> TYPE: PRT
<213> ORGANISM: Salmonella enterica

<400> SEQUENCE: 57

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ser
                85                  90                  95
```

```
Val Gln Ala Thr Asn Gly Thr Asn Ser Asp Ser Asp Leu Lys Ser Ile
            100                 105                 110

Gln Asp Glu Ile Gln Gln Arg Leu Glu Ile Asp Arg Val Ser Asn
            115                 120                 125

Gln Thr Gln Phe Asn Gly Val Lys Val Leu Ser Gln Asp Asn Gln Met
            130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn
                165                 170
```

<210> SEQ ID NO 58
<211> LENGTH: 189
<212> TYPE: PRT
<213> ORGANISM: Pseudomonas aeruginosa

<400> SEQUENCE: 58

```
Met Ala Leu Thr Val Asn Thr Asn Ile Ala Ser Leu Asn Thr Gln Arg
1               5                   10                  15

Asn Leu Asn Ala Ser Ser Asn Asp Leu Asn Thr Ser Leu Gln Arg Leu
            20                  25                  30

Thr Thr Gly Tyr Arg Ile Asn Ser Ala Lys Asp Asp Ala Ala Gly Leu
            35                  40                  45

Gln Ile Ser Asn Arg Leu Ser Asn Gln Ile Ser Gly Leu Asn Val Ala
        50                  55                  60

Thr Arg Asn Ala Asn Asp Gly Ile Ser Leu Ala Gln Thr Ala Glu Gly
65                  70                  75                  80

Ala Leu Gln Gln Ser Thr Asn Ile Leu Gln Arg Ile Arg Asp Leu Ala
                85                  90                  95

Leu Gln Ser Ala Asn Gly Ser Asn Ser Asp Ala Asp Arg Ala Ala Leu
            100                 105                 110

Gln Lys Glu Val Ala Ala Gln Ala Glu Leu Thr Arg Ile Ser Asp
            115                 120                 125

Thr Thr Thr Phe Gly Gly Arg Lys Leu Leu Asp Gly Ser Phe Gly Thr
130                 135                 140

Thr Ser Phe Gln Val Gly Ser Asn Ala Tyr Glu Thr Ile Asp Ile Ser
145                 150                 155                 160

Leu Gln Asn Ala Ser Ala Ser Ala Ile Gly Ser Tyr Gln Val Gly Ser
                165                 170                 175

Asn Gly Ala Gly Thr Val Ala Ser Val Ala Gly Thr Ala
            180                 185
```

<210> SEQ ID NO 59
<211> LENGTH: 179
<212> TYPE: PRT
<213> ORGANISM: Legionella pneumophila

<400> SEQUENCE: 59

```
Met Ala Gln Val Ile Asn Thr Asn Val Ala Ser Leu Thr Ala Gln Arg
1               5                   10                  15

Asn Leu Gly Val Ser Gly Asn Met Met Gln Thr Ser Ile Gln Arg Leu
            20                  25                  30

Ser Ser Gly Leu Arg Ile Asn Ser Ala Lys Asp Asp Ala Ala Gly Leu
            35                  40                  45

Ala Ile Ser Gln Arg Met Thr Ala Gln Ile Arg Gly Met Asn Gln Ala
        50                  55                  60
```

-continued

```
Val Arg Asn Ala Asn Asp Gly Ile Ser Leu Ala Gln Val Ala Glu Gly
 65                  70                  75                  80

Ala Met Gln Glu Thr Thr Asn Ile Leu Gln Arg Met Arg Glu Leu Ser
                 85                  90                  95

Val Gln Ala Ala Asn Ser Thr Asn Asn Ser Ser Asp Arg Ala Ser Ile
            100                 105                 110

Gln Ser Glu Ile Ser Gln Leu Lys Ser Glu Leu Glu Arg Ile Ala Gln
        115                 120                 125

Asn Thr Glu Phe Asn Gly Gln Arg Ile Leu Asp Gly Ser Phe Ser Gly
    130                 135                 140

Ala Ser Phe Gln Val Gly Ala Asn Ser Asn Gln Thr Ile Asn Phe Ser
145                 150                 155                 160

Ile Gly Ser Ile Lys Ala Ser Ser Ile Gly Gly Ile Ala Thr Ala Thr
                165                 170                 175

Gly Thr Glu

<210> SEQ ID NO 60
<211> LENGTH: 174
<212> TYPE: PRT
<213> ORGANISM: Escherichia coli

<400> SEQUENCE: 60

Met Ala Gln Val Ile Asn Thr Asn Ser Leu Ser Leu Leu Thr Gln Asn
1               5                  10                  15

Asn Leu Asn Lys Ser Gln Ser Ser Leu Ser Ser Ala Ile Glu Arg Leu
                 20                  25                  30

Ser Ser Gly Leu Arg Ile Asn Ser Ala Lys Asp Asp Ala Ala Gly Gln
             35                  40                  45

Ala Ile Ala Asn Arg Phe Thr Ala Asn Ile Lys Gly Leu Thr Gln Ala
         50                  55                  60

Ser Arg Asn Ala Asn Asp Gly Ile Ser Val Ala Gln Thr Thr Glu Gly
 65                  70                  75                  80

Ala Leu Asn Glu Ile Asn Asn Asn Leu Gln Arg Val Arg Glu Leu Thr
                 85                  90                  95

Val Gln Ala Thr Asn Gly Thr Asn Ser Asp Ser Asp Leu Ser Ser Ile
            100                 105                 110

Gln Ala Glu Ile Thr Gln Arg Leu Glu Glu Ile Asp Arg Val Ser Glu
        115                 120                 125

Gln Thr Gln Phe Asn Gly Val Lys Val Leu Ala Glu Asn Asn Glu Met
    130                 135                 140

Lys Ile Gln Val Gly Ala Asn Asp Gly Glu Thr Ile Thr Ile Asn Leu
145                 150                 155                 160

Ala Lys Ile Asp Ala Lys Thr Leu Gly Leu Asp Gly Phe Asn
                165                 170

<210> SEQ ID NO 61
<211> LENGTH: 173
<212> TYPE: PRT
<213> ORGANISM: Serratia marcescens

<400> SEQUENCE: 61

Met Ala Gln Val Ile Asn Thr Asn Ser Leu Ser Leu Met Ala Gln Asn
1               5                  10                  15

Asn Leu Asn Lys Ser Gln Ser Ser Leu Gly Thr Ala Ile Glu Arg Leu
                 20                  25                  30

Ser Ser Gly Leu Arg Ile Asn Ser Ala Lys Asp Asp Ala Ala Gly Gln
```

```
            35                  40                  45
Ala Ile Ser Asn Arg Phe Thr Ala Asn Ile Lys Gly Leu Thr Gln Ala
         50                  55                  60

Ser Arg Asn Ala Asn Asp Gly Ile Ser Leu Ala Gln Thr Thr Glu Gly
 65                  70                  75                  80

Ala Leu Asn Glu Val Asn Asp Asn Leu Gln Asn Ile Arg Arg Leu Thr
                 85                  90                  95

Val Gln Ala Gln Asn Gly Ser Asn Ser Thr Ser Asp Leu Lys Ser Ile
            100                 105                 110

Gln Asp Glu Ile Thr Gln Arg Leu Ser Glu Ile Asn Arg Ile Ser Glu
        115                 120                 125

Gln Thr Asp Phe Asn Gly Val Lys Val Leu Ser Ser Asp Gln Lys Leu
    130                 135                 140

Thr Ile Gln Val Gly Ala Asn Asp Gly Thr Thr Asp Ile Asp Leu
145                 150                 155                 160

Lys Lys Ile Asp Ala Lys Gln Leu Gly Met Asp Thr Phe
                165                 170
```

<210> SEQ ID NO 62
<211> LENGTH: 168
<212> TYPE: PRT
<213> ORGANISM: Bacillus subtilis

<400> SEQUENCE: 62

```
Met Arg Ile Asn His Asn Ile Ala Ala Leu Asn Thr Ser Arg Gln Leu
 1               5                  10                  15

Asn Ala Gly Ser Asn Ser Ala Ala Lys Asn Met Glu Lys Leu Ser Ser
             20                  25                  30

Gly Leu Arg Ile Asn Arg Ala Gly Asp Asp Ala Ala Gly Leu Ala Ile
         35                  40                  45

Ser Glu Lys Met Arg Ser Gln Ile Arg Gly Leu Asp Met Ala Ser Lys
     50                  55                  60

Asn Ala Gln Asp Gly Ile Ser Leu Ile Gln Thr Ser Glu Gly Ala Leu
 65                  70                  75                  80

Asn Glu Thr His Ser Ile Leu Gln Arg Met Ser Glu Leu Ala Thr Gln
                 85                  90                  95

Ala Ala Asn Asp Thr Asn Thr Asp Ser Asp Arg Ser Glu Leu Gln Lys
            100                 105                 110

Glu Met Asp Gln Leu Ala Ser Glu Val Thr Arg Ile Ser Thr Asp Thr
        115                 120                 125

Glu Phe Asn Thr Lys Lys Leu Leu Asp Gly Thr Ala Gln Asn Leu Thr
    130                 135                 140

Phe Gln Ile Gly Ala Asn Glu Gly Gln Thr Met Ser Leu Ser Ile Asn
145                 150                 155                 160

Lys Met Asp Ser Glu Ser Leu Lys
                165
```

<210> SEQ ID NO 63
<211> LENGTH: 192
<212> TYPE: PRT
<213> ORGANISM: Listeria monocytogenes

<400> SEQUENCE: 63

```
Met Lys Val Asn Thr Asn Ile Ile Ser Leu Lys Thr Gln Glu Tyr Leu
 1               5                  10                  15

Arg Lys Asn Asn Glu Gly Met Thr Gln Ala Gln Glu Arg Leu Ala Ser
```

```
            20                  25                  30
Gly Lys Arg Ile Asn Ser Ser Leu Asp Asp Ala Ala Gly Leu Ala Val
             35                  40                  45

Val Thr Arg Met Asn Val Lys Ser Thr Gly Leu Asp Ala Ala Ser Lys
 50                  55                  60

Asn Ser Ser Met Gly Ile Asp Leu Leu Gln Thr Ala Asp Ser Ala Leu
 65                  70                  75                  80

Ser Ser Met Ser Ser Ile Leu Gln Arg Met Arg Gln Leu Ala Val Gln
                 85                  90                  95

Ser Ser Asn Gly Ser Phe Ser Asp Glu Asp Arg Lys Gln Tyr Thr Ala
            100                 105                 110

Glu Phe Gly Ser Leu Ile Lys Glu Leu Asp His Val Ala Asp Thr Thr
             115                 120                 125

Asn Tyr Asn Asn Ile Lys Leu Leu Asp Gln Thr Ala Thr Gly Ala Ala
            130                 135                 140

Thr Gln Val Ser Ile Gln Ala Ser Asp Lys Ala Asn Asp Leu Ile Asn
145                 150                 155                 160

Ile Asp Leu Phe Asn Ala Lys Gly Leu Ser Ala Gly Thr Ile Thr Leu
                165                 170                 175

Gly Ser Gly Ser Thr Val Ala Gly Tyr Ser Ala Leu Ser Val Ala Asp
            180                 185                 190

<210> SEQ ID NO 64
<211> LENGTH: 174
<212> TYPE: PRT
<213> ORGANISM: Shigella sonnei

<400> SEQUENCE: 64

Met Ala Gln Val Ile Asn Thr Asn Ser Leu Ser Leu Leu Thr Gln Asn
 1               5                  10                  15

Asn Leu Asn Lys Ser Gln Ser Ser Leu Ser Ser Ala Ile Glu Arg Leu
             20                  25                  30

Ser Ser Gly Leu Arg Ile Asn Ser Ala Lys Asp Asp Ala Ala Gly Gln
             35                  40                  45

Ala Ile Ala Asn Arg Phe Thr Ala Asn Ile Lys Gly Leu Thr Gln Ala
         50                  55                  60

Ser Arg Asn Ala Asn Asp Gly Ile Ser Val Ala Gln Thr Thr Glu Gly
 65                  70                  75                  80

Ala Leu Ser Glu Ile Asn Asn Asn Leu Gln Arg Ile Arg Glu Leu Ser
                 85                  90                  95

Val Gln Ala Thr Asn Gly Thr Asn Ser Asp Ser Asp Leu Asn Ser Ile
            100                 105                 110

Gln Asp Glu Ile Thr Gln Arg Leu Ser Glu Ile Asp Arg Val Ser Asn
            115                 120                 125

Gln Thr Gln Phe Asn Gly Val Lys Val Leu Ala Ser Asp Gln Thr Met
            130                 135                 140

Lys Ile Gln Val Gly Ala Asn Asp Gly Glu Thr Ile Glu Ile Ala Leu
145                 150                 155                 160

Asp Lys Ile Asp Ala Lys Thr Leu Gly Leu Asp Asn Phe Ser
                165                 170

<210> SEQ ID NO 65
<211> LENGTH: 174
<212> TYPE: PRT
<213> ORGANISM: Edwardsiella tarda
```

<400> SEQUENCE: 65

Met Ala Gln Val Ile Asn Thr Asn Ser Leu Ser Leu Met Ala Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ser Asn Arg Phe Thr Ala Asn Ile Asn Gly Leu Thr Gln Ala
    50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Ser Asp Leu Gln Ser Ile
            100                 105                 110

Gln Asp Glu Ile Thr Gln Arg Leu Ser Glu Ile Asp Arg Ile Ser Gln
        115                 120                 125

Gln Thr Asp Phe Asn Gly Val Lys Val Leu Ser Lys Asp Gln Lys Leu
    130                 135                 140

Thr Ile Gln Val Gly Ala Asn Asp Gly Glu Thr Ile Asp Ile Asp Leu
145                 150                 155                 160

Lys Asn Ile Asn Ala Gln Ser Leu Gly Leu Asp Lys Phe Asn
            165                 170

<210> SEQ ID NO 66
<211> LENGTH: 186
<212> TYPE: PRT
<213> ORGANISM: Acidovorax avenae

<400> SEQUENCE: 66

Met Ala Ser Thr Ile Asn Thr Asn Val Ser Ser Leu Thr Ala Gln Arg
1               5                   10                  15

Asn Leu Ser Leu Ser Gln Ser Ser Leu Asn Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Phe Thr Ser Gln Ile Arg Gly Leu Asn Gln Ala
    50                  55                  60

Val Arg Asn Ala Asn Asp Gly Ile Ser Leu Ala Gln Thr Ala Glu Gly
65                  70                  75                  80

Ala Leu Lys Ser Thr Gly Asp Ile Leu Gln Arg Val Arg Glu Leu Ala
                85                  90                  95

Val Gln Ser Ala Asn Ala Thr Asn Ser Ser Gly Asp Arg Lys Ala Ile
            100                 105                 110

Gln Ala Glu Val Gly Gln Leu Leu Ser Glu Met Asp Arg Ile Ala Gly
        115                 120                 125

Asn Thr Glu Phe Asn Gly Gln Lys Leu Leu Asp Gly Ser Phe Gly Ser
    130                 135                 140

Ala Thr Phe Gln Val Gly Ala Asn Ala Asn Gln Thr Ile Thr Ala Thr
145                 150                 155                 160

Thr Gly Asn Phe Arg Thr Asn Asn Tyr Gly Ala Gln Leu Thr Ala Ser
                165                 170                 175

Ala Ser Gly Ala Ala Thr Ser Gly Ala Ser
            180                 185

<210> SEQ ID NO 67
<211> LENGTH: 173
<212> TYPE: PRT
<213> ORGANISM: Yersinia pestis

<400> SEQUENCE: 67

Met Ala

```
Lys Lys Ile Asp Lys Glu Ala Leu Asn Leu Gly Lys Phe Thr
            165                 170
```

<210> SEQ ID NO 69
<211> LENGTH: 189
<212> TYPE: PRT
<213> ORGANISM: Rhodobacter sphaeroides

<400> SEQUENCE: 69

```
Met Thr Thr Ile Asn Thr Asn Ile Gly Ala Ile Ala Ala Gln Ala Asn
1               5                   10                  15

Met Thr Lys Val Asn Asp Gln Phe Asn Thr Ala Met Thr Arg Leu Ser
            20                  25                  30

Thr Gly Leu Arg Ile Asn Ala Ala Lys Asp Asp Ala Ala Gly Met Ala
        35                  40                  45

Ile Gly Glu Lys Met Thr Ala Gln Val Met Gly Leu Asn Gln Ala Ile
50                  55                  60

Arg Asn Ala Gln Asp Gly Lys Asn Leu Val Asp Thr Thr Glu Gly Ala
65                  70                  75                  80

His Val Glu Val Ser Ser Met Leu Gln Arg Leu Arg Glu Leu Ala Val
                85                  90                  95

Gln Ser Ser Asn Asp Thr Asn Thr Ala Ala Asp Arg Gly Ser Leu Ala
            100                 105                 110

Ala Glu Gly Lys Gln Leu Ile Ala Glu Ile Asn Arg Val Ala Glu Ser
        115                 120                 125

Thr Thr Phe Asn Gly Met Lys Val Leu Asp Gly Ser Phe Thr Gly Lys
    130                 135                 140

Gln Leu Gln Ile Gly Ala Asp Ser Gly Gln Thr Met Ala Ile Asn Val
145                 150                 155                 160

Asp Ser Ala Ala Ala Thr Asp Ile Gly Ala His Lys Ile Ser Ser Ala
                165                 170                 175

Ser Thr Val Val Ala Asp Ala Ala Leu Thr Asp Thr Thr
            180                 185
```

<210> SEQ ID NO 70
<211> LENGTH: 175
<212> TYPE: PRT
<213> ORGANISM: Xenorhabdus nematophila

<400> SEQUENCE: 70

```
Met Ala Ser Val Ile Asn Thr Asn Asp Ser Ala Leu Leu Ala Gln Asn
1               5                   10                  15

Asn Leu Thr Lys Ser Lys Gly Ile Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ser Glu Asn Gly Ser Asn Ser Lys Ser Asp Leu Asp Ser Ile
            100                 105                 110

Gln Lys Glu Val Thr Gln Arg Leu Glu Glu Ile Asp Arg Ile Ser Thr
        115                 120                 125
```

```
Gln Thr Gln Phe Asn Gly Ile Lys Val Leu Asn Gly Asp Val Thr Glu
            130                 135                 140

Met Lys Ile Gln Val Gly Ala Asn Asp Asn Glu Thr Ile Gly Ile Lys
145                 150                 155                 160

Leu Gly Lys Ile Asn Ser Glu Lys Leu Asn Leu Lys Glu Phe Ser
                165                 170                 175

<210> SEQ ID NO 71
<211> LENGTH: 175
<212> TYPE: PRT
<213> ORGANISM: Proteus mirabilis

<400> SEQUENCE: 71

Met Ala Gln Val Ile Asn Thr Asn Tyr Leu Ser Leu Val Thr Gln Asn
1               5                   10                  15

Asn Leu Asn Arg Ser Gln Ser Ala Leu Gly Asn Ala Ile Glu Arg Leu
            20                  25                  30

Ser Ser Gly Met Arg Ile Asn Ser Ala Lys Asp Asp Ala Ala Gly Gln
        35                  40                  45

Ala Ile Ala Asn Arg Phe Thr Ser Asn Ile Asn Gly Leu Thr Gln Ala
    50                  55                  60

Ser Arg Asn Ala Asn Asp Gly Ile Ser Val Ser Gln Thr Thr Glu Gly
65                  70                  75                  80

Ala Leu Asn Glu Ile Asn Asn Leu Gln Arg Ile Arg Glu Leu Thr
                85                  90                  95

Val Gln Ala Lys Asn Gly Thr Asn Ser Asn Ser Asp Ile Asn Ser Ile
            100                 105                 110

Gln Asn Glu Val Asn Gln Arg Leu Asp Glu Ile Asn Arg Val Ser Glu
        115                 120                 125

Gln Thr Gln Phe Asn Gly Val Lys Val Leu Ser Gly Glu Lys Ser Lys
    130                 135                 140

Met Thr Ile Gln Val Gly Thr Asn Asp Asn Glu Val Ile Glu Phe Asn
145                 150                 155                 160

Leu Asp Lys Ile Asp Asn Asp Thr Leu Gly Val Ala Ser Asp Lys
                165                 170                 175

<210> SEQ ID NO 72
<211> LENGTH: 200
<212> TYPE: PRT
<213> ORGANISM: Butyrivibrio fibrisolvens

<400> SEQUENCE: 72

Met Val Val Gln His Asn Met Gln Ala Ala Asn Ala Ser Arg Met Leu
1               5                   10                  15

Gly Ile Thr Thr Gly Asp Gln Ser Lys Ser Thr Glu Lys Leu Ser Ser
            20                  25                  30

Gly Phe Lys Ile Asn Arg Ala Ala Asp Asp Ala Ala Gly Leu Ser Ile
        35                  40                  45

Ser Glu Lys Met Arg Lys Gln Ile Arg Gly Leu Asp Gln Ala Ser Thr
    50                  55                  60

Asn Ala Ser Asp Gly Ile Ser Ala Val Gln Thr Ala Glu Gly Ala Leu
65                  70                  75                  80

Thr Glu Val His Ser Met Leu Gln Arg Met Asn Glu Leu Ala Val Gln
                85                  90                  95

Ala Ala Asn Gly Thr Asn Ser Glu Ser Asp Arg Ser Ser Ile Gln Asp
            100                 105                 110
```

```
Glu Ile Asn Gln Leu Thr Thr Glu Ile Asp Arg Val Ala Glu Thr Thr
                115                 120                 125

Lys Phe Asn Glu Thr Tyr Leu Leu Lys Gly Gly Asn Gly Asp Arg Thr
            130                 135                 140

Val Arg Val Tyr Ala His Asp Ala Gly Leu Val Gly Ser Leu Ser Gln
145                 150                 155                 160

Asn Thr Thr Lys Ala Thr Phe Gln Met Arg Lys Leu Glu Ile Gly Asp
                165                 170                 175

Ser Tyr Thr Ile Gly Gly Thr Thr Tyr Lys Ile Gly Ala Glu Thr Val
            180                 185                 190

Lys Glu Ala Met Thr Ala Leu Lys
        195                 200

<210> SEQ ID NO 73
<211> LENGTH: 177
<212> TYPE: PRT
<213> ORGANISM: Bordetella pertussis

<400> SEQUENCE: 73

Met Ala Ala Val Ile Asn Thr Asn Tyr Leu Ser Leu Val Ala Gln Asn
1               5                   10                  15

Asn Leu Asn Lys Ser Gln Ser Ala Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Leu Gln Arg Ile Arg Glu Leu Thr
                85                  90                  95

Val Gln Ala Ser Asn Gly Thr Asn Ser Ala Ser Asp Ile Asp Ser Ile
            100                 105                 110

Gln Gln Glu Val Asn Gln Arg Leu Glu Glu Ile Asn Arg Ile Ala Glu
        115                 120                 125

Gln Thr Asp Phe Asn Gly Ile Lys Val Leu Lys Ser Asn Ala Thr Asp
    130                 135                 140

Met Thr Leu Ser Ile Gln Val Gly Ala Lys Asp Asn Glu Thr Ile Asp
145                 150                 155                 160

Ile Lys Ile Asp Arg Asn Ser Asn Trp Asn Leu Tyr Asp Ala Val Gly
                165                 170                 175

Thr

<210> SEQ ID NO 74
<211> LENGTH: 167
<212> TYPE: PRT
<213> ORGANISM: Clostridium chauvoei

<400> SEQUENCE: 74

Met Ile Ile Asn His Asn Met Asn Ala Leu Asn Ala His Arg Asn Met
1               5                   10                  15

Met Gly Asn Ile Ala Thr Ala Gly Lys Ser Met Glu Lys Leu Ser Ser
            20                  25                  30

Gly Leu Arg Ile Asn Arg Ala Gly Asp Asp Ala Ala Gly Leu Ala Ile
        35                  40                  45

Ser Glu Lys Met Arg Gly Gln Ile Arg Gly Leu Asp Gln Ala Ser Arg
```

```
Asn Ala Gln Asp Gly Ile Ser Leu Ile Gln Thr Ala Glu Gly Ala Leu
 65                  70                  75                  80

Ala Glu Thr His Ser Ile Leu Gln Arg Met Arg Glu Leu Ser Val Gln
                 85                  90                  95

Ser Ala Asn Asp Thr Asn Val Ala Val Asp Arg Thr Ala Ile Gln Asp
            100                 105                 110

Glu Ile Asn Ser Leu Thr Glu Glu Ile Asn Arg Ile Ser Gly Asp Thr
                115                 120                 125

Glu Phe Asn Thr Gln Lys Leu Leu Asp Gly Gly Phe Lys Gly Glu Phe
            130                 135                 140

Gln Ile Gly Ala Asn Ser Asn Gln Thr Val Lys Leu Asp Ile Gly Asn
145                 150                 155                 160

Met Ser Ala Ala Ser Leu Gly
                165
```

<210> SEQ ID NO 75
<211> LENGTH: 178
<212> TYPE: PRT
<213> ORGANISM: Xanthomonas campestris

<400> SEQUENCE: 75

```
Met Ala Gln Val Ile Asn Thr Asn Val Met Ser Leu Asn Ala Gln Arg
  1               5                  10                  15

Asn Leu Asn Thr Asn Ser Ser Ser Met Ala Leu Ser Ile Gln Gln Leu
                 20                  25                  30

Ser Ser Gly Lys Arg Ile Thr Ser Ala Ser Val Asp Ala Ala Gly Leu
             35                  40                  45

Ala Ile Ser Glu Arg Phe Thr Thr Gln Ile Arg Gly Leu Asp Val Ala
         50                  55                  60

Ser Arg Asn Ala Asn Asp Gly Ile Ser Leu Ala Gln Thr Ala Glu Gly
 65                  70                  75                  80

Ala Met Val Glu Ile Gly Asn Asn Leu Gln Arg Ile Arg Glu Leu Ser
                 85                  90                  95

Val Gln Ser Ala Asn Ala Thr Asn Ser Ala Thr Asp Arg Glu Ala Leu
            100                 105                 110

Asn Ser Glu Val Lys Gln Leu Thr Ser Glu Ile Asp Arg Val Ala Asn
                115                 120                 125

Gln Thr Ser Phe Asn Gly Thr Lys Leu Leu Asn Gly Asp Phe Ser Gly
            130                 135                 140

Ala Leu Phe Gln Val Gly Ala Asp Ala Gly Gln Thr Ile Gly Ile Asn
145                 150                 155                 160

Ser Ile Val Asp Ala Asn Val Asp Ser Leu Gly Lys Ala Asn Phe Ala
                165                 170                 175

Ala Ser
```

<210> SEQ ID NO 76
<211> LENGTH: 161
<212> TYPE: PRT
<213> ORGANISM: Nitrosomonas europaea

<400> SEQUENCE: 76

```
Met Pro Gln Val Ile Asn Thr Asn Ile Ala Ser Leu Asn Ala Gln Arg
  1               5                  10                  15

Asn Leu Asn Val Ser Gln Asn Ser Leu Ser Thr Ala Leu Gln Arg Leu
                 20                  25                  30
```

```
Ser Ser Gly Leu Arg Ile Asn Ser Ala Lys Asp Asp Ala Ala Gly Leu
        35                  40                  45

Ala Ile Ser Glu Arg Met Thr Ser Gln Ile Arg Gly Met Asn Gln Ala
 50                  55                  60

Ala Arg Asn Ala Asn Asp Gly Ile Ser Leu Ala Gln Thr Ala Glu Gly
 65                  70                  75                  80

Ala Leu Val Glu Ile Gly Asn Asn Leu Gln Arg Ile Arg Glu Leu Ala
                 85                  90                  95

Val Gln Ser Ala Asn Ala Thr Asn Ser Glu Asp Arg Glu Ala Leu
                100                 105                 110

Gln Lys Glu Val Thr Gln Leu Ile Asp Glu Ile Gln Arg Val Gly Glu
            115                 120                 125

Gln Thr Ser Phe Asn Gly Thr Lys Leu Leu Asp Gly Ser Phe Ala Ser
            130                 135                 140

Gln Ile Phe Gln Val Gly Ala Asn Glu Gly Glu Thr Ile Asp Phe Thr
145                 150                 155                 160

Asp
```

<210> SEQ ID NO 77
<211> LENGTH: 178
<212> TYPE: PRT
<213> ORGANISM: Campylobacter lari

<400> SEQUENCE: 77

```
Gly Phe Arg Ile Asn Thr Asn Gly Ala Ser Leu Asn Ala Gln Val Asn
 1                   5                  10                  15

Ala Gly Leu Asn Ser Arg Asn Leu Asp Ser Ser Leu Ala Arg Leu Ser
                 20                  25                  30

Ser Gly Leu Arg Ile Asn Ser Ala Ala Asp Asp Ala Ser Gly Leu Ala
            35                  40                  45

Ile Ala Asp Ser Leu Lys Thr Gln Ala Asn Ser Leu Gly Gln Ala Ile
 50                  55                  60

Asn Asn Ala Asn Asp Ala Asn Ser Met Leu Gln Ile Ala Asp Lys Ala
 65                  70                  75                  80

Met Asp Glu Gln Leu Lys Ile Leu Asp Thr Ile Lys Val Lys Ala Thr
                 85                  90                  95

Gln Ala Ala Gln Asp Gly Gln Thr Ala Lys Thr Arg Ala Met Ile Gln
            100                 105                 110

Gly Glu Ile Asn Lys Leu Met Glu Glu Leu Asp Asn Ile Ala Asn Thr
            115                 120                 125

Thr Thr Tyr Asn Gly Lys Gln Leu Leu Ser Gly Ser Phe Ser Asn Ala
130                 135                 140

Gln Phe Gln Ile Gly Asp Lys Ala Asn Gln Thr Val Asn Ala Thr Ile
145                 150                 155                 160

Gly Ser Thr Asn Ser Ala Lys Val Gly Gln Thr Arg Phe Glu Thr Gly
                165                 170                 175

Ala Val
```

<210> SEQ ID NO 78
<211> LENGTH: 88
<212> TYPE: PRT
<213> ORGANISM: Salmonella enterica

<400> SEQUENCE: 78

Pro Leu Ala Ser Ile Asp Ser Ala Leu Ser Lys Val Asp Ala Val Arg

```
  1               5                   10                  15
Ser Ser Leu Gly Ala Ile Gln Asn Arg Phe Asp Ser Ala Ile Thr Asn
                20                  25                  30

Leu Gly Asn Thr Val Thr Asn Leu Asn Ser Ala Arg Ser Arg Ile Glu
            35                  40                  45

Asp Ala Asp Tyr Ala Thr Glu Val Ser Asn Met Ser Lys Ala Gln Ile
     50                  55                  60

Leu Gln Gln Ala Gly Thr Ser Val Leu Ala Gln Ala Asn Gln Val Pro
 65                  70                  75                  80

Gln Asn Val Leu Ser Leu Leu Arg
                85
```

<210> SEQ ID NO 79
<211> LENGTH: 88
<212> TYPE: PRT
<213> ORGANISM: Pseudomonas aeruginosa

<400> SEQUENCE: 79

```
Ala Ile Ala Val Val Asp Asn Ala Leu Ala Ala Ile Asp Ala Gln Arg
 1               5                   10                  15

Ala Asp Leu Gly Ala Val Gln Asn Arg Phe Lys Asn Thr Ile Asp Asn
                20                  25                  30

Leu Thr Asn Ile Ser Glu Asn Ala Thr Asn Ala Arg Ser Arg Ile Lys
            35                  40                  45

Asp Thr Asp Phe Ala Ala Glu Thr Ala Ala Leu Ser Lys Asn Gln Val
     50                  55                  60

Leu Gln Gln Ala Gly Thr Ala Ile Leu Ala Gln Ala Asn Gln Leu Pro
 65                  70                  75                  80

Gln Ala Val Leu Ser Leu Leu Arg
                85
```

<210> SEQ ID NO 80
<211> LENGTH: 89
<212> TYPE: PRT
<213> ORGANISM: Legionella pneumophila

<400> SEQUENCE: 80

```
Ala Ile Lys Arg Ile Asp Ala Ala Leu Asn Ser Val Asn Ser Asn Arg
 1               5                   10                  15

Ala Asn Met Gly Ala Leu Gln Asn Arg Phe Glu Ser Thr Ile Ala Asn
                20                  25                  30

Leu Gln Asn Val Ser Asp Asn Leu Ser Ala Ala Arg Ser Arg Ile Gln
            35                  40                  45

Asp Ala Asp Tyr Ala Ala Glu Met Ala Ser Leu Thr Lys Asn Gln Ile
     50                  55                  60

Leu Gln Gln Ala Gly Thr Ala Met Leu Ala Gln Ala Asn Ser Leu Pro
 65                  70                  75                  80

Gln Ser Val Leu Ser Leu Leu Gly Arg
                85
```

<210> SEQ ID NO 81
<211> LENGTH: 89
<212> TYPE: PRT
<213> ORGANISM: Escherichia coli

<400> SEQUENCE: 81

```
Pro Leu Glu Thr Ile Asp Lys Ala Leu Ala Lys Val Asp Asn Leu Arg
 1               5                   10                  15
```

Ser Asp Leu Gly Ala Val Gln Asn Arg Phe Asp Ser Ala Ile Thr Asn
            20                  25                  30

Leu Gly Asn Thr Val Asn Asn Leu Ser Ser Ala Arg Ser Arg Ile Glu
        35                  40                  45

Asp Ala Asp Tyr Ala Thr Glu Val Ser Asn Met Ser Arg Ala Gln Ile
 50                  55                  60

Leu Gln Gln Ala Gly Thr Ser Val Leu Ala Gln Ala Asn Gln Thr Thr
 65                  70                  75                  80

Gln Asn Val Leu Ser Leu Leu Gln Gly
                85

<210> SEQ ID NO 82
<211> LENGTH: 88
<212> TYPE: PRT
<213> ORGANISM: Serratia marcescens

<400> SEQUENCE: 82

Pro Leu Ala Thr Leu Asp Lys Ala Leu Ala Gln Val Asp Gly Leu Arg
 1               5                  10                  15

Ser Ser Leu Gly Ala Val Gln Asn Arg Phe Asp Ser Val Ile Asn Asn
            20                  25                  30

Leu Asn Ser Thr Val Asn Asn Leu Ser Ala Ser Gln Ser Arg Ile Gln
        35                  40                  45

Asp Ala Asp Tyr Ala Thr Glu Val Ser Asn Met Ser Arg Ala Asn Ile
 50                  55                  60

Leu Gln Gln Ala Gly Thr Ser Val Leu Ala Gln Ala Asn Gln Ser Thr
 65                  70                  75                  80

Gln Asn Val Leu Ser Leu Leu Arg
                85

<210> SEQ ID NO 83
<211> LENGTH: 89
<212> TYPE: PRT
<213> ORGANISM: Bacillus subtilis

<400> SEQUENCE: 83

Ala Leu Thr Thr Ile Lys Thr Ala Ile Asp Thr Val Ser Ser Glu Arg
 1               5                  10                  15

Ala Lys Leu Gly Ala Val Gln Asn Arg Leu Glu His Thr Ile Asn Asn
            20                  25                  30

Leu Gly Thr Ser Ser Glu Asn Leu Thr Ser Ala Glu Ser Arg Ile Arg
        35                  40                  45

Asp Val Asp Met Ala Ser Glu Met Met Glu Tyr Thr Lys Asn Asn Ile
 50                  55                  60

Leu Thr Gln Ala Ser Gln Ala Met Leu Ala Gln Ala Asn Gln Gln Pro
 65                  70                  75                  80

Gln Gln Val Leu Gln Leu Leu Lys Gly
                85

<210> SEQ ID NO 84
<211> LENGTH: 90
<212> TYPE: PRT
<213> ORGANISM: Leptospira interrogans

<400> SEQUENCE: 84

Val Ile Gly Leu Ala Asp Ala Ala Leu Thr Lys Ile Met Lys Gln Arg
 1               5                  10                  15

```
Ala Asp Met Gly Ala Tyr Tyr Asn Arg Leu Glu Tyr Thr Ala Lys Gly
            20                  25                  30

Leu Met Gly Ala Tyr Glu Asn Met Gln Ala Ser Glu Ser Arg Ile Arg
            35                  40                  45

Asp Ala Asp Met Ala Glu Glu Val Val Ser Leu Thr Thr Lys Gln Ile
            50                  55                  60

Leu Val Gln Ser Gly Thr Ala Met Leu Ala Gln Ala Asn Met Lys Pro
65                  70                  75                  80

Asn Ser Val Leu Lys Leu Leu Gln Gln Ile
                85                  90
```

<210> SEQ ID NO 85
<211> LENGTH: 88
<212> TYPE: PRT
<213> ORGANISM: Shigella sonnei

<400> SEQUENCE: 85

```
Pro Leu Ser Lys Leu Asp Glu Ala Leu Ala Lys Val Asp Lys Leu Arg
1               5                   10                  15

Ser Ser Leu Gly Ala Val Gln Asn Arg Phe Asp Ser Ala Ile Thr Asn
            20                  25                  30

Leu Gly Asn Thr Val Asn Asp Leu Ser Ser Ala Arg Ser Arg Ile Glu
            35                  40                  45

Asp Ala Asp Tyr Ala Thr Glu Val Ser Asn Met Ser Arg Ala Gln Ile
            50                  55                  60

Leu Gln Gln Ala Gly Thr Ser Val Leu Ala Gln Ala Asn Gln Thr Thr
65                  70                  75                  80

Gln Asn Val Leu Ser Leu Leu Arg
                85
```

<210> SEQ ID NO 86
<211> LENGTH: 88
<212> TYPE: PRT
<213> ORGANISM: Edwardsiella tarda

<400> SEQUENCE: 86

```
Pro Leu Ala Thr Leu Asp Lys Ala Leu Ser Gln Val Asp Asp Leu Arg
1               5                   10                  15

Ser Gly Leu Gly Ala Val Gln Asn Arg Phe Asp Ser Val Ile Asn Asn
            20                  25                  30

Leu Asn Ser Thr Val Asn Asn Leu Ser Ala Ser Arg Ser Arg Ile Gln
            35                  40                  45

Asp Ala Asp Tyr Ala Thr Glu Val Ser Asn Met Ser Arg Ala Gln Ile
            50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
                85
```

<210> SEQ ID NO 87
<211> LENGTH: 88
<212> TYPE: PRT
<213> ORGANISM: Acidovorax avenae

<400> SEQUENCE: 87

```
Ala Leu Lys Ile Ile Asp Ala Ala Leu Ser Ala Val Asn Gly Gln Arg
1               5                   10                  15

Ala Ser Phe Gly Ala Leu Gln Ser Arg Phe Glu Thr Thr Val Asn Asn
```

20                  25                  30

Leu Gln Ser Thr Ser Glu Asn Met Ser Ala Ser Arg Ser Arg Ile Gln
            35                  40                  45

Asp Ala Asp Phe Ala Ala Glu Thr Ala Asn Leu Ser Arg Ser Gln Ile
        50                  55                  60

Leu Gln Gln Ala Gly Thr Ala Met Val Ala Gln Ala Asn Gln Leu Pro
65                  70                  75                  80

Gln Gly Val Leu Ser Leu Leu Lys
                85

<210> SEQ ID NO 88
<211> LENGTH: 88
<212> TYPE: PRT
<213> ORGANISM: Yersinia pestis

<400> SEQUENCE: 88

Pro Leu Glu Thr Leu Asp Asp Ala Ile Lys Gln Val Asp Gly Leu Arg
1               5                   10

Leu Thr Asn Ile Ser Thr Ser Val Gln Ala Ala Lys Ser Gln Val Met
        35                  40                  45

Asp Ala Asp Phe Ala Ala Glu Ser Thr Asn Leu Ala Arg Ser Gln Ile
 50                  55                  60

Leu Ser Gln Ala Ser Thr Ala Met Leu Ala Gln Ala Asn Ser Ser Lys
 65                  70                  75                  80

Gln Asn Val Leu Ser Leu Leu Arg Gly
                85

<210> SEQ ID NO 91
<211> LENGTH: 88
<212> TYPE: PRT
<213> ORGANISM: Xenorhabdus nematophila

<400> SEQUENCE: 91

Pro Leu Asp Thr Leu Asp Lys Ala Leu Ala Gln Val Asp Asp Met Arg
 1               5                  10                  15

Ser Ser Leu Gly Ala Val Gln Asn Arg Leu Glu Ser Thr Val Asn Asn
                20                  25                  30

Leu Asn Asn Thr Val Asn Asn Leu Ser Ala Ala Arg Ser Arg Ile Glu
        35                  40                  45

Asp Ala Asp Tyr Ala Val Glu Val Ser Asn Met Ser Arg Gly Gln Ile
 50                  55                  60

Leu Gln Gln Ala Gly Thr Ser Val Leu Ala Gln Ala Asn Gln Val Pro
 65                  70                  75                  80

Gln Thr Val Leu Ser Leu Leu Arg
                85

<210> SEQ ID NO 92
<211> LENGTH: 88
<212> TYPE: PRT
<213> ORGANISM: Proteus mirabilis

<400> SEQUENCE: 92

Ala Leu Ala Thr Leu Asp Asn Ala Ile Ser Lys Val Asp Glu Ser Arg
 1               5                  10                  15

Ser Lys Leu Gly Ala Ile Gln Asn Arg Phe Gln Ser Thr Ile Asn Asn
                20                  25                  30

Leu Asn Asn Thr Val Asn Asn Leu Ser Ala Ser Arg Ser Arg Ile Leu
        35                  40                  45

Asp Ala Asp Tyr Ala Thr Glu Val Ser Asn Met Ser Lys Asn Gln Ile
 50                  55                  60

Leu Gln Gln Ala Gly Thr Ala Val Leu Ala Gln Ala Asn Gln Val Pro
 65                  70                  75                  80

Gln Thr Val Leu Ser Leu Leu Arg
                85

<210> SEQ ID NO 93
<211> LENGTH: 88
<212> TYPE: PRT
<213> ORGANISM: Butyrivibrio fibrisolvens

<400> SEQUENCE: 93

Ala Ile Asp Ala Ile Ser Asp Ala Leu Ala Lys Val Ser Ala Gln Arg
 1               5                  10                  15

Ser Ala Leu Gly Ser Ile Gln Asn Arg Leu Glu His Ser Ile Ala Asn
                20                  25                  30

```
Leu Asp Asn Val Val Glu Asn Thr Asn Ala Ala Glu Ser Arg Ile Arg
        35                  40                  45

Asp Thr Asp Met Ala Asp Glu Met Val Thr Tyr Ser Lys Asn Asn Ile
 50                  55                  60

Leu Met Gln Ala Gly Gln Ser Met Leu Ala Gln Ala Asn Gln Ala Thr
 65                  70                  75                  80

Gln Gly Val Leu Ser Ile Leu Gln
                85

<210> SEQ ID NO 94
<211> LENGTH: 88
<212> TYPE: PRT
<213> ORGANISM: Bordetella pertussis

<400> SEQUENCE: 94

Ala Leu Ser Lys Leu Asp Asp Ala Met Lys Ala Val Asp Glu Gln Arg
 1               5                  10                  15

Ser Ser Leu Gly Ala Ile Gln Asn Arg Phe Glu Ser Thr Val Ala Asn
                20                  25                  30

Leu Asn Asn Thr Ile Thr Asn Leu Ser Ala Ala Arg Ser Arg Ile Glu
        35                  40                  45

Asp Ser Asp Tyr Ala Thr Glu Val Ser Asn Met Thr Lys Asn Gln Ile
 50                  55                  60

Leu Gln Gln Ala Gly Thr Ser Val Leu Ala Gln Ala Asn Gln Val Pro
 65                  70                  75                  80

Gln Asn Val Leu Ser Leu Leu Arg
                85

<210> SEQ ID NO 95
<211> LENGTH: 88
<212> TYPE: PRT
<213> ORGANISM: Clostridium chauvoei

<400> SEQUENCE: 95

Ser Ile Lys Thr Ile Asn Ser Ala Ile Glu Gln Val Ser Thr Gln Arg
 1               5                  10                  15

Ser Lys Leu Gly Ala Val Gln Asn Arg Leu Glu His Thr Ile Asn Asn
                20                  25                  30

Leu Asn Thr Ser Ser Glu Asn Leu Thr Ala Ala Glu Ser Arg Val Arg
        35                  40                  45

Asp Val Asp Met Ala Lys Glu Met Met Ala Phe Ser Lys Asn Asn Ile
 50                  55                  60

Leu Ser Gln Ala Ala Gln Ala Met Leu Gly Gln Ala Asn Gln Gln Pro
 65                  70                  75                  80

Gln Gly Val Leu Gln Leu Leu Arg
                85

<210> SEQ ID NO 96
<211> LENGTH: 88
<212> TYPE: PRT
<213> ORGANISM: Xanthomonas campestris

<400> SEQUENCE: 96

Ala Leu Glu Ile Val Asp Lys Ala Leu Thr Ser Val Asn Ser Ser Arg
 1               5                  10                  15

Ala Asp Met Gly Ala Val Gln Asn Arg Phe Thr Ser Thr Ile Ala Asn
                20                  25                  30

Leu Ala Ala Thr Ser Glu Asn Leu Thr Ala Ser Arg Ser Arg Ile Ala
```

-continued

```
                35                  40                  45

Asp Thr Asp Tyr Ala Lys Thr Thr Ala Glu Leu Thr Arg Thr Gln Ile
 50                  55                  60

Leu Gln Gln Ala Gly Thr Ala Met Leu Ala Gln Ala Lys Ser Val Pro
 65                  70                  75                  80

Gln Asn Val Leu Ser Leu Leu Gln
                 85

<210> SEQ ID NO 97
<211> LENGTH: 84
<212> TYPE: PRT
<213> ORGANISM: Nitrosomonas europaea

<400> SEQUENCE: 97

Ile Asp Asp Ala Leu Lys Ile Val Asn Ser Thr Arg Ala Asp Leu Gly
 1               5                  10                  15

Ala Ile Gln Asn Arg Phe Ser Ser Ala Ile Ala Asn Leu Gln Thr Ser
                20                  25                  30

Ala Glu Asn Leu Ser Ala Ser Arg Ser Arg Ile Gln Asp Ala Asp Phe
             35                  40                  45

Ala Ala Glu Thr Ala Ala Leu Thr Arg Ala Gln Ile Leu Gln Gln Ala
 50                  55                  60

Gly Val Ala Met Leu Ser Gln Ala Asn Ala Leu Pro Asn Asn Val Leu
 65                  70                  75                  80

Ser Leu Leu Arg

<210> SEQ ID NO 98
<211> LENGTH: 88
<212> TYPE: PRT
<213> ORGANISM: Campylobacter lari

<400> SEQUENCE: 98

Val Met Asp Ile Ala Asp Thr Ala Ile Ala Asn Leu Asp Thr Ile Arg
 1               5                  10                  15

Ala Asn Ile Gly Ala Thr Gln Asn Gln Ile Thr Ser Thr Ile Asn Asn
                20                  25                  30

Ile Ser Val Thr Gln Val Asn Val Lys Ala Ala Glu Ser Gln Ile Arg
             35                  40                  45

Asp Val Asp Phe Ala Ser Glu Ser Ala Asn Tyr Ser Lys Ala Asn Ile
 50                  55                  60

Leu Ala Gln Ser Gly Ser Tyr Ala Met Ala Gln Ala Asn Ala Ala Ser
 65                  70                  75                  80

Gln Asn Val Leu Arg Leu Leu Gln
                 85

<210> SEQ ID NO 99
<211> LENGTH: 20
<212> TYPE: DNA
<213> ORGANISM: Artificial Sequence
<220> FEATURE:
<223> OTHER INFORMATION: primer

<400> SEQUENCE: 99
agtcccccag ctccagtttc                                              20

<210> SEQ ID NO 100
<211> LENGTH: 20
<212> TYPE: DNA
<213> ORGANISM: Artificial Sequence
```

```
<220> FEATURE:
<223> OTHER INFORMATION: primer

<400> SEQUENCE: 100
ggagccccct agcagtgagt                                                    20

<210> SEQ ID NO 101
<211> LENGTH: 51
<212> TYPE: DNA
<213> ORGANISM: Artificial Sequence
<220> FEATURE:
<223> OTHER INFORMATION: leader

<400> SEQUENCE: 101
atgctgctgc tgctgctgct gctgggcctg aggctacagc tctccctggg c                 51

<210> SEQ ID NO 102
<211> LENGTH: 22
<212> TYPE: DNA
<213> ORGANISM: Artificial Sequence
<220> FEATURE:
<223> OTHER INFORMATION: primer

<400> SEQUENCE: 102
actcgcgcaa ccatctccac ac                                                 22

<210> SEQ ID NO 103
<211> LENGTH: 22
<212> TYPE: DNA
<213> ORGANISM: Artificial Sequence
<220> FEATURE:
<223> OTHER INFORMATION: primer

<400> SEQUENCE: 103
ctcgcaccag gtacccatcc at                                                 22

<210> SEQ ID NO 104
<211> LENGTH: 20
<212> TYPE: DNA
<213> ORGANISM: Artificial Sequence
<220> FEATURE:
<223> OTHER INFORMATION: primer

<400> SEQUENCE: 104
taggtgggca gcagcagtca                                                    20

<210> SEQ ID NO 105
<211> LENGTH: 20
<212> TYPE: DNA
<213> ORGANISM: Artificial Sequence
<220> FEATURE:
<223> OTHER INFORMATION: primer

<400> SEQUENCE: 105
ctccattccg ccgtatccat                                                    20

<210> SEQ ID NO 106
<211> LENGTH: 21
<212> TYPE: DNA
<213> ORGANISM: Artificial Sequence
<220> FEATURE:
<223> OTHER INFORMATION: primer

<400> SEQUENCE: 106
tctaggtggg cagcagcagt c                                                  21
```

<210> SEQ ID NO 107
<211> LENGTH: 21
<212> TYPE: DNA
<213> ORGANISM: Artificial Sequence
<220> FEATURE:
<223> OTHER INFORMATION: primer

<400> SEQUENCE: 107
attccgccgt atccattctc c                                              21

<210> SEQ ID NO 108
<211> LENGTH: 22
<212> TYPE: DNA
<213> ORGANISM: Artificial Sequence
<220> FEATURE:
<223> OTHER INFORMATION: primer

<400> SEQUENCE: 108
tgaagccaag ggtacacaag at                                             22

<210> SEQ ID NO 109
<211> LENGTH: 22
<212> TYPE: DNA
<213> ORGANISM: Artificial Sequence
<220> FEATURE:
<223> OTHER INFORMATION: primer

<400> SEQUENCE: 109
ggacacccaa acaaacaaac at                                             22

<210> SEQ ID NO 110
<211> LENGTH: 22
<212> TYPE: DNA
<213> ORGANISM: Artificial Sequence
<220> FEATURE:
<223> OTHER INFORMATION: primer

<400> SEQUENCE: 110
gagcgcagag catcggcaga ag                                             22

<210> SEQ ID NO 111
<211> LENGTH: 22
<212> TYPE: DNA
<213> ORGANISM: Artificial Sequence
<220> FEATURE:
<223> OTHER INFORMATION: primer

<400> SEQUENCE: 111
ttgagaaggg gcagggtgaa gg                                             22

<210> SEQ ID NO 112
<211> LENGTH: 22
<212> TYPE: DNA
<213> ORGANISM: Artificial Sequence
<220> FEATURE:
<223> OTHER INFORMATION: primer

<400> SEQUENCE: 112
agccctggca gcctgtctct ac                                             22

<210> SEQ ID NO 113
<211> LENGTH: 22
<212> TYPE: DNA
<213> ORGANISM: Artificial Sequence
<220> FEATURE:
<223> OTHER INFORMATION: primer

<400> SEQUENCE: 113
gtgatcacgc cgttgctgtt gg         22

<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
accacagtcc atgccatcac         20

<210> SEQ ID NO 115
<211> LENGTH: 20
<212> TYPE: DNA
<213> ORGANISM: Artificial Sequence
<220> FEATURE:
<223> OTHER INFORMATION: primer

<400> SEQUENCE: 115
tccaccacca tgttgctgta         20

<210> SEQ ID NO 116
<211> LENGTH: 58
<212> TYPE: DNA
<213> ORGANISM: Artificial Sequence
<220> FEATURE:
<223> OTHER INFORMATION: shRNA

<400> SEQUENCE: 116
ccggccttgc ctacaacaag ataaactcga gtttatcttg ttgtaggcaa ggttttttg         58

<210> SEQ ID NO 117
<211> LENGTH: 858
<212> TYPE: PRT
<213> ORGANISM: Homo sapiens

<400> SEQUENCE: 117

Met Gly Asp His Leu Asp Leu Leu Gly Val Val Leu Met Ala Gly
1               5                   10                  15

Pro Val Phe Gly Ile Pro Ser Cys Ser Phe Asp Gly Arg Ile Ala Phe
                20                  25                  30

Tyr Arg Phe Cys Asn Leu Thr Gln Val Pro Gln Val Leu Asn Thr Thr
            35                  40                  45

Glu Arg Leu Leu Leu Ser Phe Asn Tyr Ile Arg Thr Val Thr Ala Ser
        50                  55                  60

Ser Phe Pro Phe Leu Glu Gln Leu Gln Leu Leu Glu Leu Gly Ser Gln
65                  70                  75                  80

Tyr Thr Pro Leu Thr Ile Asp Lys Glu Ala Phe Arg Asn Leu Pro Asn
                85                  90                  95

Leu Arg Ile Leu Asp Leu Gly Ser Ser Lys Ile Tyr Phe Leu His Pro
            100                 105                 110

Asp Ala Phe Gln Gly Leu Phe His Leu Phe Glu Leu Arg Leu Tyr Phe
        115                 120                 125

Cys Gly Leu Ser Asp Ala Val Leu Lys Asp Gly Tyr Phe Arg Asn Leu
    130                 135                 140

Lys Ala Leu Thr Arg Leu Asp Leu Ser Lys Asn Gln Ile Arg Ser Leu
145                 150                 155                 160

Tyr Leu His Pro Ser Phe Gly Lys Leu Asn Ser Leu Lys Ser Ile Asp
            165                 170                 175

Phe Ser Ser Asn Gln Ile Phe Leu Val Cys Glu His Glu Leu Glu Pro
            180                 185                 190

Leu Gln Gly Lys Thr Leu Ser Phe Phe Ser Leu Ala Ala Asn Ser Leu
            195                 200                 205

Tyr Ser Arg Val Ser Val Asp Trp Gly Lys Cys Met Asn Pro Phe Arg
            210                 215                 220

Asn Met Val Leu Glu Ile Leu Asp Val Ser Gly Asn Gly Trp Thr Val
225                 230                 235                 240

Asp Ile Thr Gly Asn Phe Ser Asn Ala Ile Ser Lys Ser Gln Ala Phe
            245                 250                 255

Ser Leu Ile Leu Ala His His Ile Met Gly Ala Gly Phe Gly Phe His
            260                 265                 270

Asn Ile Lys Asp Pro Asp Gln Asn Thr Phe Ala Gly Leu Ala Arg Ser
            275                 280                 285

Ser Val Arg His Leu Asp Leu Ser His Gly Phe Val Phe Ser Leu Asn
            290                 295                 300

Ser Arg Val Phe Glu Thr Leu Lys Asp Leu Lys Val Leu Asn Leu Ala
305                 310                 315                 320

Tyr Asn Lys Ile Asn Lys Ile Ala Asp Glu Ala Phe Tyr Gly Leu Asp
            325                 330                 335

Asn Leu Gln Val Leu Asn Leu Ser Tyr Asn Leu Leu Gly Glu Leu Tyr
            340                 345                 350

Ser Ser Asn Phe Tyr Gly Leu Pro Lys Val Ala Tyr Ile Asp Leu Gln
            355                 360                 365

Lys Asn His Ile Ala Ile Ile Gln Asp Gln Thr Phe Lys Phe Leu Glu
            370                 375                 380

Lys Leu Gln Thr Leu Asp Leu Arg Asp Asn Ala Leu Thr Thr Ile His
385                 390                 395                 400

Phe Ile Pro Ser Ile Pro Asp Ile Phe Leu Ser Gly Asn Lys Leu Val
            405                 410                 415

Thr Leu Pro Lys Ile Asn Leu Thr Ala Asn Leu Ile His Leu Ser Glu
            420                 425                 430

Asn Arg Leu Glu Asn Leu Asp Ile Leu Tyr Phe Leu Leu Arg Val Pro
            435                 440                 445

His Leu Gln Ile Leu Ile Leu Asn Gln Asn Arg Phe Ser Ser Cys Ser
            450                 455                 460

Gly Asp Gln Thr Pro Ser Glu Asn Pro Ser Leu Glu Gln Leu Phe Leu
465                 470                 475                 480

Gly Glu Asn Met Leu Gln Leu Ala Trp Glu Thr Glu Leu Cys Trp Asp
            485                 490                 495

Val Phe Glu Gly Leu Ser His Leu Gln Val Leu Tyr Leu Asn His Asn
            500                 505                 510

Tyr Leu Asn Ser Leu Pro Pro Gly Val Phe Ser His Leu Thr Ala Leu
            515                 520                 525

Arg Gly Leu Ser Leu Asn Ser Asn Arg Leu Thr Val Leu Ser His Asn
530                 535                 540

Asp Leu Pro Ala Asn Leu Glu Ile Leu Asp Ile Ser Arg Asn Gln Leu
545                 550                 555                 560

Leu Ala Pro Asn Pro Asp Val Phe Val Ser Leu Ser Val Leu Asp Ile
            565                 570                 575

Thr His Asn Lys Phe Ile Cys Glu Cys Glu Leu Ser Thr Phe Ile Asn

```
            580                 585                 590
Trp Leu Asn His Thr Asn Val Thr Ile Ala Gly Pro Pro Ala Asp Ile
            595                 600                 605

Tyr Cys Val Tyr Pro Asp Ser Phe Ser Gly Val Ser Leu Phe Ser Leu
            610                 615                 620

Ser Thr Glu Gly Cys Asp Glu Glu Val Leu Lys Ser Leu Lys Phe
625                 630                 635                 640

Ser Leu Phe Ile Val Cys Thr Val Thr Leu Thr Leu Phe Leu Met Thr
                    645                 650                 655

Ile Leu Thr Val Thr Lys Phe Arg Gly Phe Cys Phe Ile Cys Tyr Lys
                    660                 665                 670

Thr Ala Gln Arg Leu Val Phe Lys Asp His Pro Gln Gly Thr Glu Pro
            675                 680                 685

Asp Met Tyr Lys Tyr Asp Ala Tyr Leu Cys Phe Ser Lys Asp Phe
            690                 695                 700

Thr Trp Val Gln Asn Ala Leu Leu Lys His Leu Asp Thr Gln Tyr Ser
705                 710                 715                 720

Asp Gln Asn Arg Phe Asn Leu Cys Phe Glu Glu Arg Asp Phe Val Pro
                    725                 730                 735

Gly Glu Asn Arg Ile Ala Asn Ile Gln Asp Ala Ile Trp Asn Ser Arg
                    740                 745                 750

Lys Ile Val Cys Leu Val Ser Arg His Phe Leu Arg Asp Gly Trp Cys
                    755                 760                 765

Leu Glu Ala Phe Ser Tyr Ala Gln Gly Arg Cys Leu Ser Asp Leu Asn
            770                 775                 780

Ser Ala Leu Ile Met Val Val Gly Ser Leu Ser Gln Tyr Gln Leu
785                 790                 795                 800

Met Lys His Gln Ser Ile Arg Gly Phe Val Gln Lys Gln Tyr Leu
                    805                 810                 815

Arg Trp Pro Glu Asp Phe Gln Asp Val Gly Trp Phe Leu His Lys Leu
            820                 825                 830

Ser Gln Gln Ile Leu Lys Lys Glu Lys Glu Lys Lys Asp Asn Asn
            835                 840                 845

Ile Pro Leu Gln Thr Val Ala Thr Ile Ser
            850                 855

<210> SEQ ID NO 118
<211> LENGTH: 174
<212> TYPE: PRT
<213> ORGANISM: Salmonella enterica

<400> SEQUENCE: 118

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
        50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95
```

```
Val Gln Ala Thr Asn Gly Thr Asn Ser Asp Ser Asp Leu Lys Ser Ile
            100                 105                 110

Gln Asp Glu Ile Gln Gln Arg Leu Glu Ile Asp Arg Val Ser Asn
            115                 120                 125

Gln Thr Gln Phe Asn Gly Val Lys Val Leu Ser Gln Asp Asn Gln Met
            130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn
                165                 170
```

<210> SEQ ID NO 119
<211> LENGTH: 189
<212> TYPE: PRT
<213> ORGANISM: Pseudomonas aeruginosa

<400> SEQUENCE: 119

```
Met Ala Leu Thr Val Asn Thr Asn Ile Ala Ser Leu Asn Thr Gln Arg
1               5                   10                  15

Asn Leu Asn Ala Ser Ser Asn Asp Leu Asn Thr Ser Leu Gln Arg Leu
            20                  25                  30

Thr Thr Gly Tyr Arg Ile Asn Ser Ala Lys Asp Asp Ala Ala Gly Leu
        35                  40                  45

Gln Ile Ser Asn Arg Leu Ser Asn Gln Ile Ser Gly Leu Asn Val Ala
    50                  55                  60

Thr Arg Asn Ala Asn Asp Gly Ile Ser Leu Ala Gln Thr Ala Glu Gly
65                  70                  75                  80

Ala Leu Gln Gln Ser Thr Asn Ile Leu Gln Arg Ile Arg Asp Leu Ala
                85                  90                  95

Leu Gln Ser Ala Asn Gly Ser Asn Ser Asp Ala Asp Arg Ala Ala Leu
            100                 105                 110

Gln Lys Glu Val Ala Ala Gln Ala Glu Leu Thr Arg Ile Ser Asp
            115                 120                 125

Thr Thr Thr Phe Gly Gly Arg Lys Leu Leu Asp Gly Ser Phe Gly Thr
            130                 135                 140

Thr Ser Phe Gln Val Gly Ser Asn Ala Tyr Glu Thr Ile Asp Ile Ser
145                 150                 155                 160

Leu Gln Asn Ala Ser Ala Ser Ala Ile Gly Ser Tyr Gln Val Gly Ser
                165                 170                 175

Asn Gly Ala Gly Thr Val Ala Ser Val Ala Gly Thr Ala
            180                 185
```

<210> SEQ ID NO 120
<211> LENGTH: 179
<212> TYPE: PRT
<213> ORGANISM: Legionella pneumophila

<400> SEQUENCE: 120

```
Met Ala Gln Val Ile Asn Thr Asn Val Ala Ser Leu Thr Ala Gln Arg
1               5                   10                  15

Asn Leu Gly Val Ser Gly Asn Met Met Gln Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Gln Arg Met Thr Ala Gln Ile Arg Gly Met Gly Asn Gln
    50                  55                  60
```

Val Arg Asn Ala Asn Asp Gly Ile Ser Leu Ala Gln Val Ala Glu Gly
 65                  70                  75                  80

Ala Met Gln Glu Thr Thr Asn Ile Leu Gln Arg Met Arg Glu Leu Ser
                 85                  90                  95

Val Gln Ala Ala Asn Ser Thr Asn Asn Ser Ser Asp Arg Ala Ser Ile
            100                 105                 110

Gln Ser Glu Ile Ser Gln Leu Lys Ser Glu Leu Glu Arg Ile Ala Gln
        115                 120                 125

Asn Thr Glu Phe Asn Gly Gln Arg Ile Leu Asp Gly Ser Phe Ser Gly
    130                 135                 140

Ala Ser Phe Gln Val Gly Ala Asn Ser Asn Gln Thr Ile Asn Phe Ser
145                 150                 155                 160

Ile Gly Ser Ile Lys Ala Ser Ser Ile Gly Gly Ile Ala Thr Ala Thr
                165                 170                 175

Gly Thr Glu

<210> SEQ ID NO 121
<211> LENGTH: 174
<212> TYPE: PRT
<213> ORGANISM: Escherichia coli

<400> SEQUENCE: 121

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Val Ala Gln Thr Thr Glu Gly
65                  70                  75                  80

Ala Leu Asn Glu Ile Asn Asn Asn Leu Gln Arg Val Arg Glu Leu Thr
                85                  90                  95

Val Gln Ala Thr Asn Gly Thr Asn Ser Asp Ser Asp Leu Ser Ser Ile
            100                 105                 110

Gln Ala Glu Ile Thr Gln Arg Leu Glu Glu Ile Asp Arg Val Ser Glu
        115                 120                 125

Gln Thr Gln Phe Asn Gly Val Lys Val Leu Ala Glu Asn Asn Glu Met
    130                 135                 140

Lys Ile Gln Val Gly Ala Asn Asp Gly Glu Thr Ile Thr Ile Asn Leu
145                 150                 155                 160

Ala Lys Ile Asp Ala Lys Thr Leu Gly Leu Asp Gly Phe Asn
                165                 170

<210> SEQ ID NO 122
<211> LENGTH: 173
<212> TYPE: PRT
<213> ORGANISM: Serratia marcescens

<400> SEQUENCE: 122

Met Ala Gln Val Ile Asn Thr Asn Ser Leu Ser Leu Met Ala Gln Asn
1               5                   10                  15

Asn Leu Asn Lys Ser Gln Ser Ser Leu Gly Thr Ala Ile Glu Arg Leu
            20                  25                  30

Ser Ser Gly Leu Arg Ile Asn Ser Ala Lys Asp Asp Ala Ala Gly Gln

-continued

```
                35                  40                  45

Ala Ile Ser Asn Arg Phe Thr Ala Asn Ile Lys Gly Leu Thr Gln Ala
 50                  55                  60

Ser Arg Asn Ala Asn Asp Gly Ile Ser Leu Ala Gln Thr Thr Glu Gly
 65                  70                  75                  80

Ala Leu Asn Glu Val Asn Asp Asn Leu Gln Asn Ile Arg Arg Leu Thr
                 85                  90                  95

Val Gln Ala Gln Asn Gly Ser Asn Ser Thr Ser Asp Leu Lys Ser Ile
                100                 105                 110

Gln Asp Glu Ile Thr Gln Arg Leu Ser Glu Ile Asn Arg Ile Ser Glu
                115                 120                 125

Gln Thr Asp Phe Asn Gly Val Lys Val Leu Ser Ser Asp Gln Lys Leu
                130                 135                 140

Thr Ile Gln Val Gly Ala Asn Asp Gly Thr Thr Asp Ile Asp Leu
145                 150                 155                 160

Lys Lys Ile Asp Ala Lys Gln Leu Gly Met Asp Thr Phe
                165                 170

<210> SEQ ID NO 123
<211> LENGTH: 168
<212> TYPE: PRT
<213> ORGANISM: Bacillus subtilis

<400> SEQUENCE: 123

Met Arg Ile Asn His Asn Ile Ala Ala Leu Asn Thr Ser Arg Gln Leu
 1               5                  10                  15

Asn Ala Gly Ser Asn Ser Ala Ala Lys Asn Met Glu Lys Leu Ser Ser
                20                  25                  30

Gly Leu Arg Ile Asn Arg Ala Gly Asp Asp Ala Ala Gly Leu Ala Ile
                35                  40                  45

Ser Glu Lys Met Arg Ser Gln Ile Arg Gly Leu Asp Met Ala Ser Lys
 50                  55                  60

Asn Ala Gln Asp Gly Ile Ser Leu Ile Gln Thr Ser Glu Gly Ala Leu
 65                  70                  75                  80

Asn Glu Thr His Ser Ile Leu Gln Arg Met Ser Glu Leu Ala Thr Gln
                 85                  90                  95

Ala Ala Asn Asp Thr Asn Thr Asp Ser Asp Arg Ser Glu Leu Gln Lys
                100                 105                 110

Glu Met Asp Gln Leu Ala Ser Glu Val Thr Arg Ile Ser Thr Asp Thr
                115                 120                 125

Glu Phe Asn Thr Lys Lys Leu Leu Asp Gly Thr Ala Gln Asn Leu Thr
                130                 135                 140

Phe Gln Ile Gly Ala Asn Glu Gly Gln Thr Met Ser Leu Ser Ile Asn
145                 150                 155                 160

Lys Met Asp Ser Glu Ser Leu Lys
                165

<210> SEQ ID NO 124
<211> LENGTH: 192
<212> TYPE: PRT
<213> ORGANISM: Listeria monocytogenes

<400> SEQUENCE: 124

Met Lys Val Asn Thr Asn Ile Ile Ser Leu Lys Thr Gln Glu Tyr Leu
 1               5                  10                  15

Arg Lys Asn Asn Glu Gly Met Thr Gln Ala Gln Glu Arg Leu Ala Ser
```

```
                20                  25                  30
Gly Lys Arg Ile Asn Ser Ser Leu Asp Asp Ala Ala Gly Leu Ala Val
            35                  40                  45

Val Thr Arg Met Asn Val Lys Ser Thr Gly Leu Asp Ala Ala Ser Lys
 50                  55                  60

Asn Ser Ser Met Gly Ile Asp Leu Leu Gln Thr Ala Asp Ser Ala Leu
 65                  70                  75                  80

Ser Ser Met Ser Ser Ile Leu Gln Arg Met Arg Gln Leu Ala Val Gln
                85                  90                  95

Ser Ser Asn Gly Ser Phe Ser Asp Glu Asp Arg Lys Gln Tyr Thr Ala
            100                 105                 110

Glu Phe Gly Ser Leu Ile Lys Glu Leu Asp His Val Ala Asp Thr Thr
        115                 120                 125

Asn Tyr Asn Asn Ile Lys Leu Leu Asp Gln Thr Ala Thr Gly Ala Ala
            130                 135                 140

Thr Gln Val Ser Ile Gln Ala Ser Asp Lys Ala Asn Asp Leu Ile Asn
145                 150                 155                 160

Ile Asp Leu Phe Asn Ala Lys Gly Leu Ser Ala Gly Thr Ile Thr Leu
                165                 170                 175

Gly Ser Gly Ser Thr Val Ala Gly Tyr Ser Ala Leu Ser Val Ala Asp
            180                 185                 190

<210> SEQ ID NO 125
<211> LENGTH: 174
<212> TYPE: PRT
<213> ORGANISM: Shigella sonnei

<400> SEQUENCE: 125

Met Ala Gln Val Ile Asn Thr Asn Ser Leu Ser Leu Leu Thr Gln Asn
 1               5                  10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
            35                  40                  45

Ala Ile Ala Asn Arg Phe Thr Ala Asn Ile Lys Gly Leu Thr Gln Ala
        50                  55                  60

Ser Arg Asn Ala Asn Asp Gly Ile Ser Val Ala Gln Thr Thr Glu Gly
 65                  70                  75                  80

Ala Leu Ser Glu Ile Asn Asn Asn Leu Gln Arg Ile Arg Glu Leu Ser
                85                  90                  95

Val Gln Ala Thr Asn Gly Thr Asn Ser Asp Ser Asp Leu Asn Ser Ile
            100                 105                 110

Gln Asp Glu Ile Thr Gln Arg Leu Ser Glu Ile Asp Arg Val Ser Asn
        115                 120                 125

Gln Thr Gln Phe Asn Gly Val Lys Val Leu Ala Ser Asp Gln Thr Met
    130                 135                 140

Lys Ile Gln Val Gly Ala Asn Asp Gly Glu Thr Ile Glu Ile Ala Leu
145                 150                 155                 160

Asp Lys Ile Asp Ala Lys Thr Leu Gly Leu Asp Asn Phe Ser
                165                 170

<210> SEQ ID NO 126
<211> LENGTH: 174
<212> TYPE: PRT
<213> ORGANISM: Edwardsiella tarda
```

```
<400> SEQUENCE: 126

Met Ala Gln Val Ile Asn Thr Asn Ser Leu Ser Leu Met Ala Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ser Asn Arg Phe Thr Ala Asn Ile Asn Gly Leu Thr Gln Ala
    50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Ser Ser Asp Leu Gln Ser Ile
            100                 105                 110

Gln Asp Glu Ile Thr Gln Arg Leu Ser Glu Ile Asp Arg Ile Ser Gln
        115                 120                 125

Gln Thr Asp Phe Asn Gly Val Lys Val Leu Ser Lys Asp Gln Lys Leu
    130                 135                 140

Thr Ile Gln Val Gly Ala Asn Asp Gly Glu Thr Ile Asp Ile Asp Leu
145                 150                 155                 160

Lys Asn Ile Asn Ala Gln Ser Leu Gly Leu Asp Lys Phe Asn
                165                 170

<210> SEQ ID NO 127
<211> LENGTH: 186
<212> TYPE: PRT
<213> ORGANISM: Acidovorax avenae

<400> SEQUENCE: 127

Met Ala Ser Thr Ile Asn Thr Asn Val Ser Ser Leu Thr Ala Gln Arg
1               5                   10                  15

Asn Leu Ser Leu Ser Gln Ser Ser Leu Asn Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Phe Thr Ser Gln Ile Arg Gly Leu Asn Gln Ala
    50                  55                  60

Val Arg Asn Ala Asn Asp Gly Ile Ser Leu Ala Gln Thr Ala Glu Gly
65                  70                  75                  80

Ala Leu Lys Ser Thr Gly Asp Ile Leu Gln Arg Val Arg Glu Leu Ala
                85                  90                  95

Val Gln Ser Ala Asn Ala Thr Asn Ser Ser Gly Asp Arg Lys Ala Ile
            100                 105                 110

Gln Ala Glu Val Gly Gln Leu Leu Ser Glu Met Asp Arg Ile Ala Gly
        115                 120                 125

Asn Thr Glu Phe Asn Gly Gln Lys Leu Leu Asp Gly Ser Phe Gly Ser
    130                 135                 140

Ala Thr Phe Gln Val Gly Ala Asn Ala Asn Gln Thr Ile Thr Ala Thr
145                 150                 155                 160

Thr Gly Asn Phe Arg Thr Asn Asn Tyr Gly Ala Gln Leu Thr Ala Ser
                165                 170                 175

Ala Ser Gly Ala Ala Thr Ser Gly Ala Ser
            180                 185
```

<210> SEQ ID NO 128
<211> LENGTH: 173
<212> TYPE: PRT
<213> ORGANISM: Yersinia pestis

<400> SEQUENCE: 128

Met Ala Val

```
Lys Lys Ile Asp Lys Glu Ala Leu Asn Leu Gly Lys Phe Thr
            165                 170

<210> SEQ ID NO 130
<211> LENGTH: 189
<212> TYPE: PRT
<213> ORGANISM: Rhodobacter sphaeroides

<400> SEQUENCE: 130

Met Thr Thr Ile Asn Thr Asn Ile Gly Ala Ile Ala Ala Gln Ala Asn
1               5                   10                  15

Met Thr Lys Val Asn Asp Gln Phe Asn Thr Ala Met Thr Arg Leu Ser
            20                  25                  30

Thr Gly Leu Arg Ile Asn Ala Ala Lys Asp Asp Ala Ala Gly Met Ala
        35                  40                  45

Ile Gly Glu Lys Met Thr Ala Gln Val Met Gly Leu Asn Gln Ala Ile
    50                  55                  60

Arg Asn Ala Gln Asp Gly Lys Asn Leu Val Asp Thr Thr Glu Gly Ala
65                  70                  75                  80

His Val Glu Val Ser Ser Met Leu Gln Arg Leu Arg Glu Leu Ala Val
                85                  90                  95

Gln Ser Ser Asn Asp Thr Asn Thr Ala Ala Asp Arg Gly Ser Leu Ala
            100                 105                 110

Ala Glu Gly Lys Gln Leu Ile Ala Glu Ile Asn Arg Val Ala Glu Ser
        115                 120                 125

Thr Thr Phe Asn Gly Met Lys Val Leu Asp Gly Ser Phe Thr Gly Lys
    130                 135                 140

Gln Leu Gln Ile Gly Ala Asp Ser Gly Gln Thr Met Ala Ile Asn Val
145                 150                 155                 160

Asp Ser Ala Ala Ala Thr Asp Ile Gly Ala His Lys Ile Ser Ser Ala
                165                 170                 175

Ser Thr Val Val Ala Asp Ala Ala Leu Thr Asp Thr Thr
            180                 185

<210> SEQ ID NO 131
<211> LENGTH: 175
<212> TYPE: PRT
<213> ORGANISM: Xenorhabdus nematophila

<400> SEQUENCE: 131

Met Ala Ser Val Ile Asn Thr Asn Asp Ser Ala Leu Leu Ala Gln Asn
1               5                   10                  15

Asn Leu Thr Lys Ser Lys Gly Ile Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ser Glu Asn Gly Ser Asn Ser Lys Ser Asp Leu Asp Ser Ile
            100                 105                 110

Gln Lys Glu Val Thr Gln Arg Leu Glu Glu Ile Asp Arg Ile Ser Thr
        115                 120                 125
```

```
Gln Thr Gln Phe Asn Gly Ile Lys Val Leu Asn Gly Asp Val Thr Glu
        130                 135                 140

Met Lys Ile Gln Val Gly Ala Asn Asp Asn Glu Thr Ile Gly Ile Lys
145                 150                 155                 160

Leu Gly Lys Ile Asn Ser Glu Lys Leu Asn Leu Lys Glu Phe Ser
                165                 170                 175

<210> SEQ ID NO 132
<211> LENGTH: 175
<212> TYPE: PRT
<213> ORGANISM: Proteus mirabilis

<400> SEQUENCE: 132

Met Ala Gln Val Ile Asn Thr Asn Tyr Leu Ser Leu Val Thr Gln Asn
1               5                   10                  15

Asn Leu Asn Arg Ser Gln Ser Ala Leu Gly Asn Ala Ile Glu Arg Leu
            20                  25                  30

Ser Ser Gly Met Arg Ile Asn Ser Ala Lys Asp Asp Ala Ala Gly Gln
        35                  40                  45

Ala Ile Ala Asn Arg Phe Thr Ser Asn Ile Asn Gly Leu Thr Gln Ala
    50                  55                  60

Ser Arg Asn Ala Asn Asp Gly Ile Ser Val Ser Gln Thr Thr Glu Gly
65                  70                  75                  80

Ala Leu Asn Glu Ile Asn Asn Leu Gln Arg Ile Arg Glu Leu Thr
                85                  90                  95

Val Gln Ala Lys Asn Gly Thr Asn Ser Asn Ser Asp Ile Asn Ser Ile
            100                 105                 110

Gln Asn Glu Val Asn Gln Arg Leu Asp Glu Ile Asn Arg Val Ser Glu
        115                 120                 125

Gln Thr Gln Phe Asn Gly Val Lys Val Leu Ser Gly Glu Lys Ser Lys
    130                 135                 140

Met Thr Ile Gln Val Gly Thr Asn Asp Asn Glu Val Ile Glu Phe Asn
145                 150                 155                 160

Leu Asp Lys Ile Asp Asn Asp Thr Leu Gly Val Ala Ser Asp Lys
                165                 170                 175

<210> SEQ ID NO 133
<211> LENGTH: 200
<212> TYPE: PRT
<213> ORGANISM: Butyrivibrio fibrisolvens

<400> SEQUENCE: 133

Met Val Val Gln His Asn Met Gln Ala Ala Asn Ala Ser Arg Met Leu
1               5                   10                  15

Gly Ile Thr Thr Gly Asp Gln Ser Lys Ser Thr Glu Lys Leu Ser Ser
            20                  25                  30

Gly Phe Lys Ile Asn Arg Ala Ala Asp Asp Ala Ala Gly Leu Ser Ile
        35                  40                  45

Ser Glu Lys Met Arg Lys Gln Ile Arg Gly Leu Asp Gln Ala Ser Thr
    50                  55                  60

Asn Ala Ser Asp Gly Ile Ser Ala Val Gln Thr Ala Glu Gly Ala Leu
65                  70                  75                  80

Thr Glu Val His Ser Met Leu Gln Arg Met Asn Glu Leu Ala Val Gln
                85                  90                  95

Ala Ala Asn Gly Thr Asn Ser Glu Ser Asp Arg Ser Ser Ile Gln Asp
            100                 105                 110
```

```
Glu Ile Asn Gln Leu Thr Thr Glu Ile Asp Arg Val Ala Glu Thr Thr
            115                 120                 125

Lys Phe Asn Glu Thr Tyr Leu Leu Lys Gly Gly Asn Gly Asp Arg Thr
130                 135                 140

Val Arg Val Tyr Ala His Asp Ala Gly Leu Val Gly Ser Leu Ser Gln
145                 150                 155                 160

Asn Thr Thr Lys Ala Thr Phe Gln Met Arg Lys Leu Glu Ile Gly Asp
                165                 170                 175

Ser Tyr Thr Ile Gly Gly Thr Thr Tyr Lys Ile Gly Ala Glu Thr Val
                180                 185                 190

Lys Glu Ala Met Thr Ala Leu Lys
            195                 200

<210> SEQ ID NO 134
<211> LENGTH: 177
<212> TYPE: PRT
<213> ORGANISM: Bordetella pertussis

<400> SEQUENCE: 134

Met Ala Ala Val Ile Asn Thr Asn Tyr Leu Ser Leu Val Ala Gln Asn
1               5                   10                  15

Asn Leu Asn Lys Ser Gln Ser Ala Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Leu Gln Arg Ile Arg Glu Leu Thr
            85                  90                  95

Val Gln Ala Ser Asn Gly Thr Asn Ser Ala Ser Asp Ile Asp Ser Ile
            100                 105                 110

Gln Gln Glu Val Asn Gln Arg Leu Glu Glu Ile Asn Arg Ile Ala Glu
        115                 120                 125

Gln Thr Asp Phe Asn Gly Ile Lys Val Leu Lys Ser Asn Ala Thr Asp
    130                 135                 140

Met Thr Leu Ser Ile Gln Val Gly Ala Lys Asp Asn Glu Thr Ile Asp
145                 150                 155                 160

Ile Lys Ile Asp Arg Asn Ser Asn Trp Asn Leu Tyr Asp Ala Val Gly
                165                 170                 175

Thr

<210> SEQ ID NO 135
<211> LENGTH: 167
<212> TYPE: PRT
<213> ORGANISM: Clostridium chauvoei

<400> SEQUENCE: 135

Met Ile Ile Asn His Asn Met Asn Ala Leu Asn Ala His Arg Asn Met
1               5                   10                  15

Met Gly Asn Ile Ala Thr Ala Gly Lys Ser Met Glu Lys Leu Ser Ser
            20                  25                  30

Gly Leu Arg Ile Asn Arg Ala Gly Asp Asp Ala Ala Gly Leu Ala Ile
        35                  40                  45

Ser Glu Lys Met Arg Gly Gln Ile Arg Gly Leu Asp Gln Ala Ser Arg
```

```
                  50                  55                  60

Asn Ala Gln Asp Gly Ile Ser Leu Ile Gln Thr Ala Glu Gly Ala Leu
 65                  70                  75                  80

Ala Glu Thr His Ser Ile Leu Gln Arg Met Arg Glu Leu Ser Val Gln
                     85                  90                  95

Ser Ala Asn Asp Thr Asn Val Ala Val Asp Arg Thr Ala Ile Gln Asp
                    100                 105                 110

Glu Ile Asn Ser Leu Thr Glu Glu Ile Asn Arg Ile Ser Gly Asp Thr
                    115                 120                 125

Glu Phe Asn Thr Gln Lys Leu Leu Asp Gly Gly Phe Lys Gly Glu Phe
                130                 135                 140

Gln Ile Gly Ala Asn Ser Asn Gln Thr Val Lys Leu Asp Ile Gly Asn
145                 150                 155                 160

Met Ser Ala Ala Ser Leu Gly
                165

<210> SEQ ID NO 136
<211> LENGTH: 178
<212> TYPE: PRT
<213> ORGANISM: Xanthomonas campestris

<400> SEQUENCE: 136

Met Ala Gln Val Ile Asn Thr Asn Val Met Ser Leu Asn Ala Gln Arg
  1               5                  10                  15

Asn Leu Asn Thr Asn Ser Ser Ser Met Ala Leu Ser Ile Gln Gln Leu
                 20                  25                  30

Ser Ser Gly Lys Arg Ile Thr Ser Ala Ser Val Asp Ala Ala Gly Leu
             35                  40                  45

Ala Ile Ser Glu Arg Phe Thr Thr Gln Ile Arg Gly Leu Asp Val Ala
         50                  55                  60

Ser Arg Asn Ala Asn Asp Gly Ile Ser Leu Ala Gln Thr Ala Glu Gly
 65                  70                  75                  80

Ala Met Val Glu Ile Gly Asn Asn Leu Gln Arg Ile Arg Glu Leu Ser
                 85                  90                  95

Val Gln Ser Ala Asn Ala Thr Asn Ser Ala Thr Asp Arg Glu Ala Leu
                100                 105                 110

Asn Ser Glu Val Lys Gln Leu Thr Ser Glu Ile Asp Arg Val Ala Asn
                115                 120                 125

Gln Thr Ser Phe Asn Gly Thr Lys Leu Leu Asn Gly Asp Phe Ser Gly
            130                 135                 140

Ala Leu Phe Gln Val Gly Ala Asp Ala Gly Gln Thr Ile Gly Ile Asn
145                 150                 155                 160

Ser Ile Val Asp Ala Asn Val Asp Ser Leu Gly Lys Ala Asn Phe Ala
                165                 170                 175

Ala Ser

<210> SEQ ID NO 137
<211> LENGTH: 161
<212> TYPE: PRT
<213> ORGANISM: Nitrosomonas europaea

<400> SEQUENCE: 137

Met Pro Gln Val Ile Asn Thr Asn Ile Ala Ser Leu Asn Ala Gln Arg
  1               5                  10                  15

Asn Leu Asn Val Ser Gln Asn Ser Leu Ser Thr Ala Leu Gln Arg Leu
                 20                  25                  30
```

```
Ser Ser Gly Leu Arg Ile Asn Ser Ala Lys Asp Asp Ala Gly Leu
        35                  40                  45

Ala Ile Ser Glu Arg Met Thr Ser Gln Ile Arg Gly Met Asn Gln Ala
 50                  55                  60

Ala Arg Asn Ala Asn Asp Gly Ile Ser Leu Ala Gln Thr Ala Glu Gly
 65                  70                  75                  80

Ala Leu Val Glu Ile Gly Asn Asn Leu Gln Arg Ile Arg Glu Leu Ala
                 85                  90                  95

Val Gln Ser Ala Asn Ala Thr Asn Ser Glu Asp Arg Glu Ala Leu
                100                 105                 110

Gln Lys Glu Val Thr Gln Leu Ile Asp Glu Ile Gln Arg Val Gly Glu
        115                 120                 125

Gln Thr Ser Phe Asn Gly Thr Lys Leu Leu Asp Gly Ser Phe Ala Ser
        130                 135                 140

Gln Ile Phe Gln Val Gly Ala Asn Glu Gly Glu Thr Ile Asp Phe Thr
145                 150                 155                 160

Asp

<210> SEQ ID NO 138
<211> LENGTH: 178
<212> TYPE: PRT
<213> ORGANISM: Campylobacter lari

<400> SEQUENCE: 138

Gly Phe Arg Ile Asn Thr Asn Gly Ala Ser Leu Asn Ala Gln Val Asn
 1               5                  10                  15

Ala Gly Leu Asn Ser Arg Asn Leu Asp Ser Ser Leu Ala Arg Leu Ser
            20                  25                  30

Ser Gly Leu Arg Ile Asn Ser Ala Ala Asp Asp Ala Ser Gly Leu Ala
        35                  40                  45

Ile Ala Asp Ser Leu Lys Thr Gln Ala Asn Ser Leu Gly Gln Ala Ile
 50                  55                  60

Asn Asn Ala Asn Asp Ala Asn Ser Met Leu Gln Ile Ala Asp Lys Ala
 65                  70                  75                  80

Met Asp Glu Gln Leu Lys Ile Leu Asp Thr Ile Lys Val Lys Ala Thr
                 85                  90                  95

Gln Ala Ala Gln Asp Gly Gln Thr Ala Lys Thr Arg Ala Met Ile Gln
                100                 105                 110

Gly Glu Ile Asn Lys Leu Met Glu Glu Leu Asp Asn Ile Ala Asn Thr
        115                 120                 125

Thr Thr Tyr Asn Gly Lys Gln Leu Leu Ser Gly Ser Phe Ser Asn Ala
        130                 135                 140

Gln Phe Gln Ile Gly Asp Lys Ala Asn Gln Thr Val Asn Ala Thr Ile
145                 150                 155                 160

Gly Ser Thr Asn Ser Ala Lys Val Gly Gln Thr Arg Phe Glu Thr Gly
                165                 170                 175

Ala Val

<210> SEQ ID NO 139
<211> LENGTH: 88
<212> TYPE: PRT
<213> ORGANISM: Salmonella enterica

<400> SEQUENCE: 139

Pro Leu Ala Ser Ile Asp Ser Ala Leu Ser Lys Val Asp Ala Val Arg
```

```
                1               5                   10                  15
Ser Ser Leu Gly Ala Ile Gln Asn Arg Phe Asp Ser Ala Ile Thr Asn
                20                  25                  30

Leu Gly Asn Thr Val Thr Asn Leu Asn Ser Ala Arg Ser Arg Ile Glu
                35                  40                  45

Asp Ala Asp Tyr Ala Thr Glu Val Ser Asn Met Ser Lys Ala Gln Ile
            50                  55                  60

Leu Gln Gln Ala Gly Thr Ser Val Leu Ala Gln Ala Asn Gln Val Pro
65                  70                  75                  80

Gln Asn Val Leu Ser Leu Leu Arg
                85
```

<210> SEQ ID NO 140
<211> LENGTH: 88
<212> TYPE: PRT
<213> ORGANISM: Pseudomonas aeruginosa

<400> SEQUENCE: 140

```
Ala Ile Ala Val Val Asp Asn Ala Leu Ala Ala Ile Asp Ala Gln Arg
1               5                   10                  15

Ala Asp Leu Gly Ala Val Gln Asn Arg Phe Lys Asn Thr Ile Asp Asn
                20                  25                  30

Leu Thr Asn Ile Ser Glu Asn Ala Thr Asn Ala Arg Ser Arg Ile Lys
                35                  40                  45

Asp Thr Asp Phe Ala Ala Glu Thr Ala Ala Leu Ser Lys Asn Gln Val
            50                  55                  60

Leu Gln Gln Ala Gly Thr Ala Ile Leu Ala Gln Ala Asn Gln Leu Pro
65                  70                  75                  80

Gln Ala Val Leu Ser Leu Leu Arg
                85
```

<210> SEQ ID NO 141
<211> LENGTH: 89
<212> TYPE: PRT
<213> ORGANISM: Legionella pneumophila

<400> SEQUENCE: 141

```
Ala Ile Lys Arg Ile Asp Ala Ala Leu Asn Ser Val Asn Ser Asn Arg
1               5                   10                  15

Ala Asn Met Gly Ala Leu Gln Asn Arg Phe Glu Ser Thr Ile Ala Asn
                20                  25                  30

Leu Gln Asn Val Ser Asp Asn Leu Ser Ala Ala Arg Ser Arg Ile Gln
                35                  40                  45

Asp Ala Asp Tyr Ala Ala Glu Met Ala Ser Leu Thr Lys Asn Gln Ile
            50                  55                  60

Leu Gln Gln Ala Gly Thr Ala Met Leu Ala Gln Ala Asn Ser Leu Pro
65                  70                  75                  80

Gln Ser Val Leu Ser Leu Leu Gly Arg
                85
```

<210> SEQ ID NO 142
<211> LENGTH: 89
<212> TYPE: PRT
<213> ORGANISM: Escherichia coli

<400> SEQUENCE: 142

```
Pro Leu Glu Thr Ile Asp Lys Ala Leu Ala Lys Val Asp Asn Leu Arg
1               5                   10                  15
```

Ser Asp Leu Gly Ala Val Gln Asn Arg Phe Asp Ser Ala Ile Thr Asn
            20                  25                  30

Leu Gly Asn Thr Val Asn Asn Leu Ser Ser Ala Arg Ser Arg Ile Glu
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Thr Thr
65                  70                  75                  80

Gln Asn Val Leu Ser Leu Leu Gln Gly
                85

<210> SEQ ID NO 143
<211> LENGTH: 88
<212> TYPE: PRT
<213> ORGANISM: Serratia marcescens

<400> SEQUENCE: 143

Pro Leu Ala Thr Leu Asp Lys Ala Leu Ala Gln Val Asp Gly Leu Arg
1               5                   10                  15

Ser Ser Leu Gly Ala Val Gln Asn Arg Phe Asp Ser Val Ile Asn Asn
            20                  25                  30

Leu Asn Ser Thr Val Asn Asn Leu Ser Ala Ser Gln Ser Arg Ile Gln
        35                  40                  45

Asp Ala Asp Tyr Ala Thr Glu Val Ser Asn Met Ser Arg Ala Asn Ile
    50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
                85

<210> SEQ ID NO 144
<211> LENGTH: 89
<212> TYPE: PRT
<213> ORGANISM: Bacillus subtilis

<400> SEQUENCE: 144

Ala Leu Thr Thr Ile Lys Thr Ala Ile Asp Thr Val Ser Ser Glu Arg
1               5                   10                  15

Ala Lys Leu Gly Ala Val Gln Asn Arg Leu Glu His Thr Ile Asn Asn
            20                  25                  30

Leu Gly Thr Ser Ser Glu Asn Leu Thr Ser Ala Glu Ser Arg Ile Arg
        35                  40                  45

Asp Val Asp Met Ala Ser Glu Met Met Glu Tyr Thr Lys Asn Asn Ile
    50                  55                  60

Leu Thr Gln Ala Ser Gln Ala Met Leu Ala Gln Ala Asn Gln Gln Pro
65                  70                  75                  80

Gln Gln Val Leu Gln Leu Leu Lys Gly
                85

<210> SEQ ID NO 145
<211> LENGTH: 90
<212> TYPE: PRT
<213> ORGANISM: Leptospira interrogans

<400> SEQUENCE: 145

Val Ile Gly Leu Ala Asp Ala Ala Leu Thr Lys Ile Met Lys Gln Arg
1               5                   10                  15

Ala Asp Met Gly Ala Tyr Tyr Asn Arg Leu Glu Tyr Thr Ala Lys Gly
            20                  25                  30

Leu Met Gly Ala Tyr Glu Asn Met Gln Ala Ser Glu Ser Arg Ile Arg
            35                  40                  45

Asp Ala Asp Met Ala Glu Glu Val Val Ser Leu Thr Thr Lys Gln Ile
        50                  55                  60

Leu Val Gln Ser Gly Thr Ala Met Leu Ala Gln Ala Asn Met Lys Pro
65                  70                  75                  80

Asn Ser Val Leu Lys Leu Leu Gln Gln Ile
            85                  90

<210> SEQ ID NO 146
<211> LENGTH: 88
<212> TYPE: PRT
<213> ORGANISM: Shigella sonnei

<400> SEQUENCE: 146

Pro Leu Ser Lys Leu Asp Glu Ala Leu Ala Lys Val Asp Lys Leu Arg
1               5                   10                  15

Ser Ser Leu Gly Ala Val Gln Asn Arg Phe Asp Ser Ala Ile Thr Asn
            20                  25                  30

Leu Gly Asn Thr Val Asn Asp Leu Ser Ser Ala Arg Ser Arg Ile Glu
            35                  40                  45

Asp Ala Asp Tyr Ala Thr Glu Val Ser Asn Met Ser Arg Ala Gln Ile
        50                  55                  60

Leu Gln Gln Ala Gly Thr Ser Val Leu Ala Gln Ala Asn Gln Thr Thr
65                  70                  75                  80

Gln Asn Val Leu Ser Leu Leu Arg
            85

<210> SEQ ID NO 147
<211> LENGTH: 88
<212> TYPE: PRT
<213> ORGANISM: Edwardsiella tarda

<400> SEQUENCE: 147

Pro Leu Ala Thr Leu Asp Lys Ala Leu Ser Gln Val Asp Asp Leu Arg
1               5                   10                  15

Ser Gly Leu Gly Ala Val Gln Asn Arg Phe Asp Ser Val Ile Asn Asn
            20                  25                  30

Leu Asn Ser Thr Val Asn Asn Leu Ser Ala Ser Arg Ser Arg Ile Gln
            35                  40                  45

Asp Ala Asp Tyr Ala Thr Glu Val Ser Asn Met Ser Arg Ala Gln Ile
        50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
            85

<210> SEQ ID NO 148
<211> LENGTH: 88
<212> TYPE: PRT
<213> ORGANISM: Acidovorax avenae

<400> SEQUENCE: 148

Ala Leu Lys Ile Ile Asp Ala Ala Leu Ser Ala Val Asn Gly Gln Arg
1               5                   10                  15

Ala Ser Phe Gly Ala Leu Gln Ser Arg Phe Glu Thr Thr Val Asn Asn

```
                20                  25                  30

Leu Gln Ser Thr Ser Glu Asn Met Ser Ala Ser Arg Ser Arg Ile Gln
            35                  40                  45

Asp Ala Asp Phe Ala Ala Glu Thr Ala Asn Leu Ser Arg Ser Gln Ile
        50                  55                  60

Leu Gln Gln Ala Gly Thr Ala Met Val Ala Gln Ala Asn Gln Leu Pro
65                  70                  75                  80

Gln Gly Val Leu Ser Leu Leu Lys
                85

<210> SEQ ID NO 149
<211> LENGTH: 88
<212> TYPE: PRT
<213> ORGANISM: Yersinia pestis

<400> SEQUENCE: 149

Pro Leu Glu Thr Leu Asp Asp Ala Ile Lys Gln Val Asp Gly Leu Arg
1               5                   10                  15

Ser Ser Leu Gly Ala Val Gln Asn Arg Phe Glu Ser Ala Val Thr Asn
            20                  25                  30

Leu Asn Asn Thr Val Thr Asn Leu Thr Ser Ala Arg Ser Arg

```
Leu Thr Asn Ile Ser Thr Ser Val Gln Ala Ala Lys Ser Gln Val Met
            35                  40                  45

Asp Ala Asp Phe Ala Ala Glu Ser Thr Asn Leu Ala Arg Ser Gln Ile
 50                  55                  60

Leu Ser Gln Ala Ser Thr Ala Met Leu Ala Gln Ala Asn Ser Ser Lys
 65                  70                  75                  80

Gln Asn Val Leu Ser Leu Leu Arg Gly
                85

<210> SEQ ID NO 152
<211> LENGTH: 88
<212> TYPE: PRT
<213> ORGANISM: Xenorhabdus nematophila

<400> SEQUENCE: 152

Pro Leu Asp Thr Leu Asp Lys Ala Leu Ala Gln Val Asp Asp Met Arg
 1               5                  10                  15

Ser Ser Leu Gly Ala Val Gln Asn Arg Leu Glu Ser Thr Val Asn Asn
            20                  25                  30

Leu Asn Asn Thr Val Asn Asn Leu Ser Ala Ala Arg Ser Arg Ile Glu
            35                  40                  45

Asp Ala Asp Tyr Ala Val Glu Val Ser Asn Met Ser Arg Gly Gln Ile
 50                  55                  60

Leu Gln Gln Ala Gly Thr Ser Val Leu Ala Gln Ala Asn Gln Val Pro
 65                  70                  75                  80

Gln Thr Val Leu Ser Leu Leu Arg
                85

<210> SEQ ID NO 153
<211> LENGTH: 88
<212> TYPE: PRT
<213> ORGANISM: Proteus mirabilis

<400> SEQUENCE: 153

Ala Leu Ala Thr Leu Asp Asn Ala Ile Ser Lys Val Asp Glu Ser Arg
 1               5                  10                  15

Ser Lys Leu Gly Ala Ile Gln Asn Arg Phe Gln Ser Thr Ile Asn Asn
            20                  25                  30

Leu Asn Asn Thr Val Asn Asn Leu Ser Ala Ser Arg Ser Arg Ile Leu
            35                  40                  45

Asp Ala Asp Tyr Ala Thr Glu Val Ser Asn Met Ser Lys Asn Gln Ile
 50                  55                  60

Leu Gln Gln Ala Gly Thr Ala Val Leu Ala Gln Ala Asn Gln Val Pro
 65                  70                  75                  80

Gln Thr Val Leu Ser Leu Leu Arg
                85

<210> SEQ ID NO 154
<211> LENGTH: 88
<212> TYPE: PRT
<213> ORGANISM: Butyrivibrio fibrisolvens

<400> SEQUENCE: 154

Ala Ile Asp Ala Ile Ser Asp Ala Leu Ala Lys Val Ser Ala Gln Arg
 1               5                  10                  15

Ser Ala Leu Gly Ser Ile Gln Asn Arg Leu Glu His Ser Ile Ala Asn
            20                  25                  30
```

Leu Asp Asn Val Val Glu Asn Thr Asn Ala Ala Glu Ser Arg Ile Arg
            35                  40                  45

Asp Thr Asp Met Ala Asp Glu Met Val Thr Tyr Ser Lys Asn Asn Ile
        50                  55                  60

Leu Met Gln Ala Gly Gln Ser Met Leu Ala Gln Ala Asn Gln Ala Thr
65                  70                  75                  80

Gln Gly Val Leu Ser Ile Leu Gln
                85

<210> SEQ ID NO 155
<211> LENGTH: 88
<212> TYPE: PRT
<213> ORGANISM: Bordetella pertussis

<400> SEQUENCE: 155

Ala Leu Ser Lys Leu Asp Asp Ala Met Lys Ala Val Asp Glu Gln Arg
1               5                   10                  15

Ser Ser Leu Gly Ala Ile Gln Asn Arg Phe Glu Ser Thr Val Ala Asn
            20                  25                  30

Leu Asn Asn Thr Ile Thr Asn Leu Ser Ala Ala Arg Ser Arg Ile Glu
        35                  40                  45

Asp Ser Asp Tyr Ala Thr Glu Val Ser Asn Met Thr Lys Asn Gln Ile
    50                  55                  60

Leu Gln Gln Ala Gly Thr Ser Val Leu Ala Gln Ala Asn Gln Val Pro
65                  70                  75                  80

Gln Asn Val Leu Ser Leu Leu Arg
                85

<210> SEQ ID NO 156
<211> LENGTH: 88
<212> TYPE: PRT
<213> ORGANISM: Clostridium chauvoei

<400> SEQUENCE: 156

Ser Ile Lys Thr Ile Asn Ser Ala Ile Glu Gln Val Ser Thr Gln Arg
1               5                   10                  15

Ser Lys Leu Gly Ala Val Gln Asn Arg Leu Glu His Thr Ile Asn Asn
            20                  25                  30

Leu Asn Thr Ser Ser Glu Asn Leu Thr Ala Ala Glu Ser Arg Val Arg
        35                  40                  45

Asp Val Asp Met Ala Lys Glu Met Met Ala Phe Ser Lys Asn Asn Ile
    50                  55                  60

Leu Ser Gln Ala Ala Gln Ala Met Leu Gly Gln Ala Asn Gln Gln Pro
65                  70                  75                  80

Gln Gly Val Leu Gln Leu Leu Arg
                85

<210> SEQ ID NO 157
<211> LENGTH: 88
<212> TYPE: PRT
<213> ORGANISM: Xanthomonas campestris

<400> SEQUENCE: 157

Ala Leu Glu Ile Val Asp Lys Ala Leu Thr Ser Val Asn Ser Ser Arg
1               5                   10                  15

Ala Asp Met Gly Ala Val Gln Asn Arg Phe Thr Ser Thr Ile Ala Asn
            20                  25                  30

Leu Ala Ala Thr Ser Glu Asn Leu Thr Ala Ser Arg Ser Arg Ile Ala

```
                    35                  40                  45
Asp Thr Asp Tyr Ala Lys Thr Thr Ala Glu Leu Thr Arg Thr Gln Ile
    50                  55                  60

Leu Gln Gln Ala Gly Thr Ala Met Leu Ala Gln Ala Lys Ser Val Pro
65                  70                  75                  80

Gln Asn Val Leu Ser Leu Leu Gln
                85

<210> SEQ ID NO 158
<211> LENGTH: 84
<212> TYPE: PRT
<213> ORGANISM: Nitrosomonas europaea

<400> SEQUENCE: 158

Ile Asp Asp Ala Leu Lys Ile Val Asn Ser Thr Arg Ala Asp Leu Gly
1               5                   10                  15

Ala Ile Gln Asn Arg Phe Ser Ser Ala Ile Ala Asn Leu Gln Thr Ser
                20                  25                  30

Ala Glu Asn Leu Ser Ala Ser Arg Ser Arg Ile Gln Asp Ala Asp Phe
            35                  40                  45

Ala Ala Glu Thr Ala Ala Leu Thr Arg Ala Gln Ile Leu Gln Gln Ala
        50                  55                  60

Gly Val Ala Met Leu Ser Gln Ala Asn Ala Leu Pro Asn Asn Val Leu
65                  70                  75                  80

Ser Leu Leu Arg

<210> SEQ ID NO 159
<211> LENGTH: 88
<212> TYPE: PRT
<213> ORGANISM: Campylobacter lari

<400> SEQUENCE: 159

Val Met Asp Ile Ala Asp Thr Ala Ile Ala Asn Leu Asp Thr Ile Arg
1               5                   10                  15

Ala Asn Ile Gly Ala Thr Gln Asn Gln Ile Thr Ser Thr Ile Asn Asn
                20                  25                  30

Ile Ser Val Thr Gln Val Asn Val Lys Ala Ala Glu Ser Gln Ile Arg
            35                  40                  45

Asp Val Asp Phe Ala Ser Glu Ser Ala Asn Tyr Ser Lys Ala Asn Ile
        50                  55                  60

Leu Ala Gln Ser Gly Ser Tyr Ala Met Ala Gln Ala Asn Ala Ala Ser
65                  70                  75                  80

Gln Asn Val Leu Arg Leu Leu Gln
                85
```

USE OF TOLL-LIKE RECEPTOR AGONIST FOR TREATING CANCER

CROSS REFERENCE TO RELATED APPLICATIONS

This application is a continuation of U.S. patent application Ser. No. 15/631,427, filed on Jun. 23, 2017, now U.S. Pat. No. 10,034,926, which is a continuation of U.S. patent application Ser. No. 15/241,757, filed on Aug. 19, 2016, which is a continuation of U.S. patent application Ser. No. 14/949,441, filed on Nov. 23, 2015, which is a continuation of U.S. patent application Ser. No. 13/979,104, filed on Feb. 3, 2014, now U.S. Pat. No. 9,376,473, which is the national stage of International Application No. PCT/US2012/20844, filed on Jan. 10, 2012, which claims the benefit of U.S. Provisional Patent Application No. 61/431,313, filed Jan. 10, 2011, the contents of all of which are incorporated herein by reference.

FIELD OF THE INVENTION

This invention relates to methods of treating cancer in Toll-Like Receptor-expressing tissues, and to methods of protecting the liver from the effects of a liver toxicity, using a TLR agonist.

REFERENCE TO THE SEQUENCE LISTING

Reference is made to the sequence listing submitted via EFS-Web, which consists of a file named, "CLE-010C4 SL_ST25.txt" (194 KB), created on Jun. 21, 2018, the contents of which are incorporated herein by reference.

BACKGROUND OF THE INVENTION

Interaction between members of the death receptor family and their cognate ligands induces apoptosis controlling the homeostasis of cell populations in tissues, particularly in the immune system. Although many tumor cell types are sensitive to death ligands, activation of Fas signaling also induces massive apoptosis in the liver leading to organ failure and death precluding its use for systemic anticancer therapy. Fas ligand is a 40 kDa physiological agonist of Fas signaling expressed on activated lymphocytes and many tumor cells which can also be secreted through metalloproteinase-mediated cleavage and kill the sensitive cells in autocrine and paracrine manner. Fas is a transmembrane receptor expressed on activated lymphocytes, variety of tissues and tumor cells. Fas signaling plays crucial role in regulation of the immune system by triggering autocrine suicide or paracrine death (apoptosis), suppressing immune reaction by eliminating activated lymphocytes. Upon binding, it induces p53 independent cell death through extrinsic pathway of apoptosis engaging DISC formation, caspase-8 and 10, and intrinsic (mitochondrial) apoptosis activating caspase-8 and Bid cleavage, and cytochrome release. Both apoptotic pathways lead to activation of caspase-3 and 7. Mitochondrial apoptosis is regulated by pro- and anti-apoptotic Bcl2 family members. In tumor cells, Fas signaling is often found deregulated either by absence of Fas receptor, or by constitutive activation of NF-kB resulting in the expression of anti-apoptotic genes, such as c-Flip, Bcl-2, Bcl-xL. C-Flip, an NF-kB responsive gene, has been demonstrated to inhibit caspase-8 and Fas mediated apoptosis in tumors (Kataoka et al 2000).

Upon discovery of p53 independent apoptotic mechanism through Fas, TRAIL and TNFα death receptor signaling, they seemed to be promising targets for anti-cancer therapy since tumor cells usually have impaired p53 function. A severe hepatotoxicity, however, is induced by death receptor ligands. This has hampered development of these anti-cancer therapies. While Fas agonists cause liver damage and TNF-a induces strong inflammation in liver, lungs and other organs, TRAIL is the least toxic in humans. TRAIL has therefore received more attention than other agonists for the clinical application for an anticancer treatment. Many tumors, however, are not sensitive to TRAIL therapy. Several approaches to resolve death receptor toxicity issue are currently undertaken, most of which are aimed to increase tumor sensitivity by blockage of NF-kB activity and increasing receptor expression thus reducing the amount of drug necessary for the effective therapy. Another direction is to localize the drug delivery to the tumors to minimize toxic effects on distant organs. To date, there is no reliable approach to the prevention of toxicity (including liver injury) that would allow the systemic application of death receptor agonists in clinical trials. Accordingly, there is a need in the art for methods of preventing the undesirable effects of death receptors when they are used to treat cancer. In particular, there is a need to protect the liver from these undesirable effects. There is also a need for protecting the liver from liver toxicities in general.

TLRs are found to be expressed on both epithelial and endothelial cells as well as immunocytes. At present, thirteen TLRs have been identified in mammals. Upon receptor stimulation, several common signaling pathways get activated such as NF-kB, AP-1, PI3K/AKT and mitogen-activated protein kinases (MAPK) leading to increased survival, stimulation of cell proliferation and the secretion of many cytokines with chemotactic and pro-inflammatory functions. Induction of TLR in cancer cells can be used to treat cancer, however, the distribution of different TLRs varies significantly among the various organs and cell types. This affects the cytokine profile and extent of the inflammatory response of cells. Accordingly, there is a need in the art for cancer immunotherapeutic methods that do not depend on the presence of TLR5 expression.

SUMMARY OF THE INVENTION

Provided herein is a method of treating cancer in a mammal, which may comprise administering to a mammal in need thereof of Toll-Like Receptor (TLR) agonist. Also provided is a method of reducing cancer recurrence in a mammal, which may comprise administering to a mammal in need thereof a TLR agonist. The cancer may be present in a tissue that expresses TLR. The cancer may be a metastasis or tumor regrowth.

The TLR agonist may be flagellin. The cancer may not express TLR, which may be TLR5. The tissue may be liver, lung, bladder, or intestinal. The cancer may be metastatic. The cancer may be melanoma, colon, breast, prostate, or a hematological malignancy, which may be lymphoma. The cancer may be tumor.

The agent may be administered as a monotherapy. The mammal may not be receiving a combination therapy. The mammal may also not be receiving chemotherapy or radiation therapy, but may be treated surgically. The mammal may have sufficient innate immunity, which may be at a level that is equivalent to the level required for eligibility for a first or subsequent round of chemotherapy. The mammal may have a white blood cell count within the range of normal, or may have a white blood cell count indicative of mild-immunosuppression. The TLR agonist may be administered to the mammal before, after or concurrent with removal of a tumor. The TLR agonist may be administered during tumor removal.

Further provided herein is a method of treating cancer in a mammal, which may comprise administering to a mammal in need thereof a FAS agonist and a TLR agonist, which may be flagellin. The FAS agonist may be a FAS agonist antibody. The cancer may be metastatic, and may be a tumor. The cancer may not express a TLR. The cancer may have metastasized to an invaded tissue that expresses TLR. The invaded tissue may be liver, bladder, lung, or intestinal.

Also provided herein is a method of protecting liver tissue in a mammal from the effects of a liver toxicity, which may comprise administering to a mammal in need thereof a TLR agonist. The toxicity may be a FAS ligand, a FAS agonistic antibody, TNFα, acetaminophen, alcohol, a viral infection of the liver, or a chemotherapeutic agent. The toxicity may also be a *Salmonella* infection, which may be from *Salmonella typhimurium*. The TLR agonist may be flagellin.

BRIEF DESCRIPTION OF THE DRAWINGS

FIGS. 4A-K show the nucleotide and amino acid sequence for the following flagellin variants: AA' (SEQ ID NO: 7-8), AB' (SEQ ID NO: 9-10), BA' (SEQ ID NO: 11-12), BB' (SEQ ID NO: 13-14), CA' (SEQ ID NO: 15-16), CB' (SEQ ID NO: 17-18), A (SEQ ID NO: 19-20), B (SEQ ID NO: 21-22), C (SEQ ID NO: 23-24), GST-A' (SEQ ID NO: 25-26), GST-B' (SEQ ID NO: 27-28), AA'n1-170 (SEQ ID NO: 29-30), AA'n1-163 (SEQ ID NO: 33-34), AA'n54-170 (SEQ ID NO: 31-32), AA'n54-163 (SEQ ID NO: 35-36), AB'n1-170 (SEQ ID NO: 37-38), AB'n1-163 (SEQ ID NO: 39-40), AA'n1-129 (SEQ ID NO: 41-42), AA'n54-129 (SEQ ID NO: 43-44), AB'n1-129 (SEQ ID NO: 45-46), AB'n54-129 (SEQ ID NO: 47-48), AA'n1-100 (SEQ ID NO: 49-50), AB'n1-100 (SEQ ID NO: 51-52), AA'n1-70 (SEQ ID NO: 53-54) and AB'n1-70 (SEQ ID NO: 55-56). The pRSETb leader sequence is shown in Italic (leader includes Met, which is also amino acid 1 of FliC). The N terminal constant domain is underlined. The amino acid linker sequence is in Bold. The C terminal constant domain is underlined. GST, if present, is highlighted.

FIGS. 5A-C show a comparison of amino acid sequences of the conserved amino (FIGS. 5A and 5B) and carboxy (FIG. 5C) terminus from 21 species of bacteria. The 13 conserved amino acids important for TLR5 activity are shown with shading. The amino acid sequences are identified by their accession numbers from TrEMBL (first letter=Q) or Swiss-Prot (first letter=P). The amino terminus sequences have SEQ ID NOs: 118-138, respectively, for each of the 21 bacterial species, and the carboxy terminus sequences have SEQ ID NOs: 139-159, respectively.

FIG. 6 shows the sequence of human TLR5 (SEQ ID NO: 117).

FIGS. 7A-E show NF-kB activation in vivo in response to CBLB502 and LPS injections. FIG. 7A. Background and NF-kB dependent luciferase expression in BALB/c-Tg (IκBα-luc)Xen reporter mice was detected by noninvasive imaging 2 hs after the treatment with CBLB502 (0.2 mg/kg). FIG. 7B. NF-kB dependent luciferase expression in liver, small intestine (ileum part), colon, spleen, kidneys, lungs and heart was assessed in the reporter mice 2 hs after s.c. injections of 100 µl of either PBS, CBLB502 (0.2 mg/kg) or LPS (1 mg/kg). Luciferase activity normalized per µg of the protein extract was detected in 3 mice in each group. Bars represent average+/−s.d. FIG. 7C. The dynamics of NF-kB nuclear translocation (p65) indicative of the bioactivity of agonists LPS and CBLB502 in liver from NIH-Swiss mice injected s.c either with CBLB502 or LPS. Control mice were injected with PBS. Tissue samples were obtained 20, 40 and 60 min after the treatments, processed into paraffin blocks. Nuclear translocation of p65 in primary mouse hepatocytes isolated from NIH-Swiss mice (FIG. 7D) and human hepatocytes purchased from (BD Biosciences) (FIG. 7E) was detected after in vitro treatment with CBLB502 (100 ng/ml) or LPS (1 µg/ml) for indicated period of time. Control hepatocytes remained intact. P65 was stained with green fluorescence, cytokeratin-8 with red fluorescence and nuclei with non-specific Dapi blue staining. Pictures are taken at ×20 magnification. Arrows indicate Kupffer and endothelial cells determined based on morphological criteria.

FIGS. 8A-G show CBLB502 protection from Fas mediated hepatotoxicity. FIG. 8A. Survival of NIH-Swiss mice after i.p. injection of 4 µg of anti-Fas antibodies alone or in combination with CBLB502 (1 µg/mouse) injected 30 min, 2 hours and 6 hours prior antibodies. In parenthesis are the numbers of mice per each treatment. FIG. 8C. Protection of livers from anti-Fas antibody toxicity. Apoptosis in livers 5 hours after injections of anti-Fas antibodies was detected using TUNEL technique. FIG. 8B. Tissue morphology with H&E staining revealed necrotic damage to livers by anti-Fas antibody injections and protection by CBLB502. FIG. 8D. Hemorrhage in liver was detected using erythrocyte autofluorescence (rhodamine channel, red), mouse IgG control (Cy5-conjugated anti-mouse IgG antibody, pseudocolored in purple) and DAPI nuclei (blue). FIG. 8E. Caspase-3/7 activity in liver samples of NIH-Swiss mice was determined in tissue protein lysates 5 hours after injection of 3 µg anti-Fas antibody with or without CBLB502 thirty minute pre-treatment. N=3. Bars represent average+/−s.d. FIG. 8F. Alanine aminotransferase (ALT) accumulation in blood serum of NIH-Swiss mice was detected 5 hours after anti- Fas antibody injections with or without CBLB502. N=3. Bars represent average+/−s.d. FIG. 8G. Caspase-8 activity in liver samples of NIH-Swiss mice was determined in tissue protein lysates 5 hours after injection of 3 µg anti-Fas antibody with or without CBLB502 thirty minute pre-treatment. N=3. Bars represent average+/−s.d.

FIGS. 9A-G show regulation of apoptosis-related factors by CBLB502 in liver and its effect on Fas-mediated antitumor activity in CT-26 tumor model. Inhibition of caspase-8 (FIG. 9A) and Bid (FIG. 9B) cleavage by CBLB502 detected in liver isolated from C57BL/6 mice 2 hours after anti-Fas antibody injections (5 µg) alone or in combination with CBLB502 by western blot. FIG. 9C. RNA expression of Bcl2A1B, Bcl2A1D, IER-3, Fos, Jun and JunB genes in livers of intact mice and treated with CBLB502 for 30 min and 2 hours was detected by RT-PCR. GAPDH was used as a control to monitor the induction of gene expression. FIG. 9D. Mice with s.c. growing CT-26 tumors were injected either with single anti-Fas antibodies (4 µg/mouse) and CBLB502 or their combination. Control mice ("intact") received PBS in replace of CBLB502 and antibodies. In parenthesis are the numbers of tumors in each group. The results represent the average tumor volumes (m+/−standard error). (*)—The difference between intact and combination treatment groups is significant (p<0.05). FIG. 9E. Mice were treated with anti-Fas antibodies alone or in combination with CBLB502 on day 5 after intrasplenic injection of luciferase expressing CT-26 tumor cells. Tumor growth in livers was determined using Xenogen IVIS Imaging System on the days 10, 15, 17, 22, 28 and 40 after tumor cell inoculation. Images of 3 mice from each group taken on day 15 are presented. The difference between proportions of mice with tumor-free livers in CBLB502-treated and control groups reaches statistical significance (p<0.05) on days indicated by asterisks. FIG. 9F. Migration and infiltration of immunocytes (arrows) into tumor nodules grown in liver of mice 5 hrs post treatment with CBLB502. FIG. 9G. Statistical comparison of animals free of liver tumor is presented.

FIGS. 10A-D. Dynamics of NF-kB activation in different organs after injections with CBLB502 (5 µg,s.c.) or LPS (20 µg, s.c.). Mice were euthanized 2, 6, 24 and 48 hours later by CO2 inhalation. Luciferase activity in protein extracts from liver (FIG. 10B), large intestine (FIG. 10A), kidneys (FIG. 10D) and lungs (FIG. 10C) was normalized per µg of the protein extract and average values were calculated per organ. Luciferase fold induction was calculated as ratio between average luciferase activity in protein extract from organs of the TLR agonist treated mice and that obtained in the extracts from the corresponding organs of the PBS injected control mice (3 mice/group). Bars represent fold induction as average±s.e.

FIG. 11. NF-kB dependent luciferase expression in primary culture of mouse hepatocytes isolated from luciferase reporter mice and treated in vitro for 3 hours with CBLB502 (100 ng/ml), LPS (5 µg/ml) or PBS control. Then hepatocytes were rinsed with PBS and collected in cell lysis buffer (Promega). Luciferase activity in the protein supernatants was determined by Promega reporter system and normalized per µg of the protein extract. Bars represent luciferase units (mean±s.d.).

FIG. 13A. Caspase-3/7 activity in Balb/c mice. FIG. 13B. Caspase-8 activity in Balb/c mice. FIG. 13C. Caspase-3/7 activity in C57Bl/6 mice.

FIG. 14B. An in vitro luciferase assay for NF-kB activation in B16 (TLR5 positive) and CT-26 TLR5 negative) tumor cells was performed.

FIG. 20C demonstrates NF-kB dependent induction of luciferase reporter expression in A549-shV and A549-shTLR5 in response to CBLB502 treatment.

FIG. 21C demonstrates IL-8 production in response to CBLB502 treatment as indicative of TLR5 function in H1299-TLR5 cells.

FIGS. 23A-E show that CBLB502 treatment delays tumor appearance and growth in livers, even in tumors that do not express TLR5.

FIGS. 24A-B show CBLB502 protection from Fas mediated hepatotoxicity.

FIGS. 25A-B show that the liver is protected from TNFα and LPS toxicity by CBLB502.

FIGS. 26A-B show that CBLB502 protects the lungs from TNF and LPS toxicity.

FIGS. 27A-B show that CBLB502 protects mice from legal oral administration of *Salmonella*.

FIGS. 28A-C show that irinotecan abrogates the antitumor effect of flagellin (CBLB502).

DETAILED DESCRIPTION

Figure 1:
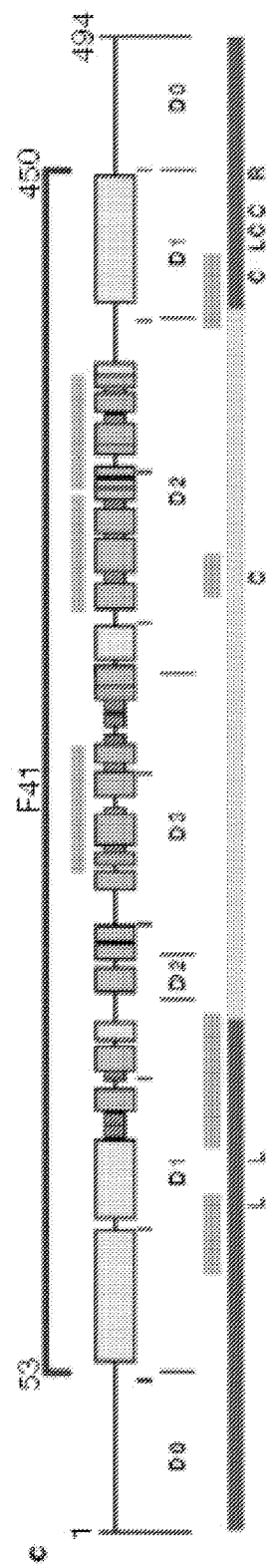
FIG. 1 shows the domain structure of bacterial flagellin. The Cα backbone trace, hydrophobic core distribution and structural information of F41. Four distinct hydrophobic cores that define domains D1, D2a, D2b and D3. All the hydrophobic side-chain atoms are displayed with the Cα backbone. Side-chain atoms are color coded: Ala, yellow; Leu, Ile or Val, orange; Phe and Tyr, purple (carbon atoms) and red (oxygen atoms). c, Position and region of various structural features in the amino-acid sequence of flagellin. Shown are, from top to bottom: the F41 fragment in blue; three b-folium folds in brown; the secondary structure distribution with a-helix in yellow, b-structure in green, and b-turn in purple; tic mark at every 50th residue in blue; domains D0, D1, D2 and D3; the axial subunit contact region within the proto-element in cyan; the well-conserved amino-acid sequence in red and variable region in violet; point mutations in F41 that produce the elements of different supercoils. Letters at the bottom indicate the morphology of mutant elements: L (D107E, R124A, R124S, G426A), L-type straight; R (A449V), R-type straight; C (D313Y, A414V, A427V, N433D), curly33.

The inventors have made the surprising discovery that the provision of a Toll-Like Receptor (TLR) agonist, such an agonist of TLR5 like flagellin, can effectively inhibit the growth of and reduce cancer cells, even when the cells do not express TLR5. The TLR agonist may be particularly useful in treating liver, bladder, lung, and intestinal cancers, whether primary or metastatic, as well as cancer affecting other TLR5-positive tissues. The TLR agonist can also be used to treat cancers that originate in tissues other than the liver, bladder, lung, intestinal, and other TLR5-positive tissues, but metastasize to these tissues. Even though the metastatic cancer cells do not express TLR5, the cancer may nonetheless be treatable with the TLR agonist when the cancer has metastasized to TLR5-expressing tissues such as the liver. While not being bound by theory, the idea implemented in this invention is that TLR agonists effectively reduce or kill cancer cells affecting a tissue that has a strong innate immunity system, thereby obviating the need for any pre-existing expression of TLR5 in the cancer cells. Unexpectedly, by providing a TLR agonist, the innate immune system is sufficiently triggered so as to treat cancers that are devoid of TLR5 expression. Thus, TLR5 does not need to be provided to the cancer cells in order for the TLR agonist to effectively reduce or kill cancer cells.

The inventors have also made the surprising discovery that a TLR agonist can protect the liver from a liver toxicity. For example, death ligands and activators of FAS-mediated apoptosis, such as FAS ligand and anti-FAS agonistic antibodies, can induce does-dependent hepatotoxicity. Administering the TLR agonist can protect the liver against such toxicities. This unexpected property of TLR agonists allows it be combined with FAS agonists or TNF for cancer treatment, such that the adverse of effects of the FAS agonist or TNF are reduced or prevented.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Administer" may mean a single dose or multiple doses of an agent or agent.

"Analog" may mean, in the context of a peptide or polypeptide, a peptide or polypeptide comprising one or more non-standard amino acids or other structural variations from the conventional set of amino acids.

"Antibody" may mean an antibody of classes IgG, IgM, IgA, IgD or IgE, or fragments, or derivatives thereof, including Fab, F(ab')2, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety.

A "derivative" may mean a peptide or polypeptide different other than in primary structure (amino acids and amino acid analogs). Derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives may include fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

A "fragment" may mean a portion of a reference peptide or polypeptide.

A "homolog" may mean a peptide or polypeptide sharing a common evolutionary ancestor.

A "leader sequence" may be a nucleic acid encoding any peptide sequence that is linked and translated with a peptide or polypeptide of interest to allow the peptide or polypeptide of interest be properly routed through a eukaryotic cell's endoplasmic reticulum and Golgi complexes for the purposed of extracellular secretion from the cell's membrane. The leader peptide sequence may be derived from alkaline phosphatase. The leader sequence may have a DNA sequence comprising atgctgctgctgctgctgctgctgggcctgaggcta-cagctct ccctgggc (SEQ ID NO: 101).

A "liposome" may mean a tiny bubble (vesicle) made out of the same material as a cell membrane. A liposome be filled with drugs and used to deliver drugs for cancer and other diseases. A liposome may be filled with a vector. A liposome membrane may be made of phospholipids, which are molecules that have a head group and a tail group. The head of the liposome may be attracted to water, and the tail, which is made of a long hydrocarbon chain, is repelled by water. The tails may be repelled by water, and line up to form a surface away from the water. The lipids in the plasma membrane may be chiefly phospholipids like phosphatidylethanolamine and phosphatidylcholine. Liposomes may be composed of naturally-derived phospholipids with mixed lipid chains (like egg phosphatidylethanolamine), or of pure surfactant components like DOPE (dioleoylphosphatidylethanolamine).

A "peptide" or "polypeptide" may mean a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%, or 99% over a region of 10, 15, 20, 25, 30, 35, 40, 45, 50, 55, 60, 65, 70, 75, 80, 85, 90, 95, 100, 200, 300, 400, 500, 600, 700, 800, 900, 1000, 1100 amino acids.

"Treating," "treatment," or "to treat" each may mean to alleviate, suppress, repress, eliminate, prevent or slow the appearance of symptoms, clinical signs, or underlying pathology of a condition or disorder on a temporary or permanent basis. Preventing a condition or disorder involves administering an agent of the present invention to a subject prior to onset of the disease. Suppressing a condition or disorder involves administering an agent of the present invention to a subject after induction of the condition or disorder but before its clinical appearance. Repressing the condition or disorder involves administering an agent of the present invention to a subject after clinical appearance of the disease.

A "variant" may mean means a peptide or polypeptide that differs in amino acid sequence by the insertion, deletion, or conservative substitution of amino acids, but retain at least one biological activity. Representative examples of "biological activity" include the ability to bind to a toll-like receptor and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A "vector" may mean a nucleic acid sequence containing an origin of replication. A vector may be a plasmid, a yeast or a mammalian artificial chromosome. A vector may be a RNA or DNA vector. A vector may be either a self-replicating extrachromosomal vector or a vector which integrates into a host genome.

2. Toll-Like Receptor Agonist

Provided herein is a TLR agonist. The TLR agonist may be a PAMP, which may be conserved molecular product derived from a pathogen. The pathogen may be a Gram-positive bacterium, Gram-negative bacterium, fungus, or virus. The TLR agonist may be a damage-associated molecular pattern (DAMP) ligand, which may be an endogenous molecule released from injured or dying cells. A DAMP or PAMP may initiate an immune response through TLR signals and recruit adapter molecules within the cytoplasm of cells in order to propagate a signal. The TLR agonist may be an agonist for the TLR, which may be a ligand from the following in Table 1:

TABLE 1

TLRs and Ligands

| TLR | Ligand DAMP | Ligand PAMP |
|---|---|---|
| TLR1 |  | Triacyl lipoproteins |
| TLR2 | Heat Shock proteins | Peptidoglycan |
|  | HMGB1 (high mobility group box 1 - amphoterin) | Lipoprotein |
|  |  | Lipoteichoic acid |
|  |  | Zymosan |
| TLR3 | Self dsRNA | Viral dsRNA |
| TLR4 | Heat shock proteins | Heat shock proteins |
|  | Fibrinogen | Lipopolysaccharides |
|  | Heparan sulfate | RSV fusion protein |
|  | Fibronectin | MMTV (Mouse mammary tumor virus) envelope proteins |
|  | Hyaluronic acid | Paclitaxel |
|  | HMGB1 |  |
| TLR5 |  | flagellin |
| TLR6 |  | Lipoteichoic acid |
|  |  | Triacyl lipoproteins |
|  |  | zymosan |
| TLR7/TLR8 | Self ssRNA | Viral ssRNA |
| TLR9 | Self DNA | Bacterial and viral DNA |
| TLR10 |  |  |
| TLR11 |  | Profilin |

The TLR agonist may be a fragment, variant, analog, homology or derivative of a PAMP or DAMP that binds a TLR and induces TLR-mediated activity, such as activation of NF-κB activity. The TLR agonist fragment, variant, analog, homolog, or derivative may be at least 30-99% identical to amino acids of a TLR-agonist and induce TLR-mediated activity.

The TLR agonist may target a TLR such as TLR-5. The TLR agonist may be an agonist of TLR-5 and stimulate TLR-5 activity. The TLR agonist may be an anti-TLR5 antibody or other small molecule. The TLR agonist may be flagellin.

Figure 3:
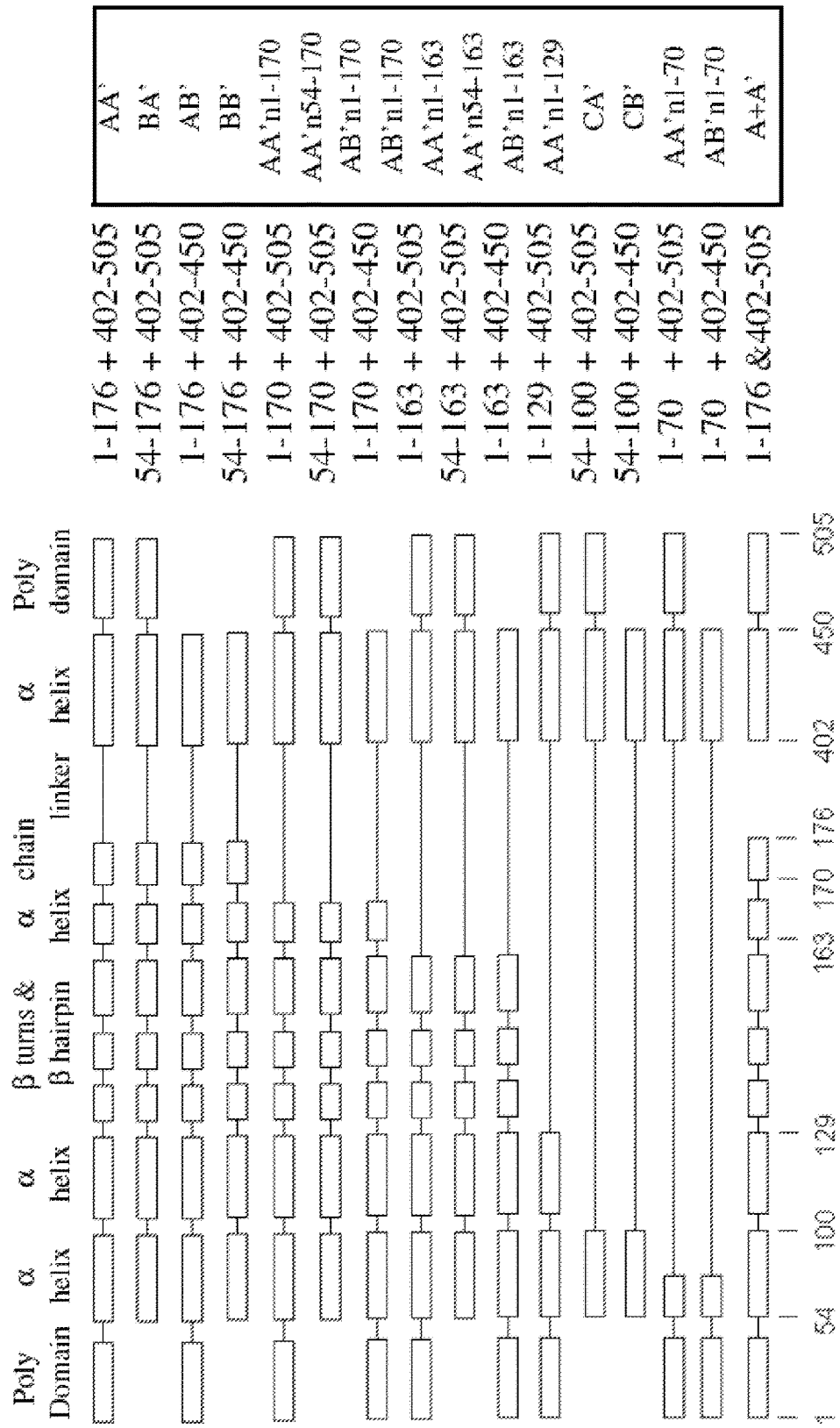
FIG. 3 depicts flagellin derivatives. The domain structure and approximate boundaries (amino acid coordinates) of selected flagellin derivatives (listed on the right). FliC flagellin of *Salmonella* dublin is encoded within 505 amino acids (aa).

The flagellin may also be a flagellin or flagellin-related polypeptide. The flagellin may be from any source, including a variety of Gram-positive and Gram-negative bacterial species. The flagellin may be a flagellin polypeptide from any Gram-positive or Gram-negative bacterial species including, but not limited to, a flagellin polypeptide disclosed in U.S. Pat. Pub. No. 2003/000044429, the contents of which are fully incorporated herein by reference. For example, the flagellin may have an amino acid sequence from a bacterial species depicted in FIG. 7 of U.S. Patent Publication No. 2003/0044429. The nucleotide sequences encoding the flagellin polypeptides listed in FIG. 7 of U.S. 2003/0044429 are publicly available at sources including the NCBI Genbank database. The flagellin may also be a flagellin peptide corresponding to an Accession number listed in the BLAST results shown in FIG. 25 of U.S. Patent Pub. 2003/000044429, or a variant thereof. The flagellin may also be a flagellin polypeptide as disclosed in U.S. Patent Appl. Publication No. 2009/0011982, the contents of which are fully incorporated herein. The flagellin maybe any one of a flagellin polypeptide as disclosed in FIGS. 3 and 4 herein.

The flagellin may be a fragment, variant, analog, homology or derivative of a flagellin that binds TLR5 and induces TLR5-mediated activity, such as activation of NF-κB activity. A fragment, variant, analog, homolog, or derivative of flagellin may be at least 30-99% identical to amino acids of a flagellin that binds TLR5 and induces TLR5-mediated activity.

The flagellin may be from a species of *Salmonella*, a representative example of which is S. dublin (encoded by GenBank Accession Number M84972). The flagellin related-polypeptide may be a fragment, variant, analog, homolog, or derivative of M84972, or combination thereof, that binds to TLR5 and induces TLR5-mediated activity, such as activation of NF-kB activity. A fragment, variant, analog, homolog, or derivative of flagellin may be obtained by rational-based design based on the domain structure of Flagellin and the conserved structure recognized by TLR5.

Figure 2:
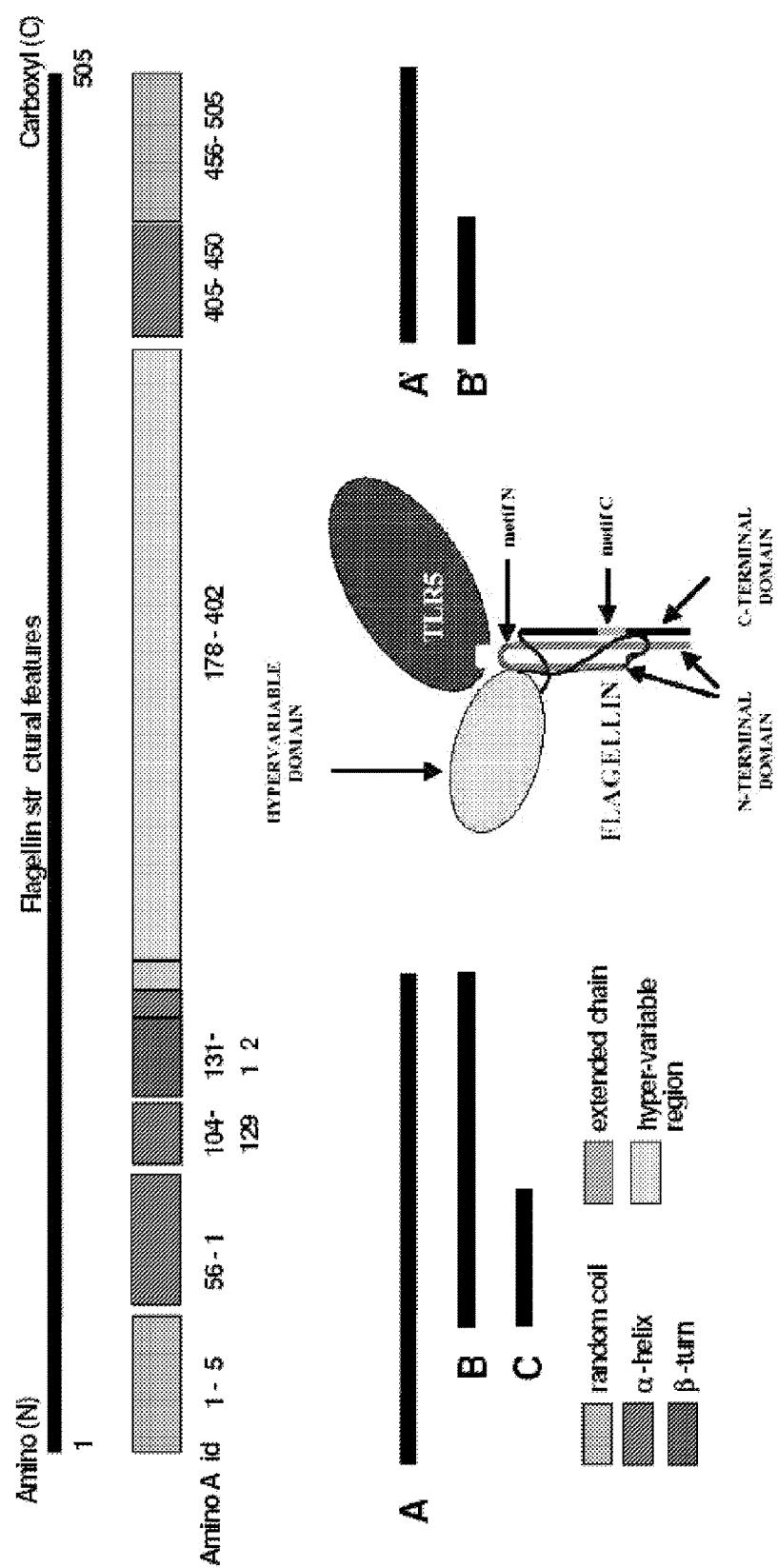
FIG. 2 shows a schematic of *Salmonella* flagellin domains, its fragments, and its interaction with TLR5. Dark bars denote regions of the flagellin gene used to construct fragments comprising A, B, C, A' and B'.

The flagellin may comprise at least 10, 11, 12, or 13 of the 13 conserved amino acids shown in FIG. 2 (positions 89, 90, 91, 95, 98, 101, 115, 422, 423, 426, 431, 436 and 452). The flagellin may be at least 30-99% identical to amino acids 1 174 and 418 505 of M84972. FIG. 26 of U.S. Patent Appl Publication No. 2009/0011982, the contents of which are fully incorporated herein, lists the percentage identity of the amino—and carboxy-terminus of flagellin with known TLR-5 stimulating activity, as compared to M84972.

The flagellin may be the major component of bacterial flagellum. The flagellin may be composed of three domains (FIG. 1). Domain 1 (D1) and domain 2 (D2) may be discontinuous and may be formed when residues in the amino terminus and carboxy terminus are juxtaposed by the formation of a hairpin structure. The amino and carboxy terminus comprising the D1 and D2 domains may be most conserved, whereas the middle hypervariable domain (D3) may be highly variable. Studies with a recombinant protein containing the amino D1 and D2 and carboxyl D1 and D2 separated by an *Escherichia coli* hinge (ND1-2/ECH/CD2) indicate that D1 and D2 may be bioactive when coupled to an ECH element. This chimera, but not the hinge alone, may induce IkBa degradation, NF-kB activation, and NO and IL-8 production in two intestinal epithelial cell lines. The non-conserved D3 domain may be on the surface of the flagellar filament and may contain the major antigenic epitopes. The potent proinflammatory activity of flagellin may reside in the highly conserved N and C D1 and D2 regions (See FIG. 1).

The flagellin may induce NF-kB activity by binding to Toll-like receptor 5 (TLR5). The TLR may recognize a conserved structure that is particular to the flagellin. The conserved structure may be composed of a large group of residues that are somewhat permissive to variation in amino acid content. Smith et al., Nat Immunol. 4:1247-53 (2003), the contents of which are incorporated herein by reference, have identified 13 conserved amino acids in flagellin that are part of the conserved structure recognized by TLR5. The 13 conserved amino acids of flagellin that may be important for TLR5 activity are shown in FIG. 2.

Numerous deletional mutants of flagellin have been made that retain at least some TLR5 stimulating activity. The flagellin may be such a deletional mutant, and may be a deletional mutant disclosed in the Examples herein. The flagellin may comprise a sequence translated from GenBank Accession number D13689 missing amino acids 185-306 or 444-492, or from GenBank Accession number M84973 missing amino acids 179-415, or a variant thereof.

The flagellin may comprise transposon insertions and changes to the variable D3 domain. The D3 domain may be substituted in part, or in whole, with a hinge or linker polypeptide that allows the D1 and D2 domains to properly fold such that the variant stimulates TLR5 activity. The variant hinge elements may be found in the *E. coli* MukB protein and may have a sequence as set forth in International Application No. PCT/US10/51646, filed on Oct. 6, 2010, the contents of which are incorporated herein by reference.

The flagellin as described above may further comprise a leader sequence. The flagellin further comprising a leader sequence may be CBLB502S.

3. Agent

This invention also relates to an agent comprising a therapeutically effective amount of a TLR agonist. The agent may be a polypeptide. The agent may also be a vector. The vector may comprise a nucleic acid encoding the TLR agonist. The vector may be capable of transducing mammalian cells. The vector may be delivered into a mammalian cell by a virus or liposome related vector system. The virus vector system may be an adenovirus or a cytomegalovirus.

The agent may be a liposome harboring the vector. The liposome maybe capable of transducing mammalian cells and delivering the vector for expression.

The agent may be a drug formulation that activates a TLR, thereby exposing tumor or infected cells to the host immune system imitating the situation of a massive penetration through the intestinal wall. The agent may be delivered systematically in solution for administration such as intramuscularly. The agent may be a drug formulation that expresses the TLR agonist in the form of a nano-particle, which may carry a functional agonist to the cell surface of a mammalian cell.

The agent may be a pharmaceutical agent comprising the drug formulation described above, which may be produced using methods well known in the art. The agent may also comprise a coagent.

The vector may comprise a nucleic acid encoding flagellin. The vector may be capable of expressing flagellin using a strong promoter. The expression vector may further comprise a leader sequence cloned upstream of the gene encoding the TLR agonist. The drug formulation may be an adenovirus expressing:

the TLR agonist, delivered systematically in solution for administration, such as intramuscularly; or the TLR agonist, expressed in the form of nano-particles carrying functional TLR agonist, such as flagellin, which may be derived from CBLB502, on their surface. The nano-particle may be on the basis of a bacteriophage T7, or fully formed to retain its biological activity. The nano-formulation may provide for dose-dependent, NF-κB-responsive reporter activation, and may result in cell internalization by endocytosis for effective immunization approach (Mobian AP-A).

a. Administration

Administration of the agents using the method described herein may be systemically, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. Administration may also be subcutaneous, intravenous, via intra-air duct, or intra-tumoral. For veterinary use, the agent may be administered as a suitably acceptable formulation in accordance with normal veterinary practice. The veterinarian can readily determine the dosing regimen and route of administration that is most appropriate for a particular animal. The agents may be administered to a human patient, cat, dog, large animal, or an avian.

The agent may be administered as a monotherapy or simultaneously or metronomically with other treatments, which may be a surgery or removal of a tumor. The term "simultaneous" or "simultaneously" as used herein, means that the agent and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The agent may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. The agent may be administered at any point prior to a second treatment of the agent including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The agent may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The agent may be administered at any point prior after a second treatment of the agent including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

b. Formulation

The method may comprise administering the agent. Agents provided herein may be in the form of tablets or lozenges formulated in a conventional manner. For example, tablets and capsules for oral administration may contain conventional excipients may be binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers may be lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants may be potato starch and sodium starch glycollate. Wetting agents may be sodium lauryl sulfate. Tablets may be coated according to methods well known in the art.

Agents provided herein may also be liquid formulations such as aqueous or oily suspensions, solutions, emulsions, syrups, and elixirs. The agents may also be formulated as a dry product for constitution with water or other suitable vehicle before use. Such liquid preparations may contain additives such as suspending agents, emulsifying agents, nonaqueous vehicles and preservatives. Suspending agent may be sorbitol syrup, methyl cellulose, glucose/sugar syrup, gelatin, hydroxyethylcellulose, carboxymethyl cellulose, aluminum stearate gel, and hydrogenated edible fats. Emulsifying agents may be lecithin, sorbitan monooleate, and acacia. Nonaqueous vehicles may be edible oils, almond oil, fractionated coconut oil, oily esters, propylene glycol, and ethyl alcohol. Preservatives may be methyl or propyl p-hydroxybenzoate and sorbic acid.

Agents provided herein may also be formulated as suppositories, which may contain suppository bases such as cocoa butter or glycerides. Agents provided herein may also be formulated for inhalation, which may be in a form such as a solution, suspension, or emulsion that may be administered as a dry powder or in the form of an aerosol using a propellant, such as dichlorodifluoromethane or trichlorofluoromethane. Agents provided herein may also be formulated as transdermal formulations comprising aqueous or nonaqueous vehicles such as creams, ointments, lotions, pastes, medicated plaster, patch, or membrane.

Agents provided herein may also be formulated for parenteral administration such as by injection, intratumor injection or continuous infusion. Formulations for injection may be in the form of suspensions, solutions, or emulsions in oily or aqueous vehicles, and may contain formulation agents including, but not limited to, suspending, stabilizing, and dispersing agents. The agent may also be provided in a powder form for reconstitution with a suitable vehicle including, but not limited to, sterile, pyrogen-free water.

Agents provided herein may also be formulated as a depot preparation, which may be administered by implantation or by intramuscular injection. The agents may be formulated with suitable polymeric or hydrophobic materials (as an emulsion in an acceptable oil, for example), ion exchange resins, or as sparingly soluble derivatives (as a sparingly soluble salt, for example).

c. Dosage

The method may comprise administering a therapeutically effective amount of the agent to a patient in need thereof. The therapeutically effective amount required for use in therapy varies with the nature of the condition being treated, the length of time desired to activate TLR activity, and the age/condition of the patient. In general, however, doses employed for adult human treatment typically are in the range of 0.001 mg/kg to about 200 mg/kg per day. The dose may be about 1 mg/kg to about 100 mg/kg per day. The desired dose may be conveniently administered in a single dose, or as multiple doses administered at appropriate intervals, for example as two, three, four or more sub-doses per day. Multiple doses may be desired, or required.

The dosage may be at any dosage such as about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 25 mg/kg, 50 mg/kg, 75 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg or 1 mg/kg.

d. Monotherapy

The agent may be administered as a monotherapy, under which the agent is not administered together with any other type of cancer treatment, such as chemotherapy, radiation therapy, another biological therapy, or other combination therapies; provided that "monotherapy" may include administration of the agent together with surgical treatment. The agent may be administered in combination with a surgery, which may be tumor removal. The agent may be administered prior to, together with, or after the surgery. The agent may be administered during the surgery.

4. Method For Treating Cancer

Provided herein is a method for treating cancer, which may be present in a tissue that expresses a TLR such as TLR5, by administering to a mammal in need thereof the agent. The cancer may be a tumor or a metastatic cancer. The cancer may also be present in liver, bladder, lung, or intestinal tissue, and also may have originated in another type of tissue such as colon, breast, or prostate. The cancer may also be melanoma or a hematological malignancy such as lymphoma. The cancer may also be any cancer that has metastasized to a TLR-expressing tissue, such as liver, lung, bladder, intestine, or other TLR-expressing tissue. The cancer may be a TLR-negative cancer, and thus lack expression of a Toll-Like Receptor. The cancer may lack both endogenous and exogenous expression of the Toll-Like Receptor. The method may comprise a step of not providing the Toll-Like Receptor to the cancer, which may include not providing the Toll-Like Receptor either exogenously or endogenously. The cancer may lack any and all Toll-Like Receptor expression.

a. Toll-Like Receptor

The Toll-Like Receptor (TLR) may recognize molecules that are conserved molecular products derived from pathogens that include Gram-positive, Gram-negative bacteria, fungi, and viruses, but are distinguishable from host molecules, collectively referred to as pathogen-associated molecular patterns (PAMPs). The TLR may also recognize endogenous molecules released from injured or dying cells, collectively referred to as damage-associated molecular pattern (DAMPs). A PAMP or DAMP may be a TLR agonist as further described below. The TLR may be a fragment, variant, analog, homolog or derivative that recruits adapter molecules within the cytoplasm of cells in order to propagate a signal. The TLR may be from a human or other mammalian species such as rhesus monkey, mouse, or rat. The TLR may be at least 30-99% identical to a TLR that recruits adapter molecules within the cytoplasm of cells in order to propagate a signal.

The TLR may be one of the between ten and fifteen types of TLR that are estimated to exist in most mammalian species. The TLR may be one of the 13 TLR (named simply TLR1 to TLR13) that have been identified in humans and mice together, or may be an equivalent form that has been found in other mammalian species. The TLR may be one of the 11 members (TLR1-TLR11) that have been identified in humans.

The TLR may ordinarily be expressed by different types of immune cells, and may be located on the cell surface or in the cell cytoplasm. The TLR may ordinarily be expressed on cancer cells. The TLR may ordinarily be expressed by normal epithelial cells in the digestive system, normal keratinocytes in the skin, alveolar and bronchial epithelial cells, and epithelial cells of the female reproductive tract. These cells lining an organ may be the first line of defense against invasion of microorganisms, and TLRs ordinarily expressed in epithelial cells may have a crucial role in the regulation of proliferation and apoptosis.

The TLR may not be expressed by the cancer cells. The TLR-negative cancer cells may not express any TLR mRNA, may not express any TLR protein, or may not express any functional TLR protein. The TLR protein may not function due to reduced ability to bind a TLR ligand or reduced ability to transmit downstream signals triggered by ligand binding. The TLR-negative cancer cells may also have reduced levels of TLR mRNA, protein, or TLR function. The reduction may be 100%, or by more than 99.9%, 99%, 95%, 90%, 85%, 80%, 75%, 70%, 65%, 60%, 55%, or 50%, as compared to a normal cell from the tissue from which the cancer cell originated, or as compared to another, known TLR-expressing cell type. The TLR-expressing cell may be a normal cell or a tumor cell, such as a tumor cell line or tumor xenograft.

The TLR ordinarily expressed on cancer cells may upregulate the NF-κB cascade and produce anti-apoptotic proteins that contribute to carcinogenesis and cancer cell proliferation.

Four adapter molecules of TLRs are known to be involved in signaling. These proteins are known as myeloid differentiation factor 88 (MyD88), Tirap (also called Mal), Trif, and Tram. The adapters activate other molecules within the cell, including certain protein kinases (IRAK1, IRAK4, TBK1, and IKKi) that amplify the signal, and ultimately lead to the induction or suppression of genes that orchestrate the inflammatory response. TLR signaling pathways during pathogen recognition may induce immune reactions via extracellular and intracellular pathways mediated by MyD88, nuclear factor kappa-light-chain-enhancer of activated B cells (NF-κB), and mitogen-associated protein kinase (MAPK). In all, thousands of genes are activated by TLR signaling, and collectively, the TLR constitute one of the most pleiotropic, yet tightly regulated gateways for gene modulation.

TLRs together with the Interleukin-1 receptors form a receptor superfamily, known as the "Interleukin-1 Receptor/Toll-Like Receptor Superfamily." All members of this family have in common a so-called TIR (Toll-IL-1 receptor) domain. Three subgroups of TIR domains may exist. Proteins with subgroup I TIR domains are receptors for interleukins that are produced by macrophages, monocytes and dendritic cells and all have extracellular Immunoglobulin (Ig) domains. Proteins with subgroup II TIR domains are classical TLRs, and bind directly or indirectly to molecules of microbial origin. A third subgroup of proteins containing TIR domains (III) consists of adaptor proteins that are exclusively cytosolic and mediate signaling from proteins of subgroups 1 and 2. The TLR may be a fragment, variant, analog, homolog or derivative that retains either a subgroup I TIR domain, subgroup II TIR domain, or subgroup III TIR domain.

The TLR may function as a dimer. For example, although most TLRs appear to function as homodimers, TLR2 forms heterodimers with TLR1 or TLR6, each dimer having a different ligand specificity. The TLR may also depend on other co-receptors for full ligand sensitivity, such as in the case of TLR4's recognition of LPS, which requires MD-2. CD14 and LPS Binding Protein (LBP) are known to facilitate the presentation of LPS to MD-2.

(1) TLR1

The TLR may be TLR1, which recognizes PAMPs with a specificity for gram-positive bacteria. TLR1 has also been designated as CD281.

(2) TLR5

The TLR may be Toll-Like Receptor 5. The protein encoded by the TLR5 may play a fundamental role in pathogen recognition and activation of innate immunity. TLR5 may recognize PAMPs that are expressed on infectious agents, and mediate the production of cytokines necessary for the development of effective immunity. TLR5 may recognize bacterial flagellin, a principal component of bacterial flagella and a virulence factor. The activation of the TLR5 may mobilize the nuclear factor NF-κB and stimulate tumor necrosis factor-alpha production.

(3) Cancer Type

The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis.

The metastatic cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The metastatic cancer may be due to a process such as lymphatic or hematogeneous spread. The metastatic cancer may also be caused by a tumor cell that comes to rest at another site, re-penetrates through the vessel or walls, continues to multiply, and eventually forms another clinically detectable tumor. The metastatic cancer may be this new tumor, which may be a metastatic (or secondary) tumor.

The metastatic cancer may be caused by tumor cells that have metastasized, which may be a secondary or metastatic tumor. The cells of the metastatic tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The metastatic cancer may have an origin from any tissue. The metastatic cancer may originate from melanoma, colon, breast, or prostate, and thus may be made up of cells that were originally skin, colon, breast, or prostate, respectively. The metastatic cancer may also be a hematological malignancy, which may be lymphoma. The metastatic cancer may invade a tissue such as liver, lung, bladder, or intestinal. The invaded tissue may express a TLR, while the metastatic cancer may or may not express a TLR.

b. Combination

The method may also comprise co-administration of the TLR agonist with an anti-cancer therapy. The anti-cancer therapy may be FAS ligand, a FAS agonistic antibody, TNFα, a TNFα agonistic antibody, TRAIL, or a TRAIL agonistic antibody. The TLR5 agonist may be used to sensitize the cancer to the anti-cancer therapy. The method may also be combined with other methods for treating cancer, including use of an immuno stimulant, cytokine, or chemotherapeutic. The immunostimulant may be a growth hormone, prolactin or vitamin D.

5. Method of Reducing Cancer Recurrence

Also provided herein is a method of reducing cancer recurrence, comprising administering to a mammal in need thereof a TLR agonist. The cancer may be or may have been present in a tissue that either does or does not express TLR, such as TLR5. The cancer, tissue, TLR, mammal, and agent may be as described above. The method may also prevent cancer recurrence. The cancer may be an oncological disease.

The cancer may be a dormant tumor, which may result from the metastasis of a cancer. The dormant tumor may also be left over from surgical removal of a tumor. The cancer recurrence may be tumor regrowth, a lung metastasis, or a liver metastasis.

6. Mammal

The mammal may have a fully-functional immune system, and may not be immunocompromised. The mammal may also have a level of immunity that is equivalent to the level sufficient to make the mammal eligible for a first or second round a chemotherapy. The mammal may not have a low white blood cell count, which may be chemotherapy-induced. The low white blood cell count may be caused by the loss of healthy cells during chemotherapy. The loss may be an expected side effect of a chemotherapy drug. The low white blood cell count may be a severe immunosuppression caused by chemotherapy. The low white blood cell count may compromise the antitumor effect of the agent. The low white blood cell count may be restored 7-14 days after a chemotherapy treatment.

The mammal may have a white blood cell count that is within a normal range. The mammal may also have a white blood cell count that is indicative of mild immunosuppression. The mammal may have not received chemotherapy treatment for 7-14 days, or at least 14 days. The mammal may also have total white blood cell count of at least 3000 or 3500 cells/ml of whole blood; a granulocyte count of at least 1800 or 2100 cells/ml of whole blood; or an albumin level of at least 3.0 or 3.5 g/100 ml of whole blood. The white blood cell count, granulocyte count, or albumin level may also fall within +/−5%, 10%, 20%, 30%, 40%, or 50% of these levels.

7. Method of Protecting Liver

As discussed above, anti-cancer treatments that trigger apoptosis through FAS, TRAIL, and TNFα death receptor signaling, such as death ligands, can cause severe liver toxicity. Thus, the use of molecules such as FAS, TRAIL, and TNFα as anti-cancer treatments has been limited, despite the efficacy of these molecules in targeting cancer cells. Accordingly, also provided herein is a method of protecting liver tissue in a mammal from the effects of a liver toxicity. The liver may be protected by administering the agent to the mammal. The death receptor signaling agonist may be FAS, TRAIL, or TNFα. The death ligand may be a liver toxicity. The FAS, TRAIL, or TNFα may be used as an anti-cancer agent.

The liver toxicity may also be a *Salmonella* infection, which may be from *Salmonella typhimurium*. The agent may also be used to protect against liver toxicity that may be FAS-mediated. The toxicity may also be FAS ligand, a FAS agonistic antibody, TNFα, acetaminophen, alcohol, a viral infection of the liver, or a chemotherapeutic agent. The agent may be administered to the mammal.

EXAMPLE 1

An Agonist of TLR5 Protects Liver from Hepatotoxicity

CBLB502, which is a pharmacologically optimized TLR5 agonist, is a powerful radioprotectant due to, at least in part, inhibition of apoptosis in radiosensitive tissues. CBLB502 was tested for liver protection from Fas-mediated apoptosis. The following examples demonstrate that upon stimulation with CBLB502 the TLR5 pathway is active in liver hepatocytes of mice and humans leading to NF-kB-dependent induction of genes encoding anti-apoptotic proteins. Pre-treatment of mice with CBLB502 protected them from lethal doses of Fas agonistic antibodies, reduced Fas-induced elevation of liver enzymes in the blood, caspase activity in liver extracts and preserved liver tissue integrity. CBLB502 did not protect tumors in syngeneic melanoma and colon carcinoma mouse models. These observations support the use of Fas agonists for cancer treatment under the protection of a TLR5 agonist, such as CBLB502.

NF-kB response was compared in different organs after administration of TLR5 agonist CBLB502 and TLR4 agonist LPS, another known activator of NF-kB. CBLB502 was found to induce fast direct activation of NF-kB in hepatocytes, while LPS activation of NF-kB in hepatocytes was mediated through different types of cells. The following data thus also demonstrate that pre-treatment with CBLB502 can reduce Fas-mediated hepatotoxicity during anti-cancer therapy in mice. The approaches described below are based on the increasing the resistance of normal tissues to damaging side effects through activation of NF-kB signaling by toll-like receptor-5 (TLR5) agonist CBLB502 derived from flagellin of Salmonella typhimurium.

1. Determination of NF-k Activation In Vivo in Response to TLR4 and TLR5 Agonists.

NF-kB response was investigated in different organs of mice to TLR5 agonist CBLB502 in comparison with bacterial LPS acting through TLR4. NF-kB dependent luciferase reporter Xenogen mouse model in which luciferase transgene is expressed under the control of NFkB-dependent natural promoter of IkBα gene (Zhang N, et al, 2005). Upon administration of NFkB-activating agents, luciferase activity was increased in cells and tissues that respond to a given agent. Using noninvasive Xenogen imaging system and ex vivo luciferase reporter assay, detected strong activation of NF-kB in liver of mice was detected 2 hours after s.c. injection of CBLB502 (FIG. 7A). The quantitative analysis of NF-kB activation in different organs revealed that in comparison with LPS, CBLB502 induced much stronger activation of NF-kB in liver, similar high NF-kB activation level in the intestine, while less NF-kB activity was found in spleen, bone marrow, kidney and lungs (FIG. 7B). The dynamics of NF-kB induced luciferase reporter activity was similar for both TLR agonists with the activation profile peaking approximately two hours after injection, reduced at the six hour time point and effectively undetectable 24 hours post-injection (FIG. 10A-D).

Immunohistochemical staining of mouse liver samples for p65 translocation to the nuclei revealed that CBLB502 directly activated NF-kB in hepatocytes as early as 20 min after injection with no response of Kupffer and endothelial cells yet (FIG. 7C). By 1 h after CBLB502 injection, all liver cells including Kupffer cells and endothelium cells demonstrated nuclear accumulation of p65 suggesting overlap of primary and secondary effects with subsequent activation of NF-kB by paracrine mechanisms. In contrast, LPS-activated NF-kB nuclear translocation in hepatocytes occurred significantly later. The activation of NF-kB was observed first in Kupffer and endothelial cells followed by the engagement of hepatocytes about 1 h after LPS administration.

Primary hepatocyte cultures (murine and human) treated with CBLB502, but not with LPS, demonstrated NF-kB translocation to the nuclei (FIG. 7D, E). CBLB502 mediated NF-kB activation was confirmed by NF-kB dependent luciferase expression with murine hepatocyte cell culture, while LPS did not induce NF-kB activation in this cells (FIG. 11). Small level of NF-kB activation found in LPS-treated hepatocytes was more likely due to contamination of primary hepatocyte culture with other stromal liver cells.

These results show that hepatocytes express TLR5 but not TLR4 allowing CBLB502 to directly activate NF-kB in hepatocytes while LPS initially activates other cell types (immune and/or stromal) and only later indirectly activates hepatocytes as a secondary event.

2. CBLB502 Protection from Fas Mediated Hepatotoxicity

Figure 12:
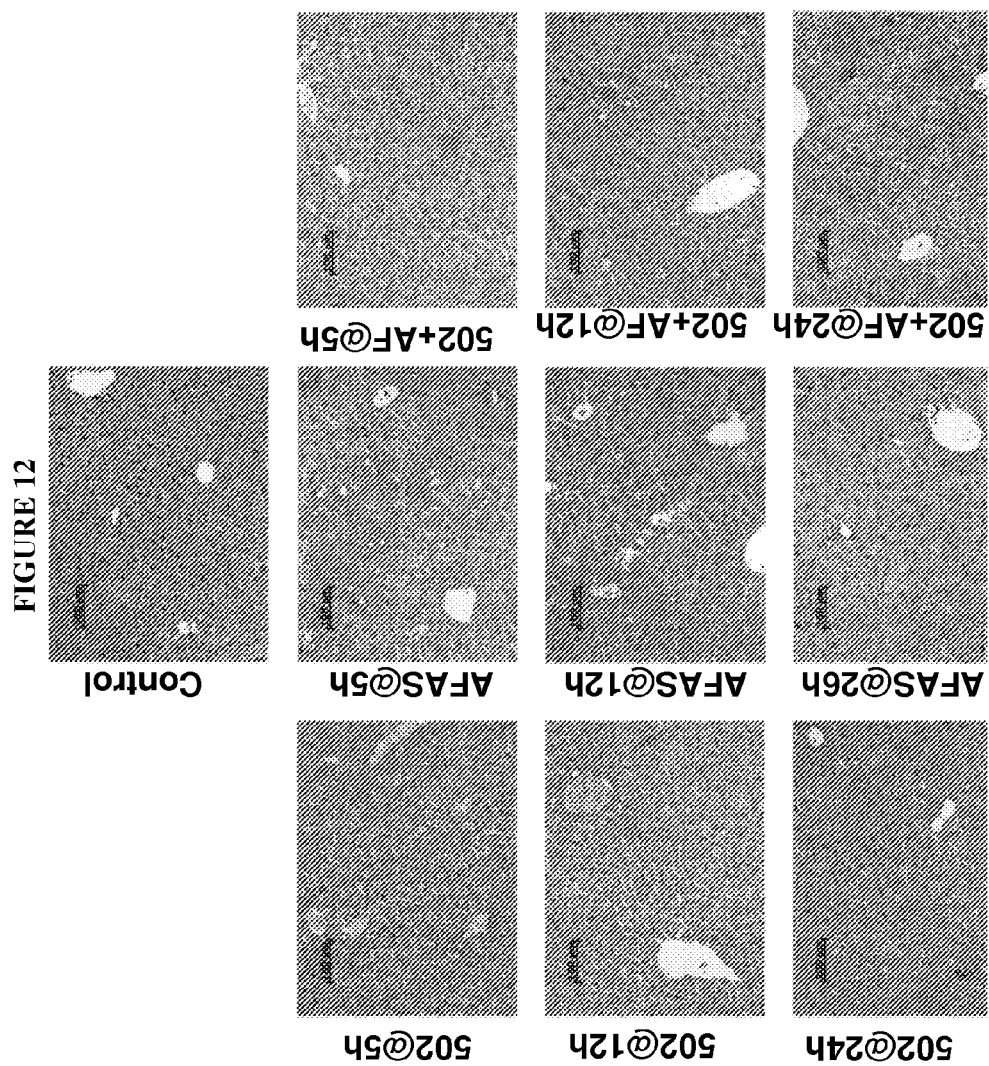
FIG. 12. H&E staining of liver samples from NIH-Swiss mice treated with CBLB502, anti-Fas antibodies (3 µg) or their combination obtained at different time-points after the treatment. Samples of livers were obtained 5, 12 and 26 hours after injections of anti-Fas antibodies, fixed in 10% formalin, embedded in paraffin and stained for tissue morphology with hematoxilin and eosin.

As it has been demonstrated, the anti-Fas antibodies can induce dose-dependent hepatotoxicity and rapidly kill mice by inducing apoptosis, liver tissue necrosis and hemorrhage (Ogasawara J et al, Nature 1993, Nishimura et al 1997). Thus, NF-kB activation in hepatocytes induced by TLR5 agonist CBLB502 may protect liver from Fas mediated apoptosis. In NIH-Swiss mice, 4 µg of anti-Fas antibodies (clone Jo2) injected i.p. induced massive apoptosis, necrosis and hemorrhage in liver (FIGS. 8B, C and D) killing mice within first 1-2 days after antibody injections (FIG. 8A). Pathomorphological examination of CBLB502-treated mice in dynamics compared to intact control mice showed that their livers had slight vacuolization of the hepatocytes (FIG. 12). The examination of mice injected with sub-lethal dose of anti-Fas antibodies (3 µg/mouse) in dynamics revealed pronounced apoptosis of the hepatocytes around the portal tracts with better preserved cells adjacent to the terminal (central) venues, most pronounced at 5 hrs and diminishing with time (12 and 24 hours post-injection). In the livers of mice treated with CBLB502 and anti-Fas antibodies the changes were minimal and the hepatocytes looked close to normal—only slight vacuolization and single apoptotic cells were visible.

CBLB502 injected mice had much less damage to the liver that deflected in better overall survival after injections of about than 80% of NIH-Swiss mice when injected 30 min before anti-Fas antibodies (FIG. 8A). All mice survived when CBLB502 was injected 2 hours before antibodies. The protection level then declined by 6 hours time-point of pre-treatment.

Figure 13:
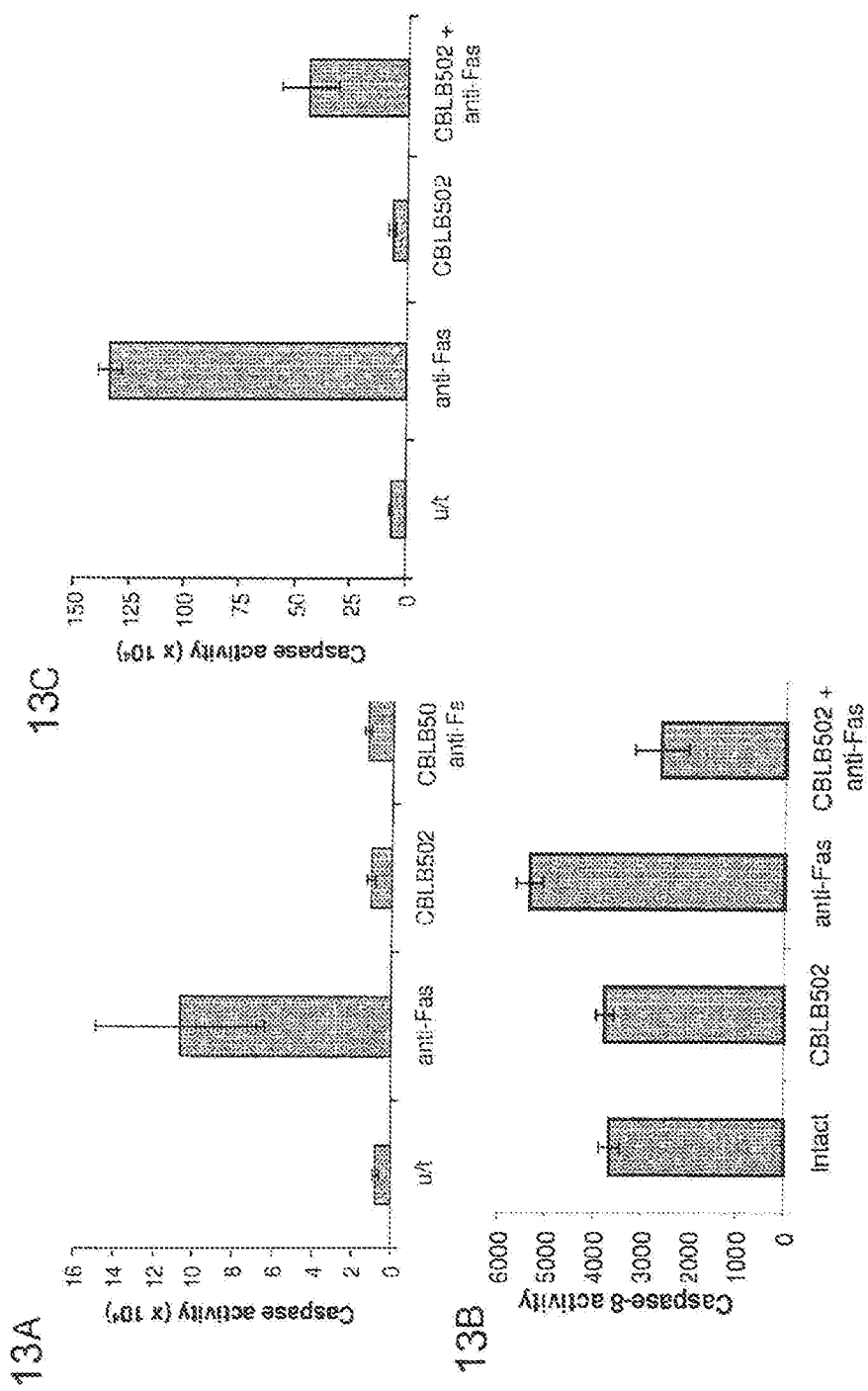
FIGS. 13A-C. Caspase-3/7 activity in liver samples of Balb/c and C57Bl/6 mice was determined in tissue protein lysates after injection of 4 µg anti-Fas antibody with or without CBLB502. Bars represent average+/−s.d.

Two and three µg of anti-Fas antibodies induced only transient liver toxicity in NIH-Swiss mice, caspase 3/7 activation in the liver and alanine aminotransferase (ALT) secretion in the blood (FIG. 8E, F). Both tests showed significant reduction of liver damage induced by anti-Fas antibodies if mice were pre-treated with CBLB502. Interestingly, Balb/c and C57Bl/6 mice appeared to be less sensitive to anti-Fas antibodies than NIH-Swiss mice. Four µg of anti-Fas antibodies, the lethal dose for NIH-Swiss mice, induced only transient caspase 3/7 activation in BALB/c and C57Bl/6 mice which was successfully prevented by CBLB502 injection 30 min before antibodies (FIG. 13A-C).

These data support the hypothesis that TLR5 mediated NF-kB activation in hepatocytes can be an indicator and a measure of increased resistance to Fas-mediated toxicity.

3. Suppression of Pro-Apoptotic and Induction of Anti-Apoptotic Factors by CBLB502 in Liver.

Caspases 3 and 7 are downstream targets of both intrinsic (mitochondrial) and extrinsic (caspase) Fas-mediated apoptosis signaling. Upon activation of the receptor, first caspase-8 becomes phosphorylated and cleaved leading to activation of mitochondrial apoptotic mechanism acting through cleavage of pro-apoptotic Bid protein and cytochrome release (Lou et al 1998). Therefore we examined whether CBLB502 suppresses this mechanism.

Western blot analysis of liver protein extracts for both caspases-8 and Bid demonstrated much less cleavage of these proteins in mice injected with combination of CBLB502 and anti-Fas antibodies in comparison with a single injection of anti-Fas antibodies (FIG. 9A, B). Consistently, caspase 8 activation was reduced to a background level, as indicated by using fluorigenic substrate assay (FIG. 8F).

The fact that the protection of mice from Fas-mediated hepatotoxicity by CBLB502 is increased with time with maximum peaking at 30 min-2 hours suggests the existing of pre-conditioning events in hepatocytes. Among the numerous of cytokines and anti-apoptotic factors, the up-regulation of two anti-apoptotic bcl2 family members bcl2A1B and bcl2A1D (Chao and Korsmeyer, 1998, Arikawa et al 2006) was found in livers by RNA array hybridization 30 min and 2 hours after CBLB502 administration that was confirmed by RT-PCR (FIG. 9C). CBLB502 also quickly induced RNA expression of another anti-apoptotic protein immediate early response protein IER-3 (FIG. 9C, IEX-1 is an alternative name) that was shown suppressing the production of reactive oxygen species and mitochondrial apoptotic pathway (Shen et al 2009). RT-PCR analysis of liver samples revealed the induction of IER-3 RNA expression by CBLB502 already 30 min after administration with significant increase by 2 hours. Several proteins of MAPK pathway were found up-regulated in livers of CBLB502 treated mice. It was demonstrated that activation of MAPK pathway in tumors mediates the resistance of these cells to Fas receptor apoptosis (REF). The up-regulation of Jun, Jun-B and Fos gene expressions directly correlated with mouse survival after anti-Fas antibody injections followed the pre-treatment with CBLB502 suggesting their possible role in CBLB502 mediated protection from Fas hepatotoxicity.

4. Effect of CBLB502 on Fas-Mediated Antitumor Activity

Figure 14:
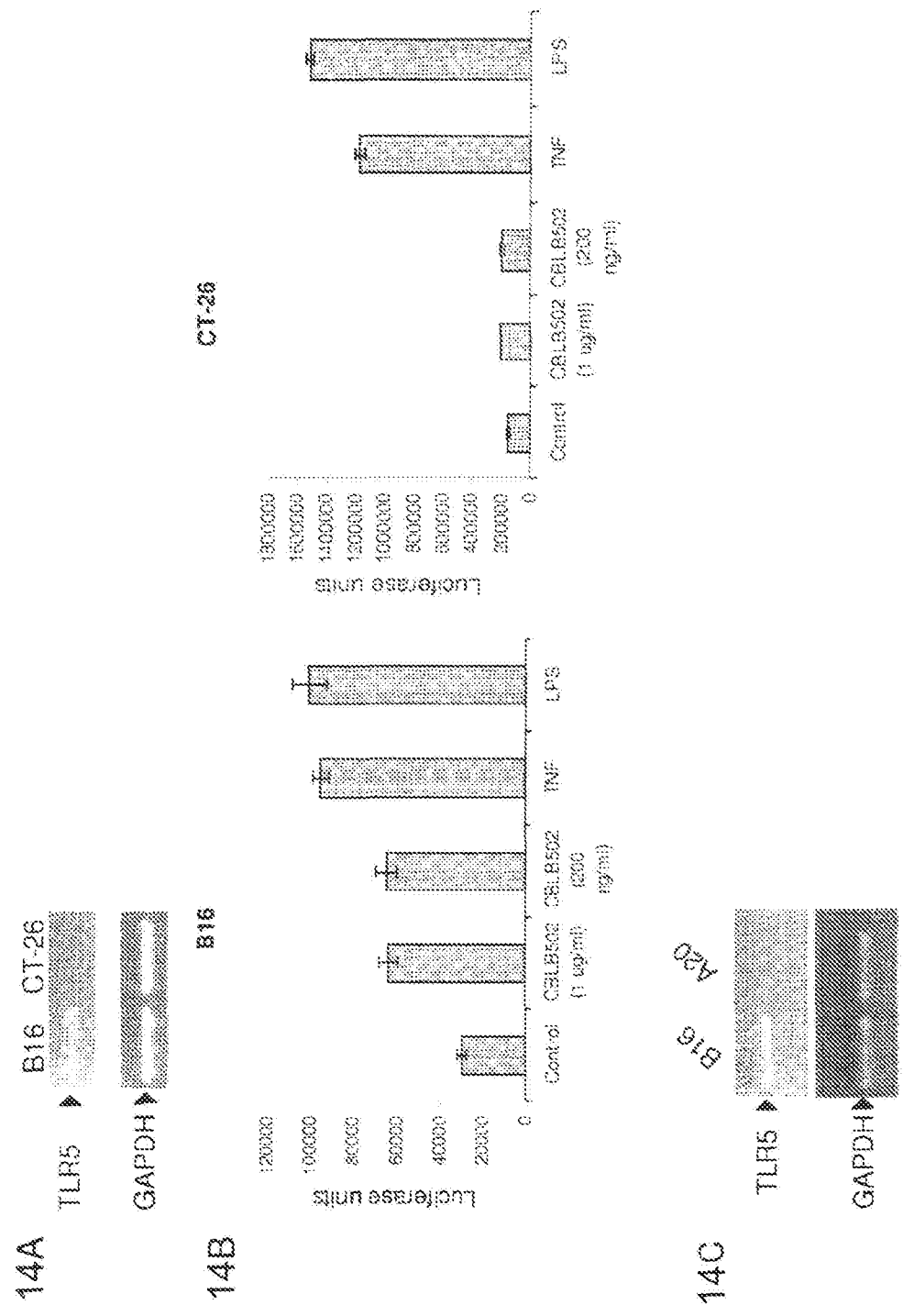
FIGS. 14A-C. TLR5 expression in B16, CT-26 tumor cells and A20 lymphoma cells. For FIGS. 14A and 14C, total RNA was extracted from CT-26 and B16 tumor cells (FIG. 14A) and CT-26 and A20 cells (FIG. 14C) using TRIzol reagent. The primers for TLR5 were designed using LaserGene software (DNASTAR, Inc., Madison, Wis.). A region of mouse TLR5 mRNA (GenBank Accession No. NM_016928.2) was amplified using primers specific for the mouse TLR5 gene: forward (5'-AGTCCCCCAGCTCCA-GTTTC-3'; SEQ ID NO: 99) and reverse (5'-GGAGC-CCCCTAGCAGTGAGT-3'; SEQ ID NO: 100). GAPDH was used as a control to monitor the induction of gene expression. cDNAs were synthesized using Superscript™ II Reverse Transcriptase and oligo(dT)12-18 primer (Invitrogen, Carlsbad, Calif.).

LPS is not a good candidate for clinical application, since it induces strong inflammation in many organs and can be directly cytotoxic through FADD/caspase-8 apoptotic pathway (REFs). CBLB502 in its turn has been tested in mice, non-human primates and human healthy volunteers and found to be a rather mild inducer of short-lasting inflammation. When evaluating a tissue protecting compounds, there is always possibility that by reducing toxic side effects it can also make tumor cells more resistant and jeopardize the efficacy of antitumor therapy. The in vivo antitumor effect of combination treatment with CBLB502 and anti-Fas antibodies was tested in CT-26 colon carcinoma mouse model of s.c. growing tumors and experimental liver metastases. This tumor model was used in a recently published study applying FasL-expressing *S. typhimurium*, total attenuated bacteria, to deliver FasL to the tropic tumors and to induce Fas mediated antitumor effect (Loeffler et al 2008). CT-26 tumor cells and A20 lymphoma cells do not express TLR5, as determined by RT-PCR and a NF-kB dependent luciferase reporter assay (FIG. 14A-C). Here, tumor-bearing mice were treated with anti-Fas antibodies alone or combination of recombinant CBLB502 given twice 24 hs and 1 h before a single injection of anti-Fas antibodies (4 μg/mouse, FIG. 9D). The volumes of s.c. growing tumors in treated mice were compared with tumors growing in the intact mice. CT-26 tumors were found to be rather resistant to the toxic but not lethal dose of anti-Fas antibodies (FIG. 9D). Pre-treatment with CBLB502 slightly sensitized tumors to anti-Fas antibodies reflecting in growth-inhibitory tumor response. Fas mediated antitumor effect was tested in the experimental model of liver metastases induced by intrasplenic injection of luciferase expressing CT-26 tumor cells followed by splenectomy. Hepatic tumor growth was assessed using Xenogen luciferase imaging every 4-6 days after the treatment. Mice remained free from liver tumor growth were counted at each imaging procedure (FIG. 9E). The results demonstrate significant delay of tumor appearance (FIG. 9G) and growth in livers by both treatments, anti-Fas antibody alone or given after pre-treatment with CBLB502. The increased sensitivity of TLR5 negative CT-26 tumors to combination treatment with anti-Fas and CBLB502 suggests the activation of antitumor immune response against CT-26 tumors. Indeed, the immunohistochemical analysis of liver sample with CT-26 tumors taken 24 hours after anti-Fas/CBLB502 treatment revealed the accumulation of neutrophils in inside and around of tumor nodules (FIG. 9F). Thus, CBLB502 does not protect tumors from anti-Fas antibodies toxicity and can even slightly enhance Fas mediated antitumor effect against CT-26 tumors. The simultaneous protection of normal liver tissue from Fas mediated toxicity may allow increasing the amount of the Fas agonist reaching complete prevention of liver metastases and the therapeutic effect against s.c. growing tumors.

Materials and Methods

Mice

NIH-Swiss female mice were purchased from NCI (Frederick, Md.), BALB/c and C57B1/6 female mice were purchased from Jackson Laboratory (Bar Harbor, Me.). All mice were used in the experiments at the age of 10-14 weeks old. Balb/C-Tg (IκBα-luc)Xen mice with NF-kB inducible luciferase reporter gene were originally purchased from Xenogen (Alameda, Calif.) and bred in our domestic colony.

Reagents

CBLB502, a bacterial flagellin derivative, was obtained from Cleveland BioLabs, Inc. Bacterial lipopolysacharide (LPS) from *Escherichia coli* 055:B5 was purchased from Sigma. Purified agonistic hamster anti-mouse Fas antibodies, clone Jo2, were purchased from BD Biosciences.

Analysis of NF-κB Activation In Vivo Using NF-kB Reporter Mouse Model

BALB/c-Tg (IκBα-luc)Xen reporter mice were injected s.c. with CBLB502 (0.2 mg/kg). The induction of NF-kB by CBLB502 was detected by noninvasive in vivo imaging 2 hours after the treatment (FIG. 1A). Mice were injected with D-luciferin (3 mg/100 μl, i.p., Promega), immediately anesthetized with isofluorane and images were taken using Xenogen IVIS Imaging System 100 series. To quantify the results, samples of liver, lungs, kidney, spleen, heart and intestine from NF-kB reporter mice injected s.c. with 100 μl of either PBS, CBLB502 (0.2 mg/kg) or LPS (1 mg/kg) were obtained 2, 6 and 24 h after injections (FIG. 7B, 10A-D). Tissue samples were covered with lysis buffer containing proteinase inhibitor cocktail (according to manufacture's recommendation, Calbiochem) to get 100 mg tissue per 1 ml lysis buffer. This was followed by homogenization and centrifugation at 14,000 rpm for 10 min at 4 C. Luciferase activity was measured in 20 μl of samples immediately after adding 30 μl of luciferin reagent (Bright-Glo Luciferase Assay System, Promega). Luciferase activity was normalized per g of the protein extract. Luciferase fold induction was calculated as ratio between average luciferase units in livers of the TLR ligand treated mice and that obtained from PBS injected control mice.

Immunohistochemical Staining for p65 Translocation.

P65 localization was detected in livers isolated from NIH-Swiss mice injected s.c either with CBLB502 (0.04 mg/kg) or LPS (1 mg/kg). Control mice were injected with PBS. Tissue samples were obtained 20, 40 and 60 min after the treatments, processed into paraffin blocks. All liver tissues were stained with rabbit polyclonal antibody against NF-kB p65 and rat monoclonal antibody against cytokeratin 8 followed by appropriate secondary fluorochrome-conjugated antibodies (p65—green, cytokeratin-8—red). The same staining was performed on the plates with primary mouse hepatocytes isolated from EGTA (0.5 mM in PBS) perfused liver tissues of NIH-Swiss mice followed by collagenase digestion and with human hepatocyte culture purchased from (BD Biosciences). Both types of hepatocytes were treated in vitro with CBLB502 (100 ng/ml) or LPS (1 µg/ml) for indicated period of time. Control hepatocytes remained intact. Pictures were taken at ×20 magnification (FIG. 7C, D, E).

Survival Assay

NIH-Swiss mice were injected i.p. with 2, 3, 4, and 5 µg of anti-Fas antibodies in 200 µl of PBS to determine a 100% lethal dose that was found to be 4 µg/mouse for this mouse strain. Then CBLB502 (0.04 mg/kg, s.c.) was injected s.c. 30 min, 2 hours and 6 hours before 4 µg of anti-Fas antibodies (i.p.) (FIG. 8A). Usually death from anti-Fas hepatotoxicity occurs during first 1-2 days after antibody injections. Mouse survival was observed and recorded during 30 days.

TUNEL Staining of Apoptotic Cells in Liver

Apoptosis in the liver of NIH-Swiss mice five hours after injections with CBLB502 (s.c., 0.04 mg/kg) or PBS 30 min before anti-Fas antibodies was detected in paraffin-embedded specimens. Apoptotic cells were stained by the indirect terminal deoxynucleotidyl transferase mediated deoxyuridine tri-phosphate nick end labeling (TUNEL) method with TUNEL POD kit (Roche Applied Science) (FIG. 8C).

Histological Assessment of Liver Morphology

Liver specimens were collected from NIH-Swiss mice five hours (FIG. 8B) or in dynamics of 5, 12 and 26 hours after anti-Fas antibody injections with or without pre-treatment with CBLB502 (0.04 mg/kg) 30 minutes before antibodies. Mice that were not treated ("intact") were used as controls. Tissue specimens were fixed in 10% buffered formalin, embedded in paraffin, sectioned and processed with H&E staining.

Histological Staining of Liver for Hemorrhage

Paraffin sections were stained with antibody against mouse IgG conjugated with Cy5 [Jackson Immunoresearch, pseudo-colored in purple] and mounted with ProLong Gold anti-fade reagent with DAPI [Invitrogen, blue nuclear stain]. Erythrocytes were visualized in red channel by red autofluorescence. (FIG. 8D). Images were captured under AxioImager Z1 fluorescent microscope (Zeiss) equipped with AxioCam HRc 13 megapixel digital camera using Axio Vision software (rel. 4.6.3).

Caspase Activation

Livers were cut to small pieces and homogenized with a tissue grinder (Bullet Blender, NextAdvance) in the buffer (10 mM Hepes, 0.4 mM EDTA, 0.2% CHAPS, 2% glycerol), supplemented with 2 mM DTT. All steps were performed on ice. Liver homogenates were centrifuged for 20 min at 13,000×g, and supernatant was stored at −20.degree. C. Caspase activities were determined by incubation of liver homogenate (containing 50 µg of total protein) with 50 µM of the fluorogenic substrate acetyl-Asp(OMe)-Glu(OMe)-Val-Asp(OMe)-aminomethylcoumarin (Ac-DEVD-amc) (ENZO, LifeSciences) in 200 µl cell-free system buffer containing 10 mM HEPES, 0.4 mM EDTA, 0.2% CHAPS, 2% glycerol and 2 mM DTT. The release of fluorescent amc was measured after at time 0 and 2 hours of incubation at 37.degree. C. by fluorometry (Ex: 355, Em: 485) (Victor3, PerkinElmer). Data are shown as the difference between twp and zero hours (FIG. 8E).

Detection of Alanine-Aminotransferase (ALT) in the Serum of Anti-Fas Antibody-Treated Mice with and without CBLB502 Injections NIH-Swiss mice (3 per group) were injected s.c. with 1 µg CBLB502 30 min before anti-Fas antibodies. The alanine aminotransferase (ALT) presence in mouse serum was determined using commercial enzyme assays according to the manufacturer's instructions (Stanbio Laboratory, Boerne, Tex., USA). Absorbance at 340 nm was measured at 60 second interval (ΔA/minute). (FIG. 8F)

Western Blot Analysis

Total protein was isolated from treated and untreated mouse liver using RIPA buffer (Sigma-Aldrich St. Louis, Mo.) supplemented with protease inhibitor cocktail (Sigma-Aldrich St. Louis, Mo.). The protein extracts were separated by electrophoresis in denaturing 4 to 20% polyacrylamide Novex gels (Invitrogen, Carlsbad, Calif.) and transferred to nylon polyvinylidene difluoride (PVDF) membranes (Immobilon-P, Millipore Billerica Mass.). The following antibodies were used: Caspase-8 antibody (Calbiochem, Darmstadt, Germany), anti-BID (AbCam, Cambridge Mass.). Horseradish peroxidase (HRP)-conjugated secondary anti-rabbit and anti-mouse antibodies were purchased from Santa Cruz Biotechnology, Inc. (Santa Cruz, Calif.). (FIGS. 9A and 9B)

RNA Analysis

Total RNA was extracted from treated and untreated mouse livers using TRIzol reagent according to manufacturer instructions (Invitrogen, Carlsbad, Calif.). To eliminate any eventual contamination with genomic DNA, isolated RNAs were treated with DNaseI (Invitrogen, Carlsbad, Calif.). cDNAs were synthesized by using SuperScript™ II Reverse Transcriptase and oligo(dT)12-18 primer (Invitrogen, Carlsbad, Calif.), according to manufacturer instructions. RNA expression of Bcl2A1B, Bcl2A1D, IER-3, Fos, Jun and JunB genes in livers of intact mice and treated with CBLB502 and LPS for 30 min and 2 hours was detected by RT-PCR. GAPDH was used as a control to monitor the induction of gene expression. The primers were designed using LaserGene software (DNASTAR, Inc., Madison, Wis.) and then UCSC Genome Browser In-Silico PCR website was used to check for locating primers. Primers specific for the IER3 gene (GenBank Accession No. NM_133662.2) (sense 5'-ACTCGCGCAACCATCTCCA-CAC-3' (SEQ ID NO: 102) and antisense 5'-CTCGCAC-CAGGTACCCATCCAT-3' (SEQ ID NO: 103)), Bcl2A1B gene (GenBank Accession No. NM_007534.3) (sense 5'-TAGGTGGGCAGCAGCAGTCA-3' (SEQ ID NO: 104) and antisense 5'-CTCCATTCCGCCGTATCCAT-3' (SEQ ID NO: 105)), Bcl2A1D gene (GenBank Accession No. NM_007536.2) (sense 5'-TCTAGGTGGGCAGCAGCA-GTC-3' (SEQ ID NO: 106) and antisense 5'-ATTCCGCCG-TATCCATTCTCC-3' (SEQ ID NO: 107)), Jun (GenBank Accession No. NM_010591.2) (sense 5'-TGAAGC-CAAGGGTACACAAGAT-3' (SEQ ID NO: 108) and antisense 5'-GGACACCCAAACAAACAAACAT-3' (SEQ ID NO: 109)), Fos (GenBank Accession No. NM_010234.2) (sense 5'-GAGCGCAGAGCATCGGCAGAAG-3' (SEQ ID NO: 110) and antisense 5'-TTGAGAAGGGGCAGGGT-GAAGG-3' (SEQ ID NO: 111)), JunB (GenBank Accession No. NM_008416.2) (sense 5'-AGCCCTGGCAGCCT-GTCTCTAC-3' (SEQ ID NO: 112) and antisense 5'-GT-GATCACGCCGTTGCTGTTGG-3' (SEQ ID NO: 113)) and GAPDH gene (sense 5'-ACCACAGTCCATGCCATCAC-3' (SEQ ID NO: 114) and antisense 5'-TCCACCACCATGT-TGCTGTA-3' (SEQ ID NO: 115)) were used. Amplification of cDNA was done for 20-30 cycles using specific primer pairs for each gene (FIG. 9C).

Experimental Therapy of CT-26 Tumor-Bearing Mice

The effect of CBLB502 on the sensitivity of tumors to anti-Fas antibodies was analyzed using two models of syngenic colon adenocarcinoma CT-26 tumor: 1) CT-26 s.c. growing tumors, and 2) Experimental liver metastatic model of CT-26 tumors. CT-26 cells were transduced with lentiviral vector carrying luciferase gene under CMV promoter for constitutive expression of luciferase. Tumors were induced by s.c. injections of CT-26 tumor cells ($2.5 \times 10^5/100$ µl) in both flanks of BALB/c mice. When the tumors reached about 4-5 mm in diameter, the mice were randomly divided into three groups and treatment was initiated. One group of mice was injected i.p. with anti-Fas antibodies (4 µg/mouse), another was treated with CBLB502 (1 µg/mouse) 24 h and 1 h before anti-Fas antibody injection (4 µg/mouse). Control mice ('intact') received PBS injections s.c. and i.p. in replace of CBLB502 and antibodies. Tumor volumes were measured every second day using calipers and calculated by formula: V=.PI./6*a2*b, where a<b. Survival was followed for 2 weeks when experiment was terminated due to large tumors in the control group (FIG. 9D). Statistical difference between tumor volumes was estimated using ANOVA one-way analysis of variances ($p<0.05$). For the development of liver tumor growth, CT-26 tumor cells ($2 \times 10^5/50$ µl) were injected directly into spleen followed by splenectomy 5 min later. Mice were treated with anti-Fas antibodies and combination of CBLB502 with antibodies the same way as described for s.c. tumors starting on day 5 after tumor cell inoculation. Noninvasive bioluminescent imaging of mice anesthetized with isoflurane and injected with D-luciferin (3 mg/100 µl,i.p.) was performed using Xenogen IVIS Imaging System 100 series on the days 14, 17, 22 and 28 after tumor cell injection. Mice were sacrificed when tumor growth in liver was determined. Statistical comparison of liver tumor-free curves was done using log-rank (Mantel-Cox) test ($p<0.05$) (FIG. 9G).

EXAMPLE 2

Figure 15:
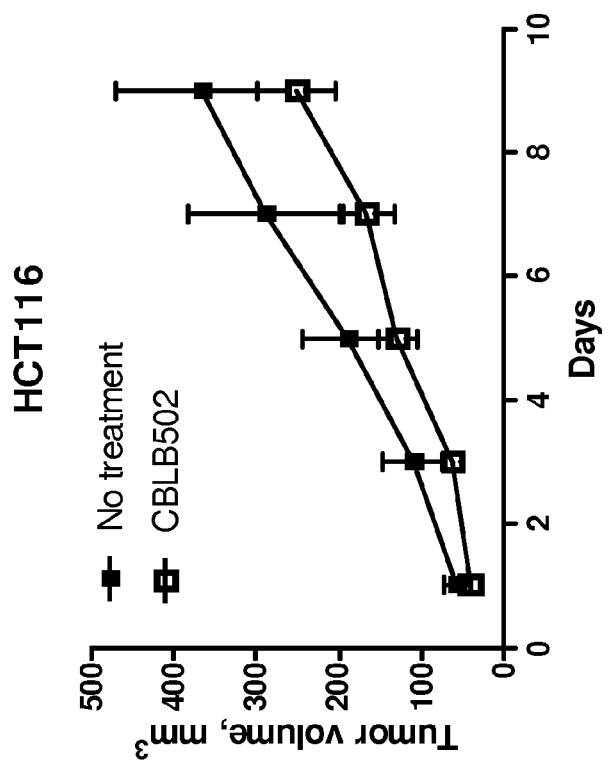
FIG. 15 shows the dynamics of TLR5 positive HCT116 tumor growth in athymic nude mice after CBLB502 or PBS (no treatment) treatments (0.2 mg/kg, s.c., days 1, 2, 3), n=6-10.

Antitumor activity of CBLB502 on colon HCT116 adenocarcinoma s.c. growth in xenogenic model of athymic mice. HCT116 were injected s.c. into 2 flanks of 8 athymic nude mice ($0.5 \times 10^6/100$ µl of PBS) to induce tumors. When tumors became of about 3-5 mm in diameter (by day 6 after injections) mice were randomly distributed into 2 groups, 5 mice for CBLB502 treated group and 3 mice in PBS control group. Suppression of tumor growth was determined in CBLB502 treated mice. Data are shown in FIG. 15.

EXAMPLE 3

Figure 16:
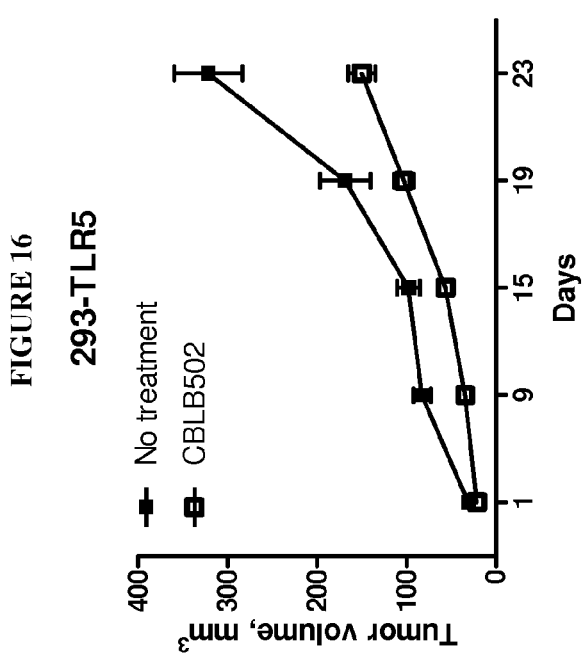
FIG. 16 shows 293-TLR5 tumor growth in athymic nude mice after CBLB502 or PBS (no treatment) treatments (0.2 mg/kg, s.c., days 1, 2, 3), n=6-10.

Antitumor activity of CBLB502 on 293-TLR5 s.c. tumor growth in xenogenic model of athymic mice. Tumor cells were injected s.c. into 2 flanks of 10 athymic nude mice ($2 \times 10^6/100$ µl of PBS) to induce tumors. When tumors became of about 3-5 mm in diameter (by day 7 after injections) mice were randomly distributed into 2 groups, 5 mice for CBLB502 treated group and 5 mice in PBS control group. Suppression of tumor growth was found in CBLB502 treated mice. Data are shown in FIG. 16.

EXAMPLE 4

Figure 17:
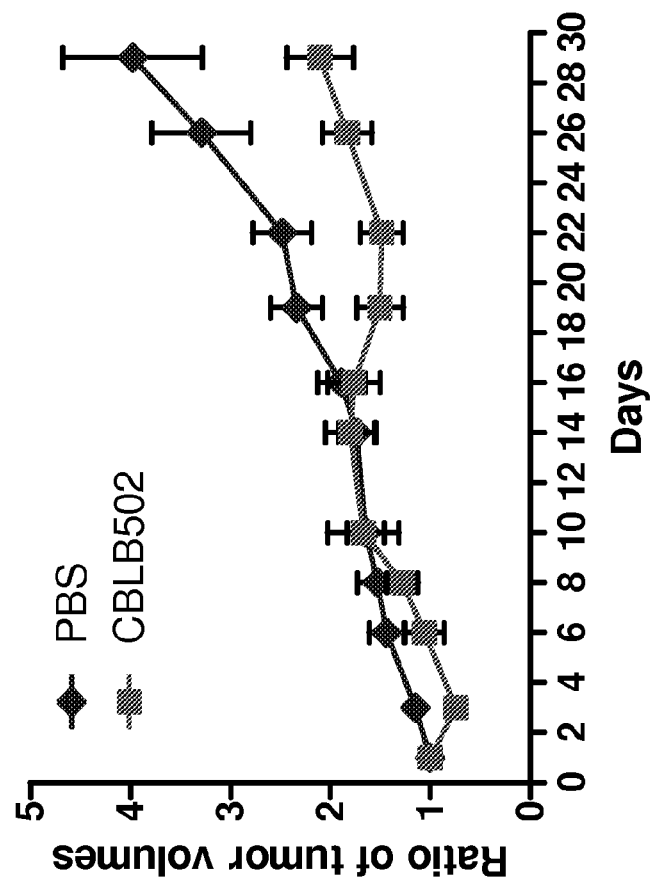
FIG. 17 shows the dynamics of xenogenic A549 tumor growth in athymic nude mice during 2 courses of CBLB502 vs. PBS (control) treatments (days 1, 2, 3, 14, 15 and 16), n=6-10. Antitumor activity of colon HCT116 adenocarcinoma s.c. Grown as a xenograft in athymic mice. HCT116 were injected s.c. into 2 flanks of 8 athymic nude mice (0.5×106/100 ml of PBS) to induce tumors. When tumors became of about 3-5 mm in diameter (by day 6 after injections) mice were randomly distributed into 2 groups, 5 mice for CBLB502 treated group and 3 mice in PBS control group.

Antitumor activity of CBLB502 on A549 adenocarcinoma s.c. growth in xenogenic model of athymic mice. The original A549 cells (ATCC, CLL-185) were injected s.c. into 2 flanks of 8 athymic nude mice ($0.5 \times 10^6/100$ µl of PBS) to induce tumors. When tumors became of about 3-5 mm in diameter (by day 6 after injections) mice were randomly distributed into 2 groups, 5 mice for CBLB502 treated group and 3 mice in PBS control group. A549 tumor-bearing mice were injected with either CBLB502 (1 µg/mouse) or PBS three times with a 24-hr time interval. In the PBS injected control group of mice, tumor volumes gradually and regularly increased. On the other hand, the CBLB502 injected mice expressed inhibited tumor growth during the first several days after injections and then tumor growth restored. The second round of CBLB502 injections 2 weeks after the first treatment (days 14, 15 and 16) induced analogous tumor growth inhibition for approximately 1-2 weeks before the restart of tumor growth. As a result, by the end of the experiment the sizes of the A549 tumors differed significantly in the two groups of mice, being much smaller in CBLB502 treated vs. PBS treated mice. Data are shown in FIG. 17.

EXAMPLE 5

Figure 18:
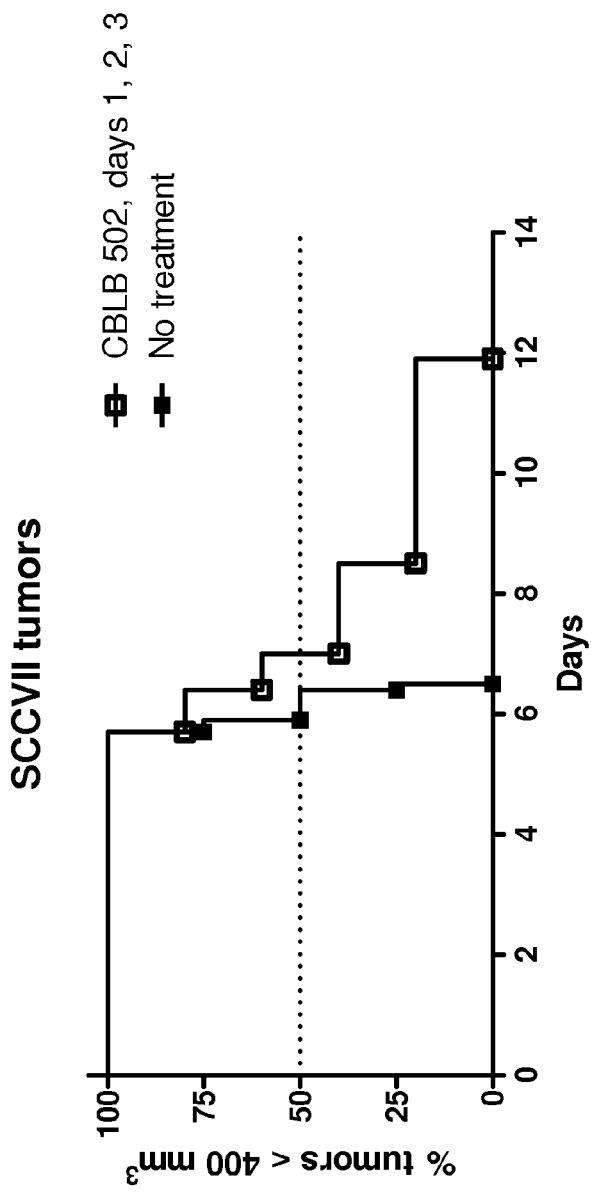
FIG. 18 shows the rate of SCCVII orthotopic tumor growth in syngenic C3H mice after CBLB502 or PBS (no treatment) treatments (0.1 mg/kg, s.c. days 1, 2, 3) to reach 400 mm³ tumor size, n=6-10. Right figure represents the amount of days needed for tumors to reach 400 mm3 volume with and without treatment with CBLB502.

Antitumor effect of CBLB502 on syngenic orthotopically (s.c.) growing squamous cell carcinoma SCCVII tumors. The rate of SCCVII orthotopic tumor growth in syngenic C3H mice after CBLB502 or PBS (no treatment) treatments (0.1 mg/kg, s.c. days 1, 2, 3) to reach 400 $mm^3$ tumor size, n=6-10. The x-axis in FIG. 18 represents the amount of days needed for tumors to reach 400 $mm^3$ volume with and without treatment with CBLB502. Data are shown in FIG. 18.

EXAMPLE 6

Figure 19:
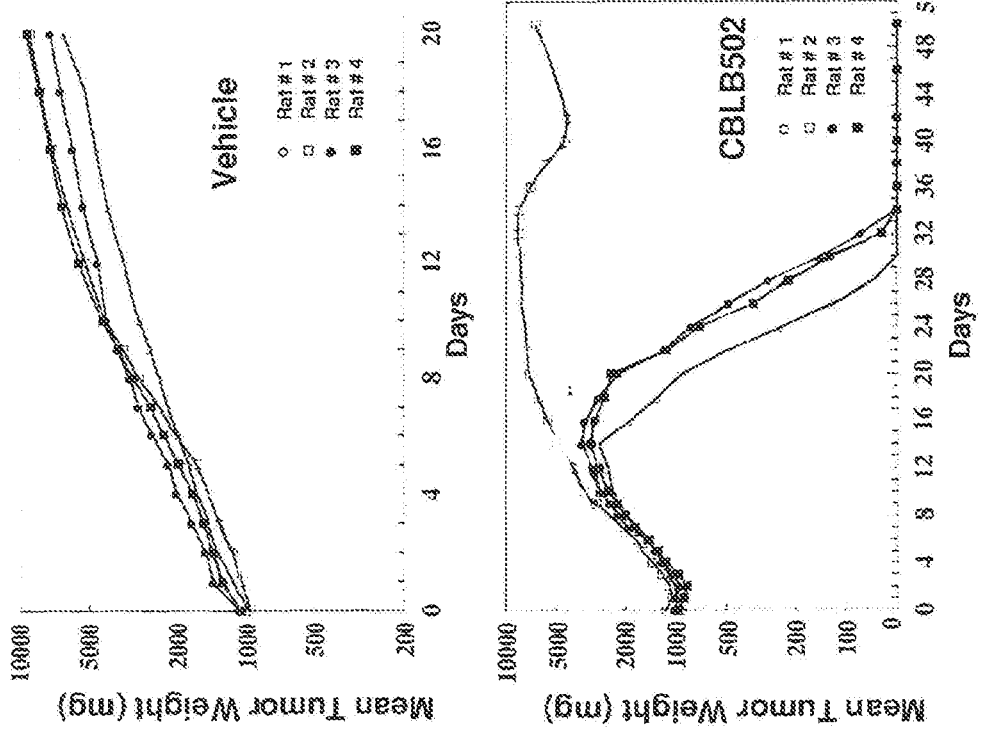
FIGS. 19A-B. Fischer rats with s.c. growing syngeneic Ward colon tumors were treated with CBLB502 (0.2 mg/kg) was administered by i.p. once a day for three days.

Antitumor activity of CBLB502 in Fischer rats bearing s.c. advanced Ward colorectal carcinoma. CBLB-502 was administered by i.p. once a day for 5 days (0.2 mg/kg×5 doses) initiated 5 days after tumor transplantation into 4 rats. Control 4 rats received PBS injection as a vehicle control. Tumor weight was measured daily. Complete response (tumor complete disappearance) was observed in 3 rats treated with CBLB502 (FIG. 19A-B). The fourth rat in this group had tumor growth similar to rats in the control group.

EXAMPLE 7

Figure 20:
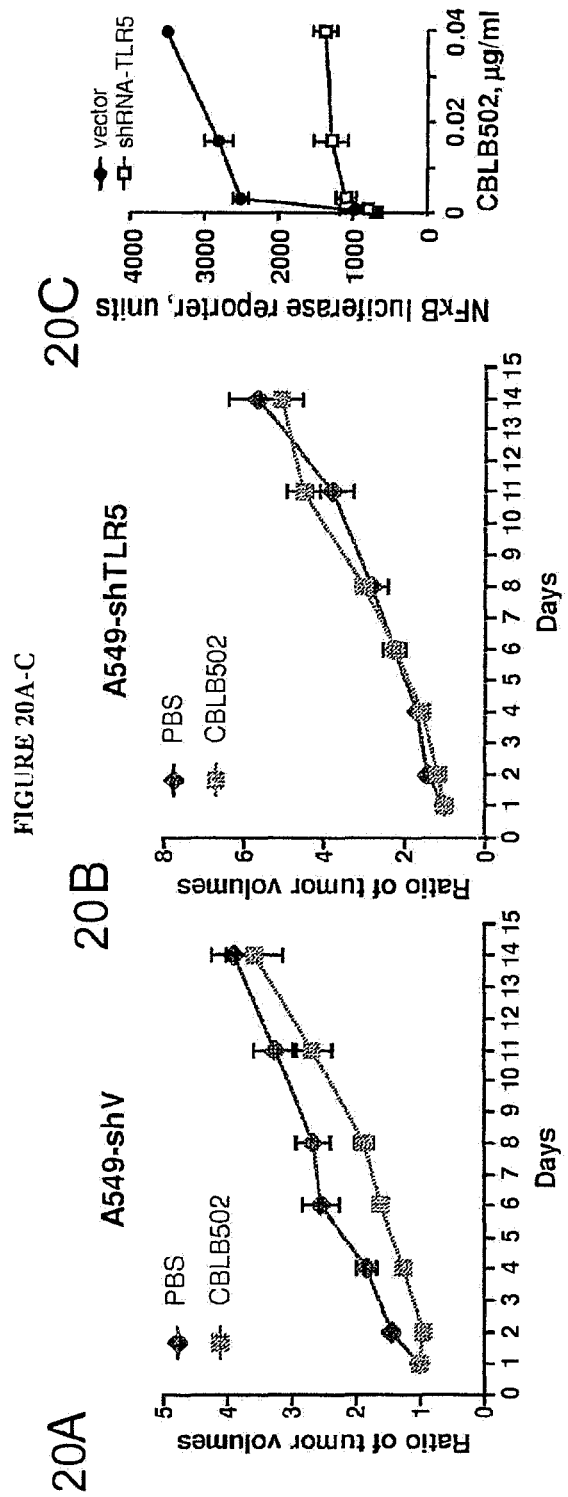
FIGS. 20A-C show the dynamics of xenogenic A549-shV (FIG. 20A) and A549-shTLR5 (FIG. 20A) tumor growth in athymic nude mice after CBLB502 or PBS (control) treatments (days 1, 2, 3). Statistical difference between tumor volumes on days 2, 4, 6 and 8 observed in A549-shV tumors (p<0.05), n=9-14.

The effect of CBLB502 injections on A549 tumors differing in TLR5 expression (A549-shTLR5 vs. A549-shV). In order to suppress TLR5 expression, A549 cells expressing Firefly luciferase gene under the control of NF-kB promoter (Cellecta, Mountain View, Calif.) were transduced with lentiviral pLKO1-puro vector expressing shRNA specific to human TLR5 gene [CCG-GCC-TTG-CCT-ACA-ACA-AGA-TAA-ACT-CGA-GTT-TAT-CTT-GTT-GTA-GGC-AAG-GTT-TTT-G (SEQ ID NO: 116)] or control empty vector (shV, Sigma-Aldrich, St. Louis, Mo.). After puromycin selection, A549-shV and A549-shTLR5 cells were tested for NF-kB activation in response to CBLB502 treatment using luciferase reporter assay according to manufacture protocol (Promega, Cat#E4530, Madison, Wis.). Then A549-shV and A549-shTLR5 cells (1×10⁶/100 µl of PBS) were injected s.c. into 2 flanks of 20 athymic nude mice to induce tumors. Mice bearing s.c. growing A549-shV and A549-shTLR5 tumor xenografts (5 mice per group) were treated with either CBLB502 or PBS acting as control The results demonstrate that the repeated administration of CBLB502 alone led to a reduction in tumor growth rates in the A549-shV (TLR5-expressing) tumor xenografts demonstrating a direct tumor suppressive effect of the drug. As shown for A549 derived tumors, this effect was TLR5 dependent since TLR5 knockdown elicited by lentiviral transduction of shRNA against human TLR5 rendered the A549 tumors no longer sensitive to the direct antitumor effect of CBLB502. Data are shown in FIG. 20A-C.

EXAMPLE 8

Figure 21:
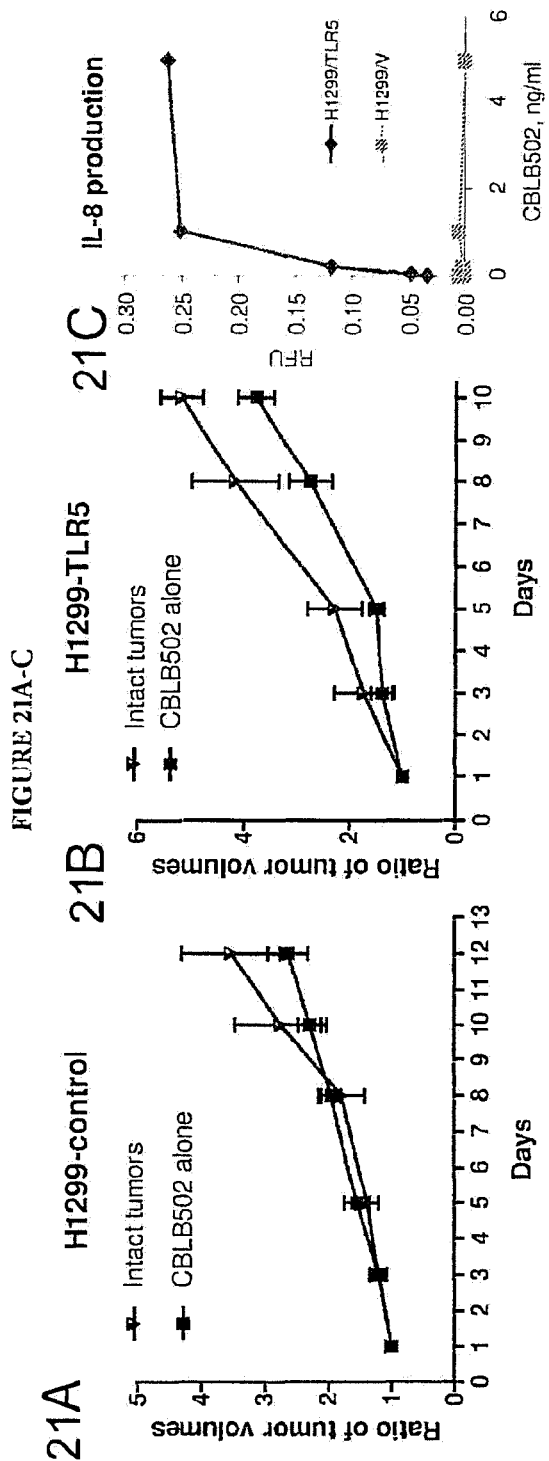
FIGS. 21A-C show the dynamics of H1299 (control, FIG. 21A) and H1299-TLR5 (FIG. 21B) tumor growth in athymic nude mice after CBLB502 or PBS (control) treatments (days 1, 2, 3), n=6.

The effect of CBLB502 injections on H1299 tumors differing in TLR5 expression (H1299-control vs. H1299-TLR5). In order to induce TLR5 expression, H1299 cells (originally TLR5 negative) were transduced with lentiviral construct expressing human TLR5 gene. The functional activity of TLR5 was checked by IL-8 production in response to CBLB502 treatment. Then both tumor cell types (1×10⁶/100 µl of PBS) were injected s.c. into 2 flanks of athymic nude mice to induce tumors. Similar to A549 model described above, mice bearing were treated with either CBLB502 or PBS acting as control. The results demonstrate that the repeated administration of CBLB502 alone led to a reduction in tumor growth rates only in H1299-TLR5 (TLR5-expressing) tumor xenografts demonstrating a direct tumor suppressive effect of the drug. As shown for the control H1299 (TLR5-negative) tumor growth was not affected CBLB502 treatment. Data are shown in FIG. 21A-C.

EXAMPLE 9

Figure 22:
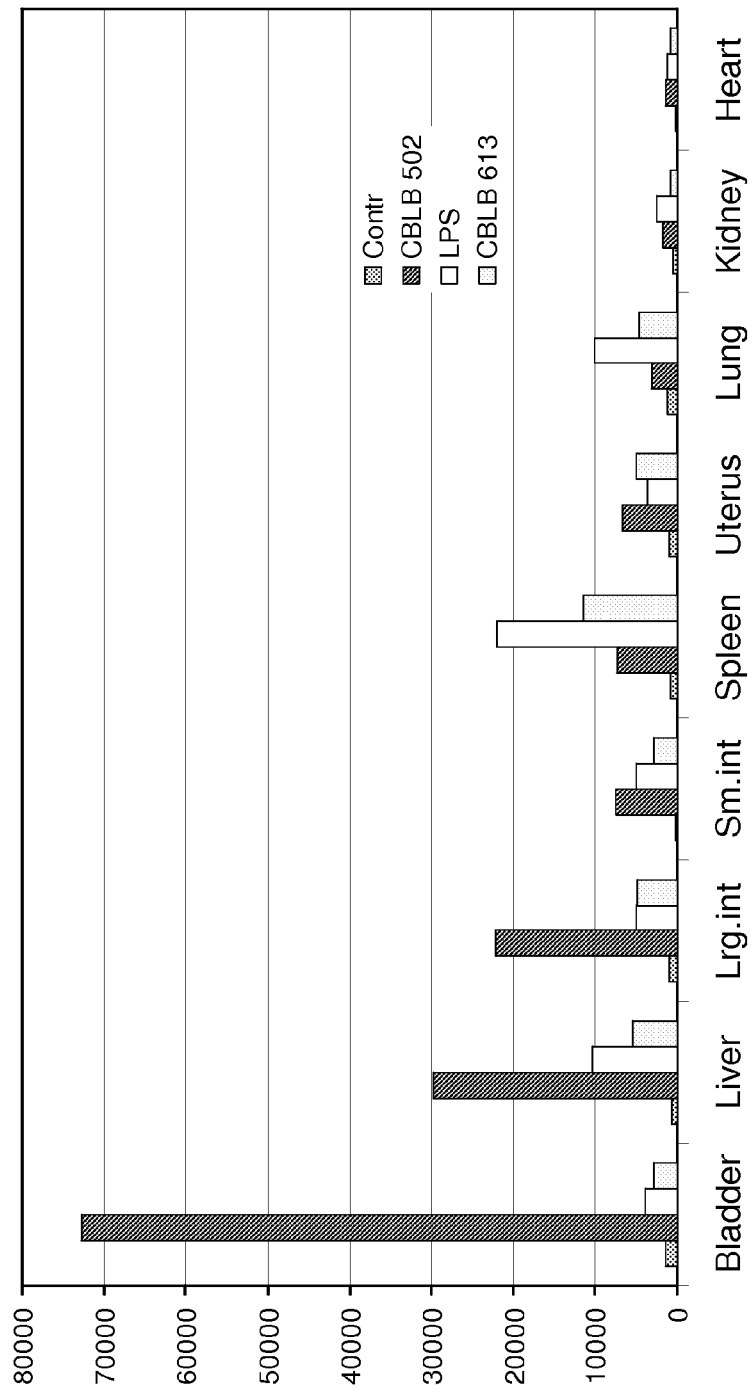
FIG. 22 shows that the bladder strongly responds to CBLB502.
Figure 23E:
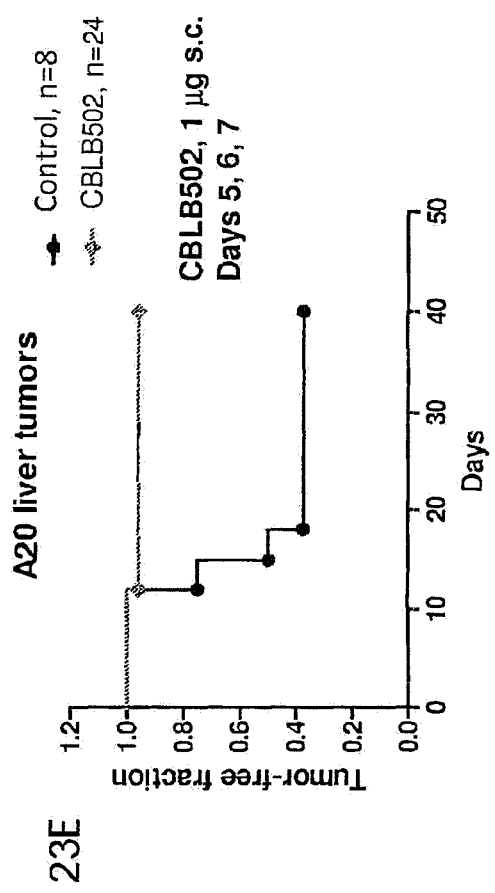

This example demonstrates that bladder tissue is a strong responder to CBLB502. The experiment was conducted as described as described above for liver tissues. NF-kB dependent luciferase expression in liver, small intestine (ileum part), colon, spleen, kidneys, lungs and heart was assessed in the reporter mice 2 hs after s.c. injections of 100 µl of either PBS, CBLB502 (0.2 mg/kg) or LPS (1 mg/kg). Luciferase activity normalized per µg of the protein extract was detected in 3 mice in each group. The data are shown in FIG. 22.

EXAMPLE 10

Table 2 shows the spectrum of genes transcriptionally activated by CBLB502 in target organs of mice (bladder results are shown). Genes that are strongly upregulated in bladders of mice treated with CBLB502, 1 and 3 hrs post-injection, are clustered according to their function. The largest group consists of chemokines, cytokines and their receptors indicative of activation of innate immunity mobilizing mechanisms.

EXAMPLE 11

CT-26 tumor cells, which do not express TLR5, were injected s.c. into syngenic BALB/c mice to induce tumors. Tumor bearing mice were treated with CBLB502 (0.04 mg/kg, s.c.) given twice 24 hour apart. The volumes of s.c. growing tumors in treated mice were compared with tumors growing in the intact mice. Pre-treatment with CBLB502 did not have any effect on tumor growth. Then CT26 tumor growth was tested in the experimental model of liver metastases induced by intrasplenic injection of luciferase expressing CT-26 tumor cells (FIGS. 23B and C) and A20 lymphoma cells (FIG. 23D) followed by splenectomy. Hepatic tumor growth was assessed using Xenogen luciferase imaging every 4-6 days after the treatment. Mice remained free from liver tumor growth were counted at each imaging procedure. The results demonstrate prevention of tumor growth and significant delay of tumor appearance in livers by CBLB502 treatment in both tumor models. The difference between CBLB502 treated and control groups in liver tumor models (B, C, D) is significant (log rank $p<0.05$). The data are shown in FIG. 23A-E.

EXAMPLE 12

CBLB502 protection from Fas mediated hepatotoxicity. A. Survival of NIH-Swiss mice after i.p. injection of 4 µg of anti-Fas antibodies alone or in combination with CBLB502 (1 µg/mouse) injected 30 min, 2 hours and 6 hours prior antibodies. In parenthesis are the numbers of mice per each treatment. B. Protection of livers from anti-Fas antibody toxicity. Apoptosis in livers 5 hours after injections of anti-Fas antibodies was detected using TUNEL technique. Tissue morphology with H&E staining revealed necrotic damage to livers by anti-Fas antibody injections and protection by CBLB502. Hemorrhage in liver was detected by erythrocyte infiltration in tissue, mouse IgG control (purple) and DAPI nuclei (blue). Data are shown in FIG. 24.

EXAMPLE 13

Liver protection from TNF-alpha and LPS toxicity. A. Caspases 3/7 were detected 5 hours after injections of TNF-a or LPS and lipis oxidation (indicative of inflammation damage) was detected 24 hours post injection in mice with and without CBLB502 treatment 30 min before TPS/TNF-a. Caspase activation and lipid oxidation in lungs induced by TNF (1 mg/mouse) was prevented by CBLB502 injection. LPS (10 mg/kg) induced damaging effect was completely abolished by CBLB502 injection 30 min before LPS. Data normalized by protein concentration, 24 hours after the treatment, n=3. It was no caspase activation (5 hours after TNF injections) and much less lipid oxidation (24 hours post-TNF injections as indicative of inflammatory damage) in livers of mice if CBLB502 was injected 30 min before h-TNF. B. Immunohistochemical analysis (H&E staining) confirmed the preservation of liver integrity by CBLB502 injection before TNF-a. Compared to the intact control, the liver of the TNF-treated mice showed vacuolization of the hepatocytes that is slightly more pronounced periportally and is dose-dependent (more severe in TNF 0.4 mg/mouse). In the livers of mice treated with CBLB502 and TNF 0.2 mg or 0.4 mg/mouse, the changes were minimal and the hepatocytes were close to normal though slight vacuolization was still visible. Data are shown in FIG. 25A-B.

EXAMPLE 14

Lung protection from TNF-a and LPS toxicity. Compared to intact control, the lungs of the TNF-treated mice showed reactive proliferation of alveolar cells, hyperemia, interstitial edema and exudates in alveoli leading to reduction of the air spaces and the alteration was dose-dependent (more severe in TNF 400). In the lungs of mice treated with CBLB502 and TNF 200 ng or 400 ng, the changes were minimal. The morphology was close to normal though slight thickening of alveolar walls was still visible (FIG. 26B). It was almost normal level of lipid oxidation (indicative of inflammatory damage) in lungs of mice if CBLB502 was injected 30 min before LPS (10 mg/kg) or h-TNF (0.05 mg/kg) (FIG. 26A). Data are shown in FIG. 26A-B.

EXAMPLE 15

Protection of mice from lethal oral *Salmonella typhimurium* administration by CBLB502 injections. Conditions of the experiments are shown in FIG. 27A-B.

EXAMPLE 16

This examples demonstrates that irinotecan abrogates the antitumor effect of flagellin. The data are shown in FIG. 28A-C. Fischer rats with s.c. growing syngeneic Ward colon tumors were treated with CBLB502 (0.2 mg/kg), which was administered by i.p. once a day for three days. Irinotecan (200 mg/kg) was injected i.v. 30 min after each CBLB502 injection. PBS was used as a vehicle control (FIG. 28A). CBLB502 rescued rats from Irinotecan toxicity with no interference with irinotecan antitumor activity (FIG. 28B). The antitumor effect of CBLB502, however, was not observed in irinotecan-treated rats (FIG. 28C). This demonstrates that the antitumor effect of CBLB502 requires sufficient innate immunity levels.

The invention claimed is:

1. A method of treating a cancer present in a tissue that expresses a Toll-Like Receptor 5 (TLR5), comprising administering an effective amount of a TLR5 agonist to a subject in need thereof,
   wherein the cancer does not express TLR5,
   wherein the TLR5 agonist is flagellin or a flagellin derivative, and
   wherein the TLR5-expressing tissue is lung.

2. The method of claim 1, wherein the cancer is metastatic.

3. The method of claim 2, wherein the metastatic cancer is selected from melanoma, colon, breast, prostate, or a hematological malignancy.

4. The method of claim 3, wherein the hematological malignancy is lymphoma.

5. The method of claim 1, wherein the cancer is a tumor.

6. The method of claim 1, wherein the TLR agonist is administered as a monotherapy.

7. The method of claim 1, wherein the subject is not receiving a combination cancer therapy.

8. The method of claim 1, wherein the subject is not receiving chemotherapy or radiation therapy.

9. The method of claim 1, wherein the subject has sufficient innate immunity.

10. The method of claim 9, wherein the sufficient innate immunity level is equivalent to the level required for eligibility for a first or subsequent round of chemotherapy.

11. The method of claim 1, wherein the subject has a white blood cell count that is within the clinically normal range.

12. The method of claim 1, wherein the TLR5 agonist is administered to the subject before, after, or concurrent with removal of a tumor.

13. The method of claim 1, wherein the flagellin derivative comprises the amino acid sequence of SEQ ID NO:8.

14. The method of claim 1, wherein the TLR5 agonist upregulates chemokines, cytokines and their receptors indicative of activation of innate immunity mobilizing mechanisms.

15. A method of reducing recurrence of a cancer that does not express Toll-Like Receptor 5 (TLR5) in a subject in need thereof, comprising administering to the subject an effective amount of a TLR5 agonist, wherein the cancer is present in a lung tissue that expresses TLR5, and wherein the TLR5 agonist is flagellin or a flagellin derivative.

16. The method of claim 15, wherein the cancer recurrence is selected from a metastasis or a tumor regrowth.

17. The method of claim 15, wherein the flagellin derivative comprises the amino acid sequence of SEQ ID NO:8.

18. A method of treating a metastatic cancer that does not express Toll-Like Receptor 5 (TLR5) but is present in a lung tissue that expresses TLR5, comprising administering an effective amount of a flagellin or a flagellin derivative to a subject in need thereof.

19. The method of claim 18, wherein the flagellin derivative comprises the amino acid sequence of SEQ ID NO:8.

* * * * *